(12) United States Patent
Hufton et al.

(10) Patent No.: US 7,348,001 B2
(45) Date of Patent: Mar. 25, 2008

(54) TIE1-BINDING LIGANDS

(75) Inventors: Simon E. Hufton, Lanes (GB); Rene Hoet, Maastricht (NL); Henk Pieters, Maastricht (NL)

(73) Assignee: Dyax Corp., Cambridge, MA (US)

( * ) Notice: Subject to any disclaimer, the term of this patent is extended or adjusted under 35 U.S.C. 154(b) by 212 days.

(21) Appl. No.: 10/916,840

(22) Filed: Aug. 12, 2004

(65) Prior Publication Data

US 2005/0136053 A1 Jun. 23, 2005

Related U.S. Application Data

(60) Provisional application No. 60/494,713, filed on Aug. 12, 2003.

(51) Int. Cl.
*A61K 39/395* (2006.01)
*C07K 16/28* (2006.01)
*C07K 16/00* (2006.01)
*C12P 21/08* (2006.01)
*G01N 33/53* (2006.01)

(52) U.S. Cl. .............. 424/130.1; 424/133.1; 424/141.1; 424/143.1; 435/7.1; 530/387.1; 530/388.1; 530/388.15; 530/388.22; 530/391.3

(58) Field of Classification Search .......... 424/130.1, 424/133.1, 141.1, 143.1; 435/7.1; 530/387.1, 530/388.2

See application file for complete search history.

(56) References Cited

U.S. PATENT DOCUMENTS

| | | | |
|---|---|---|---|
| 5,851,797 A | 12/1998 | Valenzuela et al. | |
| 5,955,291 A * | 9/1999 | Alitalo et al. | 435/7.23 |
| 6,090,382 A * | 7/2000 | Salfeld et al. | 424/133.1 |
| 6,365,154 B1 | 4/2002 | Holmes et al. | |
| 6,492,331 B1 | 12/2002 | Godowski et al. | |
| 6,551,822 B1 | 4/2003 | Godowski et al. | |
| 6,586,397 B1 | 7/2003 | Godowski et al. | |
| 7,193,064 B2 * | 3/2007 | Mikayama et al. | 530/388.73 |
| 2003/0087393 A1 | 5/2003 | O'Reilly et al. | |
| 2003/0113782 A1 | 6/2003 | Karim et al. | |

FOREIGN PATENT DOCUMENTS

| | | |
|---|---|---|
| WO | WO93/14124 | 7/1993 |
| WO | WO95/26364 | 10/1995 |
| WO | WO01/72339 | 10/2001 |

OTHER PUBLICATIONS

Rudikoff et al, Proc Natl ' Acad Sci USA 79: 1979, 1982.*
Kobrin et al, J Immunology 146: 2017-2020, 1991.*
Barrios et al, J Molecular Recognition 17: 332-338, 2004.*
Hurwitz et al., "Bevacizumab plus irinotecan, fluorouracil and leucovorin for metastatic colorectal cancer", New England Journal of Med. 350:2335-2342 (2004).*
Chen-Konak et al., "Transcriptional and post-translation regulation of the Tie1 receptor by fluid shear stress changes in vascular endothelial cells," FASEB J.(2003) 17:2121-23.
Jones et al., "Tie receptors: new modulators of angiogenic and lymphangiogenic responses," Nat Rev. Mol. Cell Biol. (Apr. 2001) 2(4):257-67.
Kontos et al., "The endothelial receptor tyrosine kinase Tie1 activates phosphatidylinositol 3-kinase and Akt to inhibit apoptosis," Mol. Cell Biol. Mar. 2002; 22(6):1704-13.
Lin et al., "tie-1 protein tyrosine kinase: a novel independent prognostic marker for gastric cancer," Clin. Cancer Res. (Jul. 1999) 5(7):1745-51.
Loughna and Sato, "A combinatorial role of angiopoietin-1 and orphan receptor TIE1 pathways in establishing vascular polarity during angiogenesis," Mol. Cell (2001) 7:233-39.
Marron et al., "Tie-1 receptor tyrosine kinase endodomain interaction with SHP2: potential signalling mechanisms and roles in angiogenesis," Adv. Exp. Med. Biol. (2000) 476:35-46.
Marron et al., "Evidence for heterotypic interaction between the receptor tyrosine kinases TIE-1 and TIE-2," J Biol Chem. (Dec. 2000) 15;275(50):39741-6.
Partanen et al., "A novel ednothelial cell surface receptor tyrosine kinase with extracellular epidermal growth factor homology domains," Mol. Cell Biol. (Apr. 1992) 12(4):1698-707.
Puri et al., "The receptor tyrosine kinase TIE is required for integrity and survival of vascular endothelial cells," EMBO J. (Dec. 1, 1995) 14(23):5884-91.
Shahrara et al., "Differential expression of the angiogenic Tie receptor family in arthritic and normal synovial tissue," Arthritis Res. (2002) 4:201-208.
Tsiamsi et al., "Characterization and regulation of the receptor tyrosine kinase Tie-1 in platelets," J. Vasc. Res. (Nov-Dec. 2000) 37:437-42.

* cited by examiner

*Primary Examiner*—Christina Chan
*Assistant Examiner*—Phuong Huynh
(74) *Attorney, Agent, or Firm*—Lowrie, Lando & Anastasi, LLP

(57) ABSTRACT

Tie1 is a receptor tyrosine kinase protein that includes a transmembrane domain. Tie1 is present on endothelial cells. This disclosure described antibodies that bind to Tie1, including ones that inhibit endothelial cell activity.

10 Claims, 3 Drawing Sheets

SEQUENCE LISTING

<160> NUMBER OF SEQ ID NOS: 161

<210> SEQ ID NO 1
<211> LENGTH: 3417
<212> TYPE: DNA
<213> ORGANISM: Homo sapiens
<220> FEATURE:
<221> NAME/KEY: CDS
<222> LOCATION: (1)...(3414)

<400> SEQUENCE: 1

```
atg gtc tgg cgg gtg ccc cct ttc ttg ctc ccc atc ctc ttc ttg gct      48
Met Val Trp Arg Val Pro Pro Phe Leu Leu Pro Ile Leu Phe Leu Ala
 1               5                  10                  15 tct cat gtg ggc gcg gcg gtg gac ctg acg ctg ctg gcc aac ctg cgg      96
Ser His Val Gly Ala Ala Val Asp Leu Thr Leu Leu Ala Asn Leu Arg
             20                  25                  30 ctc acg gac ccc cag cgc ttc ttc ctg act tgc gtg tct ggg gag gcc     144
Leu Thr Asp Pro Gln Arg Phe Phe Leu Thr Cys Val Ser Gly Glu Ala
         35                  40                  45 ggg gcg ggg agg ggc tcg gac gcc tgg ggc ccg ccc ctg ctg ctg gag     192
Gly Ala Gly Arg Gly Ser Asp Ala Trp Gly Pro Pro Leu Leu Leu Glu
     50                  55                  60 aag gac gac cgt atc gtg cgc acc ccg ccc gga cca ccc ctg cgc ctg     240
Lys Asp Asp Arg Ile Val Arg Thr Pro Pro Gly Pro Pro Leu Arg Leu
 65                  70                  75                  80 gcg cgc aac ggt tcg cac cag gtc acg ctt cgc ggc ttc tcc aag ccc     288
Ala Arg Asn Gly Ser His Gln Val Thr Leu Arg Gly Phe Ser Lys Pro
                 85                  90                  95 tcg gac ctc gtg ggc gtc ttc tcc tgc gtg ggc ggt gct ggg gcg cgg     336
Ser Asp Leu Val Gly Val Phe Ser Cys Val Gly Gly Ala Gly Ala Arg
            100                 105                 110 cgc acg cgc gtc atc tac gtg cac aac agc cct gga gcc cac ctg ctt     384
Arg Thr Arg Val Ile Tyr Val His Asn Ser Pro Gly Ala His Leu Leu
        115                 120                 125 cca gac aag gtc aca cac act gtg aac aaa ggt gac acc gct gta ctt     432
Pro Asp Lys Val Thr His Thr Val Asn Lys Gly Asp Thr Ala Val Leu
    130                 135                 140 tct gca cgt gtg cac aag gag aag cag aca gac gtg atc tgg aag agc     480
Ser Ala Arg Val His Lys Glu Lys Gln Thr Asp Val Ile Trp Lys Ser
145                 150                 155                 160 aac gga tcc tac ttc tac acc ctg gac tgg cat gaa gcc cag gat ggg     528
Asn Gly Ser Tyr Phe Tyr Thr Leu Asp Trp His Glu Ala Gln Asp Gly
                165                 170                 175 cgg ttc ctg ctg cag ctc cca aat gtg cag cca cca tcg agc ggc atc     576
Arg Phe Leu Leu Gln Leu Pro Asn Val Gln Pro Pro Ser Ser Gly Ile
            180                 185                 190 tac agt gcc act tac ctg gaa gcc agc ccc ctg ggc agc gcc ttc ttt     624
Tyr Ser Ala Thr Tyr Leu Glu Ala Ser Pro Leu Gly Ser Ala Phe Phe
        195                 200                 205 cgg ctc atc gtg cgg ggt tgt ggg gct ggg cgc tgg ggg cca ggc tgt     672
Arg Leu Ile Val Arg Gly Cys Gly Ala Gly Arg Trp Gly Pro Gly Cys
    210                 215                 220 acc aag gag tgc cca ggt tgc cta cat gga ggt gtc tgc cac gac cat     720
Thr Lys Glu Cys Pro Gly Cys Leu His Gly Gly Val Cys His Asp His
225                 230                 235                 240 gac ggc gaa tgt gta tgc ccc cct ggc ttc act ggc acc cgc tgt gaa     768
Asp Gly Glu Cys Val Cys Pro Pro Gly Phe Thr Gly Thr Arg Cys Glu
                245                 250                 255
```

-continued

| | | |
|---|---|---|
| cag gcc tgc aga gag ggc cgt ttt ggg cag agc tgc cag gag cag tgc<br>Gln Ala Cys Arg Glu Gly Arg Phe Gly Gln Ser Cys Gln Glu Gln Cys<br>260                         265                       270 | 816 |
| cca ggc ata tca ggc tgc cgg ggc ctc acc ttc tgc ctc cca gac ccc<br>Pro Gly Ile Ser Gly Cys Arg Gly Leu Thr Phe Cys Leu Pro Asp Pro<br>275                         280                       285 | 864 |
| tat ggc tgc tct tgt gga tct ggc tgg aga gga agc cag tgc caa gaa<br>Tyr Gly Cys Ser Cys Gly Ser Gly Trp Arg Gly Ser Gln Cys Gln Glu<br>290                         295                       300 | 912 |
| gct tgt gcc cct ggt cat ttt ggg gct gat tgc cga ctc cag tgc cag<br>Ala Cys Ala Pro Gly His Phe Gly Ala Asp Cys Arg Leu Gln Cys Gln<br>305                        310                     315                 320 | 960 |
| tgt cag aat ggt ggc act tgt gac cgg ttc agt ggt tgt gtc tgc ccc<br>Cys Gln Asn Gly Gly Thr Cys Asp Arg Phe Ser Gly Cys Val Cys Pro<br>                       325                       330                     335 | 1008 |
| tct ggg tgg cat gga gtg cac tgt gag aag tca gac cgg atc ccc cag<br>Ser Gly Trp His Gly Val His Cys Glu Lys Ser Asp Arg Ile Pro Gln<br>                     340                       345                     350 | 1056 |
| atc ctc aac atg gcc tca gaa ctg gag ttc aac tta gag acg atg ccc<br>Ile Leu Asn Met Ala Ser Glu Leu Glu Phe Asn Leu Glu Thr Met Pro<br>          355                     360                     365 | 1104 |
| cgg atc aac tgt gca gct gca ggg aac ccc ttc ccc gtg cgg ggc agc<br>Arg Ile Asn Cys Ala Ala Ala Gly Asn Pro Phe Pro Val Arg Gly Ser<br>370                         375                       380 | 1152 |
| ata gag cta cgc aag cca gac ggc act gtg ctc ctg tcc acc aag gcc<br>Ile Glu Leu Arg Lys Pro Asp Gly Thr Val Leu Leu Ser Thr Lys Ala<br>385                         390                     395                 400 | 1200 |
| att gtg gag cca gag aag acc aca gct gag ttc gag gtg ccc cgc ttg<br>Ile Val Glu Pro Glu Lys Thr Thr Ala Glu Phe Glu Val Pro Arg Leu<br>                       405                       410                     415 | 1248 |
| gtt ctt gcg gac agt ggg ttc tgg gag tgc cgt gtg tcc aca tct ggc<br>Val Leu Ala Asp Ser Gly Phe Trp Glu Cys Arg Val Ser Thr Ser Gly<br>                   420                       425                     430 | 1296 |
| ggc caa gac agc cgg cgc ttc aag gtc aat gtg aaa gtg ccc ccc gtg<br>Gly Gln Asp Ser Arg Arg Phe Lys Val Asn Val Lys Val Pro Pro Val<br>               435                       440                     445 | 1344 |
| ccc ctg gct gca cct cgg ctc ctg acc aag cag agc cgc cag ctt gtg<br>Pro Leu Ala Ala Pro Arg Leu Leu Thr Lys Gln Ser Arg Gln Leu Val<br>450                         455                       460 | 1392 |
| gtc tcc ccg ctg gtc tcg ttc tct ggg gat gga ccc atc tcc act gtc<br>Val Ser Pro Leu Val Ser Phe Ser Gly Asp Gly Pro Ile Ser Thr Val<br>465                         470                     475                 480 | 1440 |
| cgc ctg cac tac cgg ccc cag gac agt acc atg gac tgg tcg acc att<br>Arg Leu His Tyr Arg Pro Gln Asp Ser Thr Met Asp Trp Ser Thr Ile<br>                       485                       490                   495 | 1488 |
| gtg gtg gac ccc agt gag aac gtg acg tta atg aac ctg agg cca aag<br>Val Val Asp Pro Ser Glu Asn Val Thr Leu Met Asn Leu Arg Pro Lys<br>                   500                       505                     510 | 1536 |
| aca gga tac agt gtt cgt gtg cag ctg agc cgg cca ggg gaa gga gga<br>Thr Gly Tyr Ser Val Arg Val Gln Leu Ser Arg Pro Gly Glu Gly Gly<br>               515                       520                     525 | 1584 |
| gag ggg gcc tgg ggg cct ccc acc ctc atg acc aca gac tgt cct gag<br>Glu Gly Ala Trp Gly Pro Pro Thr Leu Met Thr Thr Asp Cys Pro Glu<br>530                         535                       540 | 1632 |
| cct ttg ttg cag ccg tgg ttg gag ggc tgg cat gtg gaa ggc act gac<br>Pro Leu Leu Gln Pro Trp Leu Glu Gly Trp His Val Glu Gly Thr Asp<br>545                         550                     555                 560 | 1680 |
| cgg ctg cga gtg agc tgg tcc ttg ccc ttg gtg ccc ggg cca ctg gtg<br>Arg Leu Arg Val Ser Trp Ser Leu Pro Leu Val Pro Gly Pro Leu Val<br>                   565                       570                     575 | 1728 |

-continued

| | |
|---|---|
| ggc gac ggt ttc ctg ctg cgc ctg tgg gac ggg aca cgg ggg cag gag<br>Gly Asp Gly Phe Leu Leu Arg Leu Trp Asp Gly Thr Arg Gly Gln Glu<br>580                              585                         590 | 1776 |
| cgg cgg gag aac gtc tca tcc ccc cag gcc cgc act gcc ctc ctg acg<br>Arg Arg Glu Asn Val Ser Ser Pro Gln Ala Arg Thr Ala Leu Leu Thr<br>     595                        600                      605 | 1824 |
| gga ctc acg cct ggc acc cac tac cag ctg gat gtg cag ctc tac cac<br>Gly Leu Thr Pro Gly Thr His Tyr Gln Leu Asp Val Gln Leu Tyr His<br>610                            615                       620 | 1872 |
| tgc acc ctc ctg ggc ccg gcc tcg ccc cct gca cac gtg ctt ctg ccc<br>Cys Thr Leu Leu Gly Pro Ala Ser Pro Pro Ala His Val Leu Leu Pro<br>625                            630                       635                640 | 1920 |
| ccc agt ggg cct cca gcc ccc cga cac ctc cac gcc cag gcc ctc tca<br>Pro Ser Gly Pro Pro Ala Pro Arg His Leu His Ala Gln Ala Leu Ser<br>                  645                       650                      655 | 1968 |
| gac tcc gag atc cag ctg aca tgg aag cac ccg gag gct ctg cct ggg<br>Asp Ser Glu Ile Gln Leu Thr Trp Lys His Pro Glu Ala Leu Pro Gly<br>660                            665                       670 | 2016 |
| cca ata tcc aag tac gtt gtg gag gtg cag gtg gct ggg ggt gca gga<br>Pro Ile Ser Lys Tyr Val Val Glu Val Gln Val Ala Gly Gly Ala Gly<br>                  675                       680                      685 | 2064 |
| gac cca ctg tgg ata gac gtg gac agg cct gag gag aca agc acc atc<br>Asp Pro Leu Trp Ile Asp Val Asp Arg Pro Glu Glu Thr Ser Thr Ile<br>690                            695                       700 | 2112 |
| atc cgt ggc ctc aac gcc agc acg cgc tac ctc ttc cgc atg cgg gcc<br>Ile Arg Gly Leu Asn Ala Ser Thr Arg Tyr Leu Phe Arg Met Arg Ala<br>705                            710                       715                720 | 2160 |
| agc att cag ggg ctc ggg gac tgg agc aac aca gta gaa gag tcc acc<br>Ser Ile Gln Gly Leu Gly Asp Trp Ser Asn Thr Val Glu Glu Ser Thr<br>                  725                       730                      735 | 2208 |
| ctg ggc aac ggg ctg cag gct gag ggc cca gtc caa gag agc cgg gca<br>Leu Gly Asn Gly Leu Gln Ala Glu Gly Pro Val Gln Glu Ser Arg Ala<br>740                            745                       750 | 2256 |
| gct gaa gag ggc ctg gat cag cag ctg atc ctg gcg gtg gtg ggc tcc<br>Ala Glu Glu Gly Leu Asp Gln Gln Leu Ile Leu Ala Val Val Gly Ser<br>                  755                       760                      765 | 2304 |
| gtg tct gcc acc tgc ctc acc atc ctg gcc gcc ctt tta acc ctg gtg<br>Val Ser Ala Thr Cys Leu Thr Ile Leu Ala Ala Leu Leu Thr Leu Val<br>770                            775                       780 | 2352 |
| tgc atc cgc aga agc tgc ctg cat cgg aga cgc acc ttc acc tac cag<br>Cys Ile Arg Arg Ser Cys Leu His Arg Arg Arg Thr Phe Thr Tyr Gln<br>785                            790                       795                800 | 2400 |
| tca ggc tcg ggc gag gag acc atc ctg cag ttc agc tca ggg acc ttg<br>Ser Gly Ser Gly Glu Glu Thr Ile Leu Gln Phe Ser Ser Gly Thr Leu<br>                  805                       810                      815 | 2448 |
| aca ctt acc cgg cgg cca aaa ctg cag ccc gag ccc ctg agc tac cca<br>Thr Leu Thr Arg Arg Pro Lys Leu Gln Pro Glu Pro Leu Ser Tyr Pro<br>820                            825                       830 | 2496 |
| gtg cta gag tgg gag gac atc acc ttt gag gac ctc atc ggg gag ggg<br>Val Leu Glu Trp Glu Asp Ile Thr Phe Glu Asp Leu Ile Gly Glu Gly<br>                  835                       840                      845 | 2544 |
| aac ttc ggc cag gtc atc cgg gcc atg atc aag aag gac ggg ctg aag<br>Asn Phe Gly Gln Val Ile Arg Ala Met Ile Lys Lys Asp Gly Leu Lys<br>850                            855                       860 | 2592 |
| atg aac gca gcc atc aaa atg ctg aaa gag tat gcc tct gaa aat gac<br>Met Asn Ala Ala Ile Lys Met Leu Lys Glu Tyr Ala Ser Glu Asn Asp<br>865                            870                       875                880 | 2640 |
| cat cgt gac ttt gcg gga gaa ctg gaa gtt ctg tgc aaa ttg ggg cat<br>His Arg Asp Phe Ala Gly Glu Leu Glu Val Leu Cys Lys Leu Gly His | 2688 |

```
                     885                 890                 895
cac ccc aac atc atc aac ctc ctg ggg gcc tgt aag aac cga ggt tac        2736
His Pro Asn Ile Ile Asn Leu Leu Gly Ala Cys Lys Asn Arg Gly Tyr
            900                 905                 910 ttg tat atc gct att gaa tat gcc ccc tac ggg aac ctg cta gat ttt        2784
Leu Tyr Ile Ala Ile Glu Tyr Ala Pro Tyr Gly Asn Leu Leu Asp Phe
        915                 920                 925 ctg cgg aaa agc cgg gtc cta gag act gac cca gct ttt gct cga gag        2832
Leu Arg Lys Ser Arg Val Leu Glu Thr Asp Pro Ala Phe Ala Arg Glu
    930                 935                 940 cat ggg aca gcc tct acc ctt agc tcc cgg cag ctg ctg cgt ttc gcc        2880
His Gly Thr Ala Ser Thr Leu Ser Ser Arg Gln Leu Leu Arg Phe Ala
945                 950                 955                 960 agt gat gcg gcc aat ggc atg cag tac ctg agt gag aag cag ttc atc        2928
Ser Asp Ala Ala Asn Gly Met Gln Tyr Leu Ser Glu Lys Gln Phe Ile
                965                 970                 975 cac agg gac ctg gct gcc cgg aat gtg ctg gtc gga gag aac cta gcc        2976
His Arg Asp Leu Ala Ala Arg Asn Val Leu Val Gly Glu Asn Leu Ala
            980                 985                 990 tcc aag att gca gac ttc ggc ctt tct cgg gga gag gag gtt tat gtg        3024
Ser Lys Ile Ala Asp Phe Gly Leu Ser Arg Gly Glu Glu Val Tyr Val
        995                 1000                1005 aag aag acg atg ggg cgt ctc cct gtg cgc tgg atg gcc att gag tcc        3072
Lys Lys Thr Met Gly Arg Leu Pro Val Arg Trp Met Ala Ile Glu Ser
    1010                1015                1020 ctg aac tac agt gtc tat acc acc aag agt gat gtc tgg tcc ttt gga        3120
Leu Asn Tyr Ser Val Tyr Thr Thr Lys Ser Asp Val Trp Ser Phe Gly
1025                1030                1035                1040 gtc ctt ctt tgg gag ata gtg agc ctt gga ggt aca ccc tac tgt ggc        3168
Val Leu Leu Trp Glu Ile Val Ser Leu Gly Gly Thr Pro Tyr Cys Gly
                1045                1050                1055 atg acc tgt gcc gag ctc tat gaa aag ctg ccc cag ggc tac cgc atg        3216
Met Thr Cys Ala Glu Leu Tyr Glu Lys Leu Pro Gln Gly Tyr Arg Met
            1060                1065                1070 gag cag cct cga aac tgt gac gat gaa gtg tac gag ctg atg cgt cag        3264
Glu Gln Pro Arg Asn Cys Asp Asp Glu Val Tyr Glu Leu Met Arg Gln
        1075                1080                1085 tgc tgg cgg gac cgt ccc tat gag cga ccc ccc ttt gcc cag att gcg        3312
Cys Trp Arg Asp Arg Pro Tyr Glu Arg Pro Pro Phe Ala Gln Ile Ala
    1090                1095                1100 cta cag cta ggc cgc atg ctg gaa gcc agg aag gcc tat gtg aac atg        3360
Leu Gln Leu Gly Arg Met Leu Glu Ala Arg Lys Ala Tyr Val Asn Met
1105                1110                1115                1120 tcg ctg ttt gag aac ttc act tac gcg ggc att gat gcc aca gct gag        3408
Ser Leu Phe Glu Asn Phe Thr Tyr Ala Gly Ile Asp Ala Thr Ala Glu
                1125                1130                1135 gag gcc tga                                                             3417
Glu Ala <210> SEQ ID NO 2
<211> LENGTH: 1138
<212> TYPE: PRT
<213> ORGANISM: Homo sapiens

<400> SEQUENCE: 2

Met Val Trp Arg Val Pro Pro Phe Leu Leu Pro Ile Leu Phe Leu Ala
  1               5                  10                  15

Ser His Val Gly Ala Ala Val Asp Leu Thr Leu Leu Ala Asn Leu Arg
             20                  25                  30
```

-continued

```
Leu Thr Asp Pro Gln Arg Phe Phe Leu Thr Cys Val Ser Gly Glu Ala
         35                  40                  45
Gly Ala Gly Arg Gly Ser Asp Ala Trp Gly Pro Pro Leu Leu Leu Glu
     50                  55                  60
Lys Asp Asp Arg Ile Val Arg Thr Pro Pro Gly Pro Pro Leu Arg Leu
 65                  70                  75                  80
Ala Arg Asn Gly Ser His Gln Val Thr Leu Arg Gly Phe Ser Lys Pro
                 85                  90                  95
Ser Asp Leu Val Gly Val Phe Ser Cys Val Gly Gly Ala Gly Ala Arg
            100                 105                 110
Arg Thr Arg Val Ile Tyr Val His Asn Ser Pro Gly Ala His Leu Leu
        115                 120                 125
Pro Asp Lys Val Thr His Thr Val Asn Lys Gly Asp Thr Ala Val Leu
    130                 135                 140
Ser Ala Arg Val His Lys Glu Lys Gln Thr Asp Val Ile Trp Lys Ser
145                 150                 155                 160
Asn Gly Ser Tyr Phe Tyr Thr Leu Asp Trp His Glu Ala Gln Asp Gly
                165                 170                 175
Arg Phe Leu Leu Gln Leu Pro Asn Val Gln Pro Pro Ser Ser Gly Ile
            180                 185                 190
Tyr Ser Ala Thr Tyr Leu Glu Ala Ser Pro Leu Gly Ser Ala Phe Phe
        195                 200                 205
Arg Leu Ile Val Arg Gly Cys Gly Ala Gly Arg Trp Gly Pro Gly Cys
    210                 215                 220
Thr Lys Glu Cys Pro Gly Cys Leu His Gly Gly Val Cys His Asp His
225                 230                 235                 240
Asp Gly Glu Cys Val Cys Pro Pro Gly Phe Thr Gly Thr Arg Cys Glu
                245                 250                 255
Gln Ala Cys Arg Glu Gly Arg Phe Gly Gln Ser Cys Gln Glu Gln Cys
            260                 265                 270
Pro Gly Ile Ser Gly Cys Arg Gly Leu Thr Phe Cys Leu Pro Asp Pro
        275                 280                 285
Tyr Gly Cys Ser Cys Gly Ser Gly Trp Arg Gly Ser Gln Cys Gln Glu
    290                 295                 300
Ala Cys Ala Pro Gly His Phe Gly Ala Asp Cys Arg Leu Gln Cys Gln
305                 310                 315                 320
Cys Gln Asn Gly Gly Thr Cys Asp Arg Phe Ser Gly Cys Val Cys Pro
                325                 330                 335
Ser Gly Trp His Gly Val His Cys Glu Lys Ser Asp Arg Ile Pro Gln
            340                 345                 350
Ile Leu Asn Met Ala Ser Glu Leu Glu Phe Asn Leu Glu Thr Met Pro
        355                 360                 365
Arg Ile Asn Cys Ala Ala Gly Asn Pro Phe Pro Val Arg Gly Ser
    370                 375                 380
Ile Glu Leu Arg Lys Pro Asp Gly Thr Val Leu Leu Ser Thr Lys Ala
385                 390                 395                 400
Ile Val Glu Pro Glu Lys Thr Thr Ala Glu Phe Glu Val Pro Arg Leu
                405                 410                 415
Val Leu Ala Asp Ser Gly Phe Trp Glu Cys Arg Val Ser Thr Ser Gly
            420                 425                 430
Gly Gln Asp Ser Arg Arg Phe Lys Val Asn Val Lys Val Pro Pro Val
        435                 440                 445
Pro Leu Ala Ala Pro Arg Leu Leu Thr Lys Gln Ser Arg Gln Leu Val
```

-continued

```
            450                 455                 460
Val Ser Pro Leu Val Ser Phe Ser Gly Asp Gly Pro Ile Ser Thr Val
465                 470                 475                 480

Arg Leu His Tyr Arg Pro Gln Asp Ser Thr Met Asp Trp Ser Thr Ile
                485                 490                 495

Val Val Asp Pro Ser Glu Asn Val Thr Leu Met Asn Leu Arg Pro Lys
                500                 505                 510

Thr Gly Tyr Ser Val Arg Val Gln Leu Ser Arg Pro Gly Glu Gly Gly
                515                 520                 525

Glu Gly Ala Trp Gly Pro Pro Thr Leu Met Thr Thr Asp Cys Pro Glu
530                 535                 540

Pro Leu Leu Gln Pro Trp Leu Glu Gly Trp His Val Glu Gly Thr Asp
545                 550                 555                 560

Arg Leu Arg Val Ser Trp Ser Leu Pro Leu Val Pro Gly Pro Leu Val
                565                 570                 575

Gly Asp Gly Phe Leu Leu Arg Leu Trp Asp Gly Thr Arg Gly Gln Glu
                580                 585                 590

Arg Arg Glu Asn Val Ser Ser Pro Gln Ala Arg Thr Ala Leu Leu Thr
            595                 600                 605

Gly Leu Thr Pro Gly Thr His Tyr Gln Leu Asp Val Gln Leu Tyr His
            610                 615                 620

Cys Thr Leu Leu Gly Pro Ala Ser Pro Pro Ala His Val Leu Leu Pro
625                 630                 635                 640

Pro Ser Gly Pro Pro Ala Pro Arg His Leu His Ala Gln Ala Leu Ser
                645                 650                 655

Asp Ser Glu Ile Gln Leu Thr Trp Lys His Pro Glu Ala Leu Pro Gly
                660                 665                 670

Pro Ile Ser Lys Tyr Val Val Glu Val Gln Val Ala Gly Gly Ala Gly
                675                 680                 685

Asp Pro Leu Trp Ile Asp Val Asp Arg Pro Glu Glu Thr Ser Thr Ile
            690                 695                 700

Ile Arg Gly Leu Asn Ala Ser Thr Arg Tyr Leu Phe Arg Met Arg Ala
705                 710                 715                 720

Ser Ile Gln Gly Leu Gly Asp Trp Ser Asn Thr Val Glu Glu Ser Thr
                725                 730                 735

Leu Gly Asn Gly Leu Gln Ala Glu Gly Pro Val Gln Glu Ser Arg Ala
                740                 745                 750

Ala Glu Glu Gly Leu Asp Gln Gln Leu Ile Leu Ala Val Val Gly Ser
            755                 760                 765

Val Ser Ala Thr Cys Leu Thr Ile Leu Ala Ala Leu Leu Thr Leu Val
            770                 775                 780

Cys Ile Arg Arg Ser Cys Leu His Arg Arg Arg Thr Phe Thr Tyr Gln
785                 790                 795                 800

Ser Gly Ser Gly Glu Glu Thr Ile Leu Gln Phe Ser Ser Gly Thr Leu
                805                 810                 815

Thr Leu Thr Arg Arg Pro Lys Leu Gln Pro Glu Pro Leu Ser Tyr Pro
                820                 825                 830

Val Leu Glu Trp Glu Asp Ile Thr Phe Glu Asp Leu Ile Gly Glu Gly
            835                 840                 845

Asn Phe Gly Gln Val Ile Arg Ala Met Ile Lys Lys Asp Gly Leu Lys
            850                 855                 860

Met Asn Ala Ala Ile Lys Met Leu Lys Glu Tyr Ala Ser Glu Asn Asp
865                 870                 875                 880
```

His Arg Asp Phe Ala Gly Glu Leu Glu Val Leu Cys Lys Leu Gly His
            885                 890                 895

His Pro Asn Ile Ile Asn Leu Leu Gly Ala Cys Lys Asn Arg Gly Tyr
        900                 905                 910

Leu Tyr Ile Ala Ile Glu Tyr Ala Pro Tyr Gly Asn Leu Leu Asp Phe
        915                 920                 925

Leu Arg Lys Ser Arg Val Leu Glu Thr Asp Pro Ala Phe Ala Arg Glu
        930                 935                 940

His Gly Thr Ala Ser Thr Leu Ser Ser Arg Gln Leu Leu Arg Phe Ala
945                 950                 955                 960

Ser Asp Ala Ala Asn Gly Met Gln Tyr Leu Ser Glu Lys Gln Phe Ile
            965                 970                 975

His Arg Asp Leu Ala Ala Arg Asn Val Leu Val Gly Glu Asn Leu Ala
            980                 985                 990

Ser Lys Ile Ala Asp Phe Gly Leu Ser Arg Gly Glu Glu Val Tyr Val
        995                 1000                1005

Lys Lys Thr Met Gly Arg Leu Pro Val Arg Trp Met Ala Ile Glu Ser
    1010                1015                1020

Leu Asn Tyr Ser Val Tyr Thr Thr Lys Ser Asp Val Trp Ser Phe Gly
1025                1030                1035                1040

Val Leu Leu Trp Glu Ile Val Ser Leu Gly Gly Thr Pro Tyr Cys Gly
            1045                1050                1055

Met Thr Cys Ala Glu Leu Tyr Glu Lys Leu Pro Gln Gly Tyr Arg Met
            1060                1065                1070

Glu Gln Pro Arg Asn Cys Asp Asp Glu Val Tyr Glu Leu Met Arg Gln
        1075                1080                1085

Cys Trp Arg Asp Arg Pro Tyr Glu Arg Pro Pro Phe Ala Gln Ile Ala
        1090                1095                1100

Leu Gln Leu Gly Arg Met Leu Glu Ala Arg Lys Ala Tyr Val Asn Met
1105                1110                1115                1120

Ser Leu Phe Glu Asn Phe Thr Tyr Ala Gly Ile Asp Ala Thr Ala Glu
            1125                1130                1135

Glu Ala

<210> SEQ ID NO 3
<211> LENGTH: 396
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(396)

<400> SEQUENCE: 3 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
 1               5                   10                  15 tct tta cgt ctt tct tgc gct gct tcc gga ttc act ttc tct att tac      96
Ser Leu Arg Leu Ser Cys Ala Ala Ser Gly Phe Thr Phe Ser Ile Tyr
            20                  25                  30 aag atg tct tgg gtt cgc caa gct cct ggt aaa ggt ttg gag tgg gtt     144
Lys Met Ser Trp Val Arg Gln Ala Pro Gly Lys Gly Leu Glu Trp Val
        35                  40                  45 tct tct atc tat cct tct ggt ggc cag act aag tat gct gac tcc gtt     192
Ser Ser Ile Tyr Pro Ser Gly Gly Gln Thr Lys Tyr Ala Asp Ser Val
    50                  55                  60

-continued

```
aaa ggt cgc ttc act atc tct aga gac aac tct aag aat act ctc tac      240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt      288
Leu Gln Met Asn Ser Leu Arg Ala Glu Asp Thr Ala Val Tyr Tyr Cys
                 85                  90                  95 gcg aga gtc aat tac tat gat agt agt ggt tac ggt cct ata gct cct      336
Ala Arg Val Asn Tyr Tyr Asp Ser Ser Gly Tyr Gly Pro Ile Ala Pro
            100                 105                 110 gga ctt gac tac tgg ggc cag gga acc ctg gtc acc gtc tca agc gcc      384
Gly Leu Asp Tyr Trp Gly Gln Gly Thr Leu Val Thr Val Ser Ser Ala
        115                 120                 125 tcc acc aag ggc                                                      396
Ser Thr Lys Gly
    130
```

<210> SEQ ID NO 4
<211> LENGTH: 132
<212> TYPE: PRT
<213> ORGANISM: Artificial Sequence
<220> FEATURE:
<223> OTHER INFORMATION: Synthetically generated peptide

<400> SEQUENCE: 4

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ile Tyr
             20                  25                  30

Lys Met Ser Trp Val Arg Gln Ala Pro Gly Lys Gly Leu Glu Trp Val
         35                  40                  45

Ser Ser Ile Tyr Pro Ser Gly Gly Gln Thr Lys Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Asn Tyr Tyr Asp Ser Ser Gly Tyr Gly Pro Ile Ala Pro
            100                 105                 110

Gly Leu Asp Tyr Trp Gly Gln Gly Thr Leu Val Thr Val Ser Ser Ala
        115                 120                 125

Ser Thr Lys Gly
    130
```

<210> SEQ ID NO 5
<211> LENGTH: 311
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(309)

<400> SEQUENCE: 5

```
caa gac atc cag atg acc cag tct cca ggc acc ctg tct ttg tct cca       48
Gln Asp Ile Gln Met Thr Gln Ser Pro Gly Thr Leu Ser Leu Ser Pro
 1               5                  10                  15 ggg gaa aga gcc acc ctc tcc tgc agg gcc agt cag agt gtt agc agc       96
Gly Glu Arg Ala Thr Leu Ser Cys Arg Ala Ser Gln Ser Val Ser Ser
             20                  25                  30
```

```
agc tac tta gcc tgg tac cag cag aaa cct ggc cag gct ccc agg ctc      144
Ser Tyr Leu Ala Trp Tyr Gln Gln Lys Pro Gly Gln Ala Pro Arg Leu
        35                  40                  45 ctc atc tat ggt gca tcc agc agg gcc act ggc atc cca gac agg ttc      192
Leu Ile Tyr Gly Ala Ser Ser Arg Ala Thr Gly Ile Pro Asp Arg Phe
 50                  55                  60 agt ggc agt ggg tct ggg aca gac ttc act ctc acc atc agc aga ctg      240
Ser Gly Ser Gly Ser Gly Thr Asp Phe Thr Leu Thr Ile Ser Arg Leu
 65                  70                  75                  80 gag cct gaa gat ttt gca gtg tat tac tgt cag cag tat ggt agc tcc      288
Glu Pro Glu Asp Phe Ala Val Tyr Tyr Cys Gln Gln Tyr Gly Ser Ser
                 85                  90                  95 cgg tgg acg ttc ggc caa ggg ac                                       311
Arg Trp Thr Phe Gly Gln Gly
            100

<210> SEQ ID NO 6
<211> LENGTH: 103
<212> TYPE: PRT
<213> ORGANISM: Artificial Sequence
<220> FEATURE:
<223> OTHER INFORMATION: Synthetically generated peptide

<400> SEQUENCE: 6

Gln Asp Ile Gln Met Thr Gln Ser Pro Gly Thr Leu Ser Leu Ser Pro
 1               5                  10                  15

Gly Glu Arg Ala Thr Leu Ser Cys Arg Ala Ser Gln Ser Val Ser Ser
                20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
 50                  55                  60

Ser Gly Ser Gly Ser Gly Thr Asp Phe Thr Leu Thr Ile Ser Arg Leu
 65                  70                  75                  80

Glu Pro Glu Asp Phe Ala Val Tyr Tyr Cys Gln Gln Tyr Gly Ser Ser
                 85                  90                  95

Arg Trp Thr Phe Gly Gln Gly
            100

<210> SEQ ID NO 7
<211> LENGTH: 396
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(396)

<400> SEQUENCE: 7 gaa gtt caa ttg tta gag tct ggt ggc ggt ctt gtt cag cct ggt ggt       48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct tat tac       96
Ser Leu Arg Leu Ser Cys Ala Ala Ser Gly Phe Thr Phe Ser Tyr Tyr
                20                  25                  30 ctt atg tat tgg gtt cgc caa gct cct ggt aaa ggt ttg gag tgg gtt      144
Leu Met Tyr Trp Val Arg Gln Ala Pro Gly Lys Gly Leu Glu Trp Val
        35                  40                  45 tct tct atc tat cct tct ggt ggc tgg act gtt tat gct gac tcc gtt      192
Ser Ser Ile Tyr Pro Ser Gly Gly Trp Thr Val Tyr Ala Asp Ser Val
 50                  55                  60
```

```
aaa ggt cgc ttc act atc tct aga gac aac tct aag aat act ctc tac    240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt    288
Leu Gln Met Asn Ser Leu Arg Ala Glu Asp Thr Ala Val Tyr Tyr Cys
                 85                  90                  95 gcg aga gtc aat tac tat gat agt agt ggt tac ggt cct ata gct cct    336
Ala Arg Val Asn Tyr Tyr Asp Ser Ser Gly Tyr Gly Pro Ile Ala Pro
            100                 105                 110 gga ctt gac tac tgg ggc cag gga acc ctg gtc acc gtc tca agc gcc    384
Gly Leu Asp Tyr Trp Gly Gln Gly Thr Leu Val Thr Val Ser Ser Ala
        115                 120                 125 tcc acc aag ggc                                                    396
Ser Thr Lys Gly
    130
```

<210> SEQ ID NO 8
<211> LENGTH: 132
<212> TYPE: PRT
<213> ORGANISM: Artificial Sequence
<220> FEATURE:
<223> OTHER INFORMATION: Synthetically generated peptide

<400> SEQUENCE: 8

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Tyr
             20                  25                  30

Leu Met Tyr Trp Val Arg Gln Ala Pro Gly Lys Gly Leu Glu Trp Val
         35                  40                  45

Ser Ser Ile Tyr Pro Ser Gly Gly Trp Thr Val Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Asn Tyr Tyr Asp Ser Ser Gly Tyr Gly Pro Ile Ala Pro
            100                 105                 110

Gly Leu Asp Tyr Trp Gly Gln Gly Thr Leu Val Thr Val Ser Ser Ala
        115                 120                 125

Ser Thr Lys Gly
    130
```

<210> SEQ ID NO 9
<211> LENGTH: 308
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(306)

<400> SEQUENCE: 9

```
caa gac atc cag atg acc cag tct cca tcc tcc ctg tct gca tct gtc     48
Gln Asp Ile Gln Met Thr Gln Ser Pro Ser Ser Leu Ser Ala Ser Val
 1               5                  10                  15 gga gac aga gtc acc atc act tgc cgg gca agt tag agc att agc acc     96
Gly Asp Arg Val Thr Ile Thr Cys Arg Ala Ser  *  Ser Ile Ser Thr
             20                  25                  30
```

-continued

```
tct tta aat tgg tat cag caa aaa tca ggg aaa gcc cct aag ctc ctg       144
Ser Leu Asn Trp Tyr Gln Gln Lys Ser Gly Lys Ala Pro Lys Leu Leu
             35                  40                  45 ata tat gct gca tcc agt ttg caa agt gaa gtc cca tca agg ttc agt       192
Ile Tyr Ala Ala Ser Ser Leu Gln Ser Glu Val Pro Ser Arg Phe Ser
         50                  55                  60 ggc agt gga tct ggg aca gat ttc act ctc acc atc acc agt ctg caa       240
Gly Ser Gly Ser Gly Thr Asp Phe Thr Leu Thr Ile Thr Ser Leu Gln
 65                  70                  75 cct gaa gat ttt gca act tac tac tgt caa cag agt tac agt acc cct       288
Pro Glu Asp Phe Ala Thr Tyr Tyr Cys Gln Gln Ser Tyr Ser Thr Pro
         80                  85                  90                  95 ccg act ttc ggc caa ggg ac                                            308
Pro Thr Phe Gly Gln Gly
                100
```

<210> SEQ ID NO 10
<211> LENGTH: 101
<212> TYPE: PRT
<213> ORGANISM: Artificial Sequence
<220> FEATURE:
<223> OTHER INFORMATION: Synthetically generated peptide

<400> SEQUENCE: 10

```
Gln Asp Ile Gln Met Thr Gln Ser Pro Ser Ser Leu Ser Ala Ser Val
 1               5                  10                  15

Gly Asp Arg Val Thr Ile Thr Cys Arg Ala Ser Ser Ile Ser Thr Ser
             20                  25                  30

Leu Asn Trp Tyr Gln Gln Lys Ser Gly Lys Ala Pro Lys Leu Leu Ile
         35                  40                  45

Tyr Ala Ala Ser Ser Leu Gln Ser Glu Val Pro Ser Arg Phe Ser Gly
     50                  55                  60

Ser Gly Ser Gly Thr Asp Phe Thr Leu Thr Ile Thr Ser Leu Gln Pro
 65                  70                  75                  80

Glu Asp Phe Ala Thr Tyr Tyr Cys Gln Gln Ser Tyr Ser Thr Pro Pro
                 85                  90                  95

Thr Phe Gly Gln Gly
            100
```

<210> SEQ ID NO 11
<211> LENGTH: 439
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(438)

<400> SEQUENCE: 11

```
gaa gtt caa ttg tta gag tct ggt ggc ggt ctt gtt cag cct ggt ggt        48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct atg tac        96
Ser Leu Arg Leu Ser Cys Ala Ala Ser Gly Phe Thr Phe Ser Met Tyr
             20                  25                  30 gtt atg aag tgg gtt cgc caa gct cct ggt aaa ggt ttg gag tgg gtt       144
Val Met Lys Trp Val Arg Gln Ala Pro Gly Lys Gly Leu Glu Trp Val
         35                  40                  45 tct tct atc tat cct tct ggt ggc tat act cgt tat gct gac tcc gtt       192
Ser Ser Ile Tyr Pro Ser Gly Gly Tyr Thr Arg Tyr Ala Asp Ser Val
     50                  55                  60
```

| | | | | | | | | | | | | | | | |
|---|---|---|---|---|---|---|---|---|---|---|---|---|---|---|---|
| aaa | ggt | cgc | ttc | act | atc | tct | aga | gac | aac | tct | aag | aat | act | ctc | tac | 240 |
| Lys | Gly | Arg | Phe | Thr | Ile | Ser | Arg | Asp | Asn | Ser | Lys | Asn | Thr | Leu | Tyr |
| 65 | | | | 70 | | | | | 75 | | | | | 80 | |

```
aaa ggt cgc ttc act atc tct aga gac aac tct aag aat act ctc tac    240
Lys Gly Arg Phe Thr Ile Ser Arg Asp Asn Ser Lys Asn Thr Leu Tyr
 65              70                  75                  80 ttg cag atg aac agc tta agg gct gag gac act gca gtc tac tat tgt    288
Leu Gln Met Asn Ser Leu Arg Ala Glu Asp Thr Ala Val Tyr Tyr Cys
                 85                  90                  95 gcg aga gtc aat tac tat gat agt agt ggt tac ggt cct ata gct cct    336
Ala Arg Val Asn Tyr Tyr Asp Ser Ser Gly Tyr Gly Pro Ile Ala Pro
                100                 105                 110 gga ctt gac tac tgg ggc cag gga acc ctg gtc acc gtc tca agc gcc    384
Gly Leu Asp Tyr Trp Gly Gln Gly Thr Leu Val Thr Val Ser Ser Ala
            115                 120                 125 tcc acc aag ggc cca tcg gtc ttc ccg cta gca ccc tcc tcc aag agc    432
Ser Thr Lys Gly Pro Ser Val Phe Pro Leu Ala Pro Ser Ser Lys Ser
        130                 135                 140 acc tct g                                                           439
Thr Ser
145
```

<210> SEQ ID NO 12
<211> LENGTH: 146
<212> TYPE: PRT
<213> ORGANISM: Artificial Sequence
<220> FEATURE:
<223> OTHER INFORMATION: Synthetically generated peptide

<400> SEQUENCE: 12

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Met Tyr
                20                  25                  30

Val Met Lys Trp Val Arg Gln Ala Pro Gly Lys Gly Leu Glu Trp Val
            35                  40                  45

Ser Ser Ile Tyr Pro Ser Gly Gly Tyr Thr Arg Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Asn Tyr Tyr Asp Ser Ser Gly Tyr Gly Pro Ile Ala Pro
                100                 105                 110

Gly Leu Asp Tyr Trp Gly Gln Gly Thr Leu Val Thr Val Ser Ser Ala
            115                 120                 125

Ser Thr Lys Gly Pro Ser Val Phe Pro Leu Ala Pro Ser Ser Lys Ser
        130                 135                 140

Thr Ser
145
```

<210> SEQ ID NO 13
<211> LENGTH: 311
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(309)

<400> SEQUENCE: 13

```
caa gac atc cag atg acc cag tct cca ggc acc ctg tct ttg tct cca     48
```

```
Gln Asp Ile Gln Met Thr Gln Ser Pro Gly Thr Leu Ser Leu Ser Pro
 1               5                  10                 15
ggg gaa aga gcc acc ctc tcc tgc agg gcc agt cag agt gtt agc agc    96
Gly Glu Arg Ala Thr Leu Ser Cys Arg Ala Ser Gln Ser Val Ser Ser
             20                  25                 30 agc tac tta gcc tgg tac cag cag aaa cct ggc cag gct ccc agg ctc   144
Ser Tyr Leu Ala Trp Tyr Gln Gln Lys Pro Gly Gln Ala Pro Arg Leu
         35                  40                  45 ctc atc tat ggt gca tcc agc agg gcc act ggc atc cca gac agg ttc   192
Leu Ile Tyr Gly Ala Ser Ser Arg Ala Thr Gly Ile Pro Asp Arg Phe
     50                  55                  60
agt ggc agt ggg tct ggg aca gac ttc act ctc acc atc agc aga ctg   240
Ser Gly Ser Gly Ser Gly Thr Asp Phe Thr Leu Thr Ile Ser Arg Leu
 65                  70                  75                  80
gag cct gaa gat ttt gca gtg tat tac tgt cag cag tat ggt agc tcc   288
Glu Pro Glu Asp Phe Ala Val Tyr Tyr Cys Gln Gln Tyr Gly Ser Ser
                 85                  90                  95 cta ttc act ttc ggc cct ggg ac                                    311
Leu Phe Thr Phe Gly Pro Gly
            100

<210> SEQ ID NO 14
<211> LENGTH: 103
<212> TYPE: PRT
<213> ORGANISM: Artificial Sequence
<220> FEATURE:
<223> OTHER INFORMATION: Synthetically generated peptide

<400> SEQUENCE: 14

Gln Asp Ile Gln Met Thr Gln Ser Pro Gly Thr Leu Ser Leu Ser Pro
 1               5                  10                 15

Gly Glu Arg Ala Thr Leu Ser Cys Arg Ala Ser Gln Ser Val Ser Ser
             20                  25                 30

Ser Tyr Leu Ala Trp Tyr Gln Gln Lys Pro Gly Gln Ala Pro Arg Leu
         35                  40                  45

Leu Ile Tyr Gly Ala Ser Ser Arg Ala Thr Gly Ile Pro Asp Arg Phe
     50                  55                  60

Ser Gly Ser Gly Ser Gly Thr Asp Phe Thr Leu Thr Ile Ser Arg Leu
 65                  70                  75                  80

Glu Pro Glu Asp Phe Ala Val Tyr Tyr Cys Gln Gln Tyr Gly Ser Ser
                 85                  90                  95

Leu Phe Thr Phe Gly Pro Gly
            100

<210> SEQ ID NO 15
<211> LENGTH: 439
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(438)

<400> SEQUENCE: 15 gaa gtt caa ttg tta gag tct ggt ggc ggt ctt gtt cag cct ggt ggt    48
Glu Val Gln Leu Leu Glu Ser Gly Gly Gly Leu Val Gln Pro Gly Gly
 1               5                  10                 15 tct tta cgt ctt tct tgc gct gct tcc gga ttc act ttc tct tct tac    96
Ser Leu Arg Leu Ser Cys Ala Ala Ser Gly Phe Thr Phe Ser Ser Tyr
             20                  25                 30 aag atg ggt tgg gtt cgc caa gct cct ggt aaa ggt ttg gag tgg gtt   144
Lys Met Gly Trp Val Arg Gln Ala Pro Gly Lys Gly Leu Glu Trp Val
         35                  40                  45
tct tgg atc tat cct tct ggt ggc ggt act act tat gct gac tcc gtt   192
```

```
Ser Trp Ile Tyr Pro Ser Gly Gly Thr Thr Tyr Ala Asp Ser Val
    50                  55                  60 aaa ggt cgc ttc act atc tct aga gac aac tct aag aat act ctc tac        240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tat tat tgt        288
Leu Gln Met Asn Ser Leu Arg Ala Glu Asp Thr Ala Val Tyr Tyr Cys
                 85                  90                  95 gcg aga gtc aat tac tat gat agt agt ggt tac ggt cct ata gct cct        336
Ala Arg Val Asn Tyr Tyr Asp Ser Ser Gly Tyr Gly Pro Ile Ala Pro
            100                 105                 110 gga ctt gac tac tgg ggc cag gga acc ctg gtc acc gtc tca agc gcc        384
Gly Leu Asp Tyr Trp Gly Gln Gly Thr Leu Val Thr Val Ser Ser Ala
                115                 120                 125 tcc acc aag ggc cca tcg gtc ttc ccg cta gca ccc tcc tcc aag agc        432
Ser Thr Lys Gly Pro Ser Val Phe Pro Leu Ala Pro Ser Ser Lys Ser
        130                 135                 140 acc tct g                                                              439
Thr Ser
145
```

<210> SEQ ID NO 16
<211> LENGTH: 146
<212> TYPE: PRT
<213> ORGANISM: Artificial Sequence
<220> FEATURE:
<223> OTHER INFORMATION: Synthetically generated peptide

<400> SEQUENCE: 16

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Lys Met Gly Trp Val Arg Gln Ala Pro Gly Lys Gly Leu Glu Trp Val
         35                  40                  45

Ser Trp Ile Tyr Pro Ser Gly Gly Thr Thr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Asn Tyr Tyr Asp Ser Ser Gly Tyr Gly Pro Ile Ala Pro
            100                 105                 110

Gly Leu Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser
145
```

<210> SEQ ID NO 17
<211> LENGTH: 311
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(309)

<400> SEQUENCE: 17

-continued

| | |
|---|---|
| caa gac atc cag atg acc cag tct cca ggc acc ctg tct ttg tct cca<br>Gln Asp Ile Gln Met Thr Gln Ser Pro Gly Thr Leu Ser Leu Ser Pro<br>1               5                   10                  15 | 48 |
| ggg gaa aga gcc acc ctc tcc tgc agg gcc agt cag agt gtt agc agc<br>Gly Glu Arg Ala Thr Leu Ser Cys Arg Ala Ser Gln Ser Val Ser Ser<br>            20                  25                  30 | 96 |
| agc tac tta gcc tgg tac cag cag aaa cct ggc cag gct ccc agg ctc<br>Ser Tyr Leu Ala Trp Tyr Gln Gln Lys Pro Gly Gln Ala Pro Arg Leu<br>        35                  40                  45 | 144 |
| ctc atc tat ggt gca tcc agc agg gcc act ggc atc cca gac agg ttc<br>Leu Ile Tyr Gly Ala Ser Ser Arg Ala Thr Gly Ile Pro Asp Arg Phe<br>    50                  55                  60 | 192 |
| agt ggc agt ggg tct ggg aca gac ttc act ctc acc atc agc aga ctg<br>Ser Gly Ser Gly Ser Gly Thr Asp Phe Thr Leu Thr Ile Ser Arg Leu<br>65                  70                  75                  80 | 240 |
| gag cct gaa gat ttt gca gtg tat tac tgt cag cag tat ggt agc tca<br>Glu Pro Glu Asp Phe Ala Val Tyr Tyr Cys Gln Gln Tyr Gly Ser Ser<br>                85                  90                  95 | 288 |
| ccg tgg acg ttc ggc caa ggg ac<br>Pro Trp Thr Phe Gly Gln Gly<br>            100 | 311 |

<210> SEQ ID NO 18
<211> LENGTH: 103
<212> TYPE: PRT
<213> ORGANISM: Artificial Sequence
<220> FEATURE:
<223> OTHER INFORMATION: Synthetically generated peptide

<400> SEQUENCE: 18

Gln Asp Ile Gln Met Thr Gln Ser Pro Gly Thr Leu Ser Leu Ser Pro
1               5                   10                  15

Gly Glu Arg Ala Thr Leu Ser Cys Arg Ala Ser Gln Ser Val Ser Ser
            20                  25                  30

Ser Tyr Leu Ala Trp Tyr Gln Gln Lys Pro Gly Gln Ala Pro Arg Leu
        35                  40                  45

Leu Ile Tyr Gly Ala Ser Ser Arg Ala Thr Gly Ile Pro Asp Arg Phe
    50                  55                  60

Ser Gly Ser Gly Ser Gly Thr Asp Phe Thr Leu Thr Ile Ser Arg Leu
65                  70                  75                  80

Glu Pro Glu Asp Phe Ala Val Tyr Tyr Cys Gln Gln Tyr Gly Ser Ser
                85                  90                  95

Pro Trp Thr Phe Gly Gln Gly
            100

<210> SEQ ID NO 19
<211> LENGTH: 446
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(444)

<400> SEQUENCE: 19

| | |
|---|---|
| gaa gtt caa ttg tta gag tct ggt ggc ggt ctt gtt cag cct ggt ggt<br>Glu Val Gln Leu Leu Glu Ser Gly Gly Gly Leu Val Gln Pro Gly Gly<br>1               5                   10                  15 | 48 |
| tct tta cgt ctt tct tgc gct gct tcc gga ttc act ttc tct cgt tac<br>Ser Leu Arg Leu Ser Cys Ala Ala Ser Gly Phe Thr Phe Ser Arg Tyr<br>            20                  25                  30 | 96 |

```
cct atg gtt tgg gtt cgc caa gct cct ggt aaa ggt ttg gag tgg gtt      144
Pro Met Val Trp Val Arg Gln Ala Pro Gly Lys Gly Leu Glu Trp Val
        35                  40                  45 tct gtt atc tct cct tct ggt ggc cag act ttt tat gct gac tcc gtt      192
Ser Val Ile Ser Pro Ser Gly Gly Gln Thr Phe Tyr Ala Asp Ser Val
    50                  55                  60 aaa ggt cgc ttc act atc tct aga gac aac tct aag aat act ctc tac      240
Lys Gly Arg Phe Thr Ile Ser Arg Asp Asn Ser Lys Asn Thr Leu Tyr
65                  70                  75                  80 ttg cag atg aac agc tta agg gct gag gac act gca gtc tac tat tgt      288
Leu Gln Met Asn Ser Leu Arg Ala Glu Asp Thr Ala Val Tyr Tyr Cys
                85                  90                  95 gcg aga ggg gtc ctc acc acc gct ttt gat atc tgg ggc caa ggg aca      336
Ala Arg Gly Val Leu Thr Thr Ala Phe Asp Ile Trp Gly Gln Gly Thr
            100                 105                 110 atg gtc acc gtc tca agc gcc tcc acc aag ggc cca tcg gtc ttc ccg      384
Met Val Thr Val Ser Ser Ala Ser Thr Lys Gly Pro Ser Val Phe Pro
        115                 120                 125 cta gca ccc tcc tcc aaa gca cct ctg ggg gca cag cgg ccc tgg gct      432
Leu Ala Pro Ser Ser Lys Ala Pro Leu Gly Ala Gln Arg Pro Trp Ala
    130                 135                 140 gcc tgg tca agg ac                                                    446
Ala Trp Ser Arg
145

<210> SEQ ID NO 20
<211> LENGTH: 148
<212> TYPE: PRT
<213> ORGANISM: Artificial Sequence
<220> FEATURE:
<223> OTHER INFORMATION: Synthetically generated peptide

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Pro Met Val Trp Val Arg Gln Ala Pro Gly Lys Gly Leu Glu Trp Val
        35                  40                  45

Ser Val Ile Ser Pro Ser Gly Gly Gln Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Val Leu Thr Thr Ala Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ala Pro Leu Gly Ala Gln Arg Pro Trp Ala
    130                 135                 140

Ala Trp Ser Arg
145

<210> SEQ ID NO 21
<211> LENGTH: 308
<212> TYPE: DNA
<213> ORGANISM: Artificial Sequence
<220> FEATURE:
```

<223> OTHER INFORMATION: Synthetically generated oligonucleotide
<220> FEATURE:
<221> NAME/KEY: CDS
<222> LOCATION: (1)...(306)

<400> SEQUENCE: 21

```
caa gac atc cag atg acc cag tct cca tcc tcc ctg tct gca tct gtg      48
Gln Asp Ile Gln Met Thr Gln Ser Pro Ser Ser Leu Ser Ala Ser Val
1               5                   10                  15 gga gac aga gtc acc atc act tgc cgg gca agt cag aac att aac agc      96
Gly Asp Arg Val Thr Ile Thr Cys Arg Ala Ser Gln Asn Ile Asn Ser
            20                  25                  30 tat tta aat tgg tat cag cag aaa cca ggg caa gcc cct aaa ctc ctg     144
Tyr Leu Asn Trp Tyr Gln Gln Lys Pro Gly Gln Ala Pro Lys Leu Leu
        35                  40                  45 atc tat gct gcc tcc aat ttg gaa act gcg gtc cca tca agg ttc agc     192
Ile Tyr Ala Ala Ser Asn Leu Glu Thr Ala Val Pro Ser Arg Phe Ser
    50                  55                  60 ggc agt gga tct ggg aca gat ttc act ctc acc atc agt agc ctg cag     240
Gly Ser Gly Ser Gly Thr Asp Phe Thr Leu Thr Ile Ser Ser Leu Gln
65                  70                  75                  80 cct gaa gat ttt gca act tat tat tgt caa caa ttt aat act tac cct     288
Pro Glu Asp Phe Ala Thr Tyr Tyr Cys Gln Gln Phe Asn Thr Tyr Pro
                85                  90                  95 ctc act ttc ggc gga ggg ac                                          308
Leu Thr Phe Gly Gly Gly
                100
```

<210> SEQ ID NO 22
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 22

```
Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asn Ile Asn Ser
            20                  25                  30

Tyr Leu Asn Trp Tyr Gln Gln Lys Pro Gly Gln Ala Pro Lys Leu Leu
        35                  40                  45

Ile Tyr Ala Ala Ser Asn Leu Glu Thr Ala Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Phe Asn Thr Tyr Pro
                85                  90                  95

Leu Thr Phe Gly Gly Gly
                100
```

<210> SEQ ID NO 23
<211> LENGTH: 393
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(393)

<400> SEQUENCE: 23

```
gaa gtt caa ttg tta gag tct ggt ggc ggt ctt gtt cag cct ggt ggt        48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct cgt tac        96
Ser Leu Arg Leu Ser Cys Ala Ala Ser Gly Phe Thr Phe Ser Arg Tyr
             20                  25                  30 ggt atg cat tgg gtt cgc caa gct cct ggt aaa ggt ttg gag tgg gtt       144
Gly Met His Trp Val Arg Gln Ala Pro Gly Lys Gly Leu Glu Trp Val
         35                  40                  45 tct gtt atc tct cct tct ggt ggc atg act tat tat gct gac tcc gtt       192
Ser Val Ile Ser Pro Ser Gly Gly Met Thr Tyr Tyr Ala Asp Ser Val
     50                  55                  60 aaa ggt cgc ttc act atc tct aga gac aac act aag aat act ctc tac       240
Lys Gly Arg Phe Thr Ile Ser Arg Asp Asn Thr Lys Asn Thr Leu Tyr
 65                  70                  75                  80 ttg cag atg aac agc tta agg gct gag gac act gca gtc tac tat tgt       288
Leu Gln Met Asn Ser Leu Arg Ala Glu Asp Thr Ala Val Tyr Tyr Cys
                 85                  90                  95 gcg aga gtg gga gct acc ggg cct ttt gat atc tgg ggc caa ggg aca       336
Ala Arg Val Gly Ala Thr Gly Pro Phe Asp Ile Trp Gly Gln Gly Thr
             100                 105                 110 atg gtc acc gtc tca agc gcc tcc acc aag ggc cca tcg gtc ttc ccg       384
Met Val Thr Val Ser Ser Ala Ser Thr Lys Gly Pro Ser Val Phe Pro
         115                 120                 125 cta gca ccc                                                            393
Leu Ala Pro
    130
```

<210> SEQ ID NO 24
<211> LENGTH: 131
<212> TYPE: PRT
<213> ORGANISM: Artificial Sequence
<220> FEATURE:
<223> OTHER INFORMATION: Synthetically generated peptide

<400> SEQUENCE: 24

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
             20                  25                  30

Gly Met His Trp Val Arg Gln Ala Pro Gly Lys Gly Leu Glu Trp Val
         35                  40                  45

Ser Val Ile Ser Pro Ser Gly Gly Met Thr Tyr Tyr Ala Asp Ser Val
     50                  55                  60

Lys Gly Arg Phe Thr Ile Ser Arg Asp Asn Thr Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Gly Ala Thr Gly Pro Phe Asp Ile Trp Gly Gln Gly Thr
             100                 105                 110

Met Val Thr Val Ser Ser Ala Ser Thr Lys Gly Pro Ser Val Phe Pro
         115                 120                 125

Leu Ala Pro
    130
```

<210> SEQ ID NO 25
<211> LENGTH: 308
<212> TYPE: DNA
<213> ORGANISM: Artificial Sequence
<220> FEATURE:

<223> OTHER INFORMATION: Synthetically generated oligonucleotide
<220> FEATURE:
<221> NAME/KEY: CDS
<222> LOCATION: (1)...(306)

<400> SEQUENCE: 25

| caa | gac | atc | cag | atg | acc | cag | tct | cca | gcc | acc | ctg | tct | ttg | tct | cca | 48 |
|---|---|---|---|---|---|---|---|---|---|---|---|---|---|---|---|---|
| Gln | Asp | Ile | Gln | Met | Thr | Gln | Ser | Pro | Ala | Thr | Leu | Ser | Leu | Ser | Pro | |
| 1 | | | | 5 | | | | | 10 | | | | | 15 | | |

| ggg | gaa | aga | gcc | acc | ctc | tcc | tgc | agg | gcc | agt | cag | agt | gtt | agc | acc | 96 |
|---|---|---|---|---|---|---|---|---|---|---|---|---|---|---|---|---|
| Gly | Glu | Arg | Ala | Thr | Leu | Ser | Cys | Arg | Ala | Ser | Gln | Ser | Val | Ser | Thr | |
| | | | | 20 | | | | | 25 | | | | | 30 | | |

| tac | tta | gcc | tgg | tac | caa | cag | aaa | cct | ggc | cag | gct | ccc | agg | ctt | ctc | 144 |
|---|---|---|---|---|---|---|---|---|---|---|---|---|---|---|---|---|
| Tyr | Leu | Ala | Trp | Tyr | Gln | Gln | Lys | Pro | Gly | Gln | Ala | Pro | Arg | Leu | Leu | |
| | | | 35 | | | | | 40 | | | | | 45 | | | |

| atc | tat | gat | gca | tcc | aac | agg | gcc | act | ggc | atc | cca | ggc | agg | ttc | agt | 192 |
|---|---|---|---|---|---|---|---|---|---|---|---|---|---|---|---|---|
| Ile | Tyr | Asp | Ala | Ser | Asn | Arg | Ala | Thr | Gly | Ile | Pro | Gly | Arg | Phe | Ser | |
| | | | 50 | | | | | 55 | | | | | 60 | | | |

| ggc | agt | ggg | tct | ggg | aca | gac | ttc | act | ctc | acc | atc | agc | agc | cta | gag | 240 |
|---|---|---|---|---|---|---|---|---|---|---|---|---|---|---|---|---|
| Gly | Ser | Gly | Ser | Gly | Thr | Asp | Phe | Thr | Leu | Thr | Ile | Ser | Ser | Leu | Glu | |
| 65 | | | | | 70 | | | | | 75 | | | | | 80 | |

| gct | gaa | gac | ttt | gca | gtt | tat | tac | tgt | cag | cag | cgt | agc | agc | tgg | ccg | 288 |
|---|---|---|---|---|---|---|---|---|---|---|---|---|---|---|---|---|
| Ala | Glu | Asp | Phe | Ala | Val | Tyr | Tyr | Cys | Gln | Gln | Arg | Ser | Ser | Trp | Pro | |
| | | | | 85 | | | | | 90 | | | | | 95 | | |

| atc | acc | ttc | ggc | caa | ggg | ac | | | | | | | | | | 308 |
|---|---|---|---|---|---|---|---|---|---|---|---|---|---|---|---|---|
| Ile | Thr | Phe | Gly | Gln | Gly | | | | | | | | | | | |
| | | | | 100 | | | | | | | | | | | | |

<210> SEQ ID NO 26
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 26

Gln Asp Ile Gln Met Thr Gln Ser Pro Ala Thr Leu Ser Leu Ser Pro
1               5                   10                  15

Gly Glu Arg Ala Thr Leu Ser Cys Arg Ala Ser Gln Ser Val Ser Thr
            20                  25                  30

Tyr Leu Ala Trp Tyr Gln Gln Lys Pro Gly Gln Ala Pro Arg Leu Leu
        35                  40                  45

Ile Tyr Asp Ala Ser Asn Arg Ala Thr Gly Ile Pro Gly Arg Phe Ser
    50                  55                  60

Gly Ser Gly Ser Gly Thr Asp Phe Thr Leu Thr Ile Ser Ser Leu Glu
65                  70                  75                  80

Ala Glu Asp Phe Ala Val Tyr Tyr Cys Gln Gln Arg Ser Ser Trp Pro
                85                  90                  95

Ile Thr Phe Gly Gln Gly
            100

<210> SEQ ID NO 27
<211> LENGTH: 429
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(429)

<400> SEQUENCE: 27

-continued

```
gaa gtt caa ttg tta gag tct ggt ggc ggt ctt gtt cag cct ggt ggt        48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct cat tac        96
Ser Leu Arg Leu Ser Cys Ala Ala Ser Gly Phe Thr Phe Ser His Tyr
             20                  25                  30 ggt atg act tgg gtt cgc caa gct cct ggt aaa ggt ttg gag tgg gtt       144
Gly Met Thr Trp Val Arg Gln Ala Pro Gly Lys Gly Leu Glu Trp Val
         35                  40                  45 tct gtt atc tct cct tct ggt ggc cag act ggt tat gct gac tcc gtt       192
Ser Val Ile Ser Pro Ser Gly Gly Gln Thr Gly Tyr Ala Asp Ser Val
     50                  55                  60 aaa ggt cgc ttc act atc tct aga gac aac tct aag aat act ctc tac       240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt       288
Leu Gln Met Asn Ser Leu Arg Ala Glu Asp Thr Ala Val Tyr Tyr Cys
                 85                  90                  95 gcg ggt ggt ggc tac gca gcc ttt gac tac tgg ggc cag gga acc ctg       336
Ala Gly Gly Gly Tyr Ala Ala Phe Asp Tyr Trp Gly Gln Gly Thr Leu
            100                 105                 110 gtc acc gtc tca agc gcc tcc acc aag ggc cca tcg gtc ttc ccg cta       384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc           429
Ala Pro Ser Ser Lys Ser Thr Ser Gly Gly Thr Ala Ala Leu Gly
    130                 135                 140
```

<210> SEQ ID NO 28
<211> LENGTH: 143
<212> TYPE: PRT
<213> ORGANISM: Artificial Sequence
<220> FEATURE:
<223> OTHER INFORMATION: Synthetically generated peptide

<400> SEQUENCE: 28

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
             20                  25                  30

Gly Met Thr Trp Val Arg Gln Ala Pro Gly Lys Gly Leu Glu Trp Val
         35                  40                  45

Ser Val Ile Ser Pro Ser Gly Gly Gln Thr Gly Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gly Gly Gly Tyr Ala Ala Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly
    130                 135                 140
```

<210> SEQ ID NO 29
<211> LENGTH: 308
<212> TYPE: DNA
<213> ORGANISM: Artificial Sequence
<220> FEATURE:

<223> OTHER INFORMATION: Synthetically generated oligonucleotide
<220> FEATURE:
<221> NAME/KEY: CDS
<222> LOCATION: (1)...(306)

<400> SEQUENCE: 29

```
caa gac atc cag atg acc cag tct cca gcc acc ctg tct ttg tct cca        48
Gln Asp Ile Gln Met Thr Gln Ser Pro Ala Thr Leu Ser Leu Ser Pro
  1               5                  10                  15 ggg gaa aga gcc acc ctc tcc tgc agg gcc agt cag agt gtt agc agc        96
Gly Glu Arg Ala Thr Leu Ser Cys Arg Ala Ser Gln Ser Val Ser Ser
             20                  25                  30 tac tta gcc tgg tac caa cag aaa cct ggc cag gct ccc agg ctc ctc       144
Tyr Leu Ala Trp Tyr Gln Gln Lys Pro Gly Gln Ala Pro Arg Leu Leu
         35                  40                  45 atc tat gat gca tcc aac agg gcc act ggc atc cca gcc agg ttc agt       192
Ile Tyr Asp Ala Ser Asn Arg Ala Thr Gly Ile Pro Ala Arg Phe Ser
     50                  55                  60 ggc agt ggg tct ggg aca gac ttc act ctc acc atc agc agc cta gag       240
Gly Ser Gly Ser Gly Thr Asp Phe Thr Leu Thr Ile Ser Ser Leu Glu
 65                  70                  75                  80 cct gaa gat ttt gca gtt tat tac tgt cag cag cgt agc aac tgg cct       288
Pro Glu Asp Phe Ala Val Tyr Tyr Cys Gln Gln Arg Ser Asn Trp Pro
                 85                  90                  95 ctc act ttc ggc gga ggg ac                                            308
Leu Thr Phe Gly Gly Gly
            100
```

<210> SEQ ID NO 30
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 30

```
Gln Asp Ile Gln Met Thr Gln Ser Pro Ala Thr Leu Ser Leu Ser Pro
  1               5                  10                  15

Gly Glu Arg Ala Thr Leu Ser Cys Arg Ala Ser Gln Ser Val Ser Ser
             20                  25                  30

Tyr Leu Ala Trp Tyr Gln Gln Lys Pro Gly Gln Ala Pro Arg Leu Leu
         35                  40                  45

Ile Tyr Asp Ala Ser Asn Arg Ala Thr Gly Ile Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Arg Ser Asn Trp Pro
                 85                  90                  95

Leu Thr Phe Gly Gly Gly
            100
```

<210> SEQ ID NO 31
<211> LENGTH: 396
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(396)

<400> SEQUENCE: 31

-continued

```
gaa gtt caa ttg tta gag tct ggt ggc ggt ctt gtt cag cct ggt ggt    48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct gct tac    96
Ser Leu Arg Leu Ser Cys Ala Ala Ser Gly Phe Thr Phe Ser Ala Tyr
             20                  25                  30 cgt atg gag tgg gtt cgc caa gct cct ggt aaa ggt ttg gag tgg gtt   144
Arg Met Glu Trp Val Arg Gln Ala Pro Gly Lys Gly Leu Glu Trp Val
         35                  40                  45 tct tct atc tat cct tct ggt ggc att act tat tat gct gac tcc gtt   192
Ser Ser Ile Tyr Pro Ser Gly Gly Ile Thr Tyr Tyr Ala Asp Ser Val
     50                  55                  60 aaa ggt cgc ttc act atc tct aga gac aac tct aag aat act ctc tac   240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt   288
Leu Gln Met Asn Ser Leu Arg Ala Glu Asp Thr Ala Val Tyr Tyr Cys
                 85                  90                  95 gcg aga gtc aat tac tat gat agt agt ggt tac ggt cct ata gct cct   336
Ala Arg Val Asn Tyr Tyr Asp Ser Ser Gly Tyr Gly Pro Ile Ala Pro
             100                 105                 110 gga ctt gac tac tgg ggc cag gga acc ctg gtc acc gtc tca agc gcc   384
Gly Leu Asp Tyr Trp Gly Gln Gly Thr Leu Val Thr Val Ser Ser Ala
         115                 120                 125 tcc acc aag ggc                                                   396
Ser Thr Lys Gly
    130
```

<210> SEQ ID NO 32
<211> LENGTH: 132
<212> TYPE: PRT
<213> ORGANISM: Artificial Sequence
<220> FEATURE:
<223> OTHER INFORMATION: Synthetically generated peptide

<400> SEQUENCE: 32

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
             20                  25                  30

Arg Met Glu Trp Val Arg Gln Ala Pro Gly Lys Gly Leu Glu Trp Val
         35                  40                  45

Ser Ser Ile Tyr Pro Ser Gly Gly Ile Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Asn Tyr Tyr Asp Ser Ser Gly Tyr Gly Pro Ile Ala Pro
             100                 105                 110

Gly Leu Asp Tyr Trp Gly Gln Gly Thr Leu Val Thr Val Ser Ser Ala
         115                 120                 125

Ser Thr Lys Gly
    130
```

<210> SEQ ID NO 33
<211> LENGTH: 308
<212> TYPE: DNA
<213> ORGANISM: Artificial Sequence
<220> FEATURE:

<223> OTHER INFORMATION: Synthetically generated oligonucleotide
<220> FEATURE:
<221> NAME/KEY: CDS
<222> LOCATION: (1)...(306)

<400> SEQUENCE: 33

```
caa gac atc cag atg acc cag tct cca tcc tcc ctg tct gca tct gta       48
Gln Asp Ile Gln Met Thr Gln Ser Pro Ser Ser Leu Ser Ala Ser Val
1               5                   10                  15 gga gac aga gtt acc atc act tgc cgg gca agt cag ggc att acc act       96
Gly Asp Arg Val Thr Ile Thr Cys Arg Ala Ser Gln Gly Ile Thr Thr
            20                  25                  30 tat tta ggc tgg tat tag cag aaa cca ggg aaa gcc cct aag ctc ctg      144
Tyr Leu Gly Trp Tyr  *  Gln Lys Pro Gly Lys Ala Pro Lys Leu Leu
        35                  40                  45 atc tat gct gca tcc act ttg caa agt ggg gtc cca gca aag ttc agc      192
Ile Tyr Ala Ala Ser Thr Leu Gln Ser Gly Val Pro Ala Lys Phe Ser
    50                  55                  60 ggc agt gga tct ggg aca ctt ttc act ctc acc atc agc ggt ctg caa      240
Gly Ser Gly Ser Gly Thr Leu Phe Thr Leu Thr Ile Ser Gly Leu Gln
65                  70                  75                  80 cct gaa gat tct gca act tac tac tgt cac cag agt tac aat acc cct      288
Pro Glu Asp Ser Ala Thr Tyr Tyr Cys His Gln Ser Tyr Asn Thr Pro
                85                  90                  95 tgg acg ttc ggc caa ggg ac                                           308
Trp Thr Phe Gly Gln Gly
                100
```

<210> SEQ ID NO 34
<211> LENGTH: 101
<212> TYPE: PRT
<213> ORGANISM: Artificial Sequence
<220> FEATURE:
<223> OTHER INFORMATION: Synthetically generated peptide

<400> SEQUENCE: 34

```
Gln Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Gly Ile Thr Thr
            20                  25                  30

Tyr Leu Gly Trp Tyr Gln Lys Pro Gly Lys Ala Pro Lys Leu Leu Ile
        35                  40                  45

Tyr Ala Ala Ser Thr Leu Gln Ser Gly Val Pro Ala Lys Phe Ser Gly
    50                  55                  60

Ser Gly Ser Gly Thr Leu Phe Thr Leu Thr Ile Ser Gly Leu Gln Pro
65                  70                  75                  80

Glu Asp Ser Ala Thr Tyr Tyr Cys His Gln Ser Tyr Asn Thr Pro Trp
                85                  90                  95

Thr Phe Gly Gln Gly
            100
```

<210> SEQ ID NO 35
<211> LENGTH: 412
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(411)

<400> SEQUENCE: 35

```
gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct ggt tac      96
Ser Leu Arg Leu Ser Cys Ala Ala Ser Gly Phe Thr Phe Ser Gly Tyr
            20                  25                  30 ggt atg cat tgg gtt cgc caa gct cct ggt aaa ggt ttg gag tgg gtt     144
Gly Met His Trp Val Arg Gln Ala Pro Gly Lys Gly Leu Glu Trp Val
         35                  40                  45 tct gtt atc tct cct tct ggt ggc cag act tgg tag gct gac tcc gtt     192
Ser Val Ile Ser Pro Ser Gly Gly Gln Thr Trp  *  Ala Asp Ser Val
     50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
 65                  70                  75 ttg cag atg aac agc tta agg gct gag gac act gca gtc tac tat tgt     288
Leu Gln Met Asn Ser Leu Arg Ala Glu Asp Thr Ala Val Tyr Tyr Cys
 80              85                  90                  95 gcg aga ggc ggg acc agt aac cca ctg ttt tac tgg ggc cag gga acc     336
Ala Arg Gly Gly Thr Ser Asn Pro Leu Phe Tyr Trp Gly Gln Gly Thr
                100                 105                 110 ctg gtc acc gtc tca agc gcc tcc acc aag ggc cca tcg gtc ttc ccg     384
Leu Val Thr Val Ser Ser Ala Ser Thr Lys Gly Pro Ser Val Phe Pro
            115                 120                 125 cta gca ccc tcc tcc aag agc acc tct g                                412
Leu Ala Pro Ser Ser Lys Ser Thr Ser
        130                 135

<210> SEQ ID NO 36
<211> LENGTH: 136
<212> TYPE: PRT
<213> ORGANISM: Artificial Sequence
<220> FEATURE:
<223> OTHER INFORMATION: Synthetically generated peptide

<400> SEQUENCE: 36

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
         35                  40                  45

Ser Val Ile Ser Pro Ser Gly Gly Gln Thr Trp Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Gly Gly Thr Ser Asn Pro Leu Phe Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser
        130                 135

<210> SEQ ID NO 37
<211> LENGTH: 308
<212> TYPE: DNA
<213> ORGANISM: Artificial Sequence
<220> FEATURE:
```

```
<223> OTHER INFORMATION: Synthetically generated oligonucleotide
<220> FEATURE:
<221> NAME/KEY: CDS
<222> LOCATION: (1)...(306)

<400> SEQUENCE: 37 caa gac atc cag atg acc cag tct cca gcc acc ctg tct ttg tct cca      48
Gln Asp Ile Gln Met Thr Gln Ser Pro Ala Thr Leu Ser Leu Ser Pro
 1               5                  10                  15 ggg gaa aga gcc acc ctc tcc tgc agg gcc agt cag agt gtt agc agc      96
Gly Glu Arg Ala Thr Leu Ser Cys Arg Ala Ser Gln Ser Val Ser Ser
             20                  25                  30 tac tta gcc tgg tac caa cag aaa cct ggc cag gct ccc agg ctc ctc     144
Tyr Leu Ala Trp Tyr Gln Gln Lys Pro Gly Gln Ala Pro Arg Leu Leu
         35                  40                  45 atc tat gat gca tcc aac agg gcc act ggc atc cca gcc agg ttc agt     192
Ile Tyr Asp Ala Ser Asn Arg Ala Thr Gly Ile Pro Ala Arg Phe Ser
     50                  55                  60 ggc agt ggg tct ggg aca gac ttc act ctc acc atc agc agc cta gag     240
Gly Ser Gly Ser Gly Thr Asp Phe Thr Leu Thr Ile Ser Ser Leu Glu
 65                  70                  75                  80 cct gaa gat ttt gca gtt tat tac tgt cag cag cgt agc aac tgg cct     288
Pro Glu Asp Phe Ala Val Tyr Tyr Cys Gln Gln Arg Ser Asn Trp Pro
                 85                  90                  95 ccg act ttt ggc cag ggg ac                                          308
Pro Thr Phe Gly Gln Gly
            100

<210> SEQ ID NO 38
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 38

Gln Asp Ile Gln Met Thr Gln Ser Pro Ala Thr Leu Ser Leu Ser Pro
 1               5                  10                  15

Gly Glu Arg Ala Thr Leu Ser Cys Arg Ala Ser Gln Ser Val Ser Ser
             20                  25                  30

Tyr Leu Ala Trp Tyr Gln Gln Lys Pro Gly Gln Ala Pro Arg Leu Leu
         35                  40                  45

Ile Tyr Asp Ala Ser Asn Arg Ala Thr Gly Ile Pro Ala Arg Phe Ser
     50                  55                  60

Gly Ser Gly Ser Gly Thr Asp Phe Thr Leu Thr Ile Ser Ser Leu Glu
 65                  70                  75                  80

Pro Glu Asp Phe Ala Val Tyr Tyr Cys Gln Gln Arg Ser Asn Trp Pro
                 85                  90                  95

Pro Thr Phe Gly Gln Gly
            100

<210> SEQ ID NO 39
<211> LENGTH: 444
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(444)

<400> SEQUENCE: 39
```

```
gaa gtt caa ttg tta gag tct ggt ggc ggt ctt gtt cag cct ggt ggt     48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct ggt tac     96
Ser Leu Arg Leu Ser Cys Ala Ala Ser Gly Phe Thr Phe Ser Gly Tyr
             20                  25                  30 ggt atg cat tgg gtt cgc caa gct cct ggt aaa ggt ttg gag tgg gtt    144
Gly Met His Trp Val Arg Gln Ala Pro Gly Lys Gly Leu Glu Trp Val
         35                  40                  45 tct gtt atc tct cct tct ggt ggc cag act tct tat gct gac tcc gtt    192
Ser Val Ile Ser Pro Ser Gly Gly Gln Thr Ser Tyr Ala Asp Ser Val
     50                  55                  60 aaa ggt cgc ttc act atc tct aga gac aac tct aag aat act ctc tac    240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt    288
Leu Gln Met Asn Ser Leu Arg Ala Glu Asp Thr Ala Val Tyr Tyr Cys
                 85                  90                  95 gcg aga gat agg cag tat tac tat ggt tcg ggg agt ctt gac tac tgg    336
Ala Arg Asp Arg Gln Tyr Tyr Tyr Gly Ser Gly Ser Leu Asp Tyr Trp
            100                 105                 110 ggc cag gga acc ctg gtc acc gtc tca agc gcc tcc acc aag ggc cca    384
Gly Gln Gly Thr Leu Val Thr Val Ser Ser Ala Ser Thr Lys Gly Pro
        115                 120                 125 tcg gtc ttc ccg cta gca ccc tcc tcc aag agc acc tct ggg ggc aca    432
Ser Val Phe Pro Leu Ala Pro Ser Ser Lys Ser Thr Ser Gly Gly Thr
    130                 135                 140 gcg gcc ctg ggc                                                    444
Ala Ala Leu Gly
145

<210> SEQ ID NO 40
<211> LENGTH: 148
<212> TYPE: PRT
<213> ORGANISM: Artificial Sequence
<220> FEATURE:
<223> OTHER INFORMATION: Synthetically generated peptide

<400> SEQUENCE: 40

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
             20                  25                  30

Gly Met His Trp Val Arg Gln Ala Pro Gly Lys Gly Leu Glu Trp Val
         35                  40                  45

Ser Val Ile Ser Pro Ser Gly Gly Gln Thr Ser Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gln Tyr Tyr Tyr Gly Ser Gly Ser Leu Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly
145
```

<210> SEQ ID NO 41
<211> LENGTH: 308
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(306)

<400> SEQUENCE: 41

```
caa gac atc cag atg acc cag tct cca tcc tcc ctg tct gca tct gta      48
Gln Asp Ile Gln Met Thr Gln Ser Pro Ser Ser Leu Ser Ala Ser Val
 1               5                  10                  15 gga gac aga gtc acc gtc act tgc cgg gca agt cag agc att agc agt      96
Gly Asp Arg Val Thr Val Thr Cys Arg Ala Ser Gln Ser Ile Ser Ser
            20                  25                  30 tat tta aat tgg tat cag cag aaa cca ggg aaa gcc cct aaa ctc ctg     144
Tyr Leu Asn Trp Tyr Gln Gln Lys Pro Gly Lys Ala Pro Lys Leu Leu
        35                  40                  45 atc tat gct gca tcc agt ttg caa agt ggg gtc cca tca agg ttc agt     192
Ile Tyr Ala Ala Ser Ser Leu Gln Ser Gly Val Pro Ser Arg Phe Ser
    50                  55                  60 ggc ggt gga tct ggg aca gat ttc act ctc acc atc agc agt ctg caa     240
Gly Gly Gly Ser Gly Thr Asp Phe Thr Leu Thr Ile Ser Ser Leu Gln
65                  70                  75                  80 cct gaa gat ttt gca act tat ttc tgt cta caa gat tac aaa tac ccg     288
Pro Glu Asp Phe Ala Thr Tyr Phe Cys Leu Gln Asp Tyr Lys Tyr Pro
                85                  90                  95 tgg acg ttc ggc caa ggg ac                                          308
Trp Thr Phe Gly Gln Gly
            100
```

<210> SEQ ID NO 42
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 42

```
Gln Asp Ile Gln Met Thr Gln Ser Pro Ser Ser Leu Ser Ala Ser Val
 1               5                  10                  15

Gly Asp Arg Val Thr Val Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Ala Ala Ser Ser Leu Gln Ser Gly Val Pro Ser Arg Phe Ser
    50                  55                  60

Gly Gly Gly Ser Gly Thr Asp Phe Thr Leu Thr Ile Ser Ser Leu Gln
65                  70                  75                  80

Pro Glu Asp Phe Ala Thr Tyr Phe Cys Leu Gln Asp Tyr Lys Tyr Pro
                85                  90                  95

Trp Thr Phe Gly Gln Gly
            100
```

<210> SEQ ID NO 43
<211> LENGTH: 375
<212> TYPE: DNA
<213> ORGANISM: Artificial Sequence
<220> FEATURE:

```
<223> OTHER INFORMATION: Synthetically generated oligonucleotide
<220> FEATURE:
<221> NAME/KEY: CDS
<222> LOCATION: (1)...(375)

<400> SEQUENCE: 43 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
1               5                   10                  15 tct tta cgt ctt tct tgc gct gct tcc gga ttc act ttc tct atg tac      96
Ser Leu Arg Leu Ser Cys Ala Ala Ser Gly Phe Thr Phe Ser Met Tyr
            20                  25                  30 ggt atg ggt tgg gtt cgc caa gct cct ggt aaa ggt ttg gag tgg gtt     144
Gly Met Gly Trp Val Arg Gln Ala Pro Gly Lys Gly Leu Glu Trp Val
        35                  40                  45 tct gtt atc tct cct tct ggt ggc cag act gct tat gct gac tcc gtt     192
Ser Val Ile Ser Pro Ser Gly Gly Gln Thr Ala Tyr Ala Asp Ser Val
    50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
65                  70                  75                  80 ttg cag atg aac agc tta agg gct gag gac act gca gtc tac tat tgt     288
Leu Gln Met Asn Ser Leu Arg Ala Glu Asp Thr Ala Val Tyr Tyr Cys
                85                  90                  95 gcg aga gtg gcc ttg ctc ctg ggc cac gct ttt gat atc tgg ggc caa     336
Ala Arg Val Ala Leu Leu Leu Gly His Ala Phe Asp Ile Trp Gly Gln
            100                 105                 110 ggg aca atg gtc acc gtc tca agc gcc tcc acc aag ggc                 375
Gly Thr Met Val Thr Val Ser Ser Ala Ser Thr Lys Gly
        115                 120                 125

<210> SEQ ID NO 44
<211> LENGTH: 125
<212> TYPE: PRT
<213> ORGANISM: Artificial Sequence
<220> FEATURE:
<223> OTHER INFORMATION: Synthetically generated peptide

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Gly Met Gly Trp Val Arg Gln Ala Pro Gly Lys Gly Leu Glu Trp Val
        35                  40                  45

Ser Val Ile Ser Pro Ser Gly Gly Gln Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Ala Leu Leu Leu Gly His Ala Phe Asp Ile Trp Gly Gln
            100                 105                 110

Gly Thr Met Val Thr Val Ser Ser Ala Ser Thr Lys Gly
        115                 120                 125

<210> SEQ ID NO 45
<211> LENGTH: 308
<212> TYPE: DNA
<213> ORGANISM: Artificial Sequence
<220> FEATURE:
```

```
<223> OTHER INFORMATION: Synthetically generated oligonucleotide
<220> FEATURE:
<221> NAME/KEY: CDS
<222> LOCATION: (1)...(306)

<400> SEQUENCE: 45 caa gac atc cag atg acc cag tct cct tcc acc ctg tct gca tct tta      48
Gln Asp Ile Gln Met Thr Gln Ser Pro Ser Thr Leu Ser Ala Ser Leu
1               5                   10                  15 gga gac aga gtc acc atc act tgc cgg gcc agt gag agt att agt agg      96
Gly Asp Arg Val Thr Ile Thr Cys Arg Ala Ser Glu Ser Ile Ser Arg
            20                  25                  30 tgg ttg gcc tgg tat cag cag aaa cca ggg aaa gcc cct aag ctc ctg     144
Trp Leu Ala Trp Tyr Gln Gln Lys Pro Gly Lys Ala Pro Lys Leu Leu
        35                  40                  45 atg tat gag gca tcc act tta gaa agt ggg gtc cca tca agg ttc acc     192
Met Tyr Glu Ala Ser Thr Leu Glu Ser Gly Val Pro Ser Arg Phe Thr
    50                  55                  60 ggc act gga tct ggg aca gaa ttc act ctc acc atc agc agc ctg cag     240
Gly Thr Gly Ser Gly Thr Glu Phe Thr Leu Thr Ile Ser Ser Leu Gln
65                  70                  75                  80 ccc gat gat ttt gca act tat tac tgt cag cag cgt agc aac tgg ccc     288
Pro Asp Asp Phe Ala Thr Tyr Tyr Cys Gln Gln Arg Ser Asn Trp Pro
                85                  90                  95 ctc act ttc ggc gga ggg ac                                          308
Leu Thr Phe Gly Gly Gly
            100

<210> SEQ ID NO 46
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 46

Gln Asp Ile Gln Met Thr Gln Ser Pro Ser Thr Leu Ser Ala Ser Leu
1               5                   10                  15

Gly Asp Arg Val Thr Ile Thr Cys Arg Ala Ser Glu Ser Ile Ser Arg
            20                  25                  30

Trp Leu Ala Trp Tyr Gln Gln Lys Pro Gly Lys Ala Pro Lys Leu Leu
        35                  40                  45

Met Tyr Glu Ala Ser Thr Leu Glu Ser Gly Val Pro Ser Arg Phe Thr
    50                  55                  60

Gly Thr Gly Ser Gly Thr Glu Phe Thr Leu Thr Ile Ser Ser Leu Gln
65                  70                  75                  80

Pro Asp Asp Phe Ala Thr Tyr Tyr Cys Gln Gln Arg Ser Asn Trp Pro
                85                  90                  95

Leu Thr Phe Gly Gly Gly
            100

<210> SEQ ID NO 47
<211> LENGTH: 429
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(429)

<400> SEQUENCE: 47
```

```
gaa gtt caa ttg tta gag tct ggt ggc ggt ctt gtt cag cct ggt ggt    48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct gct tac    96
Ser Leu Arg Leu Ser Cys Ala Ala Ser Gly Phe Thr Phe Ser Ala Tyr
             20                  25                  30 atg atg tct tgg gtt cgc caa gct cct ggt aaa ggt ttg gag tgg gtt   144
Met Met Ser Trp Val Arg Gln Ala Pro Gly Lys Gly Leu Glu Trp Val
         35                  40                  45 tct tct atc tat cct tct ggt ggc tat act tat tat gct gac tcc gtt   192
Ser Ser Ile Tyr Pro Ser Gly Gly Tyr Thr Tyr Tyr Ala Asp Ser Val
     50                  55                  60 aaa ggt cgc ttc act atc tct aga gac aac tct aag aat act ctc tac   240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt   288
Leu Gln Met Asn Ser Leu Arg Ala Glu Asp Thr Ala Val Tyr Tyr Cys
                 85                  90                  95 gcg aga ggc tta cgg gga ggt cct gac tac tgg ggc cag gga acc ctg   336
Ala Arg Gly Leu Arg Gly Gly Pro Asp Tyr Trp Gly Gln Gly Thr Leu
            100                 105                 110 gtc acc gtc tca agc gcc tcc acc aag ggc cca tcg gtc ttc ccg cta   384
Val Thr Val Ser Ser Ala Ser Thr Lys Gly Pro Ser Val Phe Pro Leu
        115                 120                 125 gca ccc tcc tcc aag agc acc tct ggg ggc aca gcg gcc ctg ggc       429
Ala Pro Ser Ser Lys Ser Thr Ser Gly Gly Thr Ala Ala Leu Gly
    130                 135                 140
```

<210> SEQ ID NO 48
<211> LENGTH: 143
<212> TYPE: PRT
<213> ORGANISM: Artificial Sequence
<220> FEATURE:
<223> OTHER INFORMATION: Synthetically generated peptide

<400> SEQUENCE: 48

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
             20                  25                  30

Met Met Ser Trp Val Arg Gln Ala Pro Gly Lys Gly Leu Glu Trp Val
         35                  40                  45

Ser Ser Ile Tyr Pro Ser Gly Gly Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Arg Gly Gly Pro Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly
    130                 135                 140
```

<210> SEQ ID NO 49
<211> LENGTH: 308
<212> TYPE: DNA
<213> ORGANISM: Artificial Sequence
<220> FEATURE:

```
<223> OTHER INFORMATION: Synthetically generated oligonucleotide
<220> FEATURE:
<221> NAME/KEY: CDS
<222> LOCATION: (1)...(306)

<400> SEQUENCE: 49 caa gac atc cag atg acc cag tct cct tcc acc ctg tct gca tat gta      48
Gln Asp Ile Gln Met Thr Gln Ser Pro Ser Thr Leu Ser Ala Tyr Val
1               5                   10                  15 gga gac agt gtc acc atc act tgc cgg gcc agt cag agt gtg aga agg      96
Gly Asp Ser Val Thr Ile Thr Cys Arg Ala Ser Gln Ser Val Arg Arg
                20                  25                  30 tcg ttg gcc tgg tat cag cag aga cca ggg aaa gcc ccc aag tcc ctc     144
Ser Leu Ala Trp Tyr Gln Gln Arg Pro Gly Lys Ala Pro Lys Ser Leu
            35                  40                  45 atc tat aag gcg tct act tta gag act ggg gtc cca cca agg ttc agc     192
Ile Tyr Lys Ala Ser Thr Leu Glu Thr Gly Val Pro Pro Arg Phe Ser
        50                  55                  60 ggc agt gga tct ggg aca gaa ttc act ctc acc atc agc agc ctg cag     240
Gly Ser Gly Ser Gly Thr Glu Phe Thr Leu Thr Ile Ser Ser Leu Gln
65                  70                  75                  80 cct gaa gat tct gca att tat tac tgc caa caa tat ggt agt ttt ccg     288
Pro Glu Asp Ser Ala Ile Tyr Tyr Cys Gln Gln Tyr Gly Ser Phe Pro
                85                  90                  95 ctc act ttc ggc gga ggg ac                                           308
Leu Thr Phe Gly Gly Gly
            100

<210> SEQ ID NO 50
<211> LENGTH: 102
<212> TYPE: PRT
<213> ORGANISM: Artificial Sequence
<220> FEATURE:
<223> OTHER INFORMATION: Synthetically generated peptide

<400> SEQUENCE: 50

Gln Asp Ile Gln Met Thr Gln Ser Pro Ser Thr Leu Ser Ala Tyr Val
1               5                   10                  15

Gly Asp Ser Val Thr Ile Thr Cys Arg Ala Ser Gln Ser Val Arg Arg
                20                  25                  30

Ser Leu Ala Trp Tyr Gln Gln Arg Pro Gly Lys Ala Pro Lys Ser Leu
            35                  40                  45

Ile Tyr Lys Ala Ser Thr Leu Glu Thr Gly Val Pro Pro Arg Phe Ser
        50                  55                  60

Gly Ser Gly Ser Gly Thr Glu Phe Thr Leu Thr Ile Ser Ser Leu Gln
65                  70                  75                  80

Pro Glu Asp Ser Ala Ile Tyr Tyr Cys Gln Gln Tyr Gly Ser Phe Pro
                85                  90                  95

Leu Thr Phe Gly Gly Gly
            100

<210> SEQ ID NO 51
<211> LENGTH: 441
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(441)

<400> SEQUENCE: 51
```

```
gaa gtt caa ttg tta gag tct ggt ggc ggt ctt gtt cag cct ggt ggt        48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct cat tac        96
Ser Leu Arg Leu Ser Cys Ala Ala Ser Gly Phe Thr Phe Ser His Tyr
             20                  25                  30 atg atg gtt tgg gtt cgc caa gct cct ggt aaa ggt ttg gag tgg gtt       144
Met Met Val Trp Val Arg Gln Ala Pro Gly Lys Gly Leu Glu Trp Val
                 35                  40                  45 tct tct atc tat cct tct ggt ggc tgg act tat tat gct gac tcc gtt       192
Ser Ser Ile Tyr Pro Ser Gly Gly Trp Thr Tyr Tyr Ala Asp Ser Val
         50                  55                  60 aaa ggt cgc ttc act atc tct aga gac aac tct aag aat act ctc tac       240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt       288
Leu Gln Met Asn Ser Leu Arg Ala Glu Asp Thr Ala Val Tyr Tyr Cys
                 85                  90                  95 gcg agg ctg gac tac ggt ggt aat tcc gcc tac ttt gac tac tgg ggc       336
Ala Arg Leu Asp Tyr Gly Gly Asn Ser Ala Tyr Phe Asp Tyr Trp Gly
             100                 105                 110 cag gga acc ctg gtc acc gtc tca agc gcc tcc acc aag ggc cca tcg       384
Gln Gly Thr Leu Val Thr Val Ser Ser Ala Ser Thr Lys Gly Pro Ser
         115                 120                 125 gtc ttc ccg cta gca ccc tcc tcc aag agc acc tct ggg ggc aca gcg       432
Val Phe Pro Leu Ala Pro Ser Ser Lys Ser Thr Ser Gly Gly Thr Ala
130                 135                 140 gcc ctg ggc                                                            441
Ala Leu Gly
145
```

<210> SEQ ID NO 52
<211> LENGTH: 147
<212> TYPE: PRT
<213> ORGANISM: Artificial Sequence
<220> FEATURE:
<223> OTHER INFORMATION: Synthetically generated peptide

<400> SEQUENCE: 52

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser His Tyr
             20                  25                  30

Met Met Val Trp Val Arg Gln Ala Pro Gly Lys Gly Leu Glu Trp Val
         35                  40                  45

Ser Ser Ile Tyr Pro Ser Gly Gly Trp Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Asp Tyr Gly Gly Asn Ser Ala Tyr Phe Asp Tyr Trp Gly
             100                 105                 110

Gln Gly Thr Leu Val Thr Val Ser Ser Ala Ser Thr Lys Gly Pro Ser
         115                 120                 125

Val Phe Pro Leu Ala Pro Ser Ser Lys Ser Thr Ser Gly Gly Thr Ala
     130                 135                 140

Ala Leu Gly
145
```

```
<210> SEQ ID NO 53
<211> LENGTH: 327
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(327)

<400> SEQUENCE: 53 cag agc gtc ttg act cag ccg cac tct gtg tcg gcc tct ccg ggg aag      48
Gln Ser Val Leu Thr Gln Pro His Ser Val Ser Ala Ser Pro Gly Lys
 1               5                  10                  15 acg gta acc atc tcc tgc acc cgc agc agt ggc aac att gcc agc aac      96
Thr Val Thr Ile Ser Cys Thr Arg Ser Ser Gly Asn Ile Ala Ser Asn
            20                  25                  30 ttt gtc cag tgg tac caa cag cgc ccg ggc agt gtc ccc acc act gtg     144
Phe Val Gln Trp Tyr Gln Gln Arg Pro Gly Ser Val Pro Thr Thr Val
        35                  40                  45 att tat gaa gat gac cga aga ccc tct ggg gtc cct gat cgc ttt tct     192
Ile Tyr Glu Asp Asp Arg Arg Pro Ser Gly Val Pro Asp Arg Phe Ser
    50                  55                  60 ggc tcc atc gac agt tcc tcc aac tct gct ttc ctc agc atc tct gga     240
Gly Ser Ile Asp Ser Ser Ser Asn Ser Ala Phe Leu Ser Ile Ser Gly
65                  70                  75                  80 ctg aag act gag gac gag gca gac tat tac tgt cag tct cat gat cgt     288
Leu Lys Thr Glu Asp Glu Ala Asp Tyr Tyr Cys Gln Ser His Asp Arg
                85                  90                  95 acc acc cgt gct tgg gtg ttc ggc gga ggg acc aag ctg                 327
Thr Thr Arg Ala Trp Val Phe Gly Gly Gly Thr Lys Leu
            100                 105

<210> SEQ ID NO 54
<211> LENGTH: 109
<212> TYPE: PRT
<213> ORGANISM: Artificial Sequence
<220> FEATURE:
<223> OTHER INFORMATION: Synthetically generated peptide

<400> SEQUENCE: 54

Gln Ser Val Leu Thr Gln Pro His Ser Val Ser Ala Ser Pro Gly Lys
 1               5                  10                  15

Thr Val Thr Ile Ser Cys Thr Arg Ser Ser Gly Asn Ile Ala Ser Asn
            20                  25                  30

Phe Val Gln Trp Tyr Gln Gln Arg Pro Gly Ser Val Pro Thr Thr Val
        35                  40                  45

Ile Tyr Glu Asp Asp Arg Arg Pro Ser Gly Val Pro Asp Arg Phe Ser
    50                  55                  60

Gly Ser Ile Asp Ser Ser Ser Asn Ser Ala Phe Leu Ser Ile Ser Gly
65                  70                  75                  80

Leu Lys Thr Glu Asp Glu Ala Asp Tyr Tyr Cys Gln Ser His Asp Arg
                85                  90                  95

Thr Thr Arg Ala Trp Val Phe Gly Gly Gly Thr Lys Leu
            100                 105

<210> SEQ ID NO 55
<211> LENGTH: 413
<212> TYPE: DNA
<213> ORGANISM: Artificial Sequence
<220> FEATURE:
```

```
<223> OTHER INFORMATION: Synthetically generated oligonucleotide
<220> FEATURE:
<221> NAME/KEY: CDS
<222> LOCATION: (1)...(411)

<400> SEQUENCE: 55 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct cgt tac      96
Ser Leu Arg Leu Ser Cys Ala Ala Ser Gly Phe Thr Phe Ser Arg Tyr
                20                  25                  30 act atg atg tgg gtt cgc caa gct cct ggt aaa ggt ttg gag tgg gtt     144
Thr Met Met Trp Val Arg Gln Ala Pro Gly Lys Gly Leu Glu Trp Val
            35                  40                  45 tct ggt atc tat cct tct ggt ggc gtt act ctt tat gct gac tcc gtt     192
Ser Gly Ile Tyr Pro Ser Gly Gly Val Thr Leu Tyr Ala Asp Ser Val
        50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
 65                 70                  75                  80 ttg cag atg aac agc tta agg gct gag gac act gca gtc tac tat tgt     288
Leu Gln Met Asn Ser Leu Arg Ala Glu Asp Thr Ala Val Tyr Tyr Cys
                85                  90                  95 gcg aga gtc aat tac tat gat agt agt ggt tac ggt cct ata gct cct     336
Ala Arg Val Asn Tyr Tyr Asp Ser Ser Gly Tyr Gly Pro Ile Ala Pro
               100                 105                 110 gga ctt gac tac tgg ggc cag gga acc ctg gtc acc gtc tca agc gcc     384
Gly Leu Asp Tyr Trp Gly Gln Gly Thr Leu Val Thr Val Ser Ser Ala
           115                 120                 125 tcc acc aag ggc cca tcg gtc ttc ccg ct                              413
Ser Thr Lys Gly Pro Ser Val Phe Pro
       130                 135

<210> SEQ ID NO 56
<211> LENGTH: 137
<212> TYPE: PRT
<213> ORGANISM: Artificial Sequence
<220> FEATURE:
<223> OTHER INFORMATION: Synthetically generated peptide

<400> SEQUENCE: 56

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
                20                  25                  30

Thr Met Met Trp Val Arg Gln Ala Pro Gly Lys Gly Leu Glu Trp Val
            35                  40                  45

Ser Gly Ile Tyr Pro Ser Gly Gly Val Thr Leu Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Val Asn Tyr Tyr Asp Ser Ser Gly Tyr Gly Pro Ile Ala Pro
               100                 105                 110

Gly Leu Asp Tyr Trp Gly Gln Gly Thr Leu Val Thr Val Ser Ser Ala
           115                 120                 125

Ser Thr Lys Gly Pro Ser Val Phe Pro
       130                 135
```

<210> SEQ ID NO 57
<211> LENGTH: 339
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(339)

<400> SEQUENCE: 57

```
cac agt gca caa gac atc cag atg acc cag tct cca ggc acc ctg tct      48
His Ser Ala Gln Asp Ile Gln Met Thr Gln Ser Pro Gly Thr Leu Ser
1               5                   10                  15 ttg tct cca ggg gaa aga gcc aca ctc tcc tgc agg gcc agt cgg agt      96
Leu Ser Pro Gly Glu Arg Ala Thr Leu Ser Cys Arg Ala Ser Arg Ser
            20                  25                  30 gtg atc atc agc tac gta gcc tgg tac cag cag aaa cct ggc cag gct     144
Val Ile Ile Ser Tyr Val Ala Trp Tyr Gln Gln Lys Pro Gly Gln Ala
        35                  40                  45 ccc agg ctc ctc atc tat gga gcg tcc acc agg gcc act ggc atc cca     192
Pro Arg Leu Leu Ile Tyr Gly Ala Ser Thr Arg Ala Thr Gly Ile Pro
    50                  55                  60 gac agg ttc agt ggc agt ggg tct ggg aca gac ttc act ctc acc atc     240
Asp Arg Phe Ser Gly Ser Gly Ser Gly Thr Asp Phe Thr Leu Thr Ile
65                  70                  75                  80 agc aga ctg gag cct gaa gac ttt gca gtg tat ttc tgt cag ctt tat     288
Ser Arg Leu Glu Pro Glu Asp Phe Ala Val Tyr Phe Cys Gln Leu Tyr
                85                  90                  95 ggt agg tca cca cgg atc atc ttc ggc caa ggg aca cga ctg gag att     336
Gly Arg Ser Pro Arg Ile Ile Phe Gly Gln Gly Thr Arg Leu Glu Ile
            100                 105                 110 aaa                                                                  339
Lys
```

<210> SEQ ID NO 58
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 58

```
His Ser Ala Gln Asp Ile Gln Met Thr Gln Ser Pro Gly Thr Leu Ser
1               5                   10                  15

Leu Ser Pro Gly Glu Arg Ala Thr Leu Ser Cys Arg Ala Ser Arg Ser
            20                  25                  30

Val Ile Ile Ser Tyr Val Ala Trp Tyr Gln Gln Lys Pro Gly Gln Ala
        35                  40                  45

Pro Arg Leu Leu Ile Tyr Gly Ala Ser Thr Arg Ala Thr Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Phe Cys Gln Leu Tyr
                85                  90                  95

Gly Arg Ser Pro Arg Ile Ile Phe Gly Gln Gly Thr Arg Leu Glu Ile
            100                 105                 110

Lys
```

```
<210> SEQ ID NO 59
<211> LENGTH: 369
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(369)

<400> SEQUENCE: 59 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
  1               5                  10                  15 tct tta cgt ctt tct tgc gct gct tcc gga ttc act ttc tct aat tac      96
Ser Leu Arg Leu Ser Cys Ala Ala Ser Gly Phe Thr Phe Ser Asn Tyr
             20                  25                  30 gtt atg gtt tgg gtt cgc caa gct cct ggt aaa ggt ttg gag tgg gtt     144
Val Met Val Trp Val Arg Gln Ala Pro Gly Lys Gly Leu Glu Trp Val
         35                  40                  45 tct ggt atc tat cct tct ggt ggc cat act aag tat gct gac tcc gtt     192
Ser Gly Ile Tyr Pro Ser Gly Gly His Thr Lys Tyr Ala Asp Ser Val
     50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt     288
Leu Gln Met Asn Ser Leu Arg Ala Glu Asp Thr Ala Val Tyr Tyr Cys
                 85                  90                  95 gcg aga gtc aat tac tat gat agt agt ggt tac ggt cct ata gct cct     336
Ala Arg Val Asn Tyr Tyr Asp Ser Ser Gly Tyr Gly Pro Ile Ala Pro
            100                 105                 110 gga ctt gac tac tgg ggc cag gga acc ctg gtc                         369
Gly Leu Asp Tyr Trp Gly Gln Gly Thr Leu Val
        115                 120

<210> SEQ ID NO 60
<211> LENGTH: 123
<212> TYPE: PRT
<213> ORGANISM: Artificial Sequence
<220> FEATURE:
<223> OTHER INFORMATION: Synthetically generated peptide

<400> SEQUENCE: 60

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Val Met Val Trp Val Arg Gln Ala Pro Gly Lys Gly Leu Glu Trp Val
         35                  40                  45

Ser Gly Ile Tyr Pro Ser Gly Gly His Thr Lys Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Asn Tyr Tyr Asp Ser Ser Gly Tyr Gly Pro Ile Ala Pro
            100                 105                 110

Gly Leu Asp Tyr Trp Gly Gln Gly Thr Leu Val
        115                 120
```

```
<210> SEQ ID NO 61
<211> LENGTH: 339
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(339)

<400> SEQUENCE: 61 cac agt gca caa gac atc cag atg acc cag tct cca ggc acc ctg tct      48
His Ser Ala Gln Asp Ile Gln Met Thr Gln Ser Pro Gly Thr Leu Ser
1               5                   10                  15 ttg tct cca ggg gaa aga gcc acc ctc ttc tgc agg gcc agt cag cgt      96
Leu Ser Pro Gly Glu Arg Ala Thr Leu Phe Cys Arg Ala Ser Gln Arg
            20                  25                  30 gtt acc agc aac tcc ttg gcc tgg tac cag cag aga cct ggc cag gct     144
Val Thr Ser Asn Ser Leu Ala Trp Tyr Gln Gln Arg Pro Gly Gln Ala
        35                  40                  45 ccc agg ctc ctc atc tat gat gca tcc acc agg gcc act ggc atc cca     192
Pro Arg Leu Leu Ile Tyr Asp Ala Ser Thr Arg Ala Thr Gly Ile Pro
    50                  55                  60 gac cgc ttc agt ggc agt ggg tcg ggg agg gac ttc act ctc acc atc     240
Asp Arg Phe Ser Gly Ser Gly Ser Gly Arg Asp Phe Thr Leu Thr Ile
65                  70                  75                  80 agc aga ctg gag cct gaa gat ttt gca gtt tat tac tgt cag cga tat     288
Ser Arg Leu Glu Pro Glu Asp Phe Ala Val Tyr Tyr Cys Gln Arg Tyr
                85                  90                  95 ggt agt tca gtg ttg tac tct ttt ggc cag ggg acg aag ttg gaa atc     336
Gly Ser Ser Val Leu Tyr Ser Phe Gly Gln Gly Thr Lys Leu Glu Ile
            100                 105                 110 aca                                                                 339
Thr

<210> SEQ ID NO 62
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 62

His Ser Ala Gln Asp Ile Gln Met Thr Gln Ser Pro Gly Thr Leu Ser
1               5                   10                  15

Leu Ser Pro Gly Glu Arg Ala Thr Leu Phe Cys Arg Ala Ser Gln Arg
            20                  25                  30

Val Thr Ser Asn Ser Leu Ala Trp Tyr Gln Gln Arg Pro Gly Gln Ala
        35                  40                  45

Pro Arg Leu Leu Ile Tyr Asp Ala Ser Thr Arg Ala Thr Gly Ile Pro
    50                  55                  60

Asp Arg Phe Ser Gly Ser Gly Ser Gly Arg Asp Phe Thr Leu Thr Ile
65                  70                  75                  80

Ser Arg Leu Glu Pro Glu Asp Phe Ala Val Tyr Tyr Cys Gln Arg Tyr
                85                  90                  95

Gly Ser Ser Val Leu Tyr Ser Phe Gly Gln Gly Thr Lys Leu Glu Ile
            100                 105                 110

Thr

<210> SEQ ID NO 63
<211> LENGTH: 383
```

<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(381)

<400> SEQUENCE: 63

| | | | | | | | | | | | | | | | | |
|---|---|---|---|---|---|---|---|---|---|---|---|---|---|---|---|---|
| gaa | gtt | caa | ttg | tta | gag | tct | ggt | ggc | ggt | ctt | gtt | cag | cct | ggt | ggt | 48 |
| Glu | Val | Gln | Leu | Leu | Glu | Ser | Gly | Gly | Gly | Leu | Val | Gln | Pro | Gly | Gly | |
| 1 | | | | 5 | | | | | 10 | | | | | 15 | | |
| tct | tta | cgt | ctt | tct | tgc | gct | gct | tcc | gga | ttc | act | ttc | tct | att | tac | 96 |
| Ser | Leu | Arg | Leu | Ser | Cys | Ala | Ala | Ser | Gly | Phe | Thr | Phe | Ser | Ile | Tyr | |
| | | | 20 | | | | | 25 | | | | | 30 | | | |
| ggt | atg | gct | tgg | gtt | cgc | caa | gct | cct | ggt | aaa | ggt | ttg | gag | tgg | gtt | 144 |
| Gly | Met | Ala | Trp | Val | Arg | Gln | Ala | Pro | Gly | Lys | Gly | Leu | Glu | Trp | Val | |
| | | 35 | | | | | 40 | | | | | 45 | | | | |
| tct | gtt | atc | tct | cct | tct | ggt | ggc | cag | act | ttt | tat | gct | gac | tcc | gtt | 192 |
| Ser | Val | Ile | Ser | Pro | Ser | Gly | Gly | Gln | Thr | Phe | Tyr | Ala | Asp | Ser | Val | |
| 50 | | | | | 55 | | | | | 60 | | | | | | |
| aaa | ggt | cgc | ttc | act | atc | tct | aga | gac | aac | tct | aag | aat | act | ctc | tac | 240 |
| Lys | Gly | Arg | Phe | Thr | Ile | Ser | Arg | Asp | Asn | Ser | Lys | Asn | Thr | Leu | Tyr | |
| 65 | | | | 70 | | | | | 75 | | | | | 80 | | |
| ttg | cag | atg | aac | agc | tta | agg | gct | gag | gac | act | gca | gtc | tac | tat | tgt | 288 |
| Leu | Gln | Met | Asn | Ser | Leu | Arg | Ala | Glu | Asp | Thr | Ala | Val | Tyr | Tyr | Cys | |
| | | | 85 | | | | | 90 | | | | | 95 | | | |
| gcg | aga | gtt | tac | tac | tac | ggt | atg | gac | gtc | tgg | ggc | caa | ggg | acc | acg | 336 |
| Ala | Arg | Val | Tyr | Tyr | Tyr | Gly | Met | Asp | Val | Trp | Gly | Gln | Gly | Thr | Thr | |
| | | | 100 | | | | | 105 | | | | | 110 | | | |
| gtc | acc | gtc | tca | agc | gcc | tcc | acc | aag | ggc | cca | tcg | gtc | ttc | ccg | | 381 |
| Val | Thr | Val | Ser | Ser | Ala | Ser | Thr | Lys | Gly | Pro | Ser | Val | Phe | Pro | | |
| | 115 | | | | | 120 | | | | | 125 | | | | | |
| ct | | | | | | | | | | | | | | | | 383 |

<210> SEQ ID NO 64
<211> LENGTH: 127
<212> TYPE: PRT
<213> ORGANISM: Artificial Sequence
<220> FEATURE:
<223> OTHER INFORMATION: Synthetically generated peptide

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Gly Met Ala Trp Val Arg Gln Ala Pro Gly Lys Gly Leu Glu Trp Val
        35                  40                  45

Ser Val Ile Ser Pro Ser Gly Gly Gln Thr Phe Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro
        115                 120                 125

```
<210> SEQ ID NO 65
<211> LENGTH: 333
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(333)

<400> SEQUENCE: 65 cac agt gca caa gac atc cag atg acc cag tct cca gcc acc ctg tct      48
His Ser Ala Gln Asp Ile Gln Met Thr Gln Ser Pro Ala Thr Leu Ser
 1               5                  10                  15 ttg tct cca ggg gaa aga gcc acc ctc tcc tgc agg gcc agt cag agt      96
Leu Ser Pro Gly Glu Arg Ala Thr Leu Ser Cys Arg Ala Ser Gln Ser
            20                  25                  30 gtt agc agc tac tta gcc tgg tac caa caa aaa cct ggc cag gct ccc     144
Val Ser Ser Tyr Leu Ala Trp Tyr Gln Gln Lys Pro Gly Gln Ala Pro
        35                  40                  45 agg ctc ctc att tat gat gca tcc aac agg gcc act ggc atc cca gcc     192
Arg Leu Leu Ile Tyr Asp Ala Ser Asn Arg Ala Thr Gly Ile Pro Ala
    50                  55                  60 agg ttc agt ggc agt ggg tct gag aca gac ttc act ctc acc atc agc     240
Arg Phe Ser Gly Ser Gly Ser Glu Thr Asp Phe Thr Leu Thr Ile Ser
65                  70                  75                  80 agc cta gag cct gaa gat ttt gca gtt tat tac tgt cag cag cgt agc     288
Ser Leu Glu Pro Glu Asp Phe Ala Val Tyr Tyr Cys Gln Gln Arg Ser
                85                  90                  95 aag tgg cct cgg act ttt ggc cag ggg acc aag ctg gag atc aaa         333
Lys Trp Pro Arg Thr Phe Gly Gln Gly Thr Lys Leu Glu Ile Lys
            100                 105                 110

<210> SEQ ID NO 66
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 66

His Ser Ala Gln Asp Ile Gln Met Thr Gln Ser Pro Ala Thr Leu Ser
 1               5                  10                  15

Leu Ser Pro Gly Glu Arg Ala Thr Leu Ser Cys Arg Ala Ser Gln Ser
            20                  25                  30

Val Ser Ser Tyr Leu Ala Trp Tyr Gln Gln Lys Pro Gly Gln Ala Pro
        35                  40                  45

Arg Leu Leu Ile Tyr Asp Ala Ser Asn Arg Ala Thr Gly Ile Pro Ala
    50                  55                  60

Arg Phe Ser Gly Ser Gly Ser Glu Thr Asp Phe Thr Leu Thr Ile Ser
65                  70                  75                  80

Ser Leu Glu Pro Glu Asp Phe Ala Val Tyr Tyr Cys Gln Gln Arg Ser
                85                  90                  95

Lys Trp Pro Arg Thr Phe Gly Gln Gly Thr Lys Leu Glu Ile Lys
            100                 105                 110

<210> SEQ ID NO 67
<211> LENGTH: 413
<212> TYPE: DNA
<213> ORGANISM: Artificial Sequence
<220> FEATURE:
<223> OTHER INFORMATION: Synthetically generated oligonucleotide
<220> FEATURE:
```

```
<221> NAME/KEY: CDS
<222> LOCATION: (1)...(411)

<400> SEQUENCE: 67 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct tct tac      96
Ser Leu Arg Leu Ser Cys Ala Ala Ser Gly Phe Thr Phe Ser Ser Tyr
             20                  25                  30 gtt atg atg tgg gtt cgc caa gct cct ggt aaa ggt ttg gag tgg gtt     144
Val Met Met Trp Val Arg Gln Ala Pro Gly Lys Gly Leu Glu Trp Val
         35                  40                  45 tct ggt atc tat cct tct ggt ggc tgg act tat tat act gac tcc gtt     192
Ser Gly Ile Tyr Pro Ser Gly Gly Trp Thr Tyr Tyr Thr Asp Ser Val
 50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt     288
Leu Gln Met Asn Ser Leu Arg Ala Glu Asp Thr Ala Val Tyr Tyr Cys
             85                  90                  95 gcg aga gtc aat tac tat gat agt agt ggt tac ggt cct ata gct cct     336
Ala Arg Val Asn Tyr Tyr Asp Ser Ser Gly Tyr Gly Pro Ile Ala Pro
            100                 105                 110 gga ctt gac tac tgg ggc cag gga acc ctg gtc acc gtc tca agc gcc     384
Gly Leu Asp Tyr Trp Gly Gln Gly Thr Leu Val Thr Val Ser Ser Ala
        115                 120                 125 tcc acc aag ggc cca tcg gtc ttc ccg ct                              413
Ser Thr Lys Gly Pro Ser Val Phe Pro
    130                 135

<210> SEQ ID NO 68
<211> LENGTH: 137
<212> TYPE: PRT
<213> ORGANISM: Artificial Sequence
<220> FEATURE:
<223> OTHER INFORMATION: Synthetically generated peptide

<400> SEQUENCE: 68

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Val Met Met Trp Val Arg Gln Ala Pro Gly Lys Gly Leu Glu Trp Val
         35                  40                  45

Ser Gly Ile Tyr Pro Ser Gly Gly Trp Thr Tyr Tyr Thr Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Val Asn Tyr Tyr Asp Ser Ser Gly Tyr Gly Pro Ile Ala Pro
            100                 105                 110

Gly Leu Asp Tyr Trp Gly Gln Gly Thr Leu Val Thr Val Ser Ser Ala
        115                 120                 125

Ser Thr Lys Gly Pro Ser Val Phe Pro
    130                 135
```

```
<210> SEQ ID NO 69
<211> LENGTH: 336
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(336)

<400> SEQUENCE: 69 cac agt gca caa gac atc cag atg acc cag tct cca tcc tcc ctg tct      48
His Ser Ala Gln Asp Ile Gln Met Thr Gln Ser Pro Ser Ser Leu Ser
 1               5                  10                  15 gca tct gtt gga gat aga gtc acc atc act tgc cgg gca agt cag agt      96
Ala Ser Val Gly Asp Arg Val Thr Ile Thr Cys Arg Ala Ser Gln Ser
             20                  25                  30 gtc agc agt cat tta agt tgg ttt cag cag aga cca ggg aaa gcc ccc     144
Val Ser Ser His Leu Ser Trp Phe Gln Gln Arg Pro Gly Lys Ala Pro
         35                  40                  45 aac ctc ctg atc tat cat gca tcc agt ttg caa agt ggg gtc cca tca     192
Asn Leu Leu Ile Tyr His Ala Ser Ser Leu Gln Ser Gly Val Pro Ser
     50                  55                  60 agg ttc agt ggc agt ggg tct ggg aca gat ttc acg ctc acc atc agc     240
Arg Phe Ser Gly Ser Gly Ser Gly Thr Asp Phe Thr Leu Thr Ile Ser
 65                  70                  75                  80 agt ctg caa cct gaa gat ttt gca act tac tac tgt cag cag agt tac     288
Ser Leu Gln Pro Glu Asp Phe Ala Thr Tyr Tyr Cys Gln Gln Ser Tyr
                 85                  90                  95 gct act tcc tcg atc acc ttc ggc cag ggg aca cga ctg gac att aaa     336
Ala Thr Ser Ser Ile Thr Phe Gly Gln Gly Thr Arg Leu Asp Ile Lys
             100                 105                 110

<210> SEQ ID NO 70
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 70

His Ser Ala Gln Asp Ile Gln Met Thr Gln Ser Pro Ser Ser Leu Ser
 1               5                  10                  15

Ala Ser Val Gly Asp Arg Val Thr Ile Thr Cys Arg Ala Ser Gln Ser
             20                  25                  30

Val Ser Ser His Leu Ser Trp Phe Gln Gln Arg Pro Gly Lys Ala Pro
         35                  40                  45

Asn Leu Leu Ile Tyr His Ala Ser Ser Leu Gln Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Tyr
                 85                  90                  95

Ala Thr Ser Ser Ile Thr Phe Gly Gln Gly Thr Arg Leu Asp Ile Lys
             100                 105                 110

<210> SEQ ID NO 71
<211> LENGTH: 413
<212> TYPE: DNA
<213> ORGANISM: Artificial Sequence
<220> FEATURE:
<223> OTHER INFORMATION: Synthetically generated oligonucleotide
<220> FEATURE:
```

<221> NAME/KEY: CDS
<222> LOCATION: (1)...(411)

<400> SEQUENCE: 71

| | | | | | | | | | | | | | | | | |
|---|---|---|---|---|---|---|---|---|---|---|---|---|---|---|---|---|
| gaa | gtt | caa | ttg | tta | gag | tct | ggt | ggc | ggt | ctt | gtt | cag | cct | ggt | ggt | 48 |
| Glu | Val | Gln | Leu | Leu | Glu | Ser | Gly | Gly | Gly | Leu | Val | Gln | Pro | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tct | tta | cgt | ctt | tct | tgc | gct | gct | tcc | gga | ttc | act | ttc | tct | cgt | tac | 96 |
| Ser | Leu | Arg | Leu | Ser | Cys | Ala | Ala | Ser | Gly | Phe | Thr | Phe | Ser | Arg | Tyr | |
| | | | 20 | | | | | 25 | | | | | 30 | | | |

| | | | | | | | | | | | | | | | | |
|---|---|---|---|---|---|---|---|---|---|---|---|---|---|---|---|---|
| aag | atg | aag | tgg | gtt | cgc | caa | gct | cct | ggt | aaa | ggt | ttg | gag | tgg | gtt | 144 |
| Lys | Met | Lys | Trp | Val | Arg | Gln | Ala | Pro | Gly | Lys | Gly | Leu | Glu | Trp | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| tct | gtt | atc | tat | cct | tct | ggt | ggc | ggt | act | ggt | tat | gct | gac | tcc | gtt | 192 |
| Ser | Val | Ile | Tyr | Pro | Ser | Gly | Gly | Gly | Thr | Gly | Tyr | Ala | Asp | Ser | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| aaa | ggt | cgc | ttc | act | atc | tct | aga | gac | aac | tct | aag | aat | act | ctc | tac | 240 |
| Lys | Gly | Arg | Phe | Thr | Ile | Ser | Arg | Asp | Asn | Ser | Lys | Asn | Thr | Leu | Tyr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttg | cag | atg | aac | agc | tta | agg | gct | gag | gac | act | gca | gtc | tac | tat | tgt | 288 |
| Leu | Gln | Met | Asn | Ser | Leu | Arg | Ala | Glu | Asp | Thr | Ala | Val | Tyr | Tyr | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| gcg | aga | gtc | aat | tac | tat | gat | agt | agt | ggt | tac | ggt | cct | ata | gct | cct | 336 |
| Ala | Arg | Val | Asn | Tyr | Tyr | Asp | Ser | Ser | Gly | Tyr | Gly | Pro | Ile | Ala | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| gga | ctt | gac | tac | tgg | ggc | cag | gga | acc | ctg | gtc | acc | gtc | tca | agc | gcc | 384 |
| Gly | Leu | Asp | Tyr | Trp | Gly | Gln | Gly | Thr | Leu | Val | Thr | Val | Ser | Ser | Ala | |
| | | 115 | | | | | 120 | | | | | 125 | | | | |

| | | | | | | | | | |
|---|---|---|---|---|---|---|---|---|---|
| tcc | acc | aag | ggc | cca | tcg | gtc | ttc | ccg | ct | 413 |
| Ser | Thr | Lys | Gly | Pro | Ser | Val | Phe | Pro | | |
| | 130 | | | | | 135 | | | | |

<210> SEQ ID NO 72
<211> LENGTH: 137
<212> TYPE: PRT
<213> ORGANISM: Artificial Sequence
<220> FEATURE:
<223> OTHER INFORMATION: Synthetically generated peptide

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Lys Met Lys Trp Val Arg Gln Ala Pro Gly Lys Gly Leu Glu Trp Val
        35                  40                  45

Ser Val Ile Tyr Pro Ser Gly Gly Gly Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Asn Tyr Tyr Asp Ser Ser Gly Tyr Gly Pro Ile Ala Pro
            100                 105                 110

Gly Leu Asp Tyr Trp Gly Gln Gly Thr Leu Val Thr Val Ser Ser Ala
        115                 120                 125

Ser Thr Lys Gly Pro Ser Val Phe Pro
    130                 135

<210> SEQ ID NO 73
<211> LENGTH: 428
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(426)

<400> SEQUENCE: 73

```
cac agt gca cag agc gtc ttg act cag cct gac tcc gtg tct ggg tct        48
His Ser Ala Gln Ser Val Leu Thr Gln Pro Asp Ser Val Ser Gly Ser
 1               5                  10                  15 cct gga gag tcg atc acc atc tcc tgc act gga agc agc aga gac gtt        96
Pro Gly Glu Ser Ile Thr Ile Ser Cys Thr Gly Ser Ser Arg Asp Val
             20                  25                  30 ggt ggt tat aac tat gtc tcc tgg tac caa caa cac cca ggc aaa gcc       144
Gly Gly Tyr Asn Tyr Val Ser Trp Tyr Gln Gln His Pro Gly Lys Ala
         35                  40                  45 ccc aaa ctc ttg ctt tat gat gtc act tat cgg ccc tca ggg att tct       192
Pro Lys Leu Leu Leu Tyr Asp Val Thr Tyr Arg Pro Ser Gly Ile Ser
     50                  55                  60 ggt cgc ttc tct ggc tcc aag tct ggc gac acg gcc tcc ctg acc atc       240
Gly Arg Phe Ser Gly Ser Lys Ser Gly Asp Thr Ala Ser Leu Thr Ile
 65                  70                  75                  80 tct ggg ctc cgg act gag gac gag gct gat tat tac tgc agc tca tct       288
Ser Gly Leu Arg Thr Glu Asp Glu Ala Asp Tyr Tyr Cys Ser Ser Ser
                 85                  90                  95 ata ggc acc agg act tat gtc ttc gga agt ggg acc aag gtc acc gtc       336
Ile Gly Thr Arg Thr Tyr Val Phe Gly Ser Gly Thr Lys Val Thr Val
            100                 105                 110 cta cgt cag ccc aag gcc aac ccc act gtc act ctg ttc ccg ccc tcc       384
Leu Arg Gln Pro Lys Ala Asn Pro Thr Val Thr Leu Phe Pro Pro Ser
        115                 120                 125 tct gag gag ctc caa gcc aac aag gcc aca cta gtg tgt ctg                426
Ser Glu Glu Leu Gln Ala Asn Lys Ala Thr Leu Val Cys Leu
    130                 135                 140 at                                                                     428
```

<210> SEQ ID NO 74
<211> LENGTH: 142
<212> TYPE: PRT
<213> ORGANISM: Artificial Sequence
<220> FEATURE:
<223> OTHER INFORMATION: Synthetically generated peptide

<400> SEQUENCE: 74

```
His Ser Ala Gln Ser Val Leu Thr Gln Pro Asp Ser Val Ser Gly Ser
 1               5                  10                  15

Pro Gly Glu Ser Ile Thr Ile Ser Cys Thr Gly Ser Ser Arg Asp Val
             20                  25                  30

Gly Gly Tyr Asn Tyr Val Ser Trp Tyr Gln Gln His Pro Gly Lys Ala
         35                  40                  45

Pro Lys Leu Leu Leu Tyr Asp Val Thr Tyr Arg Pro Ser Gly Ile Ser
     50                  55                  60

Gly Arg Phe Ser Gly Ser Lys Ser Gly Asp Thr Ala Ser Leu Thr Ile
 65                  70                  75                  80

Ser Gly Leu Arg Thr Glu Asp Glu Ala Asp Tyr Tyr Cys Ser Ser Ser
                 85                  90                  95

Ile Gly Thr Arg Thr Tyr Val Phe Gly Ser Gly Thr Lys Val Thr Val
```

-continued

```
                       100                 105                 110
Leu Arg Gln Pro Lys Ala Asn Pro Thr Val Thr Leu Phe Pro Pro Ser
            115                 120                 125
Ser Glu Glu Leu Gln Ala Asn Lys Ala Thr Leu Val Cys Leu
        130                 135                 140

<210> SEQ ID NO 75
<211> LENGTH: 386
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(384)

<400> SEQUENCE: 75 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
  1               5                  10                  15 tct tta cgt ctt tct tgc gct gct tcc gga ttc act ttc tct cgt tac      96
Ser Leu Arg Leu Ser Cys Ala Ala Ser Gly Phe Thr Phe Ser Arg Tyr
                 20                  25                  30 gtt atg tat tgg gtt cgc caa gct cct ggt aaa ggt ttg gag tgg gtt     144
Val Met Tyr Trp Val Arg Gln Ala Pro Gly Lys Gly Leu Glu Trp Val
             35                  40                  45 tct gtt atc tat cct tct ggt ggc gct act tat tat gct gac tcc gtt     192
Ser Val Ile Tyr Pro Ser Gly Gly Ala Thr Tyr Tyr Ala Asp Ser Val
         50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt     288
Leu Gln Met Asn Ser Leu Arg Ala Glu Asp Thr Ala Val Tyr Tyr Cys
                 85                  90                  95 gcg aga cgg gga agt agt ggt gcg ttt gac tac tgg ggc cag gga acc     336
Ala Arg Arg Gly Ser Ser Gly Ala Phe Asp Tyr Trp Gly Gln Gly Thr
            100                 105                 110 ctg gtc acc gtc tca agc gcc tcc acc aag ggc cca tcg gtc ttc ccg     384
Leu Val Thr Val Ser Ser Ala Ser Thr Lys Gly Pro Ser Val Phe Pro
        115                 120                 125 ct                                                                  386

<210> SEQ ID NO 76
<211> LENGTH: 128
<212> TYPE: PRT
<213> ORGANISM: Artificial Sequence
<220> FEATURE:
<223> OTHER INFORMATION: Synthetically generated peptide

<400> SEQUENCE: 76

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Tyr
                 20                  25                  30

Val Met Tyr Trp Val Arg Gln Ala Pro Gly Lys Gly Leu Glu Trp Val
             35                  40                  45

Ser Val Ile Tyr Pro Ser Gly Gly Ala Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Arg Arg Gly Ser Ser Gly Ala Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

<210> SEQ ID NO 77
<211> LENGTH: 434
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(432)

<400> SEQUENCE: 77 cac agt gca cag agc gtc ttg act cag cct gcc tcc gtg tct ggg tct        48
His Ser Ala Gln Ser Val Leu Thr Gln Pro Ala Ser Val Ser Gly Ser
  1               5                  10                  15 cct gga cag tcg atc acc atc tcc tgc act gga acc agc agt gac att        96
Pro Gly Gln Ser Ile Thr Ile Ser Cys Thr Gly Thr Ser Ser Asp Ile
             20                  25                  30 ggt cgt tat aac tat gcc tcc tgg tac caa caa cgc cca ggc aaa tcc       144
Gly Arg Tyr Asn Tyr Ala Ser Trp Tyr Gln Gln Arg Pro Gly Lys Ser
         35                  40                  45 ccc aaa ctc ctg att tat gag gtc agt gat cgg ccc tca ggg gtt tct       192
Pro Lys Leu Leu Ile Tyr Glu Val Ser Asp Arg Pro Ser Gly Val Ser
     50                  55                  60 aat cgc ttc tct ggc tcc aag tct ggc aac acg gcc tcc ctg atc atc       240
Asn Arg Phe Ser Gly Ser Lys Ser Gly Asn Thr Ala Ser Leu Ile Ile
 65                  70                  75                  80 tct ggg ctc cag gct gag gac gag gct gat tat tac tgc agc tca tat       288
Ser Gly Leu Gln Ala Glu Asp Glu Ala Asp Tyr Tyr Cys Ser Ser Tyr
                 85                  90                  95 tca agc acc aac agt ctc caa gtg gta ttc ggc gga ggg acc aag ctg       336
Ser Ser Thr Asn Ser Leu Gln Val Val Phe Gly Gly Gly Thr Lys Leu
            100                 105                 110 agc gtc cta ggt cag ccc aag gct gcc ccc tcg gtc act ctg ttc ccg       384
Ser Val Leu Gly Gln Pro Lys Ala Ala Pro Ser Val Thr Leu Phe Pro
        115                 120                 125 ccc tcc tct gag gag ctt caa gcc aac aag gcc aca ctg gtg tgt ctc       432
Pro Ser Ser Glu Glu Leu Gln Ala Asn Lys Ala Thr Leu Val Cys Leu
    130                 135                 140 at                                                                     434

<210> SEQ ID NO 78
<211> LENGTH: 144
<212> TYPE: PRT
<213> ORGANISM: Artificial Sequence
<220> FEATURE:
<223> OTHER INFORMATION: Synthetically generated peptide

<400> SEQUENCE: 78

His Ser Ala Gln Ser Val Leu Thr Gln Pro Ala Ser Val Ser Gly Ser
  1               5                  10                  15

Pro Gly Gln Ser Ile Thr Ile Ser Cys Thr Gly Thr Ser Ser Asp Ile
             20                  25                  30

Gly Arg Tyr Asn Tyr Ala Ser Trp Tyr Gln Gln Arg Pro Gly Lys Ser
         35                  40                  45
```

```
Pro Lys Leu Leu Ile Tyr Glu Val Ser Asp Arg Pro Ser Gly Val Ser
    50                  55                  60

Asn Arg Phe Ser Gly Ser Lys Ser Gly Asn Thr Ala Ser Leu Ile Ile
 65             70                  75                  80

Ser Gly Leu Gln Ala Glu Asp Glu Ala Asp Tyr Tyr Cys Ser Ser Tyr
                85                  90                  95

Ser Ser Thr Asn Ser Leu Gln Val Val Phe Gly Gly Gly Thr Lys Leu
            100                 105                 110

Ser Val Leu Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
    130                 135                 140

<210> SEQ ID NO 79
<211> LENGTH: 413
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(411)

<400> SEQUENCE: 79 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct gct tac      96
Ser Leu Arg Leu Ser Cys Ala Ala Ser Gly Phe Thr Phe Ser Ala Tyr
             20                  25                  30 ggt atg tct tgg gtt cgc caa gct cct ggt aaa ggt ttg gag tgg gtt     144
Gly Met Ser Trp Val Arg Gln Ala Pro Gly Lys Gly Leu Glu Trp Val
         35                  40                  45 tct gtt atc tat cct tct ggt ggc tgg act tat tat gct gac tcc gtt     192
Ser Val Ile Tyr Pro Ser Gly Gly Trp Thr Tyr Tyr Ala Asp Ser Val
     50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt     288
Leu Gln Met Asn Ser Leu Arg Ala Glu Asp Thr Ala Val Tyr Tyr Cys
             85                  90                  95 gcg aga gtc aat tac tat gat agt agt ggt tac ggt cct ata gct cct     336
Ala Arg Val Asn Tyr Tyr Asp Ser Ser Gly Tyr Gly Pro Ile Ala Pro
            100                 105                 110 gga ctt gac tac tgg ggc cag gga acc ctg gtc acc gtc tca agc gcc     384
Gly Leu Asp Tyr Trp Gly Gln Gly Thr Leu Val Thr Val Ser Ser Ala
        115                 120                 125 tcc acc aag ggc cca tcg gtc ttc ccg ct                              413
Ser Thr Lys Gly Pro Ser Val Phe Pro
    130                 135

<210> SEQ ID NO 80
<211> LENGTH: 137
<212> TYPE: PRT
<213> ORGANISM: Artificial Sequence
<220> FEATURE:
<223> OTHER INFORMATION: Synthetically generated peptide

<400> SEQUENCE: 80

Glu Val Gln Leu Leu Glu Ser Gly Gly Gly Leu Val Gln Pro Gly Gly
```

```
            1               5                  10                 15
Ser Leu Arg Leu Ser Cys Ala Ala Ser Gly Phe Thr Phe Ser Ala Tyr
                20                  25                 30

Gly Met Ser Trp Val Arg Gln Ala Pro Gly Lys Gly Leu Glu Trp Val
            35                  40                 45

Ser Val Ile Tyr Pro Ser Gly Gly Trp Thr Tyr Tyr Ala Asp Ser Val
        50                  55                  60

Lys Gly Arg Phe Thr Ile Ser Arg Asp Asn Ser Lys Asn Thr Leu Tyr
 65              70                  75                  80

Leu Gln Met Asn Ser Leu Arg Ala Glu Asp Thr Ala Val Tyr Tyr Cys
                85                  90                  95

Ala Arg Val Asn Tyr Tyr Asp Ser Ser Gly Tyr Gly Pro Ile Ala Pro
            100                 105                110

Gly Leu Asp Tyr Trp Gly Gln Gly Thr Leu Val Thr Val Ser Ser Ala
            115                 120                125

Ser Thr Lys Gly Pro Ser Val Phe Pro
            130                 135

<210> SEQ ID NO 81
<211> LENGTH: 336
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(336)

<400> SEQUENCE: 81 cac agt gca caa gac atc cag atg acc cag tct cca ggc acc ctg tct    48
His Ser Ala Gln Asp Ile Gln Met Thr Gln Ser Pro Gly Thr Leu Ser
 1               5                  10                  15 ttg tct cca ggg gaa aga gcc acc ctc tcc tgc agg gcc agt cag agt    96
Leu Ser Pro Gly Glu Arg Ala Thr Leu Ser Cys Arg Ala Ser Gln Ser
                20                  25                  30 gtt agc agc agc tac tta gcc tgg tac cag cag aaa cct ggc cag gct   144
Val Ser Ser Ser Tyr Leu Ala Trp Tyr Gln Gln Lys Pro Gly Gln Ala
            35                  40                  45 ccc agg ctc ctc atc tat ggt gca tcc agc agg gcc act ggc atc cca   192
Pro Arg Leu Leu Ile Tyr Gly Ala Ser Ser Arg Ala Thr Gly Ile Pro
        50                  55                  60 gac agg ttc agt ggc agt ggg tct ggg aca gac ttc act ctc acc atc   240
Asp Arg Phe Ser Gly Ser Gly Ser Gly Thr Asp Phe Thr Leu Thr Ile
 65                  70                  75                  80 agc aga ctg gag cct gaa gat ttt gca gtg tat tac tgt cag cag tat   288
Ser Arg Leu Glu Pro Glu Asp Phe Ala Val Tyr Tyr Cys Gln Gln Tyr
                85                  90                  95 aat aac tgg cct cgg acg ttc ggc caa ggg acc aag gtg gaa atc aaa   336
Asn Asn Trp Pro Arg Thr Phe Gly Gln Gly Thr Lys Val Glu Ile Lys
            100                 105                 110

<210> SEQ ID NO 82
<211> LENGTH: 112
<212> TYPE: PRT
<213> ORGANISM: Artificial Sequence
<220> FEATURE:
<223> OTHER INFORMATION: Synthetically generated peptide

<400> SEQUENCE: 82

His Ser Ala Gln Asp Ile Gln Met Thr Gln Ser Pro Gly Thr Leu Ser
 1               5                  10                  15
```

```
Leu Ser Pro Gly Glu Arg Ala Thr Leu Ser Cys Arg Ala Ser Gln Ser
            20                  25                  30

Val Ser Ser Ser Tyr Leu Ala Trp Tyr Gln Gln Lys Pro Gly Gln Ala
        35                  40                  45

Pro Arg Leu Leu Ile Tyr Gly Ala Ser Ser Arg Ala Thr Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Gln Gln Tyr
                85                  90                  95

Asn Asn Trp Pro Arg Thr Phe Gly Gln Gly Thr Lys Val Glu Ile Lys
            100                 105                 110

<210> SEQ ID NO 83
<211> LENGTH: 395
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(393)

<400> SEQUENCE: 83 gaa gtt caa ttg tta gag tct ggt ggc ggt ctt gtt cag cct ggt ggt        48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct ggt tac        96
Ser Leu Arg Leu Ser Cys Ala Ala Ser Gly Phe Thr Phe Ser Gly Tyr
            20                  25                  30 gct atg tgg tgg gtt cgc caa gct cct ggt aaa ggt ttg gag tgg gtt       144
Ala Met Trp Trp Val Arg Gln Ala Pro Gly Lys Gly Leu Glu Trp Val
        35                  40                  45 tct tct atc tct cct tct ggt ggc gct act gct tat gct gac tcc gtt       192
Ser Ser Ile Ser Pro Ser Gly Gly Ala Thr Ala Tyr Ala Asp Ser Val
    50                  55                  60 aaa ggt cgc ttc act atc tct aga gac aac tct aag aat act ctc tac       240
Lys Gly Arg Phe Thr Ile Ser Arg Asp Asn Ser Lys Asn Thr Leu Tyr
65                  70                  75                  80 ttg cag atg aac agc tta agg gct gag gac act gca gtc tac tat tgt       288
Leu Gln Met Asn Ser Leu Arg Ala Glu Asp Thr Ala Val Tyr Tyr Cys
                85                  90                  95 gcg aga gat gcg ggg agt tat tat tgg ggc tgg ttc gac ccc tgg ggc       336
Ala Arg Asp Ala Gly Ser Tyr Tyr Trp Gly Trp Phe Asp Pro Trp Gly
            100                 105                 110 cag gga acc ctg gtc acc gtc tca agc gcc tcc acc aag ggc cca tcg       384
Gln Gly Thr Leu Val Thr Val Ser Ser Ala Ser Thr Lys Gly Pro Ser
        115                 120                 125 gtc ttc ccg ct                                                         395
Val Phe Pro
    130

<210> SEQ ID NO 84
<211> LENGTH: 131
<212> TYPE: PRT
<213> ORGANISM: Artificial Sequence
<220> FEATURE:
<223> OTHER INFORMATION: Synthetically generated peptide

<400> SEQUENCE: 84

Glu Val Gln Leu Leu Glu Ser Gly Gly Gly Leu Val Gln Pro Gly Gly
```

```
                1               5                   10                  15
            Ser Leu Arg Leu Ser Cys Ala Ala Ser Gly Phe Thr Phe Ser Gly Tyr
                        20                  25                  30

Ala Met Trp Trp Val Arg Gln Ala Pro Gly Lys Gly Leu Glu Trp Val
                        35                  40                  45

Ser Ser Ile Ser Pro Ser Gly Gly Ala Thr Tyr Ala Asp Ser Val
                50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Val Tyr Tyr Cys
                            85                  90                  95

Ala Arg Asp Ala Gly Ser Tyr Tyr Trp Gly Trp Phe Asp Pro Trp Gly
                            100                 105                 110

Gln Gly Thr Leu Val Thr Val Ser Ala Ser Thr Lys Gly Pro Ser
                        115                 120                 125

Val Phe Pro
                130
```

<210> SEQ ID NO 85
<211> LENGTH: 333
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(333)

<400> SEQUENCE: 85

```
cac agt gca caa gac atc cag atg acc cag tct cca gcc acc ttg tct        48
His Ser Ala Gln Asp Ile Gln Met Thr Gln Ser Pro Ala Thr Leu Ser
  1               5                  10                  15 ttg tct cca ggg gaa aga gcc acc ctc tcc tgc agg gcc agt cag agt        96
Leu Ser Pro Gly Glu Arg Ala Thr Leu Ser Cys Arg Ala Ser Gln Ser
             20                  25                  30 att agc agc tac tta gcc tgg tac caa cag aaa cct ggc cag cct ccc       144
Ile Ser Ser Tyr Leu Ala Trp Tyr Gln Gln Lys Pro Gly Gln Pro Pro
         35                  40                  45 agg ctc ctc atc tat gat gca tcc agc agg gtt act ggc atc cca gcc       192
Arg Leu Leu Ile Tyr Asp Ala Ser Ser Arg Val Thr Gly Ile Pro Ala
     50                  55                  60 agg ttc agt ggc agt ggc ttt ggg aca gac ttc act ctc acc att agt       240
Arg Phe Ser Gly Ser Gly Phe Gly Thr Asp Phe Thr Leu Thr Ile Ser
 65                  70                  75                  80 agc ctg gag cct gaa gat ttt gca gtt tat tac tgt ctc cag cgt agc       288
Ser Leu Glu Pro Glu Asp Phe Ala Val Tyr Tyr Cys Leu Gln Arg Ser
                 85                  90                  95 agc tgg ccc cga act ttt ggc cag ggg acc aag ctg gag atc aaa           333
Ser Trp Pro Arg Thr Phe Gly Gln Gly Thr Lys Leu Glu Ile Lys
            100                 105                 110
```

<210> SEQ ID NO 86
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 86

```
His Ser Ala Gln Asp Ile Gln Met Thr Gln Ser Pro Ala Thr Leu Ser
  1               5                  10                  15
```

```
Leu Ser Pro Gly Glu Arg Ala Thr Leu Ser Cys Arg Ala Ser Gln Ser
            20                  25                  30

Ile Ser Ser Tyr Leu Ala Trp Tyr Gln Gln Lys Pro Gly Gln Pro Pro
        35                  40                  45

Arg Leu Leu Ile Tyr Asp Ala Ser Ser Arg Val Thr Gly Ile Pro Ala
    50                  55                  60

Arg Phe Ser Gly Ser Gly Phe Gly Thr Asp Phe Thr Leu Thr Ile Ser
65                  70                  75                  80

Ser Leu Glu Pro Glu Asp Phe Ala Val Tyr Tyr Cys Leu Gln Arg Ser
                85                  90                  95

Ser Trp Pro Arg Thr Phe Gly Gln Gly Thr Lys Leu Glu Ile Lys
            100                 105                 110
```

<210> SEQ ID NO 87
<211> LENGTH: 413
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(411)

<400> SEQUENCE: 87

```
gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
1               5                   10                  15 tct tta cgt ctt tct tgc gct gct tcc gga ttc act ttc tct ggt tac      96
Ser Leu Arg Leu Ser Cys Ala Ala Ser Gly Phe Thr Phe Ser Gly Tyr
            20                  25                  30 gtt atg ttt tgg gtt cgc caa gct cct ggt aaa ggt ttg gag tgg gtt     144
Val Met Phe Trp Val Arg Gln Ala Pro Gly Lys Gly Leu Glu Trp Val
        35                  40                  45 tct ggt atc tat cct tct ggt ggc tgg act gtt tat gct gac tcc gtt     192
Ser Gly Ile Tyr Pro Ser Gly Gly Trp Thr Val Tyr Ala Asp Ser Val
    50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
65                  70                  75                  80 ttg cag atg aac agc tta agg gct gag gac act gca gtc tac tat tgt     288
Leu Gln Met Asn Ser Leu Arg Ala Glu Asp Thr Ala Val Tyr Tyr Cys
                85                  90                  95 gcg aga gtc aat tac tat gat agt agt ggt tac ggt cct ata gct cct     336
Ala Arg Val Asn Tyr Tyr Asp Ser Ser Gly Tyr Gly Pro Ile Ala Pro
            100                 105                 110 gga ctt gac tac tgg ggc cag gga acc ctg gtc acc gtc tca agc gcc     384
Gly Leu Asp Tyr Trp Gly Gln Gly Thr Leu Val Thr Val Ser Ser Ala
        115                 120                 125 tcc acc aag ggc cca tcg gtc ttc ccg ct                              413
Ser Thr Lys Gly Pro Ser Val Phe Pro
    130                 135
```

<210> SEQ ID NO 88
<211> LENGTH: 137
<212> TYPE: PRT
<213> ORGANISM: Artificial Sequence
<220> FEATURE:
<223> OTHER INFORMATION: Synthetically generated peptide

<400> SEQUENCE: 88

Glu Val Gln Leu Leu Glu Ser Gly Gly Gly Leu Val Gln Pro Gly Gly

```
                1               5                  10                 15
              Ser Leu Arg Leu Ser Cys Ala Ala Ser Gly Phe Thr Phe Ser Gly Tyr
                          20                  25                  30

Val Met Phe Trp Val Arg Gln Ala Pro Gly Lys Gly Leu Glu Trp Val
                          35                  40                  45

Ser Gly Ile Tyr Pro Ser Gly Gly Trp Thr Val Tyr Ala Asp Ser Val
                          50                  55                  60

Lys Gly Arg Phe Thr Ile Ser Arg Asp Asn Ser Lys Asn Thr Leu Tyr
               65                  70                  75                  80

Leu Gln Met Asn Ser Leu Arg Ala Glu Asp Thr Ala Val Tyr Tyr Cys
                              85                  90                  95

Ala Arg Val Asn Tyr Tyr Asp Ser Ser Gly Tyr Gly Pro Ile Ala Pro
                          100                 105                 110

Gly Leu Asp Tyr Trp Gly Gln Gly Thr Leu Val Thr Val Ser Ser Ala
                          115                 120                 125

Ser Thr Lys Gly Pro Ser Val Phe Pro
                          130                 135
```

<210> SEQ ID NO 89
<211> LENGTH: 333
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(333)

<400> SEQUENCE: 89

```
cac agt gca caa gac atc cag atg acc cag tct cca ggc acc ctg tct        48
His Ser Ala Gln Asp Ile Gln Met Thr Gln Ser Pro Gly Thr Leu Ser
  1               5                  10                  15 ttg tct cca ggg gaa aga gcc acc ctc tcc tgc agg gcc agt cag agt        96
Leu Ser Pro Gly Glu Arg Ala Thr Leu Ser Cys Arg Ala Ser Gln Ser
             20                  25                  30 gtt agc agc agc tac tta gcc tgg tac cag cag aaa cct ggc cag gct       144
Val Ser Ser Ser Tyr Leu Ala Trp Tyr Gln Gln Lys Pro Gly Gln Ala
         35                  40                  45 ccc agg ctc ctc atc tat ggt gca tcc agc agg gcc act ggc atc cca       192
Pro Arg Leu Leu Ile Tyr Gly Ala Ser Ser Arg Ala Thr Gly Ile Pro
     50                  55                  60 gac agg ttc agt ggc agt ggg tct ggg aca gac ttc act ctc acc atc       240
Asp Arg Phe Ser Gly Ser Gly Ser Gly Thr Asp Phe Thr Leu Thr Ile
 65                  70                  75                  80 agc aga ctg gag cct gaa gat ttt gca gtg tat tac tgt cag caa tat       288
Ser Arg Leu Glu Pro Glu Asp Phe Ala Val Tyr Tyr Cys Gln Gln Tyr
                 85                  90                  95 ggt agc tca cgg acg ttc ggc caa ggg acc aac gtg gaa atc aaa           333
Gly Ser Ser Arg Thr Phe Gly Gln Gly Thr Asn Val Glu Ile Lys
             100                 105                 110
```

<210> SEQ ID NO 90
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 90

```
His Ser Ala Gln Asp Ile Gln Met Thr Gln Ser Pro Gly Thr Leu Ser
  1               5                  10                  15
```

```
Leu Ser Pro Gly Glu Arg Ala Thr Leu Ser Cys Arg Ala Ser Gln Ser
            20                  25                  30

Val Ser Ser Ser Tyr Leu Ala Trp Tyr Gln Gln Lys Pro Gly Gln Ala
        35                  40                  45

Pro Arg Leu Leu Ile Tyr Gly Ala Ser Ser Arg Ala Thr Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Gln Gln Tyr
                85                  90                  95

Gly Ser Ser Arg Thr Phe Gly Gln Gly Thr Asn Val Glu Ile Lys
            100                 105                 110

<210> SEQ ID NO 91
<211> LENGTH: 395
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(393)

<400> SEQUENCE: 91 gaa gtt caa ttg tta gag tct ggt ggc ggt ctt gtt cag cct ggt ggt        48
Glu Val Gln Leu Leu Glu Ser Gly Gly Gly Leu Val Gln Pro Gly Gly
1               5                   10                  15 tct tta cgt ctt tct tgc gct gct tcc gga ttc act ttc tct tct tac       96
Ser Leu Arg Leu Ser Cys Ala Ala Ser Gly Phe Thr Phe Ser Ser Tyr
            20                  25                  30 atg atg act tgg gtt cgc caa gct cct ggt aaa ggt ttg gag tgg gtt      144
Met Met Thr Trp Val Arg Gln Ala Pro Gly Lys Gly Leu Glu Trp Val
        35                  40                  45 tct tct atc tat cct tct ggt ggc tat act tat tat gct gac tcc gtt      192
Ser Ser Ile Tyr Pro Ser Gly Gly Tyr Thr Tyr Tyr Ala Asp Ser Val
    50                  55                  60 aaa ggt cgc ttc act atc tct aga gac aac tct aag aat act ctc tac      240
Lys Gly Arg Phe Thr Ile Ser Arg Asp Asn Ser Lys Asn Thr Leu Tyr
65                  70                  75                  80 ttg cag atg aac agc tta agg gct gag gac act gca gtc tac tat tgt      288
Leu Gln Met Asn Ser Leu Arg Ala Glu Asp Thr Ala Val Tyr Tyr Cys
                85                  90                  95 gcg aga gga ggg tat ggc gac tcg tca ttt ttt ttt gac tac tgg ggc      336
Ala Arg Gly Gly Tyr Gly Asp Ser Ser Phe Phe Phe Asp Tyr Trp Gly
            100                 105                 110 cag gga acc ctg gtc acc gtc tca agc gcc tcc acc aag ggc cca tcg      384
Gln Gly Thr Leu Val Thr Val Ser Ser Ala Ser Thr Lys Gly Pro Ser
        115                 120                 125 gtc ttc ccg ct                                                        395
Val Phe Pro
    130

<210> SEQ ID NO 92
<211> LENGTH: 131
<212> TYPE: PRT
<213> ORGANISM: Artificial Sequence
<220> FEATURE:
<223> OTHER INFORMATION: Synthetically generated peptide

<400> SEQUENCE: 92

Glu Val Gln Leu Leu Glu Ser Gly Gly Gly Leu Val Gln Pro Gly Gly
```

```
                1               5                  10                 15
            Ser Leu Arg Leu Ser Cys Ala Ala Ser Gly Phe Thr Phe Ser Ser Tyr
                        20                  25                  30

Met Met Thr Trp Val Arg Gln Ala Pro Gly Lys Gly Leu Glu Trp Val
                        35                  40                  45

Ser Ser Ile Tyr Pro Ser Gly Gly Tyr Thr Tyr Tyr Ala Asp Ser Val
                        50                  55                  60

Lys Gly Arg Phe Thr Ile Ser Arg Asp Asn Ser Lys Asn Thr Leu Tyr
             65                 70                  75                  80

Leu Gln Met Asn Ser Leu Arg Ala Glu Asp Thr Ala Val Tyr Tyr Cys
                            85                  90                  95

Ala Arg Gly Gly Tyr Gly Asp Ser Ser Phe Phe Phe Asp Tyr Trp Gly
                        100                 105                 110

Gln Gly Thr Leu Val Thr Val Ser Ala Ser Thr Lys Gly Pro Ser
                        115                 120                 125

Val Phe Pro
                    130

<210> SEQ ID NO 93
<211> LENGTH: 333
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(333)

<400> SEQUENCE: 93 cac agt gca caa gac atc cag atg acc cag tct cca gcc acc ctg tct      48
His Ser Ala Gln Asp Ile Gln Met Thr Gln Ser Pro Ala Thr Leu Ser
  1               5                  10                  15 gtg tct cca ggg gaa gga gcc acc ctc tct tgc agg gcc agt cgg agt      96
Val Ser Pro Gly Glu Gly Ala Thr Leu Ser Cys Arg Ala Ser Arg Ser
                 20                  25                  30 gtt ggc agc aac tta gcc tgg tac cag cag aag cct ggc cag gct ccc     144
Val Gly Ser Asn Leu Ala Trp Tyr Gln Gln Lys Pro Gly Gln Ala Pro
             35                  40                  45 agg ctc ctc atc tat gat gca tcc acc agg gcc act ggt atc ccc gcc     192
Arg Leu Leu Ile Tyr Asp Ala Ser Thr Arg Ala Thr Gly Ile Pro Ala
         50                  55                  60 agg ttc agt ggc agt ggg tct ggg aca aag ttc act ctc acc atc agc     240
Arg Phe Ser Gly Ser Gly Ser Gly Thr Lys Phe Thr Leu Thr Ile Ser
 65                  70                  75                  80 agc ctc cag tct gaa gat ttt gca gtt tat tac tgt cag cag cgt agc     288
Ser Leu Gln Ser Glu Asp Phe Ala Val Tyr Tyr Cys Gln Gln Arg Ser
                 85                  90                  95 aat tgg cct ctc act ttc ggc gga ggg acc aag gtg gag atc aaa         333
Asn Trp Pro Leu Thr Phe Gly Gly Gly Thr Lys Val Glu Ile Lys
                100                 105                 110

<210> SEQ ID NO 94
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 94

His Ser Ala Gln Asp Ile Gln Met Thr Gln Ser Pro Ala Thr Leu Ser
  1               5                  10                  15
```

```
Val Ser Pro Gly Glu Gly Ala Thr Leu Ser Cys Arg Ala Ser Arg Ser
         20                  25                  30

Val Gly Ser Asn Leu Ala Trp Tyr Gln Gln Lys Pro Gly Gln Ala Pro
         35                  40                  45

Arg Leu Leu Ile Tyr Asp Ala Ser Thr Arg Ala Thr Gly Ile Pro Ala
         50                  55                  60

Arg Phe Ser Gly Ser Gly Ser Gly Thr Lys Phe Thr Leu Thr Ile Ser
 65                  70                  75                  80

Ser Leu Gln Ser Glu Asp Phe Ala Val Tyr Tyr Cys Gln Gln Arg Ser
                 85                  90                  95

Asn Trp Pro Leu Thr Phe Gly Gly Gly Thr Lys Val Glu Ile Lys
                100                 105                 110

<210> SEQ ID NO 95
<211> LENGTH: 428
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(426)

<400> SEQUENCE: 95 cac agt gca cag agc gtc ttg act cag cct gcc tcc gtg tct ggg tct      48
His Ser Ala Gln Ser Val Leu Thr Gln Pro Ala Ser Val Ser Gly Ser
  1               5                  10                  15 cct gga cag tcg atc acc atc tcc tgc act gga acc agc agt gac gtt     96
Pro Gly Gln Ser Ile Thr Ile Ser Cys Thr Gly Thr Ser Ser Asp Val
             20                  25                  30 ggt gat gat aac tat gtc tcc tgg tac caa caa cac cca gac aaa gcc    144
Gly Asp Asp Asn Tyr Val Ser Trp Tyr Gln Gln His Pro Asp Lys Ala
         35                  40                  45 ccc aaa ctc atg att tat gag gtc agt tat cgg ccc tca ggg gtt tct    192
Pro Lys Leu Met Ile Tyr Glu Val Ser Tyr Arg Pro Ser Gly Val Ser
     50                  55                  60 aat cgc ttc tct ggc tcc aag tct ggc aac acg gcc tcc ctg acc atc    240
Asn Arg Phe Ser Gly Ser Lys Ser Gly Asn Thr Ala Ser Leu Thr Ile
 65                  70                  75                  80 tct ggg ctc cag act gag gac gag gct gat tat tat tgc ggc tca tat    288
Ser Gly Leu Gln Thr Glu Asp Glu Ala Asp Tyr Tyr Cys Gly Ser Tyr
                 85                  90                  95 cgc gtc agc agc tcc tat gtc ttc gga act ggg acc aag gtc acc gtc    336
Arg Val Ser Ser Ser Tyr Val Phe Gly Thr Gly Thr Lys Val Thr Val
                100                 105                 110 cta ggt cag ccc aag gcc aac ccc act gtc act ctg ttc ccg ccc tcc    384
Leu Gly Gln Pro Lys Ala Asn Pro Thr Val Thr Leu Phe Pro Pro Ser
             115                 120                 125 tct gag gag ctc caa gcc aac aag gcc aca cta gtg tgt ctg             426
Ser Glu Glu Leu Gln Ala Asn Lys Ala Thr Leu Val Cys Leu
        130                 135                 140 at                                                                  428

<210> SEQ ID NO 96
<211> LENGTH: 142
<212> TYPE: PRT
<213> ORGANISM: Artificial Sequence
<220> FEATURE:
<223> OTHER INFORMATION: Synthetically generated peptide

<400> SEQUENCE: 96
```

His Ser Ala Gln Ser Val Leu Thr Gln Pro Ala Ser Val Ser Gly Ser
1               5                   10                  15

Pro Gly Gln Ser Ile Thr Ile Ser Cys Thr Gly Thr Ser Ser Asp Val
            20                  25                  30

Gly Asp Asp Asn Tyr Val Ser Trp Tyr Gln Gln His Pro Asp Lys Ala
        35                  40                  45

Pro Lys Leu Met Ile Tyr Glu Val Ser Tyr Arg Pro Ser Gly Val Ser
    50                  55                  60

Asn Arg Phe Ser Gly Ser Lys Ser Gly Asn Thr Ala Ser Leu Thr Ile
65              70                  75                  80

Ser Gly Leu Gln Thr Glu Asp Glu Ala Asp Tyr Tyr Cys Gly Ser Tyr
                85                  90                  95

Arg Val Ser Ser Ser Tyr Val Phe Gly Thr Gly Thr Lys Val Thr Val
            100                 105                 110

Leu Gly Gln Pro Lys Ala Asn Pro Thr Val Thr Leu Phe Pro Pro Ser
        115                 120                 125

Ser Glu Glu Leu Gln Ala Asn Lys Ala Thr Leu Val Cys Leu
    130                 135                 140

<210> SEQ ID NO 97
<211> LENGTH: 363
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(363)

<400> SEQUENCE: 97 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
1               5                   10                  15 tct tta cgt ctt tct tgc gct gct tcc gga ttc act ttc tct cgt tac      96
Ser Leu Arg Leu Ser Cys Ala Ala Ser Gly Phe Thr Phe Ser Arg Tyr
            20                  25                  30 aag atg ttt tgg gtt cgc caa gct cct ggt aaa ggt ttg gag tgg gtt     144
Lys Met Phe Trp Val Arg Gln Ala Pro Gly Lys Gly Leu Glu Trp Val
        35                  40                  45 tct gtt atc tat cct tct ggt ggc cct act atg tat gct gac tcc gtt     192
Ser Val Ile Tyr Pro Ser Gly Gly Pro Thr Met Tyr Ala Asp Ser Val
    50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
65              70                  75                  80 ttg cag atg aac agc tta agg gct gag gac act gca gtc tac tat tgt     288
Leu Gln Met Asn Ser Leu Arg Ala Glu Asp Thr Ala Val Tyr Tyr Cys
                85                  90                  95 gcg aga ggg atg gtc cgt gga tat agt ggc tac gat tac cct ttc ttg     336
Ala Arg Gly Met Val Arg Gly Tyr Ser Gly Tyr Asp Tyr Pro Phe Leu
            100                 105                 110 gac tac tgg ggc cag gga acc ctg gtc                                 363
Asp Tyr Trp Gly Gln Gly Thr Leu Val
        115                 120

<210> SEQ ID NO 98
<211> LENGTH: 121
<212> TYPE: PRT
<213> ORGANISM: Artificial Sequence
<220> FEATURE:

```
<223> OTHER INFORMATION: Synthetically generated peptide

<400> SEQUENCE: 98

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Lys Met Phe Trp Val Arg Gln Ala Pro Gly Lys Gly Leu Glu Trp Val
        35                  40                  45

Ser Val Ile Tyr Pro Ser Gly Gly Pro Thr Met Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Met Val Arg Gly Tyr Ser Gly Tyr Asp Tyr Pro Phe Leu
            100                 105                 110

Asp Tyr Trp Gly Gln Gly Thr Leu Val
        115                 120

<210> SEQ ID NO 99
<211> LENGTH: 333
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(333)

<400> SEQUENCE: 99 cac agt gca caa gac atc cag atg acc cag tct cca tct tcc ctg tct        48
His Ser Ala Gln Asp Ile Gln Met Thr Gln Ser Pro Ser Ser Leu Ser
 1               5                  10                  15 gca tct gta ggg gac aga gtc acc atc act tgc cga gca agt cag acc        96
Ala Ser Val Gly Asp Arg Val Thr Ile Thr Cys Arg Ala Ser Gln Thr
            20                  25                  30 att agc agc tat tta aat tgg tat cag cag aag cca ggg aaa gcc cct       144
Ile Ser Ser Tyr Leu Asn Trp Tyr Gln Gln Lys Pro Gly Lys Ala Pro
        35                  40                  45 aag ctc ctg atc tat gct gca tcc agt ttg caa agt ggg gtc cca tca       192
Lys Leu Leu Ile Tyr Ala Ala Ser Ser Leu Gln Ser Gly Val Pro Ser
 50                  55                  60 agg ttc agt ggc agt gga tct ggg aca gat ttc act ctc acc atc agc       240
Arg Phe Ser Gly Ser Gly Ser Gly Thr Asp Phe Thr Leu Thr Ile Ser
65                  70                  75                  80 agt ctg caa cct gaa gat ttt gca act tac tac tgt caa cag agt tac       288
Ser Leu Gln Pro Glu Asp Phe Ala Thr Tyr Tyr Cys Gln Gln Ser Tyr
                85                  90                  95 agt acc cct cgt acg ttc ggc caa ggg acc aag gtg gaa atc aaa           333
Ser Thr Pro Arg Thr Phe Gly Gln Gly Thr Lys Val Glu Ile Lys
            100                 105                 110

<210> SEQ ID NO 100
<211> LENGTH: 111
<212> TYPE: PRT
<213> ORGANISM: Artificial Sequence
<220> FEATURE:
<223> OTHER INFORMATION: Synthetically generated peptide

<400> SEQUENCE: 100
```

```
His Ser Ala Gln Asp Ile Gln Met Thr Gln Ser Pro Ser Ser Leu Ser
 1               5                  10                  15

Ala Ser Val Gly Asp Arg Val Thr Ile Thr Cys Arg Ala Ser Gln Thr
            20                  25                  30

Ile Ser Ser Tyr Leu Asn Trp Tyr Gln Gln Lys Pro Gly Lys Ala Pro
        35                  40                  45

Lys Leu Leu Ile Tyr Ala Ala Ser Ser Leu Gln Ser Gly Val Pro Ser
 50                      55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln Ser Tyr
                 85                  90                  95

Ser Thr Pro Arg Thr Phe Gly Gln Gly Thr Lys Val Glu Ile Lys
                100                 105                 110
```

<210> SEQ ID NO 101
<211> LENGTH: 386
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(384)

<400> SEQUENCE: 101

```
gaa gtt caa ttg tta gag tct ggt ggc ggt ctt gtt cag cct ggt ggt    48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct gct tac    96
Ser Leu Arg Leu Ser Cys Ala Ala Ser Gly Phe Thr Phe Ser Ala Tyr
            20                  25                  30 cag atg gtt tgg gtt cgc caa gct cct ggt aaa ggt ttg gag tgg gtt   144
Gln Met Val Trp Val Arg Gln Ala Pro Gly Lys Gly Leu Glu Trp Val
        35                  40                  45 tct tct atc tat cct tct ggt ggc tgg act tat tat gct gac tcc gtt   192
Ser Ser Ile Tyr Pro Ser Gly Gly Trp Thr Tyr Tyr Ala Asp Ser Val
 50                      55                  60 aaa ggt cgc ttc act atc tct aga gac aac tct aag aat act ctc tac   240
Lys Gly Arg Phe Thr Ile Ser Arg Asp Asn Ser Lys Asn Thr Leu Tyr
 65                  70                  75                  80 ttg cag atg aac agc tta agg gct gag gac act gca gtc tac tat tgt   288
Leu Gln Met Asn Ser Leu Arg Ala Glu Asp Thr Ala Val Tyr Tyr Cys
                 85                  90                  95 gcg aga ggc acg cac ctc ccg ggg gtt gac tac tgg ggc cag gga acc   336
Ala Arg Gly Thr His Leu Pro Gly Val Asp Tyr Trp Gly Gln Gly Thr
                100                 105                 110 ctg gtc acc gtc tca agc gcc tcc acc aag ggc cca tcg gtc ttc ccg   384
Leu Val Thr Val Ser Ser Ala Ser Thr Lys Gly Pro Ser Val Phe Pro
            115                 120                 125 ct                                                                386
```

<210> SEQ ID NO 102
<211> LENGTH: 128
<212> TYPE: PRT
<213> ORGANISM: Artificial Sequence
<220> FEATURE:
<223> OTHER INFORMATION: Synthetically generated peptide

<400> SEQUENCE: 102

Glu Val Gln Leu Leu Glu Ser Gly Gly Gly Leu Val Gln Pro Gly Gly

```
                1               5                   10                  15
Ser Leu Arg Leu Ser Cys Ala Ala Ser Gly Phe Thr Phe Ser Ala Tyr
                    20                  25                  30

Gln Met Val Trp Val Arg Gln Ala Pro Gly Lys Gly Leu Glu Trp Val
                35                  40                  45

Ser Ser Ile Tyr Pro Ser Gly Gly Trp Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Arg Gly Thr His Leu Pro Gly Val Asp Tyr Trp Gly Gln Gly Thr
                100                 105                 110

Leu Val Thr Val Ser Ser Ala Ser Thr Lys Gly Pro Ser Val Phe Pro
            115                 120                 125
```

<210> SEQ ID NO 103
<211> LENGTH: 339
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(339)

<400> SEQUENCE: 103

```
cac agt gca caa gac atc cag atg acc cag tct cca ggc acc ctg tct        48
His Ser Ala Gln Asp Ile Gln Met Thr Gln Ser Pro Gly Thr Leu Ser
1               5                   10                  15 ttg tct cca ggg gaa aga gcc acc ctc tcc tgc agg gcc agt cag agt        96
Leu Ser Pro Gly Glu Arg Ala Thr Leu Ser Cys Arg Ala Ser Gln Ser
                20                  25                  30 gtt agc agc agc tac tta gcc tgg tac cag cag aaa cct ggc cag gct       144
Val Ser Ser Ser Tyr Leu Ala Trp Tyr Gln Gln Lys Pro Gly Gln Ala
            35                  40                  45 ccc agg ctc ctc atc tat ggt gca tcc agc agg gcc act ggc atc cca       192
Pro Arg Leu Leu Ile Tyr Gly Ala Ser Ser Arg Ala Thr Gly Ile Pro
        50                  55                  60 gac agg ttc agt ggc agt ggg tct ggg aca gac ttc act ctc acc atc       240
Asp Arg Phe Ser Gly Ser Gly Ser Gly Thr Asp Phe Thr Leu Thr Ile
65                  70                  75                  80 agc aga ctg gag cct gaa gat ttt gca gtg tat tac tgt cag cag tat       288
Ser Arg Leu Glu Pro Glu Asp Phe Ala Val Tyr Tyr Cys Gln Gln Tyr
                85                  90                  95 ggt agc tcc ccc atg tac act ttt ggc cag ggg acc aag ctg gag atc       336
Gly Ser Ser Pro Met Tyr Thr Phe Gly Gln Gly Thr Lys Leu Glu Ile
                100                 105                 110
aaa                                                                   339
Lys
```

<210> SEQ ID NO 104
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 104

```
His Ser Ala Gln Asp Ile Gln Met Thr Gln Ser Pro Gly Thr Leu Ser
1               5                   10                  15
```

```
Leu Ser Pro Gly Glu Arg Ala Thr Leu Ser Cys Arg Ala Ser Gln Ser
            20                  25                  30

Val Ser Ser Ser Tyr Leu Ala Trp Tyr Gln Gln Lys Pro Gly Gln Ala
        35                  40                  45

Pro Arg Leu Leu Ile Tyr Gly Ala Ser Ser Arg Ala Thr Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Gln Gln Tyr
                85                  90                  95

Gly Ser Ser Pro Met Tyr Thr Phe Gly Gln Gly Thr Lys Leu Glu Ile
            100                 105                 110

Lys

<210> SEQ ID NO 105
<211> LENGTH: 339
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(339)

<400> SEQUENCE: 105 gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
1               5                   10                  15 tct tta cgt ctt tct tgc gct gct tcc gga ttc act ttc tct tct tac      96
Ser Leu Arg Leu Ser Cys Ala Ala Ser Gly Phe Thr Phe Ser Ser Tyr
            20                  25                  30 aag atg ggt tgg gtt cgc caa gct cct ggt aaa ggt ttg gag tgg gtt     144
Lys Met Gly Trp Val Arg Gln Ala Pro Gly Lys Gly Leu Glu Trp Val
        35                  40                  45 tct tct atc tat cct tct ggt ggc tgg act cat tat gct gac tcc gtt     192
Ser Ser Ile Tyr Pro Ser Gly Gly Trp Thr His Tyr Ala Asp Ser Val
    50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
65                  70                  75                  80 ttg cag atg aac agc tta agg gct gag gac act gca gtc tac tat tgt     288
Leu Gln Met Asn Ser Leu Arg Ala Glu Asp Thr Ala Val Tyr Tyr Cys
                85                  90                  95 gca aga gta cta cta cac tac ttt gac tac tgg ggc cag gga acc ctg     336
Ala Arg Val Leu Leu His Tyr Phe Asp Tyr Trp Gly Gln Gly Thr Leu
            100                 105                 110 gtc                                                                  339
Val

<210> SEQ ID NO 106
<211> LENGTH: 113
<212> TYPE: PRT
<213> ORGANISM: Artificial Sequence
<220> FEATURE:
<223> OTHER INFORMATION: Synthetically generated peptide

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Lys Met Gly Trp Val Arg Gln Ala Pro Gly Lys Gly Leu Glu Trp Val
        35                  40                  45

Ser Ser Ile Tyr Pro Ser Gly Gly Trp Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Leu His Tyr Phe Asp Tyr Trp Gly Gln Gly Thr Leu
            100                 105                 110

Val
```

```
<210> SEQ ID NO 107
<211> LENGTH: 415
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(414)

<400> SEQUENCE: 107 cac agt gca cag agc gtc ttg act cag cct gcc tcc gtg tct ggg tct       48
His Ser Ala Gln Ser Val Leu Thr Gln Pro Ala Ser Val Ser Gly Ser
 1               5                  10                  15 cct gga cag tcg atc acc atc tcc tgc act gga acc agc agt gac gtt      96
Pro Gly Gln Ser Ile Thr Ile Ser Cys Thr Gly Thr Ser Ser Asp Val
             20                  25                  30 ggt ggt tat aaa tat gtc tcc tgg tac caa cag cac cca ggc aaa gcc     144
Gly Gly Tyr Lys Tyr Val Ser Trp Tyr Gln Gln His Pro Gly Lys Ala
         35                  40                  45 ccc aaa ctc att att tct gac gtc aat aat cgg ccc tca ggg gtt tct     192
Pro Lys Leu Ile Ile Ser Asp Val Asn Asn Arg Pro Ser Gly Val Ser
     50                  55                  60 gat cgc ttc tct ggc tcc aag tct ggc aac acg gcc tcc ctg acc atc     240
Asp Arg Phe Ser Gly Ser Lys Ser Gly Asn Thr Ala Ser Leu Thr Ile
 65                  70                  75                  80 tct ggg ctc cag gct gag gac gac ggt gat tat tac tgc agt tcc tac     288
Ser Gly Leu Gln Ala Glu Asp Asp Gly Asp Tyr Tyr Cys Ser Ser Tyr
                 85                  90                  95 gca agt agt tcc tat aca agc agt acc act tgg gtg ttc ggc ggg ggg     336
Ala Ser Ser Ser Tyr Thr Ser Ser Thr Thr Trp Val Phe Gly Gly Gly
            100                 105                 110 acc aag ctg acc gtc cta ggt cag ccc aag gct gcc ccc ttg gtc act     384
Thr Lys Leu Thr Val Leu Gly Gln Pro Lys Ala Ala Pro Leu Val Thr
        115                 120                 125 ctg ttc cca ccc tcc tct gag gag ctt caa g                           415
Leu Phe Pro Pro Ser Ser Glu Glu Leu Gln
    130                 135
```

```
<210> SEQ ID NO 108
<211> LENGTH: 138
<212> TYPE: PRT
<213> ORGANISM: Artificial Sequence
<220> FEATURE:
<223> OTHER INFORMATION: Synthetically generated peptide

<400> SEQUENCE: 108

His Ser Ala Gln Ser Val Leu Thr Gln Pro Ala Ser Val Ser Gly Ser
 1               5                  10                  15
```

```
Pro Gly Gln Ser Ile Thr Ile Ser Cys Thr Gly Thr Ser Ser Asp Val
        20                  25                  30

Gly Gly Tyr Lys Tyr Val Ser Trp Tyr Gln Gln His Pro Gly Lys Ala
    35                  40                  45

Pro Lys Leu Ile Ile Ser Asp Val Asn Asn Arg Pro Ser Gly Val Ser
    50                  55                  60

Asp Arg Phe Ser Gly Ser Lys Ser Gly Asn Thr Ala Ser Leu Thr Ile
65                  70                  75                  80

Ser Gly Leu Gln Ala Glu Asp Asp Gly Asp Tyr Tyr Cys Ser Ser Tyr
                85                  90                  95

Ala Ser Ser Ser Tyr Thr Ser Thr Thr Trp Val Phe Gly Gly Gly
                100                 105                 110

Thr Lys Leu Thr Val Leu Gly Gln Pro Lys Ala Ala Pro Leu Val Thr
            115                 120                 125

Leu Phe Pro Pro Ser Ser Glu Glu Leu Gln
            130                 135
```

<210> SEQ ID NO 109
<211> LENGTH: 471
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(471)

<400> SEQUENCE: 109

```
gaa gtt caa ttg tta gag tct ggt ggc ggt ctt gtt cag cct ggt ggt        48
Glu Val Gln Leu Leu Glu Ser Gly Gly Gly Leu Val Gln Pro Gly Gly
1               5                   10                  15 tct tta cgt ctt tct tgc gct gct tcc gga ttc act ttc tct tct tac        96
Ser Leu Arg Leu Ser Cys Ala Ala Ser Gly Phe Thr Phe Ser Ser Tyr
            20                  25                  30 aag atg ggt tgg gtt cgc caa gct cct ggt aga ggt ttg gag tgg gtt       144
Lys Met Gly Trp Val Arg Gln Ala Pro Gly Arg Gly Leu Glu Trp Val
        35                  40                  45 tct tct atc tat cct tct ggt ggc tgg act cat tat gct gac tcc gtt       192
Ser Ser Ile Tyr Pro Ser Gly Gly Trp Thr His Tyr Ala Asp Ser Val
    50                  55                  60 aaa ggt cgc ttc act atc tct aga gac aac tct aag aat act ctc tac       240
Lys Gly Arg Phe Thr Ile Ser Arg Asp Asn Ser Lys Asn Thr Leu Tyr
65                  70                  75                  80 ttg cag atg aac agc tta agg gct gag gac act gca gtc tac tat tgt       288
Leu Gln Met Asn Ser Leu Arg Ala Glu Asp Thr Ala Val Tyr Tyr Cys
                85                  90                  95 gca aga gta cta cta cac tac ttt gac tac tgg ggc cag gga acc ctg       336
Ala Arg Val Leu Leu His Tyr Phe Asp Tyr Trp Gly Gln Gly Thr Leu
                100                 105                 110 gtc acc gtc tca agc gcc tcc acc aag ggc cca tcg gtc ttc ccc ctg       384
Val Thr Val Ser Ser Ala Ser Thr Lys Gly Pro Ser Val Phe Pro Leu
            115                 120                 125 gca ccc tcc tcc aag agc acc tcg ggg gca cag cgg ccc tgg gct gcc       432
Ala Pro Ser Ser Lys Ser Thr Ser Gly Ala Gln Arg Pro Trp Ala Ala
        130                 135                 140 tgg tca agg act act tcc cgc gat acc ggt gac ggt gtc                   471
Trp Ser Arg Thr Thr Ser Arg Asp Thr Gly Asp Gly Val
145                 150                 155
```

<210> SEQ ID NO 110
<211> LENGTH: 157
<212> TYPE: PRT
<213> ORGANISM: Artificial Sequence
<220> FEATURE:
<223> OTHER INFORMATION: Synthetically generated peptide

<400> SEQUENCE: 110

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Lys Met Gly Trp Val Arg Gln Ala Pro Gly Arg Gly Leu Glu Trp Val
        35                  40                  45

Ser Ser Ile Tyr Pro Ser Gly Gly Trp Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Leu Leu His Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Ala Gln Arg Pro Trp Ala Ala
    130                 135                 140

Trp Ser Arg Thr Thr Ser Arg Asp Thr Gly Asp Gly Val
145                 150                 155
```

<210> SEQ ID NO 111
<211> LENGTH: 325
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(324)

<400> SEQUENCE: 111

```
cag agc gtc ttg act cag cct gcc tcc gtg tct ggg tct cct gga cag        48
Gln Ser Val Leu Thr Gln Pro Ala Ser Val Ser Gly Ser Pro Gly Gln
 1               5                  10                  15 tcg atc acc atc tcc tgc act gga acc agc agt gac gtt ggt ggt tat       96
Ser Ile Thr Ile Ser Cys Thr Gly Thr Ser Ser Asp Val Gly Gly Tyr
            20                  25                  30 aaa tat gtc tcc tgg tac caa cag cac cca ggc aaa gcc ccc aaa ctc      144
Lys Tyr Val Ser Trp Tyr Gln Gln His Pro Gly Lys Ala Pro Lys Leu
        35                  40                  45 att att tct gac gtc aat aat cgg ccc tca ggg gtt tct gat cgc ttc      192
Ile Ile Ser Asp Val Asn Asn Arg Pro Ser Gly Val Ser Asp Arg Phe
    50                  55                  60 tct ggc tcc aag tct ggc aac acg gcc tcc ctg acc atc tct ggg ctc      240
Ser Gly Ser Lys Ser Gly Asn Thr Ala Ser Leu Thr Ile Ser Gly Leu
65                  70                  75                  80 cag gct gag gac gac ggt gat tat tac tgc agt tcc tac gca agt agt      288
Gln Ala Glu Asp Asp Gly Asp Tyr Tyr Cys Ser Ser Tyr Ala Ser Ser
                85                  90                  95 tcc tat aca agc agt acc act tgg gtg ttc ggc ggg g                    325
Ser Tyr Thr Ser Ser Thr Thr Trp Val Phe Gly Gly
            100                 105
```

<210> SEQ ID NO 112
<211> LENGTH: 108
<212> TYPE: PRT
<213> ORGANISM: Artificial Sequence
<220> FEATURE:
<223> OTHER INFORMATION: Synthetically generated peptide

<400> SEQUENCE: 112

```
Gln Ser Val Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Lys Tyr Val Ser Trp Tyr Gln Gln His Pro Gly Lys Ala Pro Lys Leu
        35                  40                  45

Ile Ile Ser Asp Val Asn Asn Arg Pro Ser Gly Val Ser Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Gly Asp Tyr Tyr Cys Ser Ser Tyr Ala Ser Ser
                85                  90                  95

Ser Tyr Thr Ser Ser Thr Thr Trp Val Phe Gly Gly
            100                 105
```

<210> SEQ ID NO 113
<211> LENGTH: 425
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(423)

<400> SEQUENCE: 113

```
gaa gtt caa ttg tta gag tct ggt ggc ggt ctt gtt cag cct ggt ggt      48
Glu Val Gln Leu Leu Glu Ser Gly Gly Gly Leu Val Gln Pro Gly Gly
 1               5                  10                  15 tct tta cgt ctt tct tgc gct gct tcc gga ttc act ttc tct atg tac      96
Ser Leu Arg Leu Ser Cys Ala Ala Ser Gly Phe Thr Phe Ser Met Tyr
            20                  25                  30 ggt atg gtt tgg gtt cgc caa gct cct ggt aaa ggt ttg gag tgg gtt     144
Gly Met Val Trp Val Arg Gln Ala Pro Gly Lys Gly Leu Glu Trp Val
        35                  40                  45 tct gtt atc tct cct tct ggt ggc aat act ggt tat gct gac tcc gtt     192
Ser Val Ile Ser Pro Ser Gly Gly Asn Thr Gly Tyr Ala Asp Ser Val
    50                  55                  60 aaa ggt cgc ttc act atc tct aga gac aac tct aag aat act ctc tac     240
Lys Gly Arg Phe Thr Ile Ser Arg Asp Asn Ser Lys Asn Thr Leu Tyr
65                  70                  75                  80 ttg cag gtg aac agc tta agg gct gag gac act gca gtc tac tat tgt     288
Leu Gln Val Asn Ser Leu Arg Ala Glu Asp Thr Ala Val Tyr Tyr Cys
                85                  90                  95 gcg aga gcc cca cgt gga tac agc tat ggt tac tac tac tgg ggc cag     336
Ala Arg Ala Pro Arg Gly Tyr Ser Tyr Gly Tyr Tyr Tyr Trp Gly Gln
            100                 105                 110 gga acc ctg gtc acc gtc tca agc gcc tcc acc aag ggc cca tcg gtc     384
Gly Thr Leu Val Thr Val Ser Ser Ala Ser Thr Lys Gly Pro Ser Val
        115                 120                 125 ttc ccg cta gca ccc tcc tcc aag agc acc tct ggg ggc ac              425
Phe Pro Leu Ala Pro Ser Ser Lys Ser Thr Ser Gly Gly
```

130               135               140

<210> SEQ ID NO 114
<211> LENGTH: 141
<212> TYPE: PRT
<213> ORGANISM: Artificial Sequence
<220> FEATURE:
<223> OTHER INFORMATION: Synthetically generated peptide

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Gly Met Val Trp Val Arg Gln Ala Pro Gly Lys Gly Leu Glu Trp Val
        35                  40                  45

Ser Val Ile Ser Pro Ser Gly Gly Asn Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Val Asn Ser Leu Arg Ala Glu Asp Thr Ala Val Tyr Tyr Cys
                85                  90                  95

Ala Arg Ala Pro Arg Gly Tyr Ser Tyr Gly Tyr Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly
    130                 135                 140

<210> SEQ ID NO 115
<211> LENGTH: 322
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(321)

<400> SEQUENCE: 115 gac atc cag atg acc cag tct cca ctc tcc ctg tct gca tct gta gga      48
Asp Ile Gln Met Thr Gln Ser Pro Leu Ser Leu Ser Ala Ser Val Gly
1               5                   10                  15 gac aga gtc acc atc act tgc cgg gcg agt cag ggc att ggc cat tat      96
Asp Arg Val Thr Ile Thr Cys Arg Ala Ser Gln Gly Ile Gly His Tyr
            20                  25                  30 tta gcc tgg tat cag cag aaa cca ggg aaa gtt cct aag ctc ctg atc     144
Leu Ala Trp Tyr Gln Gln Lys Pro Gly Lys Val Pro Lys Leu Leu Ile
        35                  40                  45 tat act gca tcc act ttg caa tca ggg gtc cca tct cgg ttc agt ggc     192
Tyr Thr Ala Ser Thr Leu Gln Ser Gly Val Pro Ser Arg Phe Ser Gly
    50                  55                  60 agt gga tct ggg aca gat ttc act ctc acc atc aac agc ctg cag cct     240
Ser Gly Ser Gly Thr Asp Phe Thr Leu Thr Ile Asn Ser Leu Gln Pro
65                  70                  75                  80 gag gat gtt gca act tat tac tgt caa cag ttt aat agt tac cct cac     288
Glu Asp Val Ala Thr Tyr Tyr Cys Gln Gln Phe Asn Ser Tyr Pro His
                85                  90                  95 acc ttc ggc caa ggg aca cga ctg gat att aaa c                        322
Thr Phe Gly Gln Gly Thr Arg Leu Asp Ile Lys
            100                 105

```
<210> SEQ ID NO 116
<211> LENGTH: 107
<212> TYPE: PRT
<213> ORGANISM: Artificial Sequence
<220> FEATURE:
<223> OTHER INFORMATION: Synthetically generated peptide

<400> SEQUENCE: 116

Asp Ile Gln Met Thr Gln Ser Pro Leu Ser Leu Ser Ala Ser Val Gly
 1               5                  10                  15

Asp Arg Val Thr Ile Thr Cys Arg Ala Ser Gln Gly Ile Gly His Tyr
            20                  25                  30

Leu Ala Trp Tyr Gln Gln Lys Pro Gly Lys Val Pro Lys Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Val Ala Thr Tyr Tyr Cys Gln Gln Phe Asn Ser Tyr Pro His
                85                  90                  95

Thr Phe Gly Gln Gly Thr Arg Leu Asp Ile Lys
            100                 105

<210> SEQ ID NO 117
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, Gly, Ser, Arg
<220> FEATURE:
<221> NAME/KEY: VARIANT
<222> LOCATION: 3
<223> OTHER INFORMATION: Xaa = Gly, Val, Lys
<220> FEATURE:
<221> NAME/KEY: VARIANT
<222> LOCATION: 5
<223> OTHER INFORMATION: Xaa = Gly, Ser, Val, Phe

<400> SEQUENCE: 117

Xaa Tyr Xaa Met Xaa
 1               5

<210> SEQ ID NO 118
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, Gly, Ser, Ile, Met, Arg, His
<220> FEATURE:
<221> NAME/KEY: VARIANT
<222> LOCATION: 3
<223> OTHER INFORMATION: Xaa = Gly, Val, Met, Lys
<220> FEATURE:
<221> NAME/KEY: VARIANT
<222> LOCATION: 5
<223> OTHER INFORMATION: Xaa = Gly, Ser, Val, Met, Phe, His

<400> SEQUENCE: 118
```

```
Xaa Tyr Xaa Met Xaa
 1               5

<210> SEQ ID NO 119
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, Gly, Ser, Ile, Met, Arg, Asn, His
<220> FEATURE:
<221> NAME/KEY: VARIANT
<222> LOCATION: 3
<223> OTHER INFORMATION: Ala, Gly, Thr, Val, Met, Lys, Pro, Gln
<220> FEATURE:
<221> NAME/KEY: VARIANT
<222> LOCATION: 5
<223> OTHER INFORMATION: Xaa = Ala, Gly, Ser, Thr, Val, Met, Tyr, Trp,
      Phe, Lys, His

<400> SEQUENCE: 119

Xaa Tyr Xaa Met Xaa
 1               5

<210> SEQ ID NO 120
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 8, 10
<223> OTHER INFORMATION: Xaa = any amino acid

<400> SEQUENCE: 120

Xaa Ile Tyr Pro Ser Gly Gly Xaa Thr Xaa Tyr Ala Asp Ser Val Lys
 1               5                  10                  15
Gly

<210> SEQ ID NO 121
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Ser, Val
<220> FEATURE:
<221> NAME/KEY: VARIANT
<222> LOCATION: 3
<223> OTHER INFORMATION: Xaa = Ser, Tyr
<220> FEATURE:
<221> NAME/KEY: VARIANT
<222> LOCATION: 8
<223> OTHER INFORMATION: Xaa = Trp, Gln
<220> FEATURE:
<221> NAME/KEY: VARIANT
<222> LOCATION: 10
<223> OTHER INFORMATION: Xaa = Gly, Tyr

<400> SEQUENCE: 121

Xaa Ile Xaa Pro Ser Gly Gly Xaa Thr Xaa
 1               5                  10

<210> SEQ ID NO 122
```

```
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Ser, Val, Trp
<220> FEATURE:
<221> NAME/KEY: VARIANT
<222> LOCATION: 3
<223> OTHER INFORMATION: Xaa = Ser, Tyr
<220> FEATURE:
<221> NAME/KEY: VARIANT
<222> LOCATION: 8
<223> OTHER INFORMATION: Xaa = Trp, Gln
<220> FEATURE:
<221> NAME/KEY: VARIANT
<222> LOCATION: 10
<223> OTHER INFORMATION: Xaa = Gly, Tyr

<400> SEQUENCE: 122

Xaa Ile Xaa Pro Ser Gly Gly Xaa Thr Xaa Tyr Ala Asp Ser Val Lys
 1               5                  10                  15
Gly

<210> SEQ ID NO 123
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Ser, Val, Trp
<220> FEATURE:
<221> NAME/KEY: VARIANT
<222> LOCATION: 3
<223> OTHER INFORMATION: Xaa = Ser, Tyr
<220> FEATURE:
<221> NAME/KEY: VARIANT
<222> LOCATION: 8
<223> OTHER INFORMATION: Xaa = Ala, Gly, val, Met, Tyr, Trp, Pro, Gln,
      His
<220> FEATURE:
<221> NAME/KEY: VARIANT
<222> LOCATION: 10
<223> OTHER INFORMATION: Xaa = Ala, Gly, Ser, Thr, Leu, Val, Met, Tyr,
      Phe, Lys, His

<400> SEQUENCE: 123

Xaa Ile Xaa Pro Ser Gly Gly Xaa Thr Xaa
 1               5                  10

<210> SEQ ID NO 124
<211> LENGTH: 5
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = four or five residues
<220> FEATURE:
<221> NAME/KEY: VARIANT
<222> LOCATION: 5
<223> OTHER INFORMATION: Xaa = Ile or Tyr

<400> SEQUENCE: 124

Val Xaa Phe Asp Xaa
```

```
                          1               5

<210> SEQ ID NO 125
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 125

Gly Tyr Gly Pro Ile Ala Pro Gly Leu Asp Tyr
 1               5                  10

<210> SEQ ID NO 126
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Val
<220> FEATURE:
<221> NAME/KEY: VARIANT
<222> LOCATION: 5
<223> OTHER INFORMATION: Xaa = Gly, Tyr, Asp
<220> FEATURE:
<221> NAME/KEY: VARIANT
<222> LOCATION: 7
<223> OTHER INFORMATION: Xaa = Ser, Asp

<400> SEQUENCE: 126

Xaa Asn Tyr Tyr Xaa Ser Xaa Gly Tyr Gly Pro Ile Ala Pro Gly Leu
 1               5                  10                  15

Asp Tyr

<210> SEQ ID NO 127
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Val, Asp
<220> FEATURE:
<221> NAME/KEY: VARIANT
<222> LOCATION: 2
<223> OTHER INFORMATION: Xaa = Ala, Gly, Leu, Asn
<220> FEATURE:
<221> NAME/KEY: VARIANT
<222> LOCATION: 3
<223> OTHER INFORMATION: Xaa = Leu, Tyr, Arg
<220> FEATURE:
<221> NAME/KEY: VARIANT
<222> LOCATION: 4
<223> OTHER INFORMATION: Xaa = Gly, Ser, Thr, Leu, Tyr, His
<220> FEATURE:
<221> NAME/KEY: VARIANT
<222> LOCATION: 5
<223> OTHER INFORMATION: Xaa = Gly, Tyr, Asp
<220> FEATURE:
<221> NAME/KEY: VARIANT
<222> LOCATION: 6
<223> OTHER INFORMATION: Xaa = Ala, Gly, Ser, Tyr, Phe, Pro
<220> FEATURE:
<221> NAME/KEY: VARIANT
<222> LOCATION: 7
<223> OTHER INFORMATION: Xaa = Ser, Phe, Asp
<220> FEATURE:
<221> NAME/KEY: VARIANT
```

```
<222> LOCATION: 8
<223> OTHER INFORMATION: Xaa = Ala, Gly, Tyr, Asp
<220> FEATURE:
<221> NAME/KEY: VARIANT
<222> LOCATION: 9
<223> OTHER INFORMATION: Xaa = Ile, Tyr
<220> FEATURE:
<221> NAME/KEY: VARIANT
<222> LOCATION: 10
<223> OTHER INFORMATION: Xaa = Gly, Phe, Asp
<220> FEATURE:
<221> NAME/KEY: VARIANT
<222> LOCATION: 11
<223> OTHER INFORMATION: Xaa = Tyr, Asp, pro
<220> FEATURE:
<221> NAME/KEY: VARIANT
<222> LOCATION: 12
<223> OTHER INFORMATION: Xaa = Ile, Pro

<400> SEQUENCE: 127

Xaa Xaa Xaa Xaa Xaa Xaa Xaa Xaa Xaa Xaa Xaa Xaa Ala Pro Gly Leu
 1               5                  10                  15

Asp Tyr

<210> SEQ ID NO 128
<211> LENGTH: 18
<212> TYPE: PRT
<213> ORGANISM: Artificial Sequence
<220> FEATURE:
<223> OTHER INFORMATION: Synthetically generated peptide

<400> SEQUENCE: 128

Val Asn Tyr Tyr Asp Ser Ser Gly Tyr Gly Pro Ile Ala Pro Gly Leu
 1               5                  10                  15

Asp Tyr

<210> SEQ ID NO 129
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 6
<223> OTHER INFORMATION: Xaa = Ile, Val
<220> FEATURE:
<221> NAME/KEY: VARIANT
<222> LOCATION: 8
<223> OTHER INFORMATION: Xaa = Ser, Arg
<220> FEATURE:
<221> NAME/KEY: VARIANT
<222> LOCATION: 9
<223> OTHER INFORMATION: Xaa = Ser, or absent
<220> FEATURE:
<221> NAME/KEY: VARIANT
<222> LOCATION: 12
<223> OTHER INFORMATION: Xaa = Ala, Asn

<400> SEQUENCE: 129

Arg Ala Ser Gln Ser Xaa Ser Xaa Xaa Tyr Leu Xaa
 1               5                  10

<210> SEQ ID NO 130
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
```

<222> LOCATION: 9
<223> OTHER INFORMATION: Xaa = any amino acid

<400> SEQUENCE: 130

Arg Ala Ser Gln Ser Val Ser Ser Xaa Leu
 1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 6
<223> OTHER INFORMATION: Xaa = Ile, Val
<220> FEATURE:
<221> NAME/KEY: VARIANT
<222> LOCATION: 8
<223> OTHER INFORMATION: Ser, Arg
<220> FEATURE:
<221> NAME/KEY: VARIANT
<222> LOCATION: 9
<223> OTHER INFORMATION: Xaa = Ser, Tyr
<220> FEATURE:
<221> NAME/KEY: VARIANT
<222> LOCATION: 10
<223> OTHER INFORMATION: Xaa  = Leu, Tyr
<220> FEATURE:
<221> NAME/KEY: VARIANT
<222> LOCATION: 11
<223> OTHER INFORMATION: Xaa = Ala, Leu, Asn

<400> SEQUENCE: 131

Arg Ala Ser Gln Ser Xaa Ser Xaa Xaa Xaa Xaa
 1               5                   10

<210> SEQ ID NO 132
<211> LENGTH: 12
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 4
<223> OTHER INFORMATION: Xaa = Arg, Glu, Gln
<220> FEATURE:
<221> NAME/KEY: VARIANT
<222> LOCATION: 5
<223> OTHER INFORMATION: Xaa = Gly, Ser, Thr, Arg, Asn
<220> FEATURE:
<221> NAME/KEY: VARIANT
<222> LOCATION: 6
<223> OTHER INFORMATION: Xaa = Ile, Val
<220> FEATURE:
<221> NAME/KEY: VARIANT
<222> LOCATION: 7
<223> OTHER INFORMATION: Xaa = gly, Ser, Thr, Ile, Arg, Asn
<220> FEATURE:
<221> NAME/KEY: VARIANT
<222> LOCATION: 8
<223> OTHER INFORMATION: Xaa = Ser, Thr, Ile, Arg, His
<220> FEATURE:
<221> NAME/KEY: VARIANT
<222> LOCATION: 9
<223> OTHER INFORMATION: Xaa = Ser, or absent
<220> FEATURE:
<221> NAME/KEY: VARIANT
<222> LOCATION: 10
<223> OTHER INFORMATION: Xaa = Ser, Tyr, trp, Asn, his
<220> FEATURE:
<221> NAME/KEY: VARIANT
<222> LOCATION: 11

```
<223> OTHER INFORMATION: Xaa = Leu, Val
<220> FEATURE:
<221> NAME/KEY: VARIANT
<222> LOCATION: 12
<223> OTHER INFORMATION: Xaa = Ala, Ser, Asn

<400> SEQUENCE: 132

Arg Ala Ser Xaa Xaa Xaa Xaa Xaa Xaa Xaa Xaa Xaa
1               5                   10

<210> SEQ ID NO 133
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 4
<223> OTHER INFORMATION: Xaa = any amino acid

<400> SEQUENCE: 133

Xaa Ala Ser Xaa Arg Ala Thr
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, gly, Asp
<220> FEATURE:
<221> NAME/KEY: VARIANT
<222> LOCATION: 4
<223> OTHER INFORMATION: Xaa = Ser, Thr, Asn

<400> SEQUENCE: 134

Xaa Ala Ser Xaa Arg Ala Thr
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, Gly, Asp
<220> FEATURE:
<221> NAME/KEY: VARIANT
<222> LOCATION: 4
<223> OTHER INFORMATION: Xaa =Ser, Thr, Asn
<220> FEATURE:
<221> NAME/KEY: VARIANT
<222> LOCATION: 5
<223> OTHER INFORMATION: Xaa = Leu, Arg
<220> FEATURE:
<221> NAME/KEY: VARIANT
<222> LOCATION: 6
<223> OTHER INFORMATION: Xaa = Ala, glu, Gln
<220> FEATURE:
<221> NAME/KEY: VARIANT
<222> LOCATION: 7
<223> OTHER INFORMATION: Xaa = Ser, Thr

<400> SEQUENCE: 135
```

```
Xaa Ala Ser Xaa Xaa Xaa Xaa
 1               5

<210> SEQ ID NO 136
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ala, Gly, Thr, Lys, Asp, Glu, His
<220> FEATURE:
<221> NAME/KEY: VARIANT
<222> LOCATION: 4
<223> OTHER INFORMATION: Xaa = Ser, Thr, Asn
<220> FEATURE:
<221> NAME/KEY: VARIANT
<222> LOCATION: 5
<223> OTHER INFORMATION: Xaa =Leu, Arg
<220> FEATURE:
<221> NAME/KEY: VARIANT
<222> LOCATION: 6
<223> OTHER INFORMATION: Xaa = Ala, Val, Glu, Gln
<220> FEATURE:
<221> NAME/KEY: VARIANT
<222> LOCATION: 7
<223> OTHER INFORMATION: Ser, Thr

<400> SEQUENCE: 136

Xaa Ala Ser Xaa Xaa Xaa Xaa
 1               5

<210> SEQ ID NO 137
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Ser, Tyr, Phe, Arg
<220> FEATURE:
<221> NAME/KEY: VARIANT
<222> LOCATION: 4
<223> OTHER INFORMATION: Xaa = Gly, Ser, Tyr, Asn
<220> FEATURE:
<221> NAME/KEY: VARIANT
<222> LOCATION: 6
<223> OTHER INFORMATION: Xaa = Ser, Thr, Tyr, Trp
<220> FEATURE:
<221> NAME/KEY: VARIANT
<222> LOCATION: 7
<223> OTHER INFORMATION: Xaa = Arg, Pro
<220> FEATURE:
<221> NAME/KEY: VARIANT
<222> LOCATION: 8
<223> OTHER INFORMATION: Xaa = Leu, Trp, Arg
<220> FEATURE:
<221> NAME/KEY: VARIANT
<222> LOCATION: 9
<223> OTHER INFORMATION: Xaa = thr, Ile, tyr

<400> SEQUENCE: 137

Gln Gln Xaa Xaa Ser Xaa Xaa Xaa Xaa Thr
 1               5                  10

<210> SEQ ID NO 138
<211> LENGTH: 10
<212> TYPE: PRT
<213> ORGANISM: Artificial Sequence
<220> FEATURE:
```

```
<223> OTHER INFORMATION: Synthetically generated peptide
<220> FEATURE:
<221> NAME/KEY: VARIANT
<222> LOCATION: 1
<223> OTHER INFORMATION: Xaa = Leu, Gln
<220> FEATURE:
<221> NAME/KEY: VARIANT
<222> LOCATION: 3
<223> OTHER INFORMATION: Xaa = Ser, Tyr, Phe, Arg
<220> FEATURE:
<221> NAME/KEY: VARIANT
<222> LOCATION: 4
<223> OTHER INFORMATION: Xaa =Gly, Ser, Tyr, Asn
<220> FEATURE:
<221> NAME/KEY: VARIANT
<222> LOCATION: 5
<223> OTHER INFORMATION: Xaa = Ser, Lys, Asn
<220> FEATURE:
<221> NAME/KEY: VARIANT
<222> LOCATION: 6
<223> OTHER INFORMATION: Xaa = Ser, Thr, Tyr, Trp
<220> FEATURE:
<221> NAME/KEY: VARIANT
<222> LOCATION: 7
<223> OTHER INFORMATION: Xaa = Arg, Pro
<220> FEATURE:
<221> NAME/KEY: VARIANT
<222> LOCATION: 8
<223> OTHER INFORMATION: Xaa = Leu, Trp, Arg
<220> FEATURE:
<221> NAME/KEY: VARIANT
<222> LOCATION: 9
<223> OTHER INFORMATION: Xaa = Thr, Ile, Tyr

<400> SEQUENCE: 138

Xaa Gln Xaa Xaa Xaa Xaa Xaa Xaa Xaa Thr
 1               5                  10

<210> SEQ ID NO 139
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Tyr, Arg
<220> FEATURE:
<221> NAME/KEY: VARIANT
<222> LOCATION: 4
<223> OTHER INFORMATION: Xaa =Gly, Ser
<220> FEATURE:
<221> NAME/KEY: VARIANT
<222> LOCATION: 6
<223> OTHER INFORMATION: Xaa = Ser, Trp
<220> FEATURE:
<221> NAME/KEY: VARIANT
<222> LOCATION: 9
<223> OTHER INFORMATION: Xaa = any amino acid or absent

<400> SEQUENCE: 139

Gln Gln Xaa Xaa Ser Xaa Pro Arg Xaa Thr
 1               5                  10

<210> SEQ ID NO 140
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1, 2
<223> OTHER INFORMATION: Xaa = Leu, Gln
```

```
<220> FEATURE:
<221> NAME/KEY: VARIANT
<222> LOCATION: 3
<223> OTHER INFORMATION: Xaa =Ser, Tyr, Phe, Arg, Asp
<220> FEATURE:
<221> NAME/KEY: VARIANT
<222> LOCATION: 4
<223> OTHER INFORMATION: Xaa = Gly, Ser, Tyr, Asn
<220> FEATURE:
<221> NAME/KEY: VARIANT
<222> LOCATION: 5
<223> OTHER INFORMATION: Xaa = Ser, Thr, Arg, Lys, Asn
<220> FEATURE:
<221> NAME/KEY: VARIANT
<222> LOCATION: 6
<223> OTHER INFORMATION: Xaa = Ser, Thr, Tyr, Trp, Phe
<220> FEATURE:
<221> NAME/KEY: VARIANT
<222> LOCATION: 7
<223> OTHER INFORMATION: Xaa = Arg, Pro
<220> FEATURE:
<221> NAME/KEY: VARIANT
<222> LOCATION: 8
<223> OTHER INFORMATION: Xaa = Ile, Leu, Met, Trp, Arg, His
<220> FEATURE:
<221> NAME/KEY: VARIANT
<222> LOCATION: 9
<223> OTHER INFORMATION: Xaa = thr, Ile, Tyr
<220> FEATURE:
<221> NAME/KEY: VARIANT
<222> LOCATION: 10
<223> OTHER INFORMATION: Xaa = Thr, Ile

<400> SEQUENCE: 140

Xaa Xaa Xaa Xaa Xaa Xaa Xaa Xaa Xaa Xaa
 1               5                  10

<210> SEQ ID NO 141
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Leu, Gln
<220> FEATURE:
<221> NAME/KEY: VARIANT
<222> LOCATION: 2
<223> OTHER INFORMATION: Xaa = leu, Arg, Gln
<220> FEATURE:
<221> NAME/KEY: VARIANT
<222> LOCATION: 3
<223> OTHER INFORMATION: Xaa = Ser, Tyr, Phe, Arg, Asp
<220> FEATURE:
<221> NAME/KEY: VARIANT
<222> LOCATION: 4
<223> OTHER INFORMATION: Xaa = gly, ser, Tyr, Asn
<220> FEATURE:
<221> NAME/KEY: VARIANT
<222> LOCATION: 5
<223> OTHER INFORMATION: Xaa = Ala, Ser, Thr, Arg, Lys, Asn
<220> FEATURE:
<221> NAME/KEY: VARIANT
<222> LOCATION: 6
<223> OTHER INFORMATION: Xaa = Ser, Thr, Tyr, Trp, Phe
<220> FEATURE:
<221> NAME/KEY: VARIANT
<222> LOCATION: 7
<223> OTHER INFORMATION: Xaa = Ser, Val, Arg, Pro
<220> FEATURE:
<221> NAME/KEY: VARIANT
<222> LOCATION: 8
<223> OTHER INFORMATION: Xaa = Ser, Thr, Ile, leu, Met, Trp, Arg, His
<220> FEATURE:
<221> NAME/KEY: VARIANT
```

```
<222> LOCATION: 9
<223> OTHER INFORMATION: Xaa = Tyr, Ile, Tyr
<220> FEATURE:
<221> NAME/KEY: VARIANT
<222> LOCATION: 10
<223> OTHER INFORMATION: Xaa = Ser, thr, Ile

<400> SEQUENCE: 141

Xaa Xaa Xaa Xaa Xaa Xaa Xaa Xaa Xaa Xaa
 1               5                  10

<210> SEQ ID NO 142
<211> LENGTH: 8
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: xaa = any amino acid
<220> FEATURE:
<221> NAME/KEY: VARIANT
<222> LOCATION: 3
<223> OTHER INFORMATION: Xaa = Asn, Asp
<220> FEATURE:
<221> NAME/KEY: VARIANT
<222> LOCATION: 4
<223> OTHER INFORMATION: Xaa = Ile, Val
<220> FEATURE:
<221> NAME/KEY: VARIANT
<222> LOCATION: 5
<223> OTHER INFORMATION: Xaa = Ala, Gly
<220> FEATURE:
<221> NAME/KEY: VARIANT
<222> LOCATION: 6
<223> OTHER INFORMATION: Xaa = any amino acid (e.g., Gly or Arg)
<220> FEATURE:
<221> NAME/KEY: VARIANT
<222> LOCATION: 7
<223> OTHER INFORMATION: Xaa = any amino acid (e.g., Tyr or Asn)
<220> FEATURE:
<221> NAME/KEY: VARIANT
<222> LOCATION: 8
<223> OTHER INFORMATION: Xaa = any amino acid (e.g., Phe, Asn, or Lys)

<400> SEQUENCE: 142

Ser Xaa Xaa Xaa Xaa Xaa Xaa Xaa
 1               5

<210> SEQ ID NO 143
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 2
<223> OTHER INFORMATION: Xaa = Gly, Arg
<220> FEATURE:
<221> NAME/KEY: VARIANT
<222> LOCATION: 3
<223> OTHER INFORMATION: Xaa = Ser, Thr
<220> FEATURE:
<221> NAME/KEY: VARIANT
<222> LOCATION: 5
<223> OTHER INFORMATION: Xaa = any amino acid
<220> FEATURE:
<221> NAME/KEY: VARIANT
<222> LOCATION: 6
<223> OTHER INFORMATION: Xaa = Asn, Asp
<220> FEATURE:
<221> NAME/KEY: VARIANT
<222> LOCATION: 7
```

```
<223> OTHER INFORMATION: Xaa = Ile, Val
<220> FEATURE:
<221> NAME/KEY: VARIANT
<222> LOCATION: 8
<223> OTHER INFORMATION: Xaa = Ala, Gly
<220> FEATURE:
<221> NAME/KEY: VARIANT
<222> LOCATION: 9
<223> OTHER INFORMATION: Xaa = any amino acid (e.g., Gly or Arg)
<220> FEATURE:
<221> NAME/KEY: VARIANT
<222> LOCATION: 10
<223> OTHER INFORMATION: Xaa = any amino acid (e.g., Tyr or Asn)
<220> FEATURE:
<221> NAME/KEY: VARIANT
<222> LOCATION: 11
<223> OTHER INFORMATION: Xaa = any amino acid (e.g., Phe, Asn, or Lys)
<220> FEATURE:
<221> NAME/KEY: VARIANT
<222> LOCATION: 13
<223> OTHER INFORMATION: Xaa = any amino acid (e.g., aliphatic, e.g.,
     Val or Ala)

<400> SEQUENCE: 143

Thr Xaa Xaa Ser Xaa Xaa Xaa Xaa Xaa Xaa Xaa Tyr Xaa Ser
 1               5                  10

<210> SEQ ID NO 144
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Asp, Glu

<400> SEQUENCE: 144

Xaa Val Asn Asn Arg Pro Ser
 1               5

<210> SEQ ID NO 145
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Asp, Glu
<220> FEATURE:
<221> NAME/KEY: VARIANT
<222> LOCATION: 2
<223> OTHER INFORMATION: Xaa = Val, Asp
<220> FEATURE:
<221> NAME/KEY: VARIANT
<222> LOCATION: 3
<223> OTHER INFORMATION: Xaa = Ser, Thr, Asp, Asn
<220> FEATURE:
<221> NAME/KEY: VARIANT
<222> LOCATION: 4
<223> OTHER INFORMATION: Xaa = Tyr, Arg, Asn,p, Asn

<400> SEQUENCE: 145

Xaa Xaa Xaa Xaa Arg Pro Ser
 1               5

<210> SEQ ID NO 146
<211> LENGTH: 10
<212> TYPE: PRT
<213> ORGANISM: Artificial Sequence
```

```
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Ser, Gln
<220> FEATURE:
<221> NAME/KEY: VARIANT
<222> LOCATION: 3
<223> OTHER INFORMATION: Xaa = Ser, Tyr
<220> FEATURE:
<221> NAME/KEY: VARIANT
<222> LOCATION: 4
<223> OTHER INFORMATION: Xaa = Ala, Ser, Ile, Asp
<220> FEATURE:
<221> NAME/KEY: VARIANT
<222> LOCATION: 5
<223> OTHER INFORMATION: Xaa = Gly, Ser, Arg
<220> FEATURE:
<221> NAME/KEY: VARIANT
<222> LOCATION: 6
<223> OTHER INFORMATION: Xaa = Ser, Thr
<220> FEATURE:
<221> NAME/KEY: VARIANT
<222> LOCATION: 7
<223> OTHER INFORMATION: Xaa = Ser, Thr, Arg, Asn
<220> FEATURE:
<221> NAME/KEY: VARIANT
<222> LOCATION: 8
<223> OTHER INFORMATION: Xaa = ser, Thr, Tyr, Arg
<220> FEATURE:
<221> NAME/KEY: VARIANT
<222> LOCATION: 9
<223> OTHER INFORMATION: Xaa = Ala, Thr, Leu, Tyr
<220> FEATURE:
<221> NAME/KEY: VARIANT
<222> LOCATION: 10
<223> OTHER INFORMATION: Xaa = Ser, Val, Trp, Gln

<400> SEQUENCE: 146

Xaa Ser Xaa Xaa Xaa Xaa Xaa Xaa Xaa Xaa
 1               5                  10

<210> SEQ ID NO 147
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Ser, Val, Trp
<220> FEATURE:
<221> NAME/KEY: VARIANT
<222> LOCATION: 3
<223> OTHER INFORMATION: Xaa = Ser, Tyr
<220> FEATURE:
<221> NAME/KEY: VARIANT
<222> LOCATION: 8
<223> OTHER INFORMATION: xaa = Ala, Gly, Val, Met, Tyr, Trp, Pro, Gln,
     His
<220> FEATURE:
<221> NAME/KEY: VARIANT
<222> LOCATION: 10
<223> OTHER INFORMATION: Xaa = Ala, Gly, Ser, Thr, Leu, Val, Met, Tyr,
     Phe, Lys, His
<220> FEATURE:
<221> NAME/KEY: VARIANT
<222> LOCATION: 12
<223> OTHER INFORMATION: Xaa = Ala, Thr

<400> SEQUENCE: 147

Xaa Ile Xaa Pro Ser Gly Gly Xaa Thr Xaa Tyr Xaa Asp Ser Val Lys
 1               5                  10                  15
```

Gly

```
<210> SEQ ID NO 148
<211> LENGTH: 17
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Ser, Val
<220> FEATURE:
<221> NAME/KEY: VARIANT
<222> LOCATION: 3
<223> OTHER INFORMATION: Xaa = Ser, Tyr
<220> FEATURE:
<221> NAME/KEY: VARIANT
<222> LOCATION: 8
<223> OTHER INFORMATION: Xaa = Trp, Gln
<220> FEATURE:
<221> NAME/KEY: VARIANT
<222> LOCATION: 10
<223> OTHER INFORMATION: Xaa = Gly, Tyr
<220> FEATURE:
<221> NAME/KEY: VARIANT
<222> LOCATION: 12
<223> OTHER INFORMATION: Xaa = Ala, Thr

<400> SEQUENCE: 148

Xaa Ile Xaa Pro Ser Gly Gly Xaa Thr Xaa Tyr Xaa Asp Ser Val Lys
 1               5                  10                  15

Gly

<210> SEQ ID NO 149
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 149

Met Tyr Gly Met
 1

<210> SEQ ID NO 150
<211> LENGTH: 18
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 8
<223> OTHER INFORMATION: Xaa = a hydrophilic amino acid, e.g.,
      glutamine or asparagine
<220> FEATURE:
<221> NAME/KEY: VARIANT
<222> LOCATION: 10
<223> OTHER INFORMATION: Xaa = a small amino acid, e.g., Gly, Ala, Val,
      or Ser

<400> SEQUENCE: 150

Val Ile Ser Pro Ser Gly Gly Xaa Thr Xaa Tyr Ala Asp Ser Ala Val
 1               5                  10                  15

Lys Gly

<210> SEQ ID NO 151
<211> LENGTH: 5
<212> TYPE: PRT
```

```
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = any amino acid or optionally aliphatic,
      e.g., Ile or Val

<400> SEQUENCE: 151

Gln Ser Xaa Ser Ser
 1               5

<210> SEQ ID NO 152
<211> LENGTH: 11
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 6
<223> OTHER INFORMATION: Xaa = any amino acid or optionally aliphatic,
      e.g., Ile or Val

<400> SEQUENCE: 152

Arg Ala Ser Gln Ser Xaa Ser Ser Tyr Leu Ala
 1               5                  10

<210> SEQ ID NO 153
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = any amino acid or optionally a
      hydrophilic amino acid, e.g., serine or asparagine
<220> FEATURE:
<221> NAME/KEY: VARIANT
<222> LOCATION: 5
<223> OTHER INFORMATION: Xaa = any amino acid or optionally aliphatic or
      small aliphatic, e.g., alanine or valine

<400> SEQUENCE: 153

Ala Ser Xaa Arg Xaa Thr
 1               5

<210> SEQ ID NO 154
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 4
<223> OTHER INFORMATION: Xaa = any amino acid or optionally a
      hydrophilic amino acid, e.g., serine or asparagine
<220> FEATURE:
<221> NAME/KEY: VARIANT
<222> LOCATION: 6
<223> OTHER INFORMATION: Xaa = any amino acid or optionally aliphatic or
      small aliphatic, e.g., alanine or valine

<400> SEQUENCE: 154

Asp Ala Ser Xaa Arg Xaa Thr
 1               5
```

```
<210> SEQ ID NO 155
<211> LENGTH: 7
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 4
<223> OTHER INFORMATION: Xaa = any amino acid or optionally Lys or Ser

<400> SEQUENCE: 155

Gln Arg Ser Xaa Trp Pro Arg
 1               5

<210> SEQ ID NO 156
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = any amino acid or optionally Leu or Gln
<220> FEATURE:
<221> NAME/KEY: VARIANT
<222> LOCATION: 5
<223> OTHER INFORMATION: Xaa = any amino acid or optionally Lys or Ser

<400> SEQUENCE: 156

Xaa Gln Arg Ser Xaa Trp Pro Arg Thr
 1               5

<210> SEQ ID NO 157
<211> LENGTH: 107
<212> TYPE: PRT
<213> ORGANISM: Artificial Sequence
<220> FEATURE:
<223> OTHER INFORMATION: Synthetically generated oligonucleotide

<400> SEQUENCE: 157

Asp Ile Gln Met Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
     50                  55                  60

Ser Gly Ser Glu Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Arg
                85                  90                  95

Thr Phe Gly Gln Gly Thr Lys Leu Glu Ile Lys
                100                 105

<210> SEQ ID NO 158
<211> LENGTH: 107
<212> TYPE: PRT
<213> ORGANISM: Artificial Sequence
<220> FEATURE:
<223> OTHER INFORMATION: Synthetically generated oligonucleotide

<400> SEQUENCE: 158

Asp Ile Gln Met Thr Gln Ser Pro Ala Thr Leu Ser Leu Ser Pro Gly
```

```
                1               5                  10                 15
Glu Arg Ala Thr Leu Ser Cys Arg Ala Ser Gln Ser Ile Ser Ser Tyr
                20                 25                 30

Leu Ala Trp Tyr Gln Gln Lys Pro Gly Gln Pro Pro Arg Leu Leu Ile
            35                 40                 45

Tyr Asp Ala Ser Ser Arg Val Thr Gly Ile Pro Ala Arg Phe Ser Gly
            50                 55                 60

Ser Gly Phe Gly Thr Asp Phe Thr Leu Thr Ile Ser Ser Leu Glu Pro
 65                 70                 75                 80

Glu Asp Phe Ala Val Tyr Tyr Cys Leu Gln Arg Ser Ser Trp Pro Arg
                85                 90                 95

Thr Phe Gly Gln Gly Thr Lys Leu Glu Ile Lys
            100                105

<210> SEQ ID NO 159
<211> LENGTH: 107
<212> TYPE: PRT
<213> ORGANISM: Artificial Sequence
<220> FEATURE:
<223> OTHER INFORMATION: The germlined E3 sequence

<400> SEQUENCE: 159

Asp Ile Gln Met Thr Gln Ser Pro Ser Ser Leu Ser Ala Ser Val Gly
 1               5                  10                 15

Asp Arg Val Thr Ile Thr Cys Arg Ala Ser Gln Gly Ile Gly His Tyr
                20                 25                 30

Leu Ala Trp Tyr Gln Gln Lys Pro Gly Lys Val Pro Lys Leu Leu Ile
            35                 40                 45

Tyr Thr Ala Ser Thr Leu Gln Ser Gly Val Pro Ser Arg Phe Ser Gly
            50                 55                 60

Ser Gly Ser Gly Thr Asp Phe Thr Leu Thr Ile Ser Ser Leu Gln Pro
 65                 70                 75                 80

Glu Asp Val Ala Thr Tyr Tyr Cys Gln Gln Phe Asn Ser Tyr Pro His
                85                 90                 95

Thr Phe Gly Gln Gly Thr Arg Leu Glu Ile Lys
            100                105

<210> SEQ ID NO 160
<211> LENGTH: 10
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 1
<223> OTHER INFORMATION: Xaa = Gly, Ser, Val
<220> FEATURE:
<221> NAME/KEY: VARIANT
<222> LOCATION: 3
<223> OTHER INFORMATION: Xaa = Ser, Tyr
<220> FEATURE:
<221> NAME/KEY: VARIANT
<222> LOCATION: 8
<223> OTHER INFORMATION: Xaa = Trp, Asn, Gln
<220> FEATURE:
<221> NAME/KEY: VARIANT
<222> LOCATION: 10
<223> OTHER INFORMATION: Xaa = Gly, Tyr

<400> SEQUENCE: 160

Xaa Ile Xaa Pro Ser Gly Gly Xaa Thr Xaa
 1               5                  10
```

```
<210> SEQ ID NO 161
<211> LENGTH: 9
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: 3
<223> OTHER INFORMATION: Xaa = Ser, Tyr, Phe, Arg
<220> FEATURE:
<221> NAME/KEY: VARIANT
<222> LOCATION: 4
<223> OTHER INFORMATION: Xaa = Gly, Ser, Tyr, Asn
<220> FEATURE:
<221> NAME/KEY: VARIANT
<222> LOCATION: 6
<223> OTHER INFORMATION: Xaa = Ser, Thr,Tyr, Trp
<220> FEATURE:
<221> NAME/KEY: VARIANT
<222> LOCATION: 7
<223> OTHER INFORMATION: Xaa = Arg. Pro
<220> FEATURE:
<221> NAME/KEY: VARIANT
<222> LOCATION: 8
<223> OTHER INFORMATION: Xaa = Leu, Trp, Arg, His
<220> FEATURE:
<221> NAME/KEY: VARIANT
<222> LOCATION: 9
<223> OTHER INFORMATION: Xaa = Thr, Ile, Tyr

<400> SEQUENCE: 161

Gln Gln Xaa Xaa Ser Xaa Xaa Xaa Xaa
 1               5
```

TIE1-BINDING LIGANDS

CROSS-REFERENCE TO RELATED APPLICATIONS

This application claims priority to U.S. Application Ser. No. 60/494,713, filed on Aug. 12, 2003, the contents of which are hereby incorporated by reference in its entirety.

BACKGROUND

The oxygen and nutrients supplied by the blood vessels are crucial for tissue development and function. Indeed, the cardiovascular system is the first organ system to develop in embryos. During organogenesis and the development tissues or tumors, the proximity of the growing cells to the circulatory system is ensured by the coordinated growth of blood vessels and organ parenchyma. It may be possible to prevent or treat diseases by modulating blood vessel development or angiogenesis.

Blood vessels are composed of an inner layer of endothelial cells and an outer layer of pericytes or smooth muscle cells. The first tubular structures are formed by endothelial cells that subsequently recruit pericytes and smooth muscle cells to ensheath them. The de novo formation of blood vessels from a dispersed population of mesodermally derived endothelial precursor cells is termed vasculogenesis. This primitive network undergoes successive morphogenetic events including sprouting, splitting and remodeling to generate the hierarchical vascular network from large to branched small vessels. These successive morphogenetic events are collectively called angiogenesis. Previous studies have identified a number of endothelial cell specific receptor tyrosine kinases (RTKs) and their cognate ligands, which mediate the vasculogenic and angiogenic development of blood vessels. Members of the vascular endothelial growth factor (VEGF) family and their receptors function during the formation of the initial embryonic vascular plexus, whereas angiopoietins (Angs) and their receptor, Tie2, as well as ephrins and their Eph receptors are implicated in the subsequent remodeling processes. See, e.g., Jones et al. (2001) *Nature Reviews* 2:257 for a review of receptors involved in angiogenic and lymphangiogenic responses.

Tie1 and Tie2 are RTKs that are expressed almost exclusively in endothelial cells and hematopoietic precursor cells. These two receptors are required for the normal development of vascular structures during embryogenesis. The two Tie receptors form a RTK subfamily since, unlike other RKT family members, they include extracellular EGF-homology domains. See, e.g., Partanen (1992) *Mol Cell Biol* 12:1698 and WO 93/14124. Targeted disruption of the Tie1 gene in mice results in a lethal phenotype characterized by extensive hemorrhage and defective microvessel integrity. See, e.g., Puri et al. (1995) *EMBO J* 14:5884. Tie2 null embryos have defects in vascular remodeling and maturation, resulting from improper recruitment of periendothelial supporting cells. At least three ligands, designated the angiopoietins (Ang), have been identified for Tie2, while the ligands for Tie1 are still unknown. Mice lacking Ang1 show defects in vascular development, which are reminiscent of but slightly less severe than those of mice lacking Tie2. Binding of Ang1 induces tyrosine phosphorylation of Tie2 and activation of its signaling pathways, but Ang2 has been reported to antagonize these effects in endothelial cells. Accordingly, transgenic overexpression of Ang2 disrupts blood vessels formation in mouse embryos. So far, four angiopoietins and many related proteins have been discovered, although none of them appears to binds Tie1.

SUMMARY

In one aspect, the invention features a protein (e.g., an isolated protein) that includes a heavy chain immunoglobulin variable domain sequence and a light chain immunoglobulin variable domain sequence. The protein ligand binds to Tie1 ectodomain. For example, the protein binds with an affinity $K_D$ of less than $10^{-8}$ M, $5 \cdot 10^{-9}$ M, $10^{-9}$ M, $10^{-10}$ M, $10^{-11}$ M, or $10^{-12}$ M.

In one embodiment, one or more of the CDRs of the heavy and/or light chain variable domain sequence are human, primate, non-rodent (e.g., non-mouse or non-rat), or synthetic. In one embodiment, one or more of the framework regions of the heavy and/or light chain variable domain sequence are human, primate, or non-rodent (e.g., non-mouse or non-rat).

In one embodiment, the heavy chain includes one or more of the following properties:

i) a HC CDR1 that includes an amino acid sequence as follows:

```
(AGSR)-Y-(GVK)-M-(GSVF),           (SEQ ID NO: 117)

(AGSIMRH)-Y-(GVMK)-M-(GSVMFH), or  (SEQ ID NO: 118)

(AGSIMRNH)-Y-(AGTVMKPQ)-M-         (SEQ ID NO: 119)
(AGSTVMYWFKH);
``` ii) a HC CDR2 that includes an amino acid sequence as follows:
X-I-Y-P-S-G-G-X-T-X-Y-A-D-S-V-K-G (SEQ ID NO:120), wherein X is any amino acid,

```
(GSV)-I-(SY)-P-S-G-G-(WQ)-T-(GY),       (SEQ ID NO: 121)

(GSV)-I-(SY)-P-S-G-G-(WNQ)-T-(GY)       (SEQ ID NO: 160)

(GSV)-I-(SY)-P-S-G-G-(WQ)-T-(GY)-       (SEQ ID NO: 122)
Y-A-D-S-V-K-G, or (GSVW)-I-(SY)-P-S-G-G-(AGVMYWPQH)-      (SEQ ID NO: 123)
T-(AGSTLVMYFKH);
``` iii) a HC CDR3 that includes an amino acid sequence as follows:

```
V-(four or five residues)-F-D-          (SEQ ID NO: 124)
(I/Y),

G-Y-G-P-I-A-P-G-L-D-Y,                  (SEQ ID NO: 125)

(GV)-N-Y-Y-(GYD)-S-(SD)-G-Y-G-          (SEQ ID NO: 126)
P-I-A-P-G-L-D-Y, (GVD)-(AGLN)-(LYR)-(GSTLYH)-(GYD)-      (SEQ ID NO: 127)
(AGSYFP)-(SFD)-(AGYD)-(IY)-(GFD)-
(YDP)-(IP)-A-P-G-L-D-Y, or

VNYYDSSGYGPIAPGLDY.                     (SEQ ID NO: 128)
```

In one embodiment, the light chain includes one or more of the following properties:

i) a LC CDR1 that includes an amino acid sequence as follows:
R-A-S-Q-S-(IV)-S-(SR)-X1-Y-L-(AN) (SEQ ID NO:129),
R-A-S-Q-S-V-S-S-X-L (SEQ ID NO:130), R-A-S-Q-S-(IV)-S-(SR)-(SY)-(LY)-(ALN) (SEQ ID NO:131), or R-A-S-(REQ)-(GSTRN)-(IV)-(GSTIRN)-(STIRH)-X1-(SYWNH)-(LV)-(ASN) (SEQ ID NO:132), wherein X1 can be serine or absent;

ii) a LC CDR2 that includes an amino acid sequence as follows:

X-A-S-X-R-A-T (SEQ ID NO:133), wherein X can be any amino acid, (AGD)-A-S-(STN)-R-A-T (SEQ ID NO:134), (AGD)-A-S-(STN)-(LR)-(AEQ)-(ST) (SEQ ID NO:135), or (AGTKDEH)-A-S-(STN)-(LR)-(AVEQ)-(ST) (SEQ ID NO:136); and iii) a LC CDR3 that includes an amino acid sequence as follows:

Q-Q-(SYFR)-(GSYN)-S-(STYW)-(RP)-(LWRH)-(TIY) (SEQ ID NO:161),

Q-Q-(SYFR)-(GSYN)-S-(STYW)-(RP)-(LWR)-(TIY)-T (SEQ ID NO:137), (LQ)-Q-(SYFR)-(GSYN)-(SKN)-(STYW)-(RP)-(LWR)-(TIY)-T (SEQ ID NO:138),

Q-Q-(YR)-(GS)-S-(SW)-P-R-X1-T (SEQ ID NO:139), wherein X1 is any amino acid or absent,

```
(LQ)-(LQ)-(SYFRD)-(GSYN)-(STRKN)-    (SEQ ID NO: 140)
(STYWF)-(RP)-(ILMWRH)-(TIY)-(TI),
or (LQ)-(LRQ)-(SYFRD)-(GSYN)-           (SEQ ID NO: 141)
(ASTRKN)-(STYWF)-(SVRP)-
(STILMWRH)-(TIY)-(STI).
```

In one embodiment, the light chain includes one or more of the following properties:

i) a LC CDR1 that includes an amino acid sequence as follows:

```
S-X-(ND)-(IV)-(AG)-X1-X2-X3, or     (SEQ ID NO: 142)

T-(GR)-(ST)-S-X5-(ND)-(IV)-(AG)-    (SEQ ID NO: 143)
X1-X2-X3-Y-X4-S,
``` wherein X1 is any amino acid (e.g., G or R), X2 is any amino acid (e.g., Y or N), X3 is any amino acid (e.g., F, N, or K), X4 is any amino acid (e.g., aliphatic, e.g., V or A);

ii) a LC CDR2 that includes an amino acid sequence as follows:

```
(DE)-V-N-N-R-P-S                    (SEQ ID NO: 144)

(DE)-(VD)-(STDN)-(YRDN)-R-P-S;      (SEQ ID NO: 145)
``` iii) a LC CDR3 that includes an amino acid sequence as follows:

```
(SQ)-S-(SY)-(ASID)-(GSR)-(ST)-      (SEQ ID NO: 146)
(STRN)-(STYR)-(ATLY)-(SVWQ)
```

In one embodiment, the HC CDR2 includes an amino acid sequence as follows:

```
(GSVW)-I-(SY)-P-SG-G-(AGVMYWPQH)-   (SEQ ID NO: 147)
T-(AGSTLVMYFKH)-Y-(AT)-D-S-V-K-G
or (GSV)-I-(SY)-P-SG-G-(WQ)-T-(GY)-    (SEQ ID NO: 148)
Y-(AT)-D-S-V-K-G.
```

In one embodiment, the protein includes HC CDR1 and HC CDR2 sequences that are related to the corresponding CDR sequences of p-F3 and E3. For example, the protein includes the sequence MYGM (SEQ ID NO:149), at a position corresponding to HC CDR1. The sequence can be followed by a small amino acid, e.g., glycine, alanine, valine, or serine. In another example, the protein the sequence VISPSGGX$_1$TX$_2$YADSAVKG (SEQ ID NO:150), at a position corresponding to HC CDR2. For example, X$_1$ can be a hydrophilic amino acid, e.g., glutamine or asparagine. For example, X$_2$ can be a small amino acid, e.g., glycine, alanine, valine, or serine.

In one embodiment, two or three of the CDRs of the HC variable domain sequence match motifs that also match a HC variable domain of an antibody described herein. Similarly, in one embodiment, two or three of the CDRs of the LC variable domain sequence match motifs that also match a LC variable domain of an antibody described herein. In still another embodiment, the matched motifs for the CDRs are based on a HC and a LC that are paired in an antibody described herein.

In one embodiment, the H1 and H2 hypervariable loops have the same canonical structure as an antibody described herein. In one embodiment, the L1 and L2 hypervariable loops have the same canonical structure as an antibody described herein.

In one embodiment, the HC CDR1 amino acid sequences have a length of at least 5 amino acids of which at least 3, 4, or 5 amino acids are identical to the CDR1 sequence of the HC of clone E3, G2, p-A1, P-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the HC CDR2 amino acid sequences have a length of at least 15, 16, or 17 amino acids of which at least 10, 12, 14, 15, 16, or 17 amino acids are identical to the CDR2 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the HC CDR2 amino acid sequences have a length of at least 17 amino acids of which at least 14, 15, 16, or 17 amino acids are identical to the CDR2 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the HC CDR3 amino acid sequences have a length of at least of at least 7 or 8 amino acids of which at least 5, 6, 7, or 8 amino acids are identical to the CDR3 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, two or three of the CDRs of the HC variable domain sequence match motifs described herein such that the motifs are a set of motifs that match a HC variable domain of a clone described herein, e.g., E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. For example, the protein may include SEQ ID NO:118 and SEQ ID NO:160, e.g., motifs that match the E3 HC variable domain.

In one embodiment, the LC CDR1 amino acid sequences have a length of at least 10, 11, or 12 amino acids of which at least 7, 8, 9, 10, or 11 amino acids are identical to the CDR1 sequence of the LC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the LC CDR2 amino acid sequences have a length of at least 6 or 7 amino acids of which at least 5, 6, or 7 amino acids are identical to the CDR2 sequence of the LC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the LC CDR3 amino acid sequences have a length of at least of at least 8, 9, or 10 amino acids of which at least 7, 8, 9, or 10 amino acids are identical to the CDR3 sequence of the LC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or or s-H4.

In one embodiment, two or three of the CDRs of the LC variable domain sequence match motifs described herein such that the motifs are a set of motifs that match a LC variable domain of a clone described herein, e.g., E3, G2, p-A1, p-A10, p-B1, p-B3, p-C6, p-D12, p-F3, p-F4, p-G3, s-A10, s-H1, s-A2, s-B2, s-B9, s-C10, s-C2, s-C2, s-C7, s-D11, s-E11, s-G10, or s-H4. For example, the protein may include SEQ ID NO:132, SEQ ID NO:136, and SEQ ID NO:161, e.g., motifs that match the E3 LC variable domain.

In one embodiment, the amino acid sequence of the HC variable domain sequence is at least 70, 80, 85, 90, 92, 95, 97, 98, 99, or 100% identical to the amino acid sequence of the HC variable domain of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the amino acid sequence of the LC variable domain sequence is at least 70, 80, 85, 90, 92, 95, 97, 98, 99, or 100% identical to the amino acid sequence of the LC variable domain of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the amino acid sequences of the HC and LC variable domain sequences are at least 70, 80, 85, 90, 92, 95, 97, 98, 99, or 100% identical to the amino acid sequences of the HC and LC variable domains of a clone selected from the group consisting of E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, and s-H4.

In one embodiment, the amino acid sequences of one or more framework regions (e.g., FR1, FR2, FR3, and/or FR4) of the HC and/or LC variable domain are at least 70, 80, 85, 90, 92, 95, 97, 98, 99, or 100% identical to corresponding framework regions of the HC and LC variable domains of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the light chain variable domain sequence is human or non-immunogenic in a human. In one embodiment, the heavy chain variable domain sequence is human or non-immunogenic in a human.

The protein can bind to cells that express Tie1, e.g., endothelial cells. In one embodiment, the protein does not substantially bind (e.g., does not detectably bind) to platelets (e.g., resting and/or activated platelets).

In one embodiment, the protein inhibits tube formation by HUVECs in vitro.

In one embodiment, the protein recognizes melanoma-associated structures in a histological section, e.g., not only melanoma tissue, but antigen in surrounding structures. In one embodiment, the protein does not stain blood vessels in normal skin in a histological section.

In one embodiment, the protein specifically binds to Tie1, e.g., it binds with at least a 10, 50, 100, $10^3$, or $10^4$ fold preference for Tie1 relative to another human protein, e.g., Tie2, a natural protein other than Tie1 that has a Ig-like domain, an EGF-like domain, or fibronectin Type III repeat, or human serum albumin. In one embodiment, the protein binds to a domain of Tie1 described herein.

In another aspect, the invention features a protein (e.g., an isolated protein) that modulates activity of Tie1, e.g., the Tie1 receptor. For example, the protein is not naturally occurring. In one embodiment, the protein includes a HC and LC immunoglobulin variable domain sequence. In one embodiment, one or more of the CDRs of the heavy and/or light chain variable domain sequence are human, primate, non-rodent (e.g., non-mouse or non-rat), or synthetic. In one embodiment, one or more of the framework regions of the heavy and/or light chain variable domain sequence are human, primate, or non-rodent (e.g., non-mouse or non-rat). In another embodiment, the protein is substantially free of an immunoglobulin variable domain, e.g., the protein includes a peptide that independently interacts with Tie1.

In one embodiment, the protein activates an activity of the Tie1 protein.

In one embodiment, the protein includes the HC and LC immunoglobulin variable domains of the E3 antibody or domains that are at least 70, 80, 85, 90, 91, 92, 93, 94, 95, 96, 97, 98, 99, or 100% identical in the CDR regions. In one embodiment, the protein competes with E3 for binding to Tie1 or binds to an epitope that overlaps an epitope that is recognized by E3 or that has at least one, two or three residues in common with an epitope that is recognized by E3.

In one embodiment, the activating protein enables IL-3 dependent cells that express a chimeric receptor including the Tie1 extracellular domain and the EpoR intracellular domain to survive in the absence of IL-3.

In one embodiment, the protein can cause dimerization of Tie1. In one embodiment, the protein can cause autophosphorylation of the RTK domain of Tie1.

In one embodiment, the protein synergizes with the E3 antibody to activate an activity of Tie. In one embodiment, the protein includes the HC and LC immunoglobulin variable domains of the G2 or C7 antibody or domains that are at least 70, 80, 85, 90, 91, 92, 93, 94, 95, 96, 97, 98, 99, or 100% identical in the CDR regions. In one embodiment, the protein competes with G2 or C7 for binding to Tie1 or binds to an epitope that overlaps an epitope that is recognized by G2 or C7 or that has at least one, two or three residues in common with an epitope that is recognized by G2 or C7.

In another embodiment, the protein antagonizes an activity of the Tie1 protein. For example, the protein can at least partially inhibit the ability of the E3 antibody to agonize the Tie protein. In one embodiment, the protein can at least partially inhibit the ability of the E3 antibody to enable IL-3 dependent cells that express a chimeric receptor including the Tie1 extracellular domain and the EpoR intracellular domain to survive in the absence of IL-3.

In one embodiment, the HC and LC immunoglobulin variable domains of the protein include the amino acid sequences that are at least 70, 80, 85, 90, 91, 92, 93, 94, 95, 96, 97, 98, 99, or 100% identical to the amino acid sequences of respective immunoglobulin variable domains of B2 or D11.

In one embodiment, the Tie1 modulator protein includes the HC and LC immunoglobulin variable domains of an antibody selected from the group consisting of: B2, D11, A2, A10, P-B1, P-B3, and P-C6 or immunoglobulin domains that are at least 70, 80, 85, 90, 91, 92, 93, 94, 95, 96, 97, 98, 99, or 100% identical in the CDR regions to the CDR regions of the respective antibodies. For example, the protein binds with an affinity $K_D$ of less than $10^{-8}$ M, $5 \cdot 10^{-9}$ M, $10^{-9}$ M, $10^{-10}$ M, $10^{-11}$ M, or $10^{-12}$ M.

In one embodiment, the protein can at least partially inhibit the ability of a naturally occurring Tie1 binding protein from interacting with the Tie protein.

The protein can include other features described herein.

In another aspect, the invention features an antibody (e.g., an isolated antibody) that binds to the Tie1 ectodomain, but does not substantially bind to platelets, e.g., as detected by fluorescence activated cell sorting. For example, the antibody does not substantially bind to activated platelets and/or resting platelets. In one embodiment, the antibody binds to endothelial cells. In one embodiment, the protein is a monoclonal antibody. The antibody can be provided in a preparation that is free of other Tie1-binding antibodies that have other specificities, e.g., free of Tie1 binding antibodies that bind to platelets. The antibody can include other features described herein.

In another aspect, the invention features a protein (e.g., an isolated protein) that preferentially binds to a Tie1 protein in a conformation stabilized by the E3 antibody relative to an endogenous Tie1 protein in an unstimulated state. In one embodiment, the protein includes immunoglobulin HC and LC domains. In another embodiment, the protein includes a peptide (e.g., of length less than 30, 28, 25, 22, 20, 18, 16, or 14 amino acids) that independently binds to Tie1. For example, the peptide can include one, two, or three disulfide bonds. The protein can include other features described herein.

In another aspect, the invention features a protein (e.g., an isolated protein) that preferentially binds to a Tie1 protein in a dimeric conformation relative to a monomeric Tie1 protein. In one embodiment, the protein includes immunoglobulin HC and LC domains. In another embodiment, the protein includes a peptide (e.g., of length less than 30, 28, 25, 22, 20, 18, 16, or 14 amino acids) that independently binds to Tie1. For example, the peptide can include one, two, or three disulfide bonds. The protein can include other features described herein.

In another aspect, the invention features a protein (e.g., an isolated protein) that binds to an epitope of Tie1 ectodomain with a $K_D$ of less than $2 \times 10^{-7}$ M. The epitope overlaps, is within, or includes an epitope bound by E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4 or that includes at least one, two, or three residues in common. For example, the protein binds with an affinity $K_D$ of less than $10^{-8}$ M, $5 \cdot 10^{-9}$ M, $10^{-9}$ M, $10^{-10}$ M, $10^{-11}$ M, or $10^{-12}$ M. In one embodiment, the protein includes immunoglobulin HC and LC domains. In another embodiment, the protein includes a peptide (e.g., of length less than 30, 28, 25, 22, 20, 18, 16, or 14 amino acids) that independently binds to Tie1. For example, the peptide can include one, two, or three disulfide bonds. The protein can include other features described herein.

In another aspect, the invention features a protein (e.g., an isolated protein) that competitively inhibits binding of E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4 to a Tie1 ectodomain. In one embodiment, the protein includes immunoglobulin HC and LC domains. In another embodiment, the protein includes a peptide (e.g., of length less than 30, 28, 25, 22, 20, 18, 16, or 14 amino acids) that independently binds to Tie1. For example, the peptide can include one, two, or three disulfide bonds. The protein can include other features described herein.

In another aspect, the invention features a protein (e.g., an isolated protein) that includes a heavy chain immunoglobulin variable domain and a light chain immunoglobulin variable domain and that antagonizes an activity of the Tie1 ectodomain. In one embodiment, CDR1 of the light chain variable domain includes: Q-S-X-S-S (SEQ ID NO:151) or R-A-S-Q-S-X-S-S-Y-L-A (SEQ ID NO:152), wherein X is any amino acid or optionally aliphatic, e.g., isoleucine or valine. In one embodiment, CDR2 of the light chain variable domain includes: A-S-$X_1$-R-$X_2$-T (SEQ ID NO:153) or D-A-S-$X_1$-R-$X_2$-T (SEQ ID NO:154), wherein $X_1$ is any amino acid or optionally a hydrophilic amino acid, e.g., serine or asparagine, and $X_2$ is any amino acid or optionally aliphatic or small aliphatic, e.g., alanine or valine. In one embodiment, CDR3 of the light chain variable domain includes: Q-R-S-$X_2$-W-P-R (SEQ ID NO:155) or $X_1$-Q-R-S-$X_2$-W-P-R-T (SEQ ID NO:156), wherein $X_1$ is any amino acid or optionally leucine or glutamine, and $X_2$ is any amino acid or optionally lysine or serine.

In one embodiment, the protein competes with the B2 and/or D11 antibody for binding to Tie1 or competitively inhibits binding of B2 and/or D11 to Tie1.

In one embodiment, the protein antagonizes a Tie1 activity that is stimulated by the E3 antibody. In one embodiment, the protein inhibits dimerization of Tie1. The protein can include other features described herein.

In another aspect, the invention features an isolated, mono-specific protein including a heavy chain immunoglobulin variable domain sequence and a light chain immunoglobulin variable domain sequence, wherein the protein binds to Tie1 ectodomain and includes a human or non-mouse constant domain (e.g., a human IgG1, 2, 3, or 4 constant domain. The protein can include other features described herein.

In another aspect, the invention features an isolated, human antibody that binds to a Tie1 ectodomain. The protein can include other features described herein.

In another aspect, the invention features an isolated antibody (e.g., an isolated antibody) that binds to a Tie1 ectodomain and contains less than 5, 4, 3, or 2 peptides (of between 6-9 amino acid length) that are non-human in origin or less than 5, 4, 3, or 2 peptides that are potential human T cell epitopes. In one embodiment, the antibody contains no peptide (of 6-9 amino acid length) that is non-human in origin or that is a potential human T cell epitope.

In one embodiment, the antibody is obtained by a method that includes deimmunization. For example, the antibody is deimmunized, e.g., completely deimmunized. The protein can include other features described herein.

In another aspect, the invention features an isolated antibody that binds to a Tie1 ectodomain and that includes a modified Fc domain, e.g., a modified human Fc domain. For example, antibodies may include modifications, e.g., that alter Fc function. For example, the human IgG1 constant region can be mutated at one or more residues, e.g., one or more of residues 234 and 237, e.g., according to the number in U.S. Pat. No. 5,648,260. Other exemplary modifications include those described in U.S. Pat. No. 5,648,260. The protein can include other features described herein.

In another aspect, the invention features an isolated protein that binds to the Tie1 receptor with an affinity $K_D$ of less than $10^{-7}$ M, $10^{-8}$ M, $5\cdot10^{-9}$ M, $10^{-9}$ M, $10^{-10}$ M, $10^{-11}$ M, or $10^{-12}$ M. The protein can include other features described herein.

In another aspect, the invention features an isolated protein including a heavy chain immunoglobulin variable domain sequence and a light chain immunoglobulin variable domain sequence, wherein the protein binds to Tie1 ectodomain and, for example, includes at least one or more CDR's that are a non-primate CDR (e.g., a non-mouse or non-rabbit CDR) or a synthetic CDR. The protein can include other features described herein.

In another aspect, the invention features an isolated nucleic acid including a coding sequence that encodes a polypeptide including an immunoglobulin HC variable domain of an antigen binding protein that binds to Tie1. In one embodiment, the HC variable domain includes one or more of the following properties i) a HC CDR1 that includes an amino acid sequence as follows:

| | |
|---|---|
| (AGSR)-Y-(GVK)-M-(GSVF), | (SEQ ID NO: 117) |
| (AGSIMRH)-Y-(GVMK)-M-(GSVMFH), or | (SEQ ID NO: 118) |
| (AGSIMRNH)-Y-(AGTVMKPQ)-M-(AGSTVMYWFKH); | (SEQ ID NO: 119) | ii) a HC CDR2 that includes an amino acid sequence as follows:
X-I-Y-P-S-G-G-X-T-X-Y-A-D-S-V-K-G (SEQ ID NO:120), wherein X is any amino acid,

| | |
|---|---|
| (GSV)-I-(SY)-P-S-G-G-(WQ)-T-(GY), | (SEQ ID NO: 121) |
| (GSV)-I-(SY)-P-S-G-G-(WQ)-T-(GY)-Y-A-D-S-V-K-G, or | (SEQ ID NO: 122) |
| (GSVW)-I-(SY)-P-S-G-G-(AGVMYWPQH)-T-(AGSTLVMYFKH); | (SEQ ID NO: 123) | iii) a HC CDR3 that includes an amino acid sequence as follows:

| | |
|---|---|
| V-(four or five residues)-F-D-(I/Y), | (SEQ ID NO: 124) |
| G-Y-G-P-I-A-P-G-L-D-Y, | (SEQ ID NO: 125) |
| (GV)-N-Y-Y-(GYD)-S-(SD)-G-Y-G-P-I-A-P-G-L-D-Y, | (SEQ ID NO: 126) |
| (GVD)-(AGLN)-(LYR)-(GSTLYH)-(GYD)-(AGSYFP)-(SFD)-(AGYD)-(IY)-(GFD)-(YDP)-(IP)-A-P-G-L-D-Y, or | (SEQ ID NO: 127) |
| VNYYDSSGYGPIAPGLDY. | (SEQ ID NO: 128) |

In one embodiment, the HC CDR1 amino acid sequences have a length of at least 5 amino acids of which at least 3, 4, or 5 amino acids are identical to the CDR1 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the HC CDR2 amino acid sequences have a length of at least 15, 16, or 17 amino acids of which at least 10, 12, 14, 15, 16, or 17 amino acids are identical to the CDR2 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the HC CDR2 amino acid sequences have a length of at least 17 amino acids of which at least 14, 15, 16, or 17 amino acids are identical to the CDR2 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the HC CDR3 amino acid sequences have a length of at least of at least 7 or 8 amino acids of which at least 5, 6, 7, or 8 amino acids are identical to the CDR3 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, two or three of the CDRs of the HC variable domain sequence match motifs described herein such that the motifs are a set of motifs that match a HC variable domain of a clone described herein, e.g., E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the amino acid sequence of the HC variable domain sequence is at least 70, 80, 85, 90, 92, 95, 97, 98, 99, or 100% identical to the amino acid sequence of the HC variable domain of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the nucleic acid further includes a second coding sequence that encodes a polypeptide including an immunoglobulin LC variable domain, e.g., a LC domain described herein. In one embodiment, the nucleic acid further includes a promoter operably linked to the coding sequence.

In another aspect, the invention features an isolated nucleic acid including a coding sequence that encodes a polypeptide including an immunoglobulin LC variable domain of an antigen binding protein that binds to Tie1. In one embodiment, the LC variable domain includes one or more of the following properties: i) a LC CDR1 that includes an amino acid sequence as follows:

R-A-S-Q-S-(IV)-S-(SR)-X1-Y-L-(AN) (SEQ ID NO:129),
R-A-S-Q-S-V-S-S-X-L (SEQ ID NO:130),
R-A-S-Q-S-(IV)-S-(SR)-(SY)-(LY)-(ALN) (SEQ ID NO:131), or
R-A-S-(REQ)-(GSTRN)-(IV)-(GSTIRN)-(STIRH)-X1-(SYWNH)-(LV)-(ASN) (SEQ ID NO:132), wherein X1 can be serine or absent;

ii) a LC CDR2 that includes an amino acid sequence as follows:
X-A-S-X-R-A-T (SEQ ID NO:133), wherein X can be any amino acid,
(AGD)-A-S-(STN)-R-A-T (SEQ ID NO:134),
(AGD)-A-S-(STN)-(LR)-(AEQ)-(ST) (SEQ ID NO:135), or
(AGTKDEH)-A-S-(STN)-(LR)-(AVEQ)-(ST) (SEQ ID NO:136); and iii) a LC CDR3 that includes an amino acid sequence as follows:
Q-Q-(SYFR)-(GSYN)-S-(STYW)-(RP)-(LWR)-(TIY)-T (SEQ ID NO:137),
(LQ)-Q-(SYFR)-(GSYN)-(SKN)-(STYW)-(RP)-(LWR)-(TIY)-T (SEQ ID NO:138),
Q-Q-(YR)-(GS)-S-(SW)-P-R-X1-T (SEQ ID NO:139), wherein X1 is any amino acid or absent, (LQ)-(LQ)-(SYFRD)-(GSYN)-(STRKN)-(STYWF)-
(RP)-(ILMWRH)-(TIY)-(TI) (SEQ ID NO:140), or (LQ)-(LRQ)-(SYFRD)-(GSYN)-(ASTRKN)-(STYWF)-
(SVRP)-(STILMWRH)-(TIY)-(STI) (SEQ ID NO:141); and In one embodiment, the light chain includes one or more of the following properties:

i) a LC CDR1 that includes an amino acid sequence as follows:

```
S-X-(ND)-(IV)-(AG)-X1-X2-X3, or      (SEQ ID NO: 142)

T-(GR)-(ST)-S-X5-(ND)-(IV)-(AG)-     (SEQ ID NO: 143)
X1-X2-X3-Y-X4-S,
``` wherein X1 is any amino acid (e.g., G or R), X2 is any amino acid (e.g., Y or N), X3 is any amino acid (e.g., F, N, or K), X4 is any amino acid (e.g., aliphatic, e.g., V or A);

iii) a LC CDR2 that includes an amino acid sequence as follows:

```
(DE)-V-N-N-R-P-S                     (SEQ ID NO: 144)

(DE)-(VD)-(STDN)-(YRDN)-R-P-S;       (SEQ ID NO: 145)
``` v) a LC CDR3 that includes an amino acid sequence as follows:

```
(SQ)-S-(SY)-(ASID)-(GSR)-(ST)-       (SEQ ID NO: 146)
(STRN)-(STYR)-(ATLY)-(SVWQ)
```

In one embodiment, the HC CDR2 includes an amino acid sequence as follows:

```
(GSVW)-I-(SY)-P-SG-G-(AGVMYWPQH)-    (SEQ ID NO: 147)
T-(AGSTLVMYFKH)-Y-(AT)-D-S-V-K-G
or (GSV)-I-(SY)-P-SG-G-(WQ)-T-(GY)-Y-   (SEQ ID NO: 148)
(AT)-D-S-V-K-G.
```

In one embodiment, CDR1 of the light chain variable domain includes: Q-S-X-S-S (SEQ ID NO:151) or R-A-S-Q-S-X-S-S-Y-L-A (SEQ ID NO:152), wherein X is any amino acid or optionally aliphatic, e.g., isoleucine or valine. In one embodiment, CDR2 of the light chain variable domain includes: A-S-$X_1$-R-$X_2$-T (SEQ ID NO:153) or D-A-S-$X_1$-R-$X_2$-T (SEQ ID NO:154), wherein $X_1$ is any amino acid or optionally a hydrophilic amino acid, e.g., serine or asparagine, and $X_2$ is any amino acid or optionally aliphatic or small aliphatic, e.g., alanine or valine. In one embodiment, CDR3 of the light chain variable domain includes: Q-R-S-$X_2$-W-P-R (SEQ ID NO:155) or $X_1$-Q-R-S-$X_2$-W-P-R-T (SEQ ID NO:156), wherein $X_1$ is any amino acid or optionally leucine or glutamine, and $X_2$ is any amino acid or optionally lysine or serine.

In one embodiment, the LC CDR1 amino acid sequences have a length of at least 10, 11, or 12 amino acids of which at least 7, 8, 9, 10, or 11 amino acids are identical to the CDR1 sequence of the LC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the LC CDR2 amino acid sequences have a length of at least 6 or 7 amino acids of which at least 5, 6, or 7 amino acids are identical to the CDR2 sequence of the LC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the LC CDR3 amino acid sequences have a length of at least 8, 9, or 10 amino acids of which at least 7, 8, 9, or 10 amino acids are identical to the CDR3 sequence of the LC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the amino acid sequence of the LC variable domain sequence is at least 70, 80, 85, 90, 92, 95, 97, 98, 99, or 100% identical to the amino acid sequence of the LC variable domain of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the nucleic acid further includes a second coding sequence that encodes a polypeptide including an immunoglobulin HC variable domain, e.g., an HC domain described herein. In one embodiment, the nucleic acid further includes a promoter operably linked to the coding sequence.

In another aspect, the invention features a nucleic acid that includes one or more coding sequence that encodes one or more polypeptide chains that collectively include an immunoglobulin HC or LC variable domain of an antigen binding protein that binds to Tie1. In one embodiment, the nucleic acid segment encoding at least one of the variable domains hybridizes to a nucleic acid described herein, e.g., under stringent conditions (e.g., high stringency conditions). The nucleic acid can include other features described herein.

In another aspect, the invention features a host cell that contains a first nucleic acid sequence encoding a polypeptide including a HC variable domain of an antigen binding protein and a second nucleic acid sequence encoding a polypeptide including a LC variable domain of the antigen binding protein, wherein the antigen binding protein binds to Tie1 with a $K_D$ of less than $2\times10^{-7}$ M. In one embodiment, the HC or LC variable domain includes at least one human CDR. The antigen binding protein can include other features described herein.

In another aspect, the invention features a host cell that contains a first nucleic acid encoding a polypeptide including a HC variable region and a second nucleic acid encoding a polypeptide including a LC variable region, wherein the HC and the LC variable regions each include at least 70, 80, 85, 90, 92, 95, 97, 98, 99, or 100% identical to respective amino acid sequences of the HC and LC variable domains of a clone selected from the group consisting of E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, and s-H4. The antigen binding protein can include other features described herein.

In another aspect, the invention features a pharmaceutical composition including a protein described herein that interacts with Tie1 and a pharmaceutically acceptable carrier.

In another aspect, the invention features a therapeutic composition including a protein described herein that interacts with Tie1 wherein the composition is sterile and suitable for administration to a subject.

In another aspect, the invention features a method that includes: providing a signal-dependent or signal-responsive cell that expresses a chimeric receptor including the Tie1 extracellular domain and a heterologous intracellular sequence that can produce a signal; contacting a candidate compound to the cell; and evaluating a property of the cell that is dependent on the signal. In one embodiment, the intracellular sequence includes at least a region of an intracellular sequence of the EpoR protein. The method can be used, e.g., to evaluate activity of a candidate compound, or a plurality of compounds.

In another aspect, the invention features a method that includes: providing an IL-3 dependent cell that expresses a chimeric receptor including the Tie1 extracellular domain and the EpoR intracellular domain; contacting a candidate compound to the cell under conditions in which the concentration of IL-3 is not sufficient to sustain viability of the cell; and evaluating a property of the cell. The method can be used, e.g., to evaluate activity of a candidate compound, or a plurality of compounds. In one embodiment, the property is viability. In one embodiment, the evaluating includes an MTT assay. In one embodiment, the method further includes administering the candidate compound to a subject. For example, the candidate compound includes a protein, e.g., a protein that includes an immunoglobulin variable domain.

In another aspect, the invention features method of identifying a compound that modulates Tie1 activity. The method includes: providing a plurality of candidate compounds; and evaluating each compound of the plurality using a method described herein.

In another aspect, the invention features a culture cell that expresses a chimeric transmembrane protein including a region of the Tie1 extracellular domain and a heterologous intracellular sequence. In one embodiment, the intracellular sequence includes a region of the EpoR intracellular domain. In one embodiment, the cell requires IL-3 or Tie1 for viability. For example, the cell is IL-3 dependent in the absence of the chimeric transmembrane protein, but is viable in the presence of the E3 antibody and the absence of IL-3.

In another aspect, the invention features a preparation that includes the isolated mammalian cells (e.g., cells that expresses a chimeric transmembrane protein including a region of the Tie1 extracellular domain and a heterologous intracellular sequence) and a Tie1-binding ligand, wherein the Tie1-binding ligand is necessary to sustain viability of the cells.

In another aspect, the invention features a kit including: a Tie1-binding ligand and a culture cell that expresses a chimeric transmembrane protein including a region of the Tie1 extracellular domain and a heterologous intracellular sequence.

In another aspect, the invention features a method of evaluating a candidate compound. The method includes: providing a preparation that includes (i) a cell or membrane fraction that contains (a) an insoluble protein that includes a region of the Tie1 extracellular domain and a kinase domain and (b) ATP; (ii) a ligand that causes alters activity of the kinase domain; and (iii) the candidate compound; and evaluating phosphorylation state of the insoluble protein.

In another aspect, the invention features a method of evaluating a candidate compound. The method includes: providing a preparation that includes (i) a cell or membrane fraction that includes a Tie1 protein or a transmembrane protein that includes at least a region of the Tie1 extracellular domain and ATP; (ii) a ligand that causes autophosphorylation of Tie1 or the transmembrane protein; and (iii) the candidate compound; and evaluating phosphorylation state of the Tie1 protein.

In one embodiment, the ligand is an antibody. In one embodiment, the ligand includes the HC and LC immunoglobulin variable domains of the E3 antibody or domains that are at least 90% identical in the CDR regions. In one embodiment, the method further includes administering the candidate compound to a subject.

In another aspect, the invention features a method that includes: providing a preparation that includes (i) a cell or membrane fraction that includes a transmembrane protein that includes at least a region of the Tie1 extracellular domain and ATP; and (ii) a ligand that causes autophosphorylation of Tie1 or the transmembrane protein; and evaluating phosphorylation state of the transmembrane protein.

In another aspect, the invention features a method that includes: contacting a mammalian cell with a ligand that (i) can agonize Tie1 autophosphorylation and/or (ii) can enable an IL-3 dependent cell that expresses a chimeric receptor including the Tie1 extracellular domain and the EpoR intracellular domain to remain viable under conditions in which the concentration of IL-3 is not sufficient to sustain viability of the cell; and evaluating the mammalian cell. In one embodiment, the cell expresses an endogenous Tie1 protein. In one embodiment, the cell is an endothelial cell. In one embodiment, the method further includes contacting the mammalian cell with a test compound, other than the ligand. For example, the ligand is an antibody. For example, the ligand includes the HC and LC immunoglobulin variable domains of the E3 antibody or domains that are at least 90% identical in the CDR regions.

In another aspect, the invention features a method that includes: contacting a mammalian cell or fraction thereof with an agent that can modulate the activity of Tie1; and evaluating the mammalian cell or fraction thereof. In one embodiment, the agent is contacted to the cell while the cell is living, and the evaluating includes isolating a fraction of the cell. In one embodiment, the agent is a protein, e.g., an antibody or a peptide. In one embodiment, the agent includes the HC and LC immunoglobulin variable domains of the E3 antibody or domains that are at least 90% identical in the CDR regions to the E3 antibody. In one embodiment, the agent includes the HC and LC immunoglobulin variable domains of the B2 or D11 antibody or domains that are at least 90% identical in the CDR regions to the B2 or D11 antibody. In one embodiment, the agent includes the HC and LC immunoglobulin variable domains of the A2, A10, P-B1, P-B3, or P-C6 antibody or domains that are at least 70, 80, 85, 90, 91, 92, 93, 94, 95, 96, 97, 98, 99, or 100% identical % identical in the CDR regions to the A2, A10, P-B1, P-B3, or P-C6 antibody. In one embodiment, the agent includes the HC and LC immunoglobulin variable domains of the G2 or C7 antibody or domains that are at least 90% identical in the CDR regions to the G2, or C7 antibody. The agent can include other features described herein.

In another aspect, the invention features a method of evaluating a test compound. The method includes evaluating interaction between an agent that can modulate the activity of Tie1 and a protein that includes at least a region of the Tie1 extracellular domain in the presence of the test compound. In one embodiment, the agent is a test compound is a small organic compound with molecular weight less than 8000, 7000, 6000, 5000, or 3000 Daltons. For example, the evaluating includes contacting cells that include the protein that includes at least a region of the Tie1 extracellular domain with the agent in the presence of the test compound. In another example, the evaluating includes forming a cell-free preparation that includes the protein that includes at least a region of the Tie1 extracellular domain, the agent, and the test compound.

In another aspect, the invention features an artificial protein complex that includes (i) a protein that includes a Tie1 extracellular domain and (ii) a ligand that can agonize or antagonize an activity of Tie1. In one embodiment, the ligand is an antibody (e.g., an antibody described herein. For example, the ligand includes the HC and LC immunoglobulin variable domains of an antibody selected from the group consisting of: E3, B2, D11, A2, A10, P-B1, P-B3, P-C6, G2 and C7, or immunoglobulin domains that are at least 90% identical in the CDR regions to the CDR regions of the respective antibody. In one embodiment, the complex is present in a membrane fraction or on a mammalian cell.

In another aspect the invention features a method that includes: administering a composition that includes a protein that interacts with Tie1 (e.g., a protein described herein) to a subject in an amount effective to modulate (e.g., reduce or increase) angiogenesis in the subject.

For example, the protein binds with an affinity $K_D$ of less than $10^{-8}$ M, $5 \cdot 10^{-9}$ M, $10^{-9}$ M, $10^{-10}$ M, $10^{-11}$ M, or $10^{-12}$ M.

In one embodiment, one or more of the CDRs of the heavy and/or light chain variable domain sequence are human, primate, non-rodent (e.g., non-mouse or non-rat), or synthetic. In one embodiment, one or more of the framework regions of the heavy and/or light chain variable domain sequence are human, primate, or non-rodent (e.g., non-mouse or non-rat).

In one embodiment, the heavy chain includes one or more of the following properties:

i) a HC CDR1 that includes an amino acid sequence as follows:

```
(AGSR)-Y-(GVK)-M-(GSVF),           (SEQ ID NO: 117)

(AGSIMRH)-Y-(GVMK)-M-(GSVMFH), or  (SEQ ID NO: 118)

(AGSIMRNH)-Y-(AGTVMKPQ)-M-         (SEQ ID NO: 119)
(AGSTVMYWFKH);
``` ii) a HC CDR2 that includes an amino acid sequence as follows:
X-I-Y-P-S-G-G-X-T-X-Y-A-D-S-V-K-G (SEQ ID NO:120), wherein X is any amino acid,

```
(GSV)-I-(SY)-P-S-G-G-(WQ)-T-(GY),    (SEQ ID NO: 121)

(GSV)-I-(SY)-P-S-G-G-(WQ)-T-(GY)-    (SEQ ID NO: 122)
Y-A-D-S-V-K-G, or (GSVW)-I-(SY)-P-S-G-G-(AGVMYWPQH)-   (SEQ ID NO: 123)
T-(AGSTLVMYFKH);
``` iii) a HC CDR3 that includes an amino acid sequence as follows:

```
V-(four or five residues)-F-D-       (SEQ ID NO: 124)
(I/Y),

G-Y-G-P-I-A-P-G-L-D-Y,               (SEQ ID NO: 125)

(GV)-N-Y-Y-(GYD)-S-(SD)-G-Y-G-P-I-   (SEQ ID NO: 126)
A-P-G-L-D-Y, (GVD)-(AGLN)-(LYR)-(GSTLYH)-(GYD)-   (SEQ ID NO: 127)
(AGSYFP)-(SFD)-(AGYD)-(IY)-(GFD)-
(YDP)-(IP)-A-P-G-L-D-Y, or

VNYYDSSGYGPIAPGLDY.                  (SEQ ID NO: 128)
```

In one embodiment, the light chain includes one or more of the following properties:

i) a LC CDR1 that includes an amino acid sequence as follows:
R-A-S-Q-S-(IV)-S-(SR)-X1-Y-L-(AN) (SEQ ID NO:129),
R-A-S-Q-S-V-S-S-X-L (SEQ ID NO:130),
R-A-S-Q-S-(IV)-S-(SR)-(SY)-(LY)-(ALN) (SEQ ID NO:131), or
R-A-S-(REQ)-(GSTRN)-(IV)-(GSTIRN)-(STIRH)-X1-(SYWNH)-(LV)-(ASN) (SEQ ID NO:132), wherein X1 can be serine or absent;

ii) a LC CDR2 that includes an amino acid sequence as follows:
X-A-S-X-R-A-T (SEQ ID NO:133), wherein X can be any amino acid,
(AGD)-A-S-(STN)-R-A-T (SEQ ID NO:134),
(AGD)-A-S-(STN)-(LR)-(AEQ)-(ST) (SEQ ID NO:135), or
(AGTKDEH)-A-S-(STN)-(LR)-(AVEQ)-(ST) (SEQ ID NO:136); and iii) a LC CDR3 that includes an amino acid sequence as follows:
Q-Q-(SYFR)-(GSYN)-S-(STYW)-(RP)-(LWR)-(TIY)-T (SEQ ID NO:137),
(LQ)-Q-(SYFR)-(GSYN)-(SKN)-(STYW)-(RP)-(LWR)-(TIY)-T (SEQ ID NO:138),
Q-Q-(YR)-(GS)-S-(SW)-P-R-X1-T (SEQ ID NO:139), wherein X1 is any amino acid or absent,

```
(LQ)-(LQ)-(SYFRD)-(GSYN)-(STRKN)-   (SEQ ID NO: 140)
(STYWF)-(RP)-(ILMWRH)-(TIY)-(TI),
or (LQ)-(LRQ)-(SYFRD)-(GSYN)-           (SEQ ID NO: 141)
(ASTRKN)-(STYWF)-(SVRP)-
(STILMWRH)-(TIY)-(STI); and
```

In one embodiment, the light chain includes one or more of the following properties:

i) a LC CDR1 that includes an amino acid sequence as follows:

```
S-X-(ND)-(IV)-(AG)-X1-X2-X3, or      (SEQ ID NO: 142)

T-(GR)-(ST)-S-X5-(ND)-(IV)-(AG)-     (SEQ ID NO: 143)
X1-X2-X3-Y-X4-S,
``` wherein X1 is any amino acid (e.g., G or R), X2 is any amino acid (e.g., Y or N), X3 is any amino acid (e.g., F, N, or K), X4 is any amino acid (e.g., aliphatic, e.g., V or A);

iii) a LC CDR2 that includes an amino acid sequence as follows:
(DE)-V-N-N-R-P-S (SEQ ID NO:144)
(DE)-(VD)-(STDN)-(YRDN)-R-P-S (SEQ ID NO:145);

v) a LC CDR3 that includes an amino acid sequence as follows:
(SQ)-S-(SY)-(ASID)-(GSR)-(ST)-(STRN)-(STYR)-(ATLY)-(SVWQ) (SEQ ID NO:146)

In one embodiment, the HC CDR2 includes an amino acid sequence as follows:

```
(GSVW)-I-(SY)-P-SG-G-(AGVMYWPQH)-    (SEQ ID NO: 147)
T-(AGSTLVMYFKH)-Y-(AT)-D-S-V-K-G
or (GSV)-I-(SY)-P-SG-G-(WQ)-T-(GY)-     (SEQ ID NO: 148)
Y-(AT)-D-S-V-K-G.
```

In one embodiment, the HC CDR1 amino acid sequences have a length of at least 5 amino acids of which at least 3, 4, or 5 amino acids are identical to the CDR1 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the HC CDR2 amino acid sequences have a length of at least 15, 16, or 17 amino acids of which at least 10, 12, 14, 15, 16, or 17 amino acids are identical to the CDR2 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the HC CDR2 amino acid sequences have a length of at least 17 amino acids of which at least 14, 15, 16, or 17 amino acids are identical to the CDR2 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the HC CDR3 amino acid sequences have a length of at least of at least 7 or 8 amino acids of which at least 5, 6, 7, or 8 amino acids are identical to the CDR3 sequence of the HC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the LC CDR1 amino acid sequences have a length of at least 10, 11, or 12 amino acids of which at least 7, 8, 9, 10, or 11 amino acids are identical to the CDR1 sequence of the LC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the LC CDR2 amino acid sequences have a length of at least 6 or 7 amino acids of which at least 5, 6, or 7 amino acids are identical to the CDR2 sequence of the LC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4. In one embodiment, the LC CDR3 amino acid sequences have a length of at least of at least 8, 9, or 10 amino acids of which at least 7, 8, 9, or 10 amino acids are identical to the CDR3 sequence of the LC of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the amino acid sequence of the HC variable domain sequence is at least 70, 80, 85, 90, 92, 95, 97, 98, 99, or 100% identical to the amino acid sequence of the HC variable domain of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the amino acid sequence of the LC variable domain sequence is at least 70, 80, 85, 90, 92, 95, 97, 98, 99, or 100% identical to the amino acid sequence of the LC variable domain of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the amino acid sequences of the HC and LC variable domain sequences are at least 70, 80, 85, 90, 92, 95, 97, 98, 99, or 100% identical to the amino acid sequences of the HC and LC variable domains of a clone selected from the group consisting of E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, and s-H4.

In one embodiment, the amino acid sequences of one or more framework regions (e.g., FR1, FR2, FR3, and/or FR4) of the HC and/or LC variable domain are at least 70, 80, 85, 90, 92, 95, 97, 98, 99, or 100% identical to corresponding framework regions of the HC and LC variable domains of clone E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

In one embodiment, the light chain variable domain sequence is human or non-immunogenic in a human. In one embodiment, the heavy chain variable domain sequence is human or non-immunogenic in a human.

The protein can bind to cells that express Tie1, e.g., endothelial cells. In one embodiment, the protein does not substantially bind (e.g., does not detectably bind) to platelets.

In one embodiment, the protein specifically binds to Tie1, e.g., it binds with at least a 10, 50, 100, $10^3$, or $10^4$ fold preference for Tie1 relative to another human protein, e.g., Tie2, a natural protein other than Tie1 that has a Ig-like domain, an EGF-like domain, or fibronectin Type III repeat, or human serum albumin. In one embodiment, the protein binds to a domain of Tie1 described herein.

In one embodiment, the protein is delivered locally. In one embodiment, the protein is delivered systemically.

In one embodiment, the subject is in need of reduced angiogenesis, or identified as such. For example, the subject has an angiogenesis-related disorder. In another example, the subject has a neoplastic disorder, e.g., a metastatic cancer. For example, the subject has an angiogenesis-dependent cancer or tumor.

In another embodiment, the subject has an inflammatory disorder, e.g., rheumatoid arthritis or psoriasis.

In one embodiment, the protein is administered in an amount effective to reduce one or more of the following activities: sprouting, splitting and remodeling of blood vessels. In one embodiment, the protein is administered in an amount effective to reduce vasculogenesis or tubule formation.

In one embodiment, the method further includes, prior to the administering, identifying the subject as a subject in need of reduced angiogenesis. In one embodiment, the method further includes administering the protein continuously or in separate boluses. In one embodiment, the method further includes monitoring the subject during the course of administration. For example, the monitoring includes imaging blood vessels (locally or throughout) the subject. For example, the imaging includes administering the same or different Tie1 binding ligand to the subject.

In another aspect the invention features a method that includes: administering a composition that includes a protein described herein (e.g., a protein that reduces a Tie1 activity) to a subject in an amount effective to reduce a Tie1 activity in the subject. The method can include other features described herein.

In another aspect the invention features a method that includes: administering a composition that includes a protein described herein (e.g., a protein that increase a Tie1 activity) to a subject in an amount effective to increase Tie1 activity in the subject. The method can include other features described herein.

In one embodiment, the composition is administered locally, e.g., to a wound. For example, the subject is in need of treatment for wound healing (e.g., a burn, laceration, or surgery).

In one embodiment, the method includes administering a first antibody that includes one or more CDRs of the E3 antibody and a second antibody that includes one or more CDRs of the G2 or C7 antibody.

In another aspect, the invention features a method that includes administering a composition that includes a protein described herein that modulates an activity of Tie1 to a subject in an amount effective to modulate Tie1 activity in the subject. In one embodiment, the method includes administering first and second proteins that both interact with Tie1. For example, the first protein that agonizes Tie1 activity and second protein that antagonizes Tie1 activity is administered, e.g., to precisely titrate activity. For example, the first and second protein can be administered to different locations to inhibit angiogenesis in one area without affecting another area.

In one embodiment, the first and second proteins are administered separately. In another embodiment, the first and second proteins are administered as a combination. The method can include other features described herein.

In another aspect the invention features a method that includes: administering a composition that includes a protein described herein (e.g., a protein that can modulate an activity of Tie1) to a subject in an amount effective to modulate endothelial cell activity in the subject. In one embodiment, the protein is delivered into the circulation.

In one embodiment, the composition is effective for sensitizing endothelial cells to a treatment, and providing a treatment to the subject that inhibits, kills, ablates, or otherwise arrests the sensitized endothelial cells.

In another aspect the invention features a method that includes: (i) contacting the sample (and optionally, a reference, e.g., control, sample) with a protein that binds to Tie1, e.g., a protein described herein, under conditions that allow interaction of the Tie1-binding ligand and the Tie1 protein to occur; and (ii) detecting formation of a complex between the Tie1-binding ligand, and the sample (and optionally, the reference, e.g., control, sample).

In another aspect the invention features a method that includes: (i) administering to a subject (and optionally a control subject) an Tie1-binding ligand (e.g., an antibody or antigen binding fragment thereof), under conditions that allow interaction of the Tie1-binding ligand and the Tie1 protein to occur; and (ii) detecting formation of a complex between the Tie1-binding ligand and a Tie1 molecule of the subject or detecting distribution of Tie1-binding ligand or at least one location of the Tie1-binding ligand in the subject. In one embodiment, the Tie1-binding ligand does not modulate the activity of Tie1. The Tie1-binding ligand can be a protein described herein. In one embodiment, the ligand detects activated Tie1.

An antibody that binds to Tie1 is preferably monospecific, e.g., a monoclonal antibody, or antigen-binding fragment thereof. For example, the antibody can recognize Tie1 on a living cell, e.g., an endogenous Tie1 molecule or a Tie1 molecule that is expressed from a heterologous nucleic acid. In one embodiment, the Tie1-binding ligand interacts with primary endothelial cells. The term "monospecific antibody" refers to an antibody that displays a single binding specificity and affinity for a particular target, e.g., epitope. This term includes a "monoclonal antibody" which refers to an antibody that is produced as a single molecular species, e.g., from a population of homogenous isolated cells. A "monoclonal antibody composition" refers to a preparation of antibodies or fragments thereof of in a composition that includes a single molecular species of antibody. In one embodiment, a monoclonal antibody is produced by a mammalian cell. One or more monoclonal antibody species may be combined.

The Tie1-binding antibodies can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')$_2$ or scFv fragment), e.g., it does not include an Fc domain or a CH2, CH3, or CH4 sequence. The antibody can include two heavy chain immunoglobulins and two light chain immunoglobulins, or can be a single chain antibody. The antibodies can, optionally, include a constant region chosen from a kappa, lambda, alpha, gamma, delta, epsilon or a mu constant region gene. An Tie1-binding antibody can include a heavy and light chain constant region substantially from a human antibody, e.g., a human IgG1 constant region or a portion thereof. As used herein, "isotype" refers to the antibody class (e.g., IgM or IgG1) that is encoded by heavy chain constant region genes.

In one embodiment, the antibody (or fragment thereof) is a recombinant or modified antibody, e.g., a chimeric, a humanized, a deimmunized, or an in vitro generated antibody. The term "recombinant" or "modified" human antibody, as used herein, is intended to include all antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created or isolated by any other means that involves splicing of human immunoglobulin gene sequences to other DNA sequences. Such recombinant antibodies include humanized, CDR grafted, chimeric, deimmunized, in vitro generated antibodies, and may optionally include constant regions derived from human germline immunoglobulin sequences.

In one embodiment, the antibody binds to an epitope distinct from an epitope bound by known monoclonal antibodies that bind to Tie1, e.g., an antibody described in WO 95/26364, e.g., 3C4C7G6 and 10F11G6. In other embodiments, the antibody does not compete with known monoclonal antibodies that bind to Tie1, e.g., 3C4C7G6 and 10F11G6. In still other embodiments, the antibody does not compete with ligand described herein.

Also within the scope of the invention are antibodies or other ligands that bind overlapping epitopes of, or competitively inhibit the binding of the ligands disclosed herein to Tie1. For example, the antibodies or other ligands bind overlapping epitopes of or competitively inhibit the binding of monospecific antibodies, e.g., E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4 to Tie1, or vice versa (e.g., the monospecific antibodies competitively inhibiting binding of the ligands). Overlapping epitopes can include at least one amino acid in common. Ligands that competitively inhibit binding of one another do not necessarily bind to overlapping epitopes. For example, they may inhibit binding by steric interference or by altering the conformation of Tie1.

Any combination of Tie1-binding ligands is within the scope of the invention, e.g., two or more antibodies that bind to different regions of Tie1, e.g., antibodies that bind to two different epitopes on the extracellular domain of Tie1, e.g., a bispecific antibody.

In one embodiment, the Tie1-binding antibody or antigen-binding fragment thereof includes at least one light or heavy chain immunoglobulin (or preferably, at least one light chain immunoglobulin and at least one heavy chain immunoglobulin). Preferably, each immunoglobulin includes a light or a heavy chain variable region having at least one, two and, preferably, three complementarity determining regions (CDR's) substantially identical to a CDR from an anti-Tie1 light or heavy chain variable region, respectively, i.e., from a variable region of an antibody described herein, e.g., E3, G2, p-A1, p-A10, p-B1, p-B3, p-C6, p-D12, p-F3, p-F4, p-G3, s-A10, s-H1, s-A2, s-B2, s-B9, s-C10, s-C2, s-C7, s-D11, s-E11, s-G10, or s-H4.

An Tie1-binding ligand described herein can be used alone, e.g., can be administered to a subject or used in vitro in non-derivatized or unconjugated forms. In other embodiments, the Tie1-binding ligand can be derivatized, modified or linked to another functional molecule, e.g., another polypeptide, protein, isotope, cell, or insoluble support. For example, the Tie1-binding ligand can be functionally linked (e.g., by chemical coupling, genetic fusion, non-covalent association or otherwise) to one or more other molecular entities, such as an antibody (e.g., if the ligand is an antibody to form a bispecific or a multi-specific antibody), a toxin, a radioisotope, a therapeutic (e.g., a cytotoxic or cytostatic) agent or moiety, among others. For example, the Tie1-binding ligand can be coupled to a radioactive ion (e.g., an α-, γ-, or β-emitter), e.g., iodine ($^{131}$I or $^{125}$I), yttrium ($^{90}$Y), lutetium ($^{177}$Lu), actinium ($^{225}$Ac), rhenium ($^{186}$Re), or bismuth ($^{212}$Bi or $^{213}$Bi).

In another aspect, the invention features a nucleic acid that includes a coding sequence that encodes a polypeptide comprising an immunoglobulin heavy or light chain variable domain that binds to Tie1, e.g., an immunoglobulin heavy or light chain variable domain described herein. For example, the nucleic acid can include a particular nucleic acid sequence described herein, a nucleic acid that is at least 75, 80, 85, 90, 95, 96, 97, 98, or 99% identical to a nucleic acid sequence described herein (e.g., a particular nucleic acid sequence), or a nucleic acid that specifically hybridizes (e.g., under conditions described herein) to a a nucleic acid sequence described herein (e.g., a particular nucleic acid sequence), or fragments thereof (e.g., CDR-coding fragments).

A nucleic acid described herein can further include a promoter operably linked to the coding sequence. A nucleic acid can include a first and second coding sequence, e.g., wherein the first coding sequence encodes a polypeptide that includes an immunoglobulin heavy chain variable domain and the second coding sequence encodes a polypeptide that includes an immunoglobulin light chain variable domain.

In another aspect, the invention features a host cell that contains a first nucleic acid encoding a polypeptide comprising a heavy chain variable region and a second nucleic acid encoding a polypeptide comprising a light chain variable region. The heavy chain variable region and the light chain variable region can associate to form a Tie1 binding protein. These variable regions can have one or more properties described herein, e.g., at least 75, 80, 85, 90, 95, 96, 97, 98, or 99% identity to a sequence described herein. The invention also includes a method of providing a Tie1-binding antibody. The method can include providing a host cell described herein; and expressing said first and second nucleic acids in the host cell under conditions that allow assembly of said light and heavy chain variable regions to form an antigen binding protein that interacts with Tie1.

In another aspect, the invention provides compositions, e.g., pharmaceutical compositions, which include a pharmaceutically acceptable carrier, excipient or stabilizer, and at least one of the Tie1-binding ligands (e.g., antibodies or fragments thereof) described herein. In one embodiment, the compositions, e.g., the pharmaceutical compositions, include a combination of two or more of the aforesaid Tie1-binding ligands.

In another aspect, the invention features a kit that includes an Tie1-binding antibody (or fragment thereof), e.g., an Tie1-binding antibody (or fragment thereof) as described herein, for use alone or in combination with other therapeutic modalities, e.g., a cytotoxic or labeling agent, e.g., a cytotoxic or labeling agent as described herein, along with instructions on how to use the Tie1 antibody or the combination of such agents to treat, prevent or detect a Tie1-related disorder, e.g., an endothelial cell related disorder, e.g., rheumatoid arthritis or metastatic cancer.

In another aspect, the protein ligand that binds to Tie1 is a polypeptide that is not an immunoglobulin. For example, the polypeptide can be of variable length, e.g., 4 to 100 amino acid residues in length, preferably 5 to 75, 6 to 50, or 7 to 40 amino acid residues in length, or more preferably 8 to 30 or 10 to 25 amino acid residues in length. In some embodiments, the polypeptide includes non-standard or synthetic amino acid residues, e.g., norleucine, selenocysteine, pyrrolysine, etc. In some embodiments, the polypeptide includes cross-linking groups, e.g., two cysteine residues that can form a disulfide bond or some other type of chemical cross-linking moieties that can be used to cyclize the peptide. In other preferred embodiments, the polypeptide can be modified, e.g., using polyethylene glycol or fusion to a soluble protein, e.g., to increase the solubility or circulatory half-life of the polypeptide.

In another aspect, the invention features a method of identifying a protein that specifically binds to Tie1. In preferred embodiments, the invention includes: providing a Tie1 antigen; providing a display library (e.g., a phage display library member); identifying a member present in the library, wherein the member expresses a protein that specifically binds to the Tie1 antigen. The term "Tie1 antigen" refers to any antigenic fragment of Tie1 that is at least 8 amino acids in length. For example, a Tie1 antigen can include a fragment of the Tie1 ectodomain, e.g., a fragment that includes a folded protein domain such as a fragment described herein. In some embodiments, the Tie1 antigen is of human origin and includes, e.g., the extracellular domain of human Tie1 or a fragment thereof (e.g., a fragment described herein. The Tie1 antigen can be a recombinant polypeptide optionally fused to another polypeptide, e.g., a Fc domain, or it can be a cell that expresses Tie1 on its surface (e.g., an endothelial cell). In other preferred embodiments, the Tie1 antigen has an activated conformation, e.g., the Tie1 antigen is a dimeric conformation or a conformation stabilized by the E3 antibody described herein.

The methods described here are, for example, applicable to libraries that are based on bacteriophage with a substantially complete genome (e.g., including a modified gene III) and to libraries that are based on bacteriophage particles that include a phagemid nucleic acid. The terms "bacteriophage library member" and "phage" encompass members of both types of libraries. The term "bacteriophage particle" refers to a particle formed of bacteriophage coat proteins that packages a nucleic acid. The packaged nucleic acid can be a modified bacteriophage genome or a phagemid, e.g., a nucleic acid that includes a bacteriophage origin of replication but lacks essential phage genes and cannot propagate in *E. coli* without help from "helper phage" or phage genes supplied in trans.

In other embodiments, the invention features a method of identifying a protein that specifically binds to Tie1. The method includes: providing a Tie1 antigen (e.g., an region of the Tie1 ectodomain); immunizing a non-human animal with the Tie1 antigen; and isolating a cell that produces a immunoglobulin that interacts with Tie1. For example, the method can include producing hybridoma cells from the spleen of the animal (e.g., an immunized mouse); and identifying individual hybridoma cell lines expressing an antibody that specifically binds to the Tie1 antigen. For example, the In preferred embodiments, the Tie1 antigen is of human origin and includes, e.g., the extracellular domain of human Tie1 or some fragment thereof, e.g., the HA binding domain of Tie1. The Tie1 antigen can be a recombinant polypeptide optionally fused to another polypeptide, e.g., a purification handle, or it can be a cell that expresses Tie1 (e.g., an endothelial cell) on its surface. In other preferred embodiments, the Tie1 antigen has an activated conformation, e.g., dimerized.

In preferred embodiments, the methods further include isolating a nucleic acid molecule from the identified phage or hybridoma, wherein the nucleic acid molecule encodes the polypeptide or antibody that specifically binds to the Tie1 antigen. The isolated nucleic acid molecules can be used to produce therapeutic agents, as described herein.

In another aspect, the invention features nucleic acids that encode proteins identified by the methods described herein. In preferred embodiments, the nucleic acids include sequences encoding a heavy and light chain immunoglobulin or immunoglobulin fragment described herein. For example, the invention features, a first and second nucleic acid encoding a heavy and light chain variable region, respectively, of an Tie1-binding antibody molecule as described herein. Sequences encoding a heavy and light chain that function together can be present on separate nucleic acid molecules or on the same nucleic acid molecule. In another aspect, the invention features host cells and vectors containing a nucleic acid described herein.

In yet another aspect, the invention features a method of producing an Tie1-binding antibody, or antigen-binding fragment thereof. The method includes: providing a host cell that contains a first nucleic acid encoding a polypeptide comprising a heavy chain variable region, e.g., a heavy chain variable region as described herein; providing a second nucleic acid encoding a polypeptide comprising a light chain variable region, e.g., a light chain variable region as described herein; and expressing said first and second nucleic acids in the host cell under conditions that allow assembly of said light and heavy chain variable regions to form an antigen binding protein that interacts with Tie1. The first and second nucleic acids can be linked or unlinked, e.g., expressed on the same or different vector, respectively. The first and second nucleic acids can be components of the same molecule or can reside on different molecules (e.g., different chromosomes or plasmids).

The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell. For example, nucleic acids encoding the antibodies described herein can be expressed in a transgenic animal. In one embodiment, the nucleic acids are placed under the control of a tissue-specific promoter (e.g., a mammary specific promoter) and the antibody is produced in the transgenic animal. For example, the antibody molecule is secreted into the milk of the transgenic animal, such as a transgenic cow, pig, horse, sheep, goat or rodent. To produce a single chain antibody, the nucleic acid is configured to encode a single polypeptide that comprises both the heavy and light chain variable domains.

Tie1 has been found to be overexpressed in association with a wide range of cancers. Targeting Tie1 on the tumor vasculature with Tie1-binding ligands (e.g., antibodies) can be used to inhibit, destroy, or otherwise antagonize the vasculature so that tumor growth and metastasis is reduced. The ligands can be, for example, associated with a toxic payload or can mediate direct functional inhibition.

In another aspect, the invention features a method of inhibiting an activity of a cell, e.g., an endothelial cell, e.g., proliferation, adhesion, growth or survival of a cell, e.g., an endothelial cell, e.g., an endothelial cell in the vicinity of a cancer, e.g., a tumor. Methods of the invention include contacting the cell with a Tie1-binding ligand, in an amount sufficient to inhibit the adhesion, migration, growth or proliferation of the cell. Methods of the invention can be used, for example, to treat or prevent a disorder, e.g., an inflammatory disorder (e.g., rheumatoid arthritis, lupus, restenosis, psoriasis, graft v. host response, or multiple sclerosis), or a cancerous disorder (e.g., a malignant or metastatic disorder), by administering to a subject (e.g., an experimental animal or a human patient) a Tie1-binding ligand in an amount effective to treat or prevent such disorder. a Tie1-bidning ligand can also be used to treat or prevent stroke, heart disease, ulcers, scleroderma, infertility, and other diseases that are associated with insufficient angiogenesis.

A Tie1-binding ligand can be used to treat or prevent angiogenesis-related disorders, particularly angiogenesis-dependent cancers and tumors.

Angiogenesis-related disorders include, but are not limited to, solid tumors; blood born tumors such as leukemias; tumor metastasis; benign tumors (e.g., hemangiomas, acoustic neuromas, neurofibromas, trachomas, and pyogenic granulomas; rheumatoid arthritis); psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation.

"Angiogenesis-dependent cancers and tumors" are cancers tumors that require, for their growth (expansion in volume and/or mass), an increase in the number and density of the blood vessels supplying then with blood. In one embodiment a Tie1-binding ligand causes regression of such cancers and tumors. "Regression" refers to the reduction of tumor mass and size, e.g., a reduction of at least 2, 5, 10, or 25%.

In another aspect, the invention features a method of contacting a cell (in vitro, ex vivo, or in vivo), e.g., an endothelial cell, e.g., an endothelial cell in the vicinity of a cancer, e.g., a tumor. The method can include providing a ligand that interacts with Tie1, e.g., a ligand described herein, and contacting the cell with the ligand, in an amount sufficient to form at least one detectable ligand-cell complex. The ligand can include, for example, a label or cytotoxic entity, e.g., an immunoglobulin Fc domain or a cytotoxic drug.

In another aspect, the invention features a method of treating, e.g., inhibiting, ablating or killing, a cell or impairing at least one activity of the cell. The method includes providing an Tie1-binding ligand, e.g. a ligand described herein, and contacting the cell with the ligand, in an amount sufficient to impair at least one activity of the cell, inhibit, ablate or kill the cell. The contacting can be in vitro or in vivo. For example, the cell can be a e.g., an endothelial cell, e.g., an endothelial cell in the vicinity of a cancer, e.g., a tumor. The ligand can include a cytotoxic entity. Methods of the invention can be used, for example, to treat or prevent a disorder, e.g., a endothelial cell-based disorder, a blood vessel disorder, wound healing, or a cancerous disorder (e.g., a malignant or metastatic disorder), by administering to a subject (e.g., an experimental animal or a human patient) an Tie1-binding ligand in an amount effective to treat or prevent such disorder.

The subject methods can be used on cells in culture, e.g. in vitro or ex vivo. For example, an endothelial cell, e.g., an endothelial cell in cancer biopsy, can be cultured in vitro in culture medium and the contacting step can be effected by adding the Tie1-binding ligand to the culture medium. The method can be performed on cells (e.g., cancerous or metastatic cells) present in a subject, as part of an in vivo (e.g., therapeutic or prophylactic) protocol. For in vivo embodiments, the contacting step is effected in a subject and includes administering the Tie1-binding ligand to the subject under conditions effective to permit both binding of the ligand to the cell, and the inhibition of adhesion, migration, growth or proliferation of the cell.

The method of the invention can be used to treat or prevent cancerous disorders, e.g., including but are not limited to, solid tumors, soft tissue tumors, and metastatic lesions, particularly tumors that require a blood supply or angiogenesis. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, as well as adenocarcinomas which include malignancies such as most colon cancers, rectal cancer, renal-cell carcinoma, liver cancer, non-small cell carcinoma of the lung, cancer of the small intestine and cancer of the esophagus. The subject can be a mammal, e.g., a primate, preferably a higher primate, e.g., a human (e.g., a patient having, or at risk of, a disorder described herein, e.g., an endothelial cell-based disorder, e.g., cancer).

The Tie1-binding antibody or fragment thereof, e.g., an Tie1-binding antibody or fragment thereof as described herein, can be administered to the subject systemically (e.g., orally, parenterally, subcutaneously, intravenously, intramuscularly, intraperitoneally, intranasally, transdermally, or by inhalation), topically, or by application to mucous membranes, such as the nose, throat and bronchial tubes.

The methods can further include the step of monitoring the subject, e.g., for a reduction in one or more of: a reduction in tumor size; reduction in cancer markers, e.g., levels of cancer specific antigen; reduction in the appearance of new lesions, e.g., in a bone scan; a reduction in the appearance of new disease-related symptoms; or decreased or stabilization of size of soft tissue mass; or any parameter related to improvement in clinical outcome. The subject can be monitored in one or more of the following periods: prior to beginning of treatment; during the treatment; or after one or more elements of the treatment have been administered. Monitoring can be used to evaluate the need for further treatment with the same Tie1-binding ligand or for additional treatment with additional agents. Generally, a decrease in one or more of the parameters described above is indicative of the improved condition of the subject. Information about the monitoring can be recorded, e.g., in electronic or digital form.

The Tie1-binding ligand can be used alone in unconjugated form to thereby inhibit adhesion, migration, or extravasation of the Tie1-expressing cells, or ablate or kill the Tie1-expressing cells. If the ligand is an antibody, the ablation or killing can be mediated, e.g., by an antibody-dependent cell killing mechanisms such as complement-mediated cell lysis and/or effector cell-mediated cell killing. In other embodiments, the Tie1-binding ligand can be bound (e.g., physically associated, either directly or indirectly, covalently or non-covalently) to a substance, e.g., a cytotoxic agent or moiety, effective to kill or ablate the Tie1-expressing cells. For example, the Tie1-binding ligand can be coupled to a radioactive ion (e.g., an $\alpha$-, $\gamma$-, or $\beta$-emitter), e.g., iodine ($^{131}$I or $^{125}$I), yttrium ($^{90}$Y), lutetium ($^{177}$Lu), actinium ($^{225}$Ac), or bismuth ($^{213}$Bi). The methods and compositions of the invention can be used in combination with other therapeutic modalities. In one embodiment, the methods of the invention include administering to the subject an Tie1-binding ligand, e.g., an Tie1-binding antibody or fragment thereof, in combination with a cytotoxic agent, in an amount effective to treat or prevent said disorder. The ligand and the cytotoxic agent can be administered simultaneously or sequentially. In other embodiments, the methods and compositions of the invention are used in combination with surgical and/or radiation procedures.

In another aspect, the invention features methods for detecting the presence of a Tie1 protein or a cell expressing Tie1 (e.g., an endothelial cell) in a sample, in vitro (e.g., a biological sample, a tissue biopsy, e.g., a cancerous lesion). The subject method can be used to evaluate, e.g., diagnose or stage a disorder described herein, e.g., a cancerous disorder. The method includes: (i) contacting the sample (and optionally, a reference, e.g., control sample) with an Tie1-binding ligand, as described herein, under conditions that allow interaction of the Tie1-binding ligand and the Tie1 protein to occur; and (ii) detecting formation of a complex between the Tie1-binding ligand, and the sample (and optionally, the reference, e.g., control, sample). Formation of the complex is indicative of the presence of Tie1 protein (e.g., activated Tie1 protein), and can indicate the suitability or need for a treatment described herein. For example, a statistically significant change in the formation of the complex in the sample relative to the reference sample, e.g., the control sample, is indicative of the presence of Tie1 (e.g., activated Tie1) in the sample.

In yet another aspect, the invention provides a method for detecting the presence of Tie1 (e.g., activated Tie1) in vivo (e.g., in vivo imaging in a subject). The subject method can be used to evaluate, e.g., diagnose, localize, or stage a disorder described herein, e.g., a cancerous disorder. The method includes: (i) administering to a subject (and optionally a control subject) an Tie1-binding ligand (e.g., an antibody or antigen binding fragment thereof), under conditions that allow interaction of the Tie1-binding ligand and the Tie1 protein to occur; and (ii) detecting formation of a complex between the ligand and Tie1, wherein a statistically significant change in the formation of the complex in the subject relative to the reference, e.g., the control subject or subject's baseline, is indicative of the presence of the Tie1. The presence of activated Tie1 in particular locations within a subject can be indicative of an endothelial-cell related disorder, e.g., an angiogenesis-related disorder, e.g., a cancer, e.g., metastatic cancer, or other angiogenesis-related disorder described herein.

In other embodiments, a method of diagnosing or staging, a disorder as described herein (e.g., an inflammatory or cancerous disorder), is provided. The method includes: (i) identifying a subject having, or at risk of having, the disorder; (ii) obtaining a sample of a tissue or cell affected with the disorder; (iii) contacting said sample or a control sample with an Tie1-binding ligand, under conditions that allow interaction of the binding agent and the Tie1 protein to occur, and (iv) detecting formation of a complex. A statistically significant increase in the formation of the complex between the ligand with respect to a reference sample, e.g., a control sample, is indicative of the disorder or the stage of the disorder. For example, the finding of activated Tie1 on tumor cells located in a solid tumor can indicate that the tumor is progressing into a metastatic tumor.

Preferably, the Tie1-binding ligand used in the in vivo and in vitro diagnostic methods is directly or indirectly labeled with a detectable substance to facilitate detection of the bound or unbound binding agent. Suitable detectable substances include various enzymes, prosthetic groups, fluorescent materials, luminescent materials and radioactive materials. In one embodiment, the Tie1-binding ligand is coupled to a radioactive ion, e.g., indium ($^{111}$In), iodine ($^{131}$I or $^{125}$I), yttrium ($^{90}$Y), actinium ($^{225}$Ac), bismuth ($^{213}$Bi), sulfur ($^{35}$S), carbon ($^{14}$C), tritium ($^{3}$H), rhodium ($^{188}$Rh), or phosphorous ($^{32}$P). In another embodiment, the ligand is labeled with an NMR contrast agent.

The invention also provides polypeptides and nucleic acids that encompass a range of amino acid and nucleic acid sequences, e.g., sequences described herein or sequences related to those described herein. For example, the invention features nucleic acids that encodes each of the polypeptides described herein. The nucleic acid can include the cognate codons or any set of codons that can be translated to produce the respective polypeptide. Such polypeptides include individual subunits of a multi-chain protein, e.g., an antibody that includes a plurality of different polypeptide chains. The nucleic acid may also be a nucleic acid fragment or vector that is not expressed, but includes a sequence encoding at least a part of an immunoglobulin variable region (e.g., including a CDR described herein) or a complement thereof. Such nucleic acids can be used to prepare useful constructs, cells, and proteins. In addition, the invention features a host cell that includes a nucleic acid described herein. The cell can express a protein described herein, e.g., on its surface.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$, a Fd fragment, a Fv fragments, and dAb fragments) as well as complete antibodies.

The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest*, Fifth Edition, U.S. Department of Health and Human Services, NIH Publication No. 91-3242, and Chothia, C. et al. (1987) J. Mol. Biol. 196:901-917). Kabat definitions are used herein. Each VH and VL is typically composed of three CDR's and four FR's, arranged from amino-terminus to carboxy-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405). The canonical structures of hypervariable loops of an immunoglobulin variable can be inferred from its sequence, as described in Chothia et al. (1992) *J. Mol. Biol.* 227:799-817; Tomlinson et al. (1992) *J. Mol. Biol.* 227:776-798); and Tomlinson et al. (1995) EMBO J. 14(18):4628-38.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form a target binding structure (or "antigen binding site"), e.g., a structure that interacts with Tie1, e.g., binds to or inhibits Tie1.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human or effectively human. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human or effectively human. For example, FR1, FR2, and FR3 collectively can be at least 70, 75, 80, 85, 90, 92, 95, 98, or 99% identical to a human sequence encoded by a human germline V segment of a locus encoding a light or heavy chain sequence.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" of a full length antibody (or simply "antibody portion," or "fragment"), as used herein, refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition. As used herein, "isotype" refers to the antibody class (e.g., IgM or IgG1) that is encoded by heavy chain constant region genes.

In one embodiment, the HC or LC of an antibody includes sequences that correspond to an amino acid sequence encoded by a human germline sequence, e.g., the framework regions and/or in the CDRs. For example, the antibody can include sequences from the human DP47 antibody. In one embodiment, one or more codons for the antibody are altered relative to the germline nucleic acid sequence, but are chosen to encode the same amino acid sequence. Codons can be selected, e.g., to optimize expression in a particular system, create restriction enzyme sites, create a silent fingerprint, etc.

In one embodiment, CDR2 of the antibody HC includes at least 11, 12, 13, 14, or 15 amino acid positions that are identical to the amino acids found in CDR2 of DP47.

A "humanized" immunoglobulin variable region is an immunoglobulin variable region that includes sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

The term "Tie1 ectodomain" refers to any extracellular region of a Tie1 protein, e.g., a region that includes about amino acids 25-759 of SEQ ID NO:2. Other exemplary regions are regions that include one or more EGF domains (e.g., 214-256, 258-303, 303-345, 214-303, 258-345, or 214-345 of SEQ ID NO:2); one or more IG-Like C2 domains (e.g., 43-105, 43-426, 372-426); one or more Fibronectin Type III repeats (e.g., 446-540, 543-639, 643-744, 446-639, 543-744, or 446-744 of SEQ ID NO:2); and combinations thereof.

As used herein, "binding affinity" refers to the apparent association constant or $K_a$. The $K_a$ is the reciprocal of the dissociation constant ($K_d$). A ligand may, for example, have a binding affinity of at least $10^5$, $10^6$, $10^7$ or $10^8$ M$^{-1}$ for a particular target molecule. Higher affinity binding of a ligand to a first target relative to a second target can be indicated by a higher $K_a$ (or a smaller numerical value $K_d$) for binding the first target than the $K_a$ (or numerical value $K_d$) for binding the second target. In such cases the ligand has specificity for the first target relative to the second target. Differences in binding affinity (e.g., for specificity or other comparisons) can be at least 1.5, 2, 5, 10, 50, 100, or 1000-fold. For example, a Tie1 binding ligand may preferentially bind to Tie at least 1.5, 2, 5, 10, 50, 100, or 1000-fold better than to another antigen, e.g., Tie2, EGF, fibronectin, or human serum albumin. A Tie1 binding ligand may also be species-specific or species-general (e.g., can bind to a Tie1 protein from more than one species).

Binding affinity can be determined by a variety of methods including equilibrium dialysis, equilibrium binding, gel filtration, ELISA, surface plasmon resonance, or spectroscopy (e.g., using a fluorescence assay). These techniques can be used to measure the concentration of bound and free ligand as a function of ligand (or target) concentration. The concentration of bound ligand ([Bound]) is related to the concentration of free ligand ([Free]) and the concentration of binding sites for the ligand on the target where (N) is the number of binding sites per target molecule by the following equation:

$$[Bound]=N \cdot [Free]/((1/Ka)+[Free])$$

Although quantitative measurements of Ka are routine, it is not always necessary to make an exact determination of $K_a$, though, since sometimes it is sufficient to obtain a qualitative measurement of affinity, e.g., determined using a method such as ELISA or FACS analysis, is proportional to $K_a$, and thus can be used for comparisons, such as determining whether a higher affinity is, e.g., 2, 5, 10, 20, or 50 fold higher than a reference. Binding affinity is typically evaluated in 0.01 M HEPES pH 7.4, 0.15 M NaCl, 3 mM EDTA and 0.005% (v/v) surfactant P20.

An "isolated composition" refers to a composition that is removed from at least 90% of at least one component of a natural sample from which the isolated composition can be obtained. Compositions produced artificially or naturally can be "compositions of at least" a certain degree of purity if the species or population of species of interests is at least 5, 10, 25, 50, 75, 80, 90, 95, 98, or 99% pure on a weight-weight basis.

An "epitope" refers to the site on a target compound that is bound by a ligand, e.g., a polypeptide ligand or an antigen-binding ligand (e.g., a Fab or antibody). In the case where the target compound is a protein, for example, an epitope may refer to the amino acids that are bound by the ligand. Overlapping epitopes include at least one common amino acid residue.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Sequences similar or homologous (e.g., at least about 85% sequence identity) to the sequences disclosed herein are also part of this application. In some embodiment, the sequence identity can be about 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

As used herein, the term "homologous" is synonymous with "similarity" and means that a sequence of interest differs from a reference sequence by the presence of one or more amino acid substitutions (although modest amino acid insertions or deletions) may also be present. Presently preferred means of calculating degrees of homology or similarity to a reference sequence are through the use of BLAST algorithms (available from the National Center of Biotechnology Information (NCBI), National Institutes of Health, Bethesda Md.), in each case, using the algorithm default or recommended parameters for determining significance of calculated sequence relatedness. The percent identity between two amino acid or nucleotide sequences can also be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6× SSC at about 45° C., followed by one or more washes in 0.2× SSC, 0.1% SDS at 60° C.; 3) high stringency hybridization conditions in 6× SSC at about 45° C., followed by one or more washes in 0.2×SSC, 0.1% SDS at 65° C.; and 4) very high stringency hybridization conditions are 0.5 M sodium phosphate, 7% SDS at 65° C., followed by one or more washes at 0.2× SSC, 1% SDS at 65° C.

It is understood that the ligands described herein may have mutations relative to a ligand described herein (e.g., a conservative or non-essential amino acid substitutions), which do not have a substantial effect on the polypeptide functions. Whether or not a particular substitution will be tolerated, i.e., will not adversely affect desired biological properties, such as binding activity can be determined as described in Bowie, et al. (1990) *Science* 247:1306-1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). It is possible for framework and CDR amino acid residues to include one or more conservative substitutions.

A "non-essential" amino acid residue is a residue that can be altered from the wild-type sequence of the binding agent, e.g., the antibody, without abolishing or more preferably, without substantially altering a biological activity, whereas an "essential" amino acid residue results in such a change.

Generally, where "X" is used to represent an amino acid residue, any amino acid (e.g., any of the twenty naturally occurring amino acids) can be used at that position, or at least a subset thereof (e.g., any of the nineteen non-cysteine amino acids).

The terms "polypeptide" or "peptide" (which may be used interchangeably) refer to a polymer of three or more amino acids linked by a peptide bond, e.g., between 3 and 30, 12 and 60, or 30 and 300, or over 300 amino acids in length. The polypeptide may include one or more unnatural amino acids. Typically, the polypeptide includes only natural amino acids. A "protein" can include one or more polypeptide chains. Accordingly, the term "protein" encompasses polypeptides. A protein or polypeptide can also include one or more modifications, e.g., a glycosylation, amidation, phosphorylation, and so forth. The term "small peptide" can be used to describe a polypeptide that is between 3 and 30 amino acids in length, e.g., between 8 and 24 amino acids in length.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05, or 0.02. Particular ligands may show a difference, e.g., in specificity or binding, that are statistically significant (e.g., P value<0.05 or 0.02).

Other features and advantages of the instant invention will become more apparent from the following detailed description and claims. Embodiments of the invention can include any combination of features described herein. The contents of all references, pending patent applications and published patents, cited throughout this application are hereby expressly incorporated by reference.

DETAILED DESCRIPTION

Figure 1:
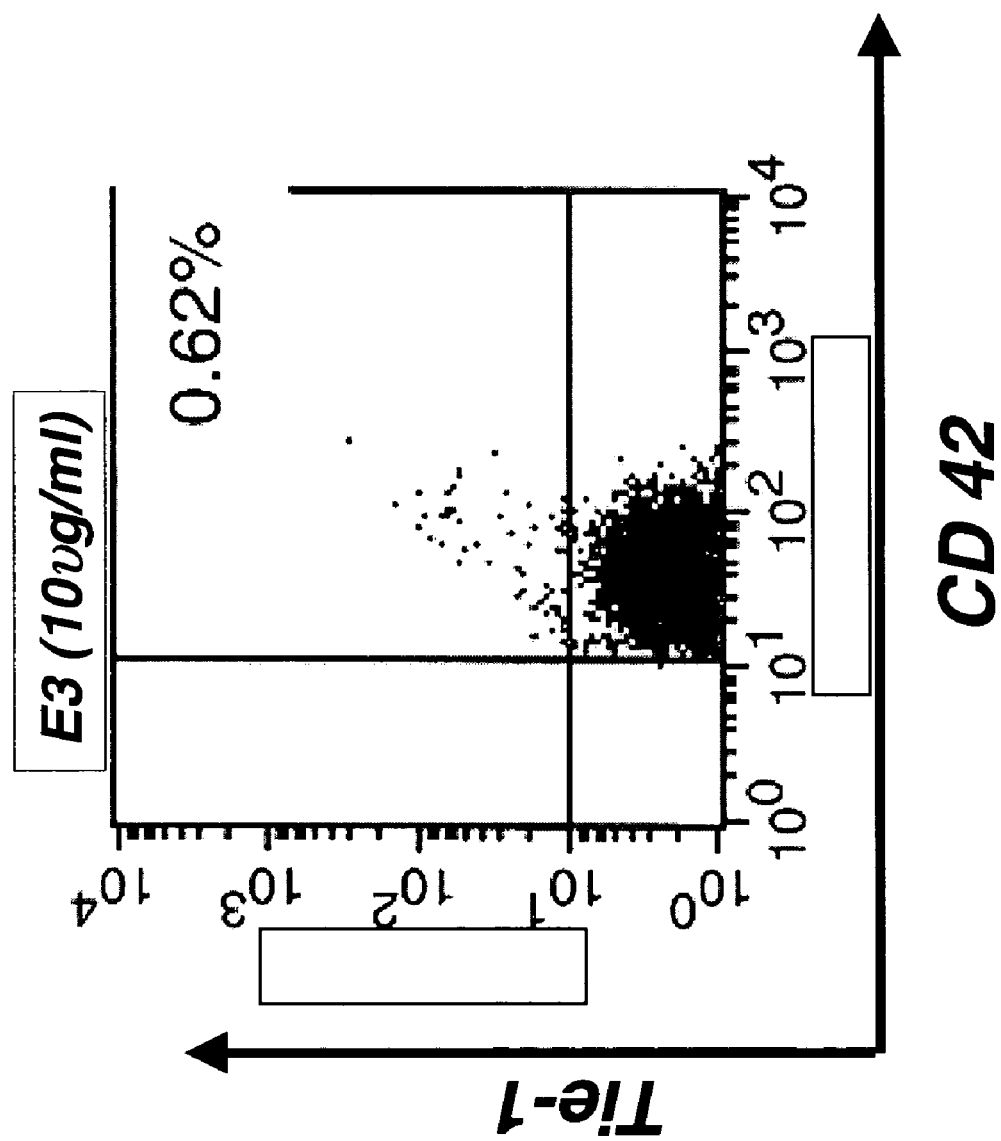
FIG. 1 illustrates a bivariant FACS plot showing labelling with the platelet specific marker CD42 with Tie1 and labelling with the E3 antibody. Only a background number of CD42 positive cells are labelled by the E3 antibody.
Figures 2A, 2B:
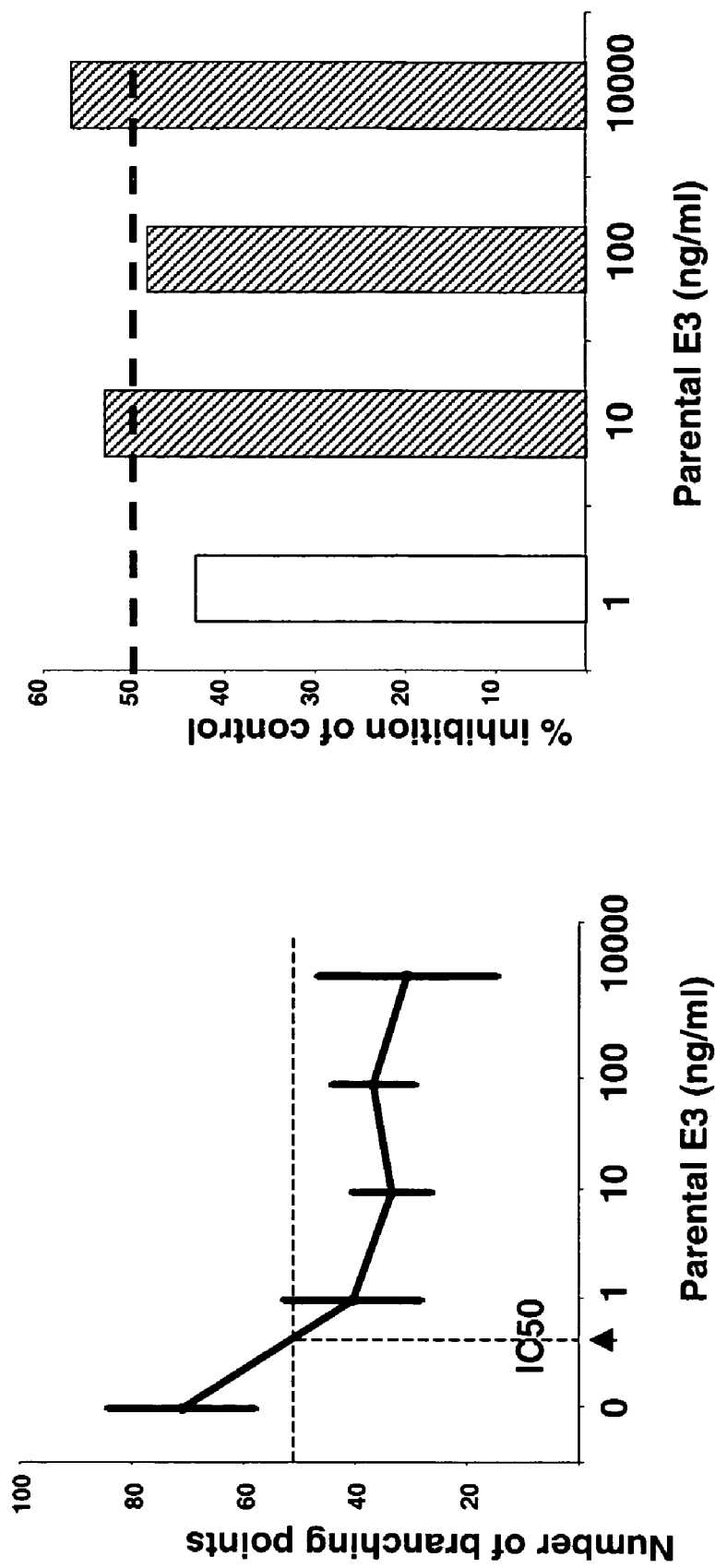
FIGS. 2A, 2B, 3A, and 3B are plots of the number of branching points verses antibody concentration comparing germlined E3 (3A and 3B) with parental E3 (2A and 2B)
Figure 3B:
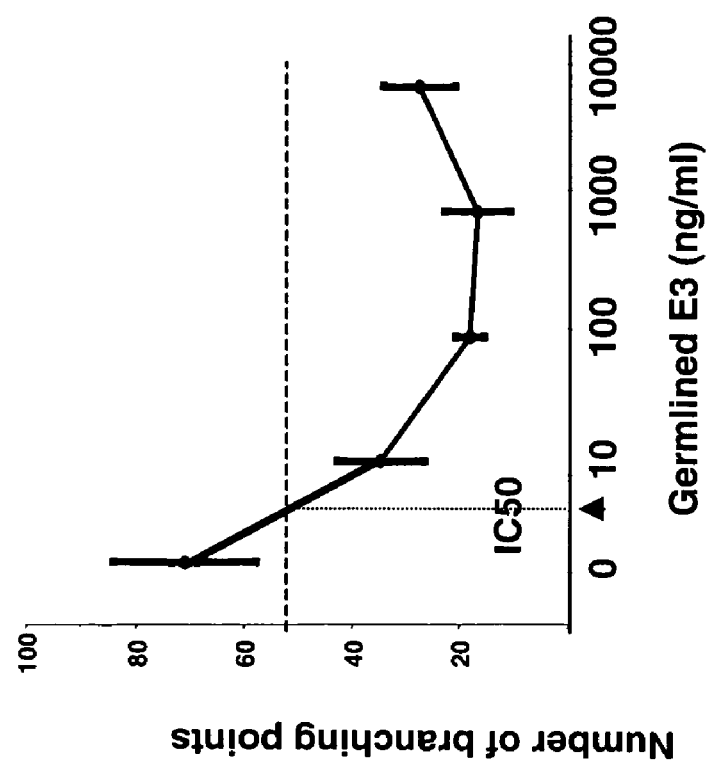
Figure 3A:
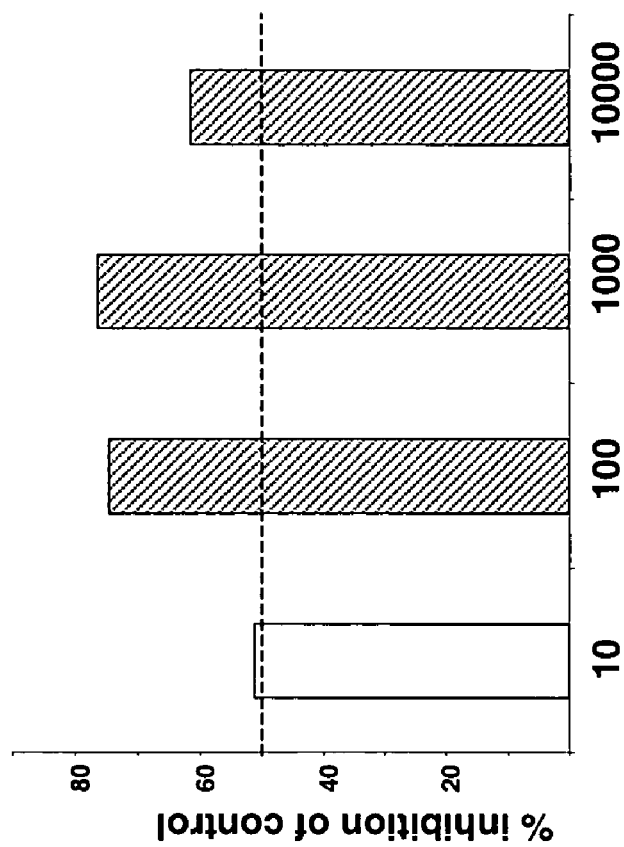

This disclosure provides, inter alia, methods for identifying proteins that bind to Tie1 and Tie1 binding proteins. The identified protein may be, for example, a small peptide (e.g., a cyclic or linear peptide, e.g., of between 7 and 25 amino acids), a polypeptide (e.g., a polypeptide of at least 20 amino acids), or a multi-chain protein (e.g., including at least two peptides or polypeptides). An example of a multi-chain protein is an antibody that has separate heavy and light chains. An example of a polypeptide is a single chain antibody.

Tie1 is a receptor tyrosine kinase protein that includes a transmembrane domain. Tie1 is present almost exclusively on endothelial cells. Accordingly, a Tie1 binding ligand can be used, e.g., to specifically recognize or target an endothelial cell. Some Tie1 binding ligands can also be used to agonize or antagonize endothelial cells. In some embodiments, these Tie1-binding ligands have an affinity for particular structural features (e.g., a feature listed below), a combination of features listed below, and/or an epitope that includes at least one amino acid in a structural feature listed below:

| Key | From | To | Length | Description |
|---|---|---|---|---|
| SIGNAL | 1 | 24 | 24 | POTENTIAL. |
| CHAIN | 25 | 1138 | 1114 | TYROSINE-PROTEIN KINASE RECEPTOR TIE1. |
| DOMAIN | 25 | 759 | 735 | EXTRACELLULAR (POTENTIAL). |
| TRANSMEM | 760 | 784 | 25 | POTENTIAL. |
| DOMAIN | 785 | 1138 | 354 | CYTOPLASMIC (POTENTIAL). |
| DOMAIN | 43 | 105 | 63 | IG-LIKE C2-TYPE 1. |
| DOMAIN | 214 | 256 | 43 | EGF-LIKE 1. |
| DOMAIN | 258 | 303 | 46 | EGF-LIKE 2. |
| DOMAIN | 305 | 345 | 41 | EGF-LIKE 3. |
| DOMAIN | 372 | 426 | 55 | IG-LIKE C2-TYPE 2. |
| DOMAIN | 446 | 540 | 95 | FIBRONECTIN TYPE-III 1. |
| DOMAIN | 543 | 639 | 97 | FIBRONECTIN TYPE-III 2. |
| DOMAIN | 643 | 744 | 102 | FIBRONECTIN TYPE-III 3. |
| DOMAIN | 839 | 1118 | 280 | PROTEIN KINASE. |
| NP_BIND | 845 | 853 | 9 | ATP (BY SIMILARITY). |
| BINDING | 870 | 870 | | ATP (BY SIMILARITY). |
| ACT_SITE | 979 | 979 | | BY SIMILARITY. |
| CARBOHYD | 83 | 83 | | N-LINKED (GLCNAC . . . ) (POTENTIAL). |
| CARBOHYD | 161 | 161 | | N-LINKED (GLCNAC . . . ) (POTENTIAL). |
| CARBOHYD | 503 | 503 | | N-LINKED (GLCNAC . . . ) (POTENTIAL). |
| CARBOHYD | 596 | 596 | | N-LINKED (GLCNAC . . . ) (POTENTIAL). |
| CARBOHYD | 709 | 709 | | N-LINKED (GLCNAC . . . ) (POTENTIAL). |
| MOD_RES | 1007 | 1007 | | PHOSPHORYLATION (AUTO-) (BY SIMILARITY). |

The sequence is relative to the amino acid sequence provided in SEQ ID NO:2 (Example 1, below).

One method for identifying proteins that bind to Tie1 includes: providing a library and selecting from the library one or more members that encode a protein that binds to the Tie1 antigen or a fragment thereof (e.g., the extracellular domain, an EGF domain, a fibronectin repeat, or an Ig-superfamily domain (e.g., a Ig-like C2-type 2 domain). The selection can be performed in a number of ways. For example, the library can be a display library.

The Tie1 can be tagged and recombinantly expressed. The Tie1 is purified and attached to a support, e.g., to affinity beads, or paramagnetic beads or other magnetically responsive particles.

The Tie1 can also be expressed on the surface of a cell. Members of the display library that specifically bind to the cell, e.g., only if the Tie1 is activated, can be selected.

Tie1 Agonists and Antagonists

In one embodiment, a Tie1-binding ligand can modulate a Tie1 activity. For example, the Tie1-binding ligand is a Tie1 agonist or antagonist.

Tie1 agonists can be used, e.g., to stimulate an activity of an endothelial cell. For example, a Tie1 agonist can be used to increase phosphatidylinosoitol 3-kinase (PI3 kinase) activity in an endothelial cell and/or Akt kinase activity. Kontos et al. suggest that the cytoplasmic domain of Tie1 can associate with the p85 subunit of PI3 kinase and activate PI3 kinase activity. Kontos (2002) Mol. Cell. Biol. 22:1704-1713. The Tie cytoplasmic domain may also associate with a protein tyrosine phosphatase Shp2. See, e.g., Marron et al. (2000) Adv. Exp. Med. Biol. 476:35-46. A Tie1 agonist may also increase dimerization, and/or tyrosine phosphorylation (e.g., as a result of auto-phosphorylation) of the Tie1 cytoplasmic domain, e.g., the tyrosine in the motif YVN at about amino acid 1117.

Tie1-binding ligand can be evaluated for agonist activity in a cell assay (e.g., in the BaF3 cell assay as described below in Example 2). An exemplary cell assay uses a growth factor dependent cell in which a chimeric receptor that includes the Tie1 ectodomain fused to the intracellular domain of the growth factor receptor is expressed. Cells are evaluated for ability to grow in the absence of the essential growth factor, but in the presence of a test compound, e.g., a Tie1-binding ligand. If the Tie1-binding ligand agonizes Tie1, a signalling activity of the Tie1 chimera can substitute for stimulation by the required growth factor thorough its cognate receptor. Thus, survival of the cell in the absence of the required growth factor can be used as an indication that the Tie1-binding ligand agonizes Tie1.

Tie1 antagonists can be used, e.g., to reduce an activity of an endothelial cell. For example, a Tie1 antagonists can be used to decrease phosphatidylinosoitol 3-kinase (PI3 kinase) activity in an endothelial cell, Shp2 activity, and/or Akt kinase activity. A Tie1 antagonists may also reduce dimerization, and/or tyrosine phosphorylation (e.g., as a result of auto-phosphorylation) of the Tie1 cytoplasmic domain, e.g., the tyrosine in the motif YVN at about amino acid 1117.

Tie1-binding ligand can be evaluated for antagonist activity in a cell assay. For example, the antagonist can be assayed for ability to prevent a Tie1 agonist (such as the E3 antibody) to stimulate Tie1 in a cell assay described herein. (e.g., the BaF3 cell assay as described below in Example 2).

Display Libraries

A number of methods can be used to identify proteins that bind to Tie1. In one embodiment, a display library is used to identify proteins that bind to Tie1. A display library is a collection of entities; each entity includes an accessible protein component and a recoverable component that encodes or identifies the protein component. The protein component can be of any length, e.g. from three amino acids to over 300 amino acids. In a selection, the protein component of each member of the library is probed with Tie1 protein and if the protein component binds to Tie1, the display library member is identified, e.g., by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the protein component and purification of the protein component for detailed characterization.

A variety of formats can be used for display libraries. Examples include the following.

Phage Display. One format utilizes viruses, particularly bacteriophages. This format is termed "phage display." The protein component is typically covalently linked to a bacteriophage coat protein. The linkage results form translation of a nucleic acid encoding the protein component fused to the coat protein. The linkage can include a flexible peptide linker, a protease site, or an amino acid incorporated as a result of suppression of a stop codon. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technology* 9:1373-1377; Rebar et al. (1996) *Methods Enzymol.* 267:129-49; Hoogenboom et al. (1991) *Nuc Acid Res* 19:4133-4137; and Barbas et al. (1991) *PNAS* 88:7978-7982.

Phage display systems have been developed for filamentous phage (phage f1, fd, and M13) as well as other bacteriophage (e.g. T7 bacteriophage and lambdoid phages; see, e.g., Santini (1998) *J. Mol. Biol.* 282:125-135; Rosenberg et al. (1996) *Innovations* 6:1-6; Houshmet al. (1999) *Anal Biochem* 268:363-370). The filamentous phage display systems typically use fusions to a minor coat protein, such as gene III protein, and gene VIII protein, a major coat protein, but fusions to other coat proteins such as gene VI protein, gene VII protein, gene IX protein, or domains thereof can also been used (see, e.g., WO 00/71694). In one embodiment, the fusion is to a domain of the gene III protein, e.g., the anchor domain or "stump," (see, e.g., U.S. Pat. No. 5,658,727 for a description of the gene III protein anchor domain). It is also possible to physically associate the protein being displayed to the coat using a non-peptide linkage, e.g., a non-covalent bond or a non-peptide covalent bond. For example, a disulfide bond and/or c-fos and c-jun coiled-coils can be used for physical associations (see, e.g., Crameri et al. (1993) *Gene* 137:69 and WO 01/05950).

The valency of the protein component can also be controlled. Cloning of the sequence encoding the protein component into the complete phage genome results in multivariant display since all replicates of the gene m protein are fused to the protein component. For reduced valency, a phagemid system can be utilized. In this system, the nucleic acid encoding the protein component fused to gene III is provided on a plasmid, typically of length less than 7000 nucleotides. The plasmid includes a phage origin of replication so that the plasmid is incorporated into bacteriophage particles when bacterial cells bearing the plasmid are infected with helper phage, e.g. M13K01. The helper phage provides an intact copy of gene III and other phage genes required for phage replication and assembly. The helper phage has a defective origin such that the helper phage genome is not efficiently incorporated into phage particles relative to the plasmid that has a wild type origin.

Bacteriophage displaying the protein component can be grown and harvested using standard phage preparatory methods, e.g. PEG precipitation from growth media.

After selection of individual display phages, the nucleic acid encoding the selected protein components, by infecting cells using the selected phages. Individual colonies or plaques can be picked, the nucleic acid isolated and sequenced.

Cell-based Display. In still another format the library is a cell-display library. Proteins are displayed on the surface of a cell, e.g., a eukaryotic or prokaryotic cell. Exemplary prokaryotic cells include *E. coli* cells, *B. subtilis* cells, and spores (see, e.g., Lu et al. (1995) *Biotechnology* 13:366). Exemplary eukaryotic cells include yeast (e.g., *Saccharomyces cerevisiae, Schizosaccharomyces pombe, Hanseula*, or *Pichia pastoris*). Yeast surface display is described, e.g., in Boder and Wittrup (1997) *Nat. Biotechnol.* 15:553-557 and WO 03/029456, which describes a yeast display system that can be used to display immunoglobulin proteins such as Fab fragments and the use of mating to generate combinations of heavy and light chains.

In one embodiment, variegate nucleic acid sequences are cloned into a vector for yeast display. The cloning joins the variegated sequence with a domain (or complete) yeast cell surface protein, e.g., Aga2, Aga1, Flo1, or Gas1. A domain of these proteins can anchor the polypeptide encoded by the variegated nucleic acid sequence by a transmembrane domain (e.g., Flo1) or by covalent linkage to the phospholipid bilayer (e.g., Gas1). The vector can be configured to express two polypeptide chains on the cell surface such that one of the chains is linked to the yeast cell surface protein. For example, the two chains can be immunoglobulin chains.

In one embodiment, nucleic acids encoding immunoglobulin heavy chains that have been mutagenized based on an initial Tie1-binding immunoglobulin are introduced into yeast cells of one cell type, and nucleic acids encoding immunoglobulin light chains that have been mutagenized based on an initial Tie1-binding immunoglobulin are introduced into yeast cells of the other cell type. These two populations of cells can be combined to form diploid yeast that each express an immunoglobulin heavy and light chain. The yeast cells can be selected and/or screened for cells that bind to Tie1, e.g., bind with improved affinity.

Ribosome Display. RNA and the polypeptide encoded by the RNA can be physically associated by stabilizing ribosomes that are translating the RNA and have the nascent polypeptide still attached. Typically, high divalent $Mg^{2+}$ concentrations and low temperature are used. See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2): 119-35.

Polypeptide-Nucleic Acid Fusions. Another format utilizes polypeptide-nucleic acid fusions. Polypeptide-nucleic acid fusions can be generated by the in vitro translation of mRNA that include a covalently attached puromycin group, e.g., as described in Roberts and Szostak (1997) *Proc. Natl. Acad. Sci. USA* 94:12297-12302, and U.S. Pat. No. 6,207, 446. The mRNA can then be reverse transcribed into DNA and crosslinked to the polypeptide.

Other Display Formats. Yet another display format is a non-biological display in which the protein component is attached to a non-nucleic acid tag that identifies the polypeptide. For example, the tag can be a chemical tag attached to a bead that displays the polypeptide or a radiofrequency tag (see, e.g., U.S. Pat. No. 5,874,214).

Display technology can also be used to obtain ligands, e.g., antibody ligands, particular epitopes of a target. This can be done, for example, by using competing non-target molecules that lack the particular epitope or are mutated within the epitope, e.g., with alanine. Such non-target molecules can be used in a negative selection procedure as described below, as competing molecules when binding a display library to the target, or as a pre-elution agent, e.g., to capture in a wash solution dissociating display library members that are not specific to the target.

Iterative Selection. In one preferred embodiment, display library technology is used in an iterative mode. A first display library is used to identify one or more ligands for a target. These identified ligands are then varied, e.g., using a mutagenesis method, to form a second display library. Higher affinity ligands are then selected from the second library, e.g., by using higher stringency or more competitive binding and washing conditions.

In some implementations, the mutagenesis is targeted to regions known or likely to be at the binding interface. If, for example, the identified ligands are antibodies, then mutagenesis can be directed to the CDR regions of the heavy or light chains as described herein. Further, mutagenesis can be directed to framework regions near or adjacent to the CDRs, e.g., framework regions, particular within ten, five, or three amino acids of a CDR junction. In the case of antibodies, mutagenesis can also be limited to one or a few of the CDRs, e.g., to make precise step-wise improvements.

Some exemplary mutagenesis techniques include: error-prone PCR (Leung et al. (1989) *Technique* 1:11-15), recombination (see, e.g., U.S. Ser. No. 10/279,633), DNA shuffling using random cleavage (Stemmer (1994) *Nature* 389-391; termed "nucleic acid shuffling"), RACHITT™ (Coco et al. (2001) *Nature Biotech.* 19:354), site-directed mutagenesis (Zoller et al. (1987) *Nucl Acids Res* 10:6487-6504), cassette mutagenesis (Reidhaar-Olson (1991) *Methods Enzymol.* 208:564-586) and incorporation of degenerate oligonucleotides. (Griffiths et al. (1994) *EMBO J* 13:3245).

In one example of iterative selection, the methods described herein are used to first identify a protein ligand from a display library that binds a Tie1 with at least a minimal binding specificity for a target or a minimal activity, e.g., an equilibrium dissociation constant for binding of greater than 1 nM, 10 nM, or 100 nM. The nucleic acid sequence encoding the initial identified protein ligand are used as a template nucleic acid for the introduction of variations, e.g., to identify a second protein ligand that has enhanced properties (e.g., binding affinity, kinetics, or stability) relative to the initial protein ligand.

Off-Rate Selection. Since a slow dissociation rate can be predictive of high affinity, particularly with respect to interactions between polypeptides and their targets, the methods described herein can be used to isolate ligands with a desired kinetic dissociation rate (i.e. reduced) for a binding interaction to a target.

To select for slow dissociating ligands from a display library, the library is contacted to an immobilized target. The immobilized target is then washed with a first solution that removes non-specifically or weakly bound biomolecules. Then the immobilized target is eluted with a second solution that includes a saturation amount of free target, i.e., replicates of the target that are not attached to the particle. The free target binds to biomolecules that dissociate from the target. Rebinding is effectively prevented by the saturating amount of free target relative to the much lower concentration of immobilized target.

The second solution can have solution conditions that are substantially physiological or that are stringent. Typically, the solution conditions of the second solution are identical to the solution conditions of the first solution. Fractions of the second solution are collected in temporal order to distinguish early from late fractions. Later fractions include biomolecules that dissociate at a slower rate from the target than biomolecules in the early fractions.

Further, it is also possible to recover display library members that remain bound to the target even after extended incubation. These can either be dissociated using chaotropic conditions or can be amplified while attached to the target. For example, phage bound to the target can be contacted to bacterial cells.

Selecting and Screening for Specificity. "Selection" refers to a process in which many members of a display library are allowed to contact the target and those that bind are recovered and propagated. The selection can be from a library having numerous members, e.g., more than $10^{10}$ members. "Screening" refers to a process in which isolated members of the library are tested singly for binding to the target. Through automation, thousands of candidates may be screened in a highly parallel process. The display library selection methods described herein can include a selection process that discards display library members that bind to a non-target molecule. Examples of non-target molecules include, e.g., extracellular domains of molecules that include an immunoglobulin super-family domain or an EGF domain and receptor tyrosine kinases other than Tie1, e.g., Tie2. In one implementation, a so-called "negative selection" step is used to discriminate between the target and related non-target molecule and a related, but distinct non-target molecules. The display library or a pool thereof is contacted to the non-target molecule. Members of the sample that do not bind the non-target are collected and used in subsequent selections for binding to the target molecule or even for subsequent negative selections. The negative selection step can be prior to or after selecting library members that bind to the target molecule.

In another implementation, a screening step is used. After display library members are isolated for binding to the target molecule, each isolated library member is tested for its ability to bind to a non-target molecule (e.g., a non-target listed above). For example, a high-throughput ELISA screen can be used to obtain this data. The ELISA screen can also be used to obtain quantitative data for binding of each library member to the target. The non-target and target binding data are compared (e.g., using a computer and software) to identify library members that specifically bind to Tie1.

The display library selection and screening methods described herein can include a selection or screening process that selects for display library members that bind to specific sites on the target molecule. For example, elution with high concentration of an antibody described herein can be used to select for phage that bind to an epitope that is near or overlaps with the epitope bound by the antibody used for elution. Accordingly, one can screen for a phage that binds to the E3-binding site of Tie1 by performing ELISAs with and without E3 antibody in the buffer.

Selection and Screening for Tie1-binding Antibodies:

The following provides one exemplary method for identifying antibodies that bind to Tie1 using a phagemid Fab library. For example, three rounds of selection can be performed with decreasing amounts of target protein (e.g., 100, 50 and 50 µg for first, second, and third rounds, respectively). The target is immobilized on streptavidin coated magnetic beads (Dynal). The library is depleted against streptavidin coated magnetic beads prior to each round of selection and optionally against an unrelated protein which may include a common purification handle. For example, if the target is produced as a fusion to a Fc domain, the library can be depleted against soluble Trail-Fc (a commercially available Fc fusion protein). The depletion process removes Fc binders.

Each round of selection can include, e.g., two cycles of streptavidin magnetic bead depletion, a cycle of binding of phage to Tie1-coated beads, ten cycles of washes, elution of bound phage, and propagation of enriched phage for the next round. Phage bound to Tie1-coated beads after ten washes can be directly amplified or eluted before amplification. After three rounds of selection, individual clones may be grown in 96-well microtiter plates and individually screened for Tie1 binding activity by phage ELISA. ELISAs can include evaluations of binding to Tie1, specificity controls, and unrelated controls. Isolates can be DNA fingerprinted to determine the diversity emerging from the selection process. For example, positive isolates can be PCR amplified with the oligonucleotide primers M13-reverse and geneIII-forward (see, e.g., Marks et al. (1991), *J. Mol. Biol.* 222:581). The products can be analyzed by BstNI fingerprinting.

An exemplary method for performing ELISA's with phage that display a ligand is as follows. Individual clones can be grown and rescued as described previously (Marks et al. (1991), *J. Mol. Biol.* 222:581). For ELISAs, 96-well Immulon 2 HB plates (Thermo Labsystems) are coated with 1 µg/well ImmunoPure™ streptavidin (Pierce) in PBS and incubated overnight at 4° C. After three washes with PBS, 100 µL of biotinylated Tie1 protein is allowed to bind to the immobilized streptavidin for 30-60 minutes at room temperature. Then, Tie1-coated wells are blocked with 300 µL of 2% milk/1× PBS/0.05% Tween (2% MPBST) for two hours at 37° C. The wells are incubated with 100 µL of phage culture supernatant that had been blocked with 2% MPBST for one hour at room temperature. The wells are washed five times with 1× PBS/Tween 0.1% (PBST), and incubated with 100 µL of anti-M13-HRP secondary antibody at a 1:5,000 dilution for one hour at room temperature. The wells are washed five times with PBST before developing with TMB-solution and read at 630 nm.

For the cell ELISAs, cells are washed once in PBS and resuspended at a concentration of $1\times10^6$ to $2\times10^6$ cells/mL of PBS. A final concentration of $1-2\times10^5$ cells per well of a 96-well tissue culture plate (Falcon, VWR) can be used. The cells are fixed by adding an equal volume of 0.2% glutaraldehyde (Sigma-Aldrich) and incubating at 37° C. for 12 minutes. They are then washed three times with PBS using an automated plate washer (Bio-Tek Instruments, Inc.) and blocked with 200 µL of 2% MPBST for one hour at room temperature. The rest of the ELISA procedure can be performed as described above except that 1× PBS/Tween 0.05% is used for the washes and incubations.

Germlining Antibodies

It is possible to modify an antibody that binds Tie1, e.g., an antibody described herein, in order to make the variable regions of the antibody more similar to one or more germline sequences. For example, an antibody can include one, two, three or more amino acid substitutions, e.g., in a framework or CDR region, to make it more similar to a reference germline sequence. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may including using two germline sequences that separately contribute to the amino-terminal portion and the carboxy-terminal portion. In other implementations more than one or two germline sequences are used, e.g., to form a consensus sequence.

In one embodiment, with respect to a particular reference variable domain sequence, e.g., a sequence described herein, a related variable domain sequence has at at least 30, 40, 50, 60, 70, 80, 90, 95 or 100% of the CDR amino acid positions that are not identical to residues in the reference CDR sequences, residues that are identical to residues at corresponding positions in a human germline sequence (i.e., an amino acid sequence encoded by a human germline nucleic acid).

In one embodiment, with respect to a particular reference variable domain sequence, e.g., a sequence described herein, a related variable domain sequence has at at least 30, 50, 60, 70, 80, 90 or 100% of the FR regions are identical to FR sequence from a human germline sequence, e.g., a germline sequence related to the reference variable domain sequence.

Accordingly, it is possible to isolate an antibody which has similar activity to a given antibody of interest, but is more similar to one or more germline sequences, particularly one or more human germline sequences. For example, an antibody can be at least 90, 91, 92, 93, 94, 95, 96, 97, 98, 99, 99.5% identical to a germline sequence in a region outside the CDRs (e.g., framework regions). Further an antibody can include at least 1, 2, 3, 4, or 5 germline residues in a CDR region, the germline residue being from a germline sequence of similar (e.g., most similar) to the variable region being modified. Germline sequences of primary interest are human germline sequences. The activity of the antibody (e.g., the binding activity) can be within a factor or 100, 10, 5, 2, 0.5, 0.1, and 0.001 of the original antibody.

Exemplary germline reference sequences for Vkappa include: O12/O2, O18/O8, A20, A30, L14, L1, L15, L4/18a, L5/L19, L8, L23, L9, L24, L11, L12, O11/O1, A17, A1, A18, A2, A19/A3, A23, A27, A11, L2/L16, L6, L20, L25, B3, B2, A26/A10, and A14. See, e.g., Tomlinson et al. (1995) EMBO J. 14(18):4628-3.

A germline reference sequence for the HC variable domain can be based on a sequence that has particular canonical structures, e.g., 1-3 structures in the H1 and H2 hypervariable loops. The canonical structures of hypervariable loops of an immunoglobulin variable domain can be inferred from its sequence, as described in Chothia et al. (1992) *J. Mol. Biol.* 227:799-817; Tomlinson et al. (1992) *J. Mol. Biol.* 227:776-798); and Tomlinson et al. (1995) *EMBO J.* 14(18):4628-38. Exemplary sequences with a 1-3 structure include: DP-1, DP-8, DP-12, DP-2, DP-25, DP-15, DP-7, DP-4, DP-31, DP-32, DP-33, DP-35, DP-40, 7-2, hv3005, hv3005f3, DP-46, DP-47, DP-58, DP-49, DP-50, DP-51, DP-53, and DP-54.

Diversity

Display libraries and other libraries include variation at one or more positions in the displayed polypeptide. The variation at a given position can be synthetic or natural. For some libraries, both synthetic and natural diversity are included.

Synthetic Diversity. Libraries can include regions of diverse nucleic acid sequence that originate from artificially synthesized sequences. Typically, these are formed from degenerate oligonucleotide populations that include a distribution of nucleotides at each given position. The inclusion of a given sequence is random with respect to the distribution. One example of a degenerate source of synthetic diversity is an oligonucleotide that includes NNN wherein N is any of the four nucleotides in equal proportion.

Synthetic diversity can also be more constrained, e.g., to limit the number of codons in a nucleic acid sequence at a given trinucleotide to a distribution that is smaller than NNN. For example, such a distribution can be constructed using less than four nucleotides at some positions of the codon. In addition, trinucleotide addition technology can be used to further constrain the distribution.

So-called "trinucleotide addition technology" is described, e.g., in Wells et al. (1985) *Gene* 34:315-323, U.S. Pat. Nos. 4,760,025 and 5,869,644. Oligonucleotides are synthesized on a solid phase support, one codon (i.e., trinucleotide) at a time. The support includes many functional groups for synthesis such that many oligonucleotides are synthesized in parallel. The support is first exposed to a solution containing a mixture of the set of codons for the first position. The unit is protected so additional units are not added. The solution containing the first mixture is washed away and the solid support is deprotected so a second mixture containing a set of codons for a second position can be added to the attached first unit. The process is iterated to sequentially assemble multiple codons. Trinucleotide addition technology enables the synthesis of a nucleic acid that at a given position can encode a number of amino acids. The frequency of these amino acids can be regulated by the proportion of codons in the mixture. Further the choice of amino acids at the given position is not restricted to quadrants of the codon table as is the case if mixtures of single nucleotides are added during the synthesis. Synthetic oligonucleotides including randomized or spiked codons can be also be used for producing a library for an affinity maturation selection.

Natural Diversity. Libraries can include regions of diverse nucleic acid sequence that originate (or are synthesized based on) from different naturally-occurring sequences. An example of natural diversity that can be included in a display library is the sequence diversity present in immune cells (see also below). Nucleic acids are prepared from these immune cells and are manipulated into a format for polypeptide display.

Antibody Display Libraries

In one embodiment, the display library presents a diverse pool of proteins, each of which includes an immunoglobulin domain, e.g., an immunoglobulin variable domain. Display libraries are particular useful, for example for identifying human or "humanized" antibodies that recognize human antigens. Such antibodies can be used as therapeutics to treat human disorders such as endothelial-related disorders, e.g., metastatic cancer. Since the constant and framework regions of the antibody are human, these therapeutic antibodies may avoid themselves being recognized and targeted as antigens. The constant regions are also optimized to recruit effector functions of the human immune system. The in vitro display selection process surmounts the inability of a normal human immune system to generate antibodies against self-antigens.

A typical antibody display library displays a polypeptide that includes a VH domain and a VL domain. An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay 1988 *Ann. Rev Immunol.* 6:381-405). The canonical structures of hypervariable loops of an immunoglobulin variable can be inferred from its sequence, as described in Chothia et al. (1992) *J. Mol. Biol.* 227:799-817; Tomlinson et al. (1992) *J. Mol. Biol.* 227:776-798); and Tomlinson et al. (1995) EMBO J. 14(18):4628-38. The display library can display the antibody as a Fab fragment (e.g., using two polypeptide chains) or a single chain Fv (e.g., using a single polypeptide chain). Other formats can also be used.

As in the case of the Fab and other formats, the displayed antibody can include a constant region as part of a light or heavy chain. In one embodiment, each chain includes one constant region, e.g., as in the case of a Fab. In other embodiments, additional constant regions are displayed.

Antibody libraries can be constructed by a number of processes (see, e.g., de Haard et al. (1999) *J. Biol. Chem* 274:18218-30; Hoogenboom et al. (1998) *Immunotechnology* 4:1-20. and Hoogenboom et al. (2000) *Immunol Today* 21:371-8). Further, elements of each process can be combined with those of other processes. The processes can be used such that variation is introduced into a single immunoglobulin domain (e.g., VH or VL) or into multiple immunoglobulin domains (e.g., VH and VL). The variation can be introduced into an immunoglobulin variable domain, e.g., in the region of one or more of CDR1, CDR2, CDR3, FR1, FR2, FR3, and FR4, referring to such regions of either or both of heavy and light chain variable domains. In one embodiment, variation is introduced into all three CDRs of a given variable domain. In another preferred embodiment, the variation is introduced into CDR1 and CDR2, e.g., of a heavy chain variable domain. Any combination is feasible. In one process, antibody libraries are constructed by inserting diverse oligonucleotides that encode CDRs into the corresponding regions of the nucleic acid. The oligonucleotides can be synthesized using monomeric nucleotides or trinucleotides. For example, Knappik et al. (2000) *J. Mol. Biol.* 296:57-86 describe a method for constructing CDR encoding oligonucleotides using trinucleotide synthesis and a template with engineered restriction sites for accepting the oligonucleotides.

In another process, an animal, e.g., a non-human animal, e.g., a rodent, is immunized with the Tie1. The animal is optionally boosted with the antigen to further stimulate the response. Then spleen cells are isolated from the animal, and nucleic acid encoding VH and/or VL domains is amplified and cloned for expression in the display library. The non-human animal can include one or more human immunoglobulin gene sequences. For example, the animal can include a complete human immunoglobulin locus. The animal may also have an inactivated endogenous immunoglobulin locus.

In yet another process, antibody libraries are constructed from nucleic acid amplified from naïve germline immunoglobulin genes (e.g., human genes). The amplified nucleic acid includes nucleic acid encoding the VH and/or VL domain. Sources of immunoglobulin-encoding nucleic acids are described below. Amplification can include PCR, e.g., with primers that anneal to the conserved constant region, or another amplification method.

Nucleic acid encoding immunoglobulin domains or fragments thereof can be obtained from the immune cells of, e.g., a human, a primate, mouse, rabbit, camel, or rodent. In one example, the cells are selected for a particular property. B cells at various stages of maturity can be selected. In another example, the B cells are naïve.

In one embodiment, fluorescent-activated cell sorting (FACS) is used to sort B cells that express surface-bound IgM, IgD, or IgG molecules. Further, B cells expressing different isotypes of IgG can be isolated. In another preferred embodiment, the B or T cell is cultured in vitro. The cells can be stimulated in vitro, e.g., by culturing with feeder cells or by adding mitogens or other modulatory reagents, such as antibodies to CD40, CD40 ligand or CD20, phorbol myristate acetate, bacterial lipopolysaccharide, concanavalin A, phytohemagglutinin or pokeweed mitogen.

In still another embodiment, the cells are isolated from a subject that has an immunological disorder, e.g., systemic lupus erythematosus (SLE), rheumatoid arthritis, vasculitis, Sjogren syndrome, systemic sclerosis, or anti-phospholipid syndrome. The subject can be a human, or an animal, e.g., an animal model for the human disease, or an animal having an analogous disorder. In yet another embodiment, the cells are isolated from a transgenic non-human animal that includes a human immunoglobulin locus.

In one preferred embodiment, the cells have activated a program of somatic hypermutation. Cells can be stimulated to undergo somatic mutagenesis of immunoglobulin genes, for example, by treatment with anti-immunoglobulin, anti-CD40, and anti-CD38 antibodies (see, e.g., Bergthorsdottir et al. (2001) *J Immunol.* 166:2228). In another embodiment, the cells are naïve.

The nucleic acid encoding an immunoglobulin variable domain can be isolated from a natural repertoire by the following exemplary method. First, RNA is isolated from the immune cell. Full length (i.e., capped) mRNAs are separated (e.g. by dephosphorylating uncapped RNAs with calf intestinal phosphatase). The cap is then removed with tobacco acid pyrophosphatase and reverse transcription is used to produce the cDNAs.

The reverse transcription of the first (antisense) strand can be done in any manner with any suitable primer. See, e.g., de Haard et al. (1999) *J. Biol. Chem* 274:18218-30. The primer binding region can be constant among different immunoglobulins, e.g., in order to reverse transcribe different isotypes of immunoglobulin. The primer binding region can also be specific to a particular isotype of immunoglobulin. Typically, the primer is specific for a region that is 3' to a sequence encoding at least one CDR. In another embodiment, poly-dT primers may be used (and may be preferred for the heavy-chain genes).

A synthetic sequence can be ligated to the 3' end of the reverse transcribed strand. The synthetic sequence can be used as a primer binding site for binding of the forward primer during PCR amplification after reverse transcription.

The use of the synthetic sequence can obviate the need to use a pool of different forward primers to fully capture the available diversity.

The variable domain-encoding gene is then amplified, e.g., using one or more rounds. If multiple rounds are used, nested primers can be used for increased fidelity. The amplified nucleic acid is then cloned into a display library vector.

Any method for amplifying nucleic acid sequences may be used for amplification. Methods that maximize and do not bias diversity are preferred. A variety of techniques can be used for nucleic acid amplification. The polymerase chain reaction (PCR; U.S. Pat. Nos. 4,683,195 and 4,683,202, Saiki, et al. (1985) *Science* 230, 1350-1354) utilizes cycles of varying temperature to drive rounds of nucleic acid synthesis. Transcription-based methods utilize RNA synthesis by RNA polymerases to amplify nucleic acid (U.S. Pat. No. 6,066,457; U.S. Pat. No. 6,132,997; U.S. Pat. No. 5,716,785; Sarkar et. al., *Science* (1989) 244: 331-34; Stofler et al., *Science* (1988) 239: 491). NASBA (U.S. Pat. Nos. 5,130,238; 5,409,818; and 5,554,517) utilizes cycles of transcription, reverse-transcription, and RNaseH-based degradation to amplify a DNA sample. Still other amplification methods include rolling circle amplification (RCA; U.S. Pat. Nos. 5,854,033 and 6,143,495) and strand displacement amplification (SDA; U.S. Pat. Nos. 5,455,166 and 5,624,825).

Secondary Screening Methods

After selecting candidate display library members that bind to a target, each candidate display library member can be further analyzed, e.g., to further characterize its binding properties for the target. Similarly candidate ligands (e.g., by immunization, etc.) obtained by other methods can also be analyzed. Each candidate ligand can be subjected to one or more secondary screening assays. The assay can be for a binding property, a catalytic property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use the display library member directly, a recombinant polypeptide produced from the nucleic acid encoding a displayed polypeptide, or a synthetic peptide synthesized based on the sequence of a displayed polypeptide. Exemplary assays for binding properties include the following.

ELISA. Proteins encoded by a display library can also be screened for a binding property using an ELISA assay. For example, each protein is contacted to a microtitre plate whose bottom surface has been coated with the target, e.g., a limiting amount of the target. The plate is washed with buffer to remove non-specifically bound polypeptides. Then the amount of the protein bound to the plate is determined by probing the plate with an antibody that can recognize the polypeptide, e.g., a tag or constant portion of the polypeptide. The antibody is linked to an enzyme such as alkaline phosphatase, which produces a colorimetric product when appropriate substrates are provided. The protein can be purified from cells or assayed in a display library format, e.g., as a fusion to a filamentous bacteriophage coat. Alternatively, cells (e.g., live or fixed) that express the target molecule, e.g., Tie1, can be plated in a microtitre plate and used to test the affinity of the peptides/antibodies present in the display library or obtained by selection from the display library.

In another version of the ELISA assay, each polypeptide of a diversity strand library is used to coat a different well of a microtitre plate. The ELISA then proceeds using a constant target molecule to query each well.

Cell Binding Assays. Tie1-binding proteins can be evaluated for their ability to interact with one or more cell types, e.g., endothelial cells or platelets. Fluorescent activated cell sorting (FACS) is one exemplary method for testing an interaction between a protein and a cell. The Tie1 binding protein is labeled directly or indirectly with a fluorophore, before or after, binding to the cells, and then cells are counted in a FACS sorter.

For example, the following method can be used to evaluate whether a Tie1 binding protein interacts with platelets or other cell types.

Isolation of Platelets. Human blood can be obtained from informed healthy volunteers. For example, venous blood is collected into one-sixth volume of ACD (2.5 g of sodium citrate, 1.5 g citric acid, and 2.5 g glucose in 100 ml dH$_2$O). The blood is centrifuged at 800×g for 15 min at room temperature and the platelet-rich plasma is removed and incubated for 60 min at 37° C. in the presence of 1 mM acetylsalicylic acid followed by centrifugation at 1000.times.g for 10 min at room temperature. The platelet pellet can be resuspended at a density of 2·10$^8$ cells/ml with HEPES-buffered Tyrode's solution (137 mM NaCl, 2.7 mM KCl, 1 mM MgCl$_2$, 3 mM NaH$_2$PO$_4$, 5 mM glucose, 10 mM HEPES pH 7.4, 0.2% bovine serum albumin, and 0.05 U/mL apyrase). See also, e.g., Kornecki et al. (1990) J Biol Chem. 265:10,042-10,048 and Naik et al. (1995) Biochem J. 310: 155-162).

FACS. For FACS analysis of platelets. Cells can be resuspended in 0.1% BSA/PBS (4×10$^5$ cells/sample) in the presence of PGE1 (1 mg/mL) and incubated with the Tie1 ligand (e.g., at about 5 μg/mL) or with a control. After a 1-hour incubation at 22° C., the cells are washed with 0.1% BSA/PBS, treated with 50 μL 1/100 diluted FITC-labeled secondary antibody, incubated for 30 minutes on ice, washed, and resuspended in 0.1% BSA/PBS. The samples are analyzed using an Immunocytometry Systems flow cytometer (FAC Sort, Becton Dickinson, San Jose, Calif.). See also, e.g., Malgorzata et al. (2000) Blood, Vol. 95 No. 8 (April 15 pp. 2600-2609.

In addition, it is possible to evaluate platelets by Westerns analysis of SDS-page separated proteins from isolated platelets and by immunoprecipitation. Still other methods involve binding cells to surfaces to which the Tie1 binding ligand is attached (e.g., coated to).

Other cell types can be prepared for FACS by methods known in the art.

Homogeneous Binding Assays. The binding interaction of candidate polypeptide with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means well known in the art (e.g., using a fluorimeter). By titrating the amount of the first or second binding molecule, a binding curve can be generated to estimate the equilibrium binding constant.

Another example of a homogenous assay is Alpha Screen (Packard Bioscience, Meriden Conn.). Alpha Screen uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding.

The homogenous assays can be performed while the candidate polypeptide is attached to the display library vehicle, e.g., a bacteriophage.

Surface Plasmon Resonance (SPR). The binding interaction of a molecule isolated from a display library and a target can be analyzed using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance (SPR)). The changes in the refractivity generate a detectable signal, which are measured as an indication of real-time reactions between biological molecules. Methods for using SPR are described, for example, in U.S. Pat. No. 5,641,640; Raether (1988) *Surface Plasmons* Springer Verlag; Sjolander and Urbaniczky (1991) *Anal. Chem.* 63:2338-2345; Szabo et al. (1995) *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_d$), and kinetic parameters, including $K_{on}$ and $K_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by crystallography or NMR). As a result, an understanding of the physical interaction between the protein and its target can be formulated and used to guide other design processes.

Protein Arrays. Proteins identified from the display library can be immobilized on a solid support, for example, on a bead or an array. For a protein array, each of the polypeptides is immobilized at a unique address on a support. Typically, the address is a two-dimensional address. Protein arrays are described below (see, e.g., Diagnostics). It is also possible to use a protein array to evaluate any plurality of proteins, e.g., for interaction with Tie1.

Cellular Assays. Candidate proteins can be selected from a library by transforming the library into a host cell; the library could have been previously identified from a display library. For example, the library can include vector nucleic acid sequences that include segments that encode the polypeptides and that direct expression, e.g., such that the proteins are produced within the cell, secreted from the cell, or attached to the cell surface. The cells can be screened or selected for proteins that bind to the Tie1, e.g., as detected by a change in a cellular phenotype or a cell-mediated activity. For example, in the case of an antibody that binds to Tie1, the activity may be autophosphorylation, activation of P13 Kinase, activation of AKT, or a change in endothelial cell activity (e.g., proliferation).

In another embodiment, the library of cells is in the form of a cellular array. The cellular array can likewise be screened for any appropriate detectable activity.

In other embodiments, competition binding assays are used to identify proteins that are compete with a reference ligand for binding to Tie1. Similarly, epitope mapping can be used to identify proteins that bind to a particular epitope of Tie. Fragments and mutants of Tie1 can be also be used in the ligand-identification process, e.g., in one or more of characterization, screening, or immunization.

Methods for Obtaining Tie1-binding Antibodies

In addition to the use of display libraries, other methods can be used to obtain a Tie1-binding antibody or in combination with the use of display libraries. For example, the Tie1 ectodomain or a region thereof can be used as an antigen in a non-human animal, e.g., a rodent.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific Mabs derived from the genes with the desired specificity may be produced and selected. See, e.g., XenoMouse™, Green et al. Nature Genetics 7:13-21 (1994), U.S. 20030070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized or deimmunized. Winter describes a CDR-grafting method that may be used to prepare the humanized antibodies of the present invention (UK Patent Application GB 2188638A, filed on Mar. 26, 1987; Winter U.S. Pat. No. 5,225,539. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen.

Humanized antibodies can be generated by replacing sequences of the Fv variable region that are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. No. 5,585,089, U.S. Pat. No. 5,693,761 and U.S. Pat. No. 5,693,762. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above. The recombinant DNA encoding the humanized antibody, or fragment thereof, can then be cloned into an appropriate expression vector.

A Tie1-binding antibody may also be modified by specific deletion of human T cell epitopes or "deimmunization" by the methods disclosed in WO 98/52976 and WO 00/34317, the contents of which are specifically incorporated by reference herein. Briefly, the heavy and light chain variable regions of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible conservative substitutions are made, often but not exclusively, an amino acid common at this position in human germline antibody sequences may be used. Human germline sequences are disclosed in Tomlinson, I. A. et al. (1992) *J. Mol. Biol.* 227:776-798; Cook, G. P. et al. (1995) *Immunol. Today* Vol. 16 (5): 237-242; Chothia, D. et al. (1992) *J. Mol. Bio.* 227:799-817. The V BASE directory provides a comprehensive directory of human immunoglobulin variable region sequences (compiled by Tomlinson, I. A. et al. MRC Centre for Protein Engineering, Cambridge, UK). After the deimmunizing changes are identified, nucleic acids encoding $V_H$ and $V_L$ can be constructed by mutagenesis or other synthetic methods (e.g., de novo synthesis, cassette replacement, and so forth). Mutagenized variable sequence can, optionally, be fused to a human constant region, e.g., human IgG1 or κ constant regions.

In some cases a potential T cell epitope will include residues which are known or predicted to be important for antibody function. For example, potential T cell epitopes are usually biased towards the CDRs. In addition, potential T cell epitopes can occur in framework residues important for antibody structure and binding. Changes to eliminate these potential epitopes will in some cases require more scrutiny, e.g., by making and testing chains with and without the change. Where possible, potential T cell epitopes that overlap the CDRs were eliminated by substitutions outside the CDRs. In some cases, an alteration within a CDR is the only option, and thus variants with and without this substitution should be tested. In other cases, the substitution required to remove a potential T cell epitope is at a residue position within the framework that might be critical for antibody binding. In these cases, variants with and without this substitution should be tested. Thus, in some cases several variant deimmunized heavy and light chain variable regions were designed and various heavy/light chain combinations tested in order to identify the optimal deimmunized antibody. The choice of the final deimmunized antibody can then be made by considering the binding affinity of the different variants in conjunction with the extent of deimmunization, i.e., the number of potential T cell epitopes remaining in the variable region. Deimmunization can be used to modify an antibody that includes a non-human sequence, e.g., a murine antibody or other non-human monoclonal antibody. Deimmunization can be used to modify an antibody isolated from a display library.

Endothelial Cell Assays

A Tie1-binding ligand or a candidate ligand can be characterized using a cellular assay, e.g., to evaluate a change in a cellular phenotype or other activity when the ligand is contacted to the cell. Typically the cell is expresses a protein that includes at least part of the ectodomain of Tie. In some embodiments, the cell expresses a full-length, mature Tie1 protein.

Endothelial cell proliferation. A candidate Tie1-binding ligand can be tested for endothelial proliferation inhibiting activity using a biological activity assay such as the bovine capillary endothelial cell proliferation assay, the chick CAM assay, the mouse corneal assay, and evaluating the effect of the ligand on implanted tumors. The chick CAM assay is described, e.g., by O'Reilly, et al. in "Angiogenic Regulation of Metastatic Growth" Cell, vol. 79 (2), Oct. 21, 1994, pp. 315-328. Briefly, three day old chicken embryos with intact yolks are separated from the egg and placed in a petri dish. After three days of incubation a methylcellulose disc containing the protein to be tested is applied to the CAM of individual embryos. After 48 hours of incubation, the embryos and CAMs are observed to determine whether endothelial growth has been inhibited. The mouse corneal assay involves implanting a growth factor-containing pellet, along with another pellet containing the suspected endothelial growth inhibitor, in the cornea of a mouse and observing the pattern of capillaries that are elaborated in the cornea.

Angiogenesis. Angiogenesis may be assayed, e.g., using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on Matrigel™ (Becton Dickinson).

Cell adhesion. Cell adhesion assays measure adhesion of cells to purified adhesion proteins or adhesion of cells to each other, in presence or absence of candidate Tie1 binding ligands. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2.times. final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays can be used to measure the ability of candidate Tie1 binding ligands to modulate binding of cells to each other. These assays can use cells that naturally or recombinantly express an adhesion protein of choice. In an exemplary assay, cells expressing the cell adhesion protein are plated in wells of a multiwell plate together with other cells (either more of the same cell type, or another type of cell to which the cells adhere). The cells that can adhere are labeled with a membrane-permeable fluorescent dye, such as BCECF, and allowed to adhere to the monolayers in the presence of candidate ligands. Unbound cells are washed off, and bound cells are detected using a fluorescence plate reader. High-throughput cell adhesion assays have also been described. See, e.g., Falsey J R et al., Bioconjug Chem. May-June 2001; 12(3):346-53.

Tubulogenesis. Tubulogenesis assays can be used to monitor the ability of cultured cells, generally endothelial cells, to form tubular structures on a matrix substrate, which generally simulates the environment of the extracellular matrix. Exemplary substrates include Matrigel™ (Becton Dickinson), an extract of basement membrane proteins containing laminin, collagen IV, and heparin sulfate proteoglycan, which is liquid at 4° C. and forms a solid gel at 37° C. Other suitable matrices comprise extracellular components such as collagen, fibronectin, and/or fibrin. Cells are stimulated with a pro-angiogenic stimulant, and their ability to form tubules is detected by imaging. Tubules can generally be detected after an overnight incubation with stimuli, but longer or shorter time frames may also be used. Tube formation assays are well known in the art (e.g., Jones M K et al., 1999, Nature Medicine 5:1418-1423). These assays have traditionally involved stimulation with serum or with the growth factors FGF or VEGF. In one embodiment, the assay is performed with cells cultured in serum free medium. In one embodiment, the assay is performed in the presence of one or more pro-angiogenic agents, e.g., inflammatory angiogenic factors such as TNF-α, or FGF, VEGF, phorbol myristate acetate (PMA), TNF-alpha, ephrin, etc.

Cell Migration. An exemplary assay for endothelial cell migration is the human microvascular endothelial (HM-VEC) migration assay. See, e.g., Tolsma et al. (1993) J. Cell Biol 122, 497-511. Migration assays are known in the art (e.g., Paik J H et al., 2001, J Biol Chem 276:11830-11837). In one example, cultured endothelial cells are seeded onto a matrix-coated porous lamina, with pore sizes generally smaller than typical cell size. The lamina is typically a membrane, such as the transwell polycarbonate membrane (Corning Costar Corporation, Cambridge, Mass.), and is generally part of an upper chamber that is in fluid contact with a lower chamber containing pro-angiogenic stimuli. Migration is generally assayed after an overnight incubation with stimuli, but longer or shorter time frames may also be used. Migration is assessed as the number of cells that crossed the lamina, and may be detected by staining cells with hemotoxylin solution (VWR Scientific.), or by any other method for determining cell number. In another exemplary set up, cells are fluorescently labeled and migration is detected using fluorescent readings, for instance using the Falcon HTS FluoroBlok (Becton Dickinson). While some migration is observed in the absence of stimulus, migration is greatly increased in response to pro-angiogenic factors. The assay can be used to test the effect of a Tie1-binding ligand on endothelial cell migration.

Sprouting assay. An exemplary sprouting assay is a three-dimensional in vitro angiogenesis assay that uses a cell-number defined spheroid aggregation of endothelial cells ("spheroid"), embedded in a collagen gel-based matrix. The spheroid can serve as a starting point for the sprouting of capillary-like structures by invasion into the extracellular matrix (termed "cell sprouting") and the subsequent formation of complex anastomosing networks (Korff and Augustin, 1999, J Cell Sci 112:3249-58). In an exemplary experimental set-up, spheroids are prepared by pipetting 400 human umbilical vein endothelial cells into individual wells of a nonadhesive 96-well plates to allow overnight spheroidal aggregation (Korff and Augustin: J Cell Biol 143: 1341-52, 1998). Spheroids are harvested and seeded in 900 μl of methocel-collagen solution and pipetted into individual wells of a 24 well plate to allow collagen gel polymerization. Test agents are added after 30 min by pipetting 100 μl of 10-fold concentrated working dilution of the test substances on top of the gel. Plates are incubated at 37° C. for 24 h. Dishes are fixed at the end of the experimental incubation period by addition of paraformaldehyde. Sprouting intensity of endothelial cells can be quantitated by an automated image analysis system to determine the cumulative sprout length per spheroid.

In some embodiments, a Tie1 binding ligand as a statistically significant effect on an assay described herein, e.g., a cellular assay desribed herein.

Ligand Production

Standard recombinant nucleic acid methods can be used to express a protein ligand that binds to Tie1. See, for example, the techniques described in Sambrook & Russell, *Molecular Cloning: A Laboratory Manual*, 3$^{rd}$ Edition, Cold Spring Harbor Laboratory, N.Y. (2001) and Ausubel et al., Current Protocols in Molecular Biology (Greene Publishing Associates and Wiley Interscience, N.Y. (1989). Generally, a nucleic acid sequence encoding the protein ligand is cloned into a nucleic acid expression vector. If the protein includes multiple polypeptide chains, each chain can be cloned into an expression vector, e.g., the same or different vectors, that are expressed in the same or different cells. Methods for producing antibodies are also provided below.

Antibody Production. Some antibodies, e.g., Fabs, can be produced in bacterial cells, e.g., *E. coli* cells. For example, if the Fab is encoded by sequences in a phage display vector that includes a suppressible stop codon between the display entity and a bacteriophage protein (or fragment thereof), the vector nucleic acid can be shuffled into a bacterial cell that cannot suppress a stop codon. In this case, the Fab is not fused to the gene III protein and is secreted into the media.

Antibodies can also be produced in eukaryotic cells. In one embodiment, the antibodies (e.g., scFv's) are expressed in a yeast cell such as Pichia (see, e.g., Powers et al. (2001) *J Immunol Methods.* 251:123-35), *Hanseula*, or *Saccharomyces*.

In one embodiment, antibodies are produced in mammalian cells. Preferred mammalian host cells for expressing the clone antibodies or antigen-binding-fragments thereof include Chinese Hamster Ovary (CHO cells) (including dhfr- CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

In an exemplary system for recombinant expression of an antibody, or antigen-binding portion thereof, of the invention, a recombinant expression vector encoding both the antibody heavy chain and the antibody light chain is introduced into dhfr- CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcγ receptors and complement C1q (Burton and Woof (1992) *Adv. Immunol.* 51:1-84; Jefferis et al. (1998) *Immunol. Rev.* 163:59-76). In a preferred embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

It is also possible to produce antibodies that bind to Tie1 by immunization, e.g., using an animal, e.g., with natural, human, or partially human immunoglobulin loci. Non-human antibodies can also be modified to include substitutions for human immunoglobulin sequences, e.g., consensus human amino acid residues at particular positions, e.g., at one or more of the following positions (preferably at least five, ten, twelve, or all): (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213.

Tie1 production. Method for producing Tie1 ectodomain protein, Tie1 protein, or Tie1 liposomes are known in the art. See, e.g., WO 93/14124.

Biotinylation Methods. A variety of methods are available to biotinylate proteins, e.g., an immunoglobulin protein or a target protein. For example, the protein can be incubated with a 5-fold molar excess of sulfo-NHS-SS-biotin in 50 mM HEPES, pH 8.0, 100 mM NaCl overnight at 4° C. Free biotin is removed by buffer exchange into PBS, 0.01% Tween 20, e.g., using a Biomax device with a 10 kDa molecular weight cut-off membrane or by dialysis. The number of biotin molecules incorporated per mole of protein can be determined using the HABA assay as described by the manufacturer (Pierce).

Pharmaceutical Compositions

In another aspect, the invention provides compositions, e.g., pharmaceutically acceptable compositions, which include an Tie1-binding ligand, e.g., an antibody molecule, other polypeptide or peptide identified as binding to Tie1, or described herein, formulated together with a pharmaceutically acceptable carrier. As used herein, "pharmaceutical compositions" encompass labeled ligands (e.g., for in vivo imaging) as well as therapeutic compositions.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., protein ligand may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for administration of humans with antibodies. The preferred mode of administration is parenteral (e.g., intravenous, subcutaneous, intraperitoneal, intramuscular). In a preferred embodiment, the Tie1-binding ligand is administered by intravenous infusion or injection. In another preferred embodiment, the Tie1-binding ligand is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutical compositions typically must be sterile and stable under the conditions of manufacture and storage. A pharmaceutical composition can also be tested to insure it meets regulatory and industry standards for administration. For example, endotoxin levels in the preparation can be tested using the Limulus amebocyte lysate assay (e.g., using the kit from Bio Whittaker lot # 7L3790, sensitivity 0.125 EU/mL) according to the USP 24/NF 19 methods. Sterility of pharmaceutical compositions can be determined using thioglycollate medium according to the USP 24/NF 19 methods. For example, the preparation is used to inoculate the thioglycollate medium and incubated at 35° C. for 14 or more days. The medium is inspected periodically to detect growth of a microorganism.

The composition can be formulated as a solution, microemulsion, dispersion, liposome, or other ordered structure suitable to high drug concentration. Sterile injectable solutions can be prepared by incorporating the active compound (i.e., the ligand) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

The anti-Tie1 protein ligands of the invention can be administered by a variety of methods known in the art, although for many applications, the preferred route/mode of administration is intravenous injection or infusion. For example, for therapeutic applications, the Tie1-binding ligand can be administered by intravenous infusion at a rate of less than 30, 20, 10, 5, or 1 mg/min to reach a dose of about 1 to 100 mg/M$^2$ or 7 to 25 mg/m$^2$. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978.

In certain embodiments, the ligand may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems, and modules are also known.

In certain embodiments, the compounds of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may include one or more moieties which are selectively transported into specific cells or organs, thus enhance targeted drug delivery (see, e.g., V. V. Ranade (1989) *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody of the invention is 0.1-20 mg/kg, more preferably 1-10 mg/kg. The Tie1-binding antibody can be administered by intravenous infusion at a rate of less than 30, 20, 10, 5, or 1 mg/min to reach a dose of about 1 to 100 mg/m$^2$ or about 5 to 30 mg/m$^2$. For ligands smaller in molecular weight than an antibody, appropriate amounts can be proportionally less. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The pharmaceutical compositions of the invention may include a "therapeutically effective amount" or a "prophylactically effective amount" of an Tie1-binding ligand of the invention. A "therapeutically effective amount" refers to an amount effective, at dosages and for periods of time necessary, to achieve the desired therapeutic result. A therapeutically effective amount of the composition may vary according to factors such as the disease state, age, sex, and weight of the individual, and the ability of the protein ligand to elicit a desired response in the individual. A therapeutically effective amount is also one in which any toxic or detrimental effects of the composition are outweighed by the therapeutically beneficial effects. A "therapeutically effective dosage" preferably inhibits a measurable parameter, e.g., inflammation or tumor growth rate by at least about 20%, more preferably by at least about 40%, even more preferably by at least about 60%, and still more preferably by at least about 80% relative to untreated subjects. The ability of a compound to inhibit a measurable parameter, e.g., cancer, can be evaluated in an animal model system predictive of efficacy in human tumors. Alternatively, this property of a composition can be evaluated by examining the ability of the compound to inhibit, such inhibition in vitro by assays known to the skilled practitioner.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention are kits including the protein ligand that binds to Tie1 and instructions for use, e.g., treatment, prophylactic, or diagnostic use. In one embodiment, the instructions for diagnostic applications include the use of the Tie1-binding ligand (e.g., antibody or antigen-binding fragment thereof, or other polypeptide or peptide) to detect Tie1, in vitro, e.g., in a sample, e.g., a biopsy or cells from a patient having an inflammatory disorder or a cancer or neoplastic disorder, or in vivo. In another embodiment, the instructions for therapeutic applications include suggested dosages and/or modes of administration in a patient with a cancer or neoplastic disorder. The kit can further contain a least one additional reagent, such as a diagnostic or therapeutic agent, e.g., a diagnostic or therapeutic agent as described herein, and/or one or more additional Tie1-binding ligands, formulated as appropriate, in one or more separate pharmaceutical preparations.

Stabilization and Retention

In one embodiment, an Tie1-binding ligand (e.g., a Tie1-binding antibody described herein) is physically associated with a moiety that improves its stabilization and/or retention in circulation, e.g., in blood, serum, lymph, or other tissues.

For example, an Tie1-binding ligand can be associated with a polymer, e.g., a substantially non-antigenic polymers, such as polyalkylene oxides or polyethylene oxides. Suitable polymers will vary substantially by weight. Polymers having molecular number average weights ranging from about 200 to about 35,000 are usually selected for the purposes of the present invention. Molecular weights of from about 1,000 to about 15,000 are preferred and 2,000 to about 12,500 are particularly preferred.

For example, an Tie1-binding ligand can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

Other compounds can also be attached to the same polymer, e.g., a cytotoxin, a label, or another targeting agent, e.g., another Tie1-binding ligand or an unrelated ligand. Mono-activated, alkoxy-terminated polyalkylene oxides (PAO's), e.g., monomethoxy-terminated polyethylene glycols (mPEG's); $C_{1-4}$ alkyl-terminated polymers; and bis-activated polyethylene oxides (glycols) can be used for crosslinking. See, e.g., U.S. Pat. No. 5,951,974.

In its most common form poly(ethylene glycol),PEG, is a linear or branched polyether terminated with hydroxyl groups and having the general structure:

$$HO\text{---}(CH_2CH_2O)_n\text{---}CH_2CH_2\text{---}OH$$

PEG can be synthesized by anionic ring opening polymerization of ethylene oxide initiated by nucleophilic attack of a hydroxide ion on the epoxide ring. Particularly useful for polypeptide modification is monomethoxy PEG, mPEG, having the general structure:

$$CH_3O\text{---}(CH_2CH_2O)_n\text{---}CH_2CH_2\text{---}OH$$

For further description, see, e.g., Roberts et al. (2002) *Advanced Drug Delivery Reviews* 54:459-476.

In one embodiment, the polymer prior to cross-linking need not be, but preferably is, water soluble. Generally, after crosslinking, the product is water soluble, e.g., exhibits a water solubility of at least about 0.01 mg/ml, and more preferably at least about 0.1 mg/ml, and still more preferably at least about 1 mg/ml. In addition, the polymer should not be highly immunogenic in the conjugate form, nor should it possess viscosity that is incompatible with intravenous infusion or injection if the conjugate is intended to be administered by such routes.

In one embodiment, the polymer contains only a single group which is reactive. This helps to avoid cross-linking of protein molecules. However, it is within the scope herein to maximize reaction conditions to reduce cross-linking, or to purify the reaction products through gel filtration or ion exchange chromatography to recover substantially homogenous derivatives. In other embodiments, the polymer contains two or more reactive groups for the purpose of linking multiple ligands to the polymer backbone. Again, gel filtration or ion exchange chromatography can be used to recover the desired derivative in substantially homogeneous form.

The molecular weight of the polymer can range up to about 500,000 D, and preferably is at least about 20,000 D, or at least about 30,000 D, or at least about 40,000 D. The molecular weight chosen can depend upon the effective size of the conjugate to be achieved, the nature (e.g. structure, such as linear or branched) of the polymer, and the degree of derivatization.

The covalent crosslink can be used to attach an Tie1-binding ligand to a polymer, for example, crosslinking to the N-terminal amino group and epsilon amino groups found on lysine residues, as well as other amino, imino, carboxyl, sulfhydryl, hydroxyl or other hydrophilic groups. The polymer may be covalently bonded directly to the Tie1-binding ligand without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylcloroformate activated PEG.) Carboxyl groups can be derivatized by coupling PEG-amine using carbodiimide. Sulfhydryl groups can be derivatized by coupling to maleimido-substituted PEG (e.g. alkoxy-PEG amine plus sulfo-succinimidyl 4-(N-maleimidomethyl)cyclohexane-1-carboxylate) WO 97/10847 or PEG-maleimide commercially available from Shearwater Polymers, Inc., Huntsville, Ala.). Alternatively, free amino groups on the ligand (e.g. epsilon amino groups on lysine residues) can be thiolated with 2-imino-thiolane (Traut's reagent) and then coupled to maleimide-containing derivatives of PEG, e.g., as described in Pedley et al., Br. J. Cancer, 70: 1126-1130 (1994).

Functionalized PEG polymers that can be attached to an Tie1-binding ligand are available, e.g., from Shearwater Polymers, Inc. (Huntsville, Ala.). Such commercially available PEG derivatives include, e.g., amino-PEG, PEG amino acid esters, PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives may vary depending on the Tie1-binding ligand, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates of an Tie1-binding ligand and a polymer can be separated from the unreacted starting materials, e.g., by gel filtration or ion exchange chromatography, e.g., HPLC. Heterologous species of the conjugates are purified from one another in the same fashion. Resolution of different species (e.g. containing one or two PEG residues) is also possible due to the difference in the ionic properties of the unreacted amino acids. See, e.g., WO 96/34015.

Treatments

Protein ligands that bind to Tie1 (e.g., those described herein) have therapeutic and prophylactic utilities. For example, these ligands can be administered to cells in culture, e.g. in vitro or ex vivo, or in a subject, e.g., in vivo, to treat, prevent, and/or diagnose a variety of disorders, such as endothelial cell disorders, blood vessel development disorders, wound healing, inflammatory diseases and cancers, particularly metastatic cancers.

As used herein, the term "treat" or "treatment" is defined as the application or administration of an Tie1-binding antibody, alone or in combination with one or more other agents (e.g., a second agent) to a subject, e.g., a patient, or application or administration of the agent to an isolated tissue or cell, e.g., cell line, from a subject, e.g., a patient, who has a disorder (e.g., a disorder as described herein), a symptom of a disorder or a predisposition toward a disorder, with the purpose to cure, heal, alleviate, relieve, alter, remedy, ameliorate, improve or affect the disorder, the symptoms of the disorder or the predisposition toward the disorder. Treating a cell refers to the inhibition of growth or activity, ablation, killing of a cell in vitro or in vivo, or otherwise reducing capacity of a cell, e.g., an aberrant cell, to mediate a disorder, e.g., a disorder as described herein (e.g., a cancerous disorder).

In one embodiment, "treating a cell" refers to a reduction in the activity and/or proliferation of a cell, e.g., a hyperproliferative cell. Such reduction does not necessarily indicate a total elimination of the cell, but a reduction, e.g., a statistically significant reduction, in the activity or the number of the cell. An example of a reduction in activity is a reduction in migration of the cell or a reduction in cell differentiation.

As used herein, an amount of an Tie1-binding ligand effective to treat a disorder, or a "therapeutically effective amount" refers to an amount of the ligand which is effective, upon single or multiple dose administration to a subject, in treating a cell, e.g., an endothelial cell (e.g., a Tie1-expressing endothelial cell) or cancer cell (particularly a metastatic cell thereof), or in prolonging curing, alleviating, relieving or improving a subject with a disorder as described herein beyond that expected in the absence of such treatment. As used herein, "inhibiting the growth" of the neoplasm refers to slowing, interrupting, arresting or stopping its growth and metastases and does not necessarily indicate a total elimination of the neoplastic growth.

As used herein, an amount of an Tie1-binding ligand effective to prevent a disorder, or a "a prophylactically effective amount" of the ligand refers to an amount of an Tie1-binding ligand, e.g., an Tie1-binding antibody described herein, which is effective, upon single- or multiple-dose administration to the subject, in preventing or delaying the occurrence of the onset or recurrence of a disorder, e.g., an endothelial cell-related disorder, a blood vessel development disorder, an inflammatory disease or a cancer.

The terms "induce", "inhibit", "potentiate", "elevate", "increase", "decrease" or the like, e.g., which denote quantitative differences between two states, refer to a difference, e.g., a statistically significant difference, between the two states. For example, "an amount effective to inhibit the proliferation of the Tie1-expressing hyperproliferative cells"

means that the rate of growth of the cells will be different, e.g., statistically significantly different, from the untreated cells.

As used herein, the term "subject" is intended to include human and non-human animals. Preferred human animals include a human patient having a disorder characterized by abnormal cell proliferation or cell differentiation. The term "non-human animals" of the invention includes all vertebrates, e.g., non-mammals (such as chickens, amphibians, reptiles) and mammals, such as non-human primates, sheep, dog, cow, pig, etc.

In one embodiment, the subject is a human subject. Alternatively, the subject can be a mammal expressing a Tie1-like antigen with which an antibody of the invention cross-reacts. A protein ligand of the invention can be administered to a human subject for therapeutic purposes (discussed further below). Moreover, an Tie1-binding ligand can be administered to a non-human mammal expressing the Tie1-like antigen to which the ligand binds (e.g., a primate, pig or mouse) for veterinary purposes or as an animal model of human disease. Regarding the latter, such animal models may be useful for evaluating the therapeutic efficacy of the ligand (e.g., testing of dosages and time courses of administration).

In one embodiment, the invention provides a method of treating (e.g., inhibiting, ablating or killing) a cell (e.g., a non-cancerous cell, e.g., a normal, benign or hyperplastic cell, or a cancerous cell, e.g., a malignant cell, e.g., cell found in a solid tumor, a soft tissue tumor, or a metastatic lesion (e.g., a cell found in renal, urothelial, colonic, rectal, pulmonary, breast or hepatic, cancers and/or metastasis)). Methods of the invention include the steps of contacting the cell with an Tie1-binding ligand, e.g., an Tie1-binding antibody described herein, in an amount sufficient to treat, e.g., inhibit, ablate or kill, the cell.

The subject method can be used on cells in culture, e.g. in vitro or ex vivo. For example, cancerous or metastatic cells (e.g., renal, urothelial, colon, rectal, lung, breast, ovarian, prostatic, or liver cancerous or metastatic cells) can be cultured in vitro in culture medium, e.g., with endothelial cells, and the contacting step can be effected by adding the Tie1-binding ligand to the culture medium. The method can be performed on cells (e.g., cancerous or metastatic cells) present in a subject, as part of an in vivo (e.g., therapeutic or prophylactic) protocol. For in vivo embodiments, the contacting step is effected in a subject and includes administering the Tie1-binding ligand to the subject under conditions effective to permit both binding of the ligand to the cell and the treating, e.g., the killing or ablating of the cell.

The method can be used to treat a cancer. As used herein, the terms "cancer", "hyperproliferative", "malignant", and "neoplastic" are used interchangeably, and refer to those cells an abnormal state or condition characterized by rapid proliferation or neoplasm. The terms include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangeably, as their context will reveal, referring generally to cells experiencing abnormal cell growth rates. Neoplasias and hyperplasias include "tumors," which may be benign, premalignant or malignant. In one embodiment, reduction in Tie1 activity by a Tie1-binding ligand can reduce or prevent angiogenesis near and around the tumor, thereby reducing or preventing tumor growth. In another embodiment, the neoplasia includes endothelial cells that are proliferating abnormally. A Tie1-binding ligand can be used to modulate the cells of the neoplasia themselves.

Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, prostate, ovary as well as adenocarcinomas which include malignancies such as most colon cancers, rectal cancer, renal-cell carcinoma, liver cancer, non-small cell carcinoma of the lung, cancer of the small intestine and so forth. Metastatic lesions of the aforementioned cancers can also be treated or prevented using the methods and compositions of the invention.

The subject method can be useful in treating malignancies of the various organ systems, such as those affecting lung, breast, lymphoid, gastrointestinal (e.g., colon), and genitourinary tract, prostate, ovary, pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. Exemplary solid tumors that can be treated include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is recognized by those skilled in the art and refers to malignant tumors of mesenchymal derivation.

The subject method can also be used to inhibit the proliferation of hyperplastic/neoplastic cells of hematopoietic origin, e.g., arising from myeloid, lymphoid or erythroid lineages, or precursor cells thereof. For instance, the invention contemplates the treatment of various myeloid disorders including, but not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97). Lymphoid malignancies which may be treated by the subject method include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the invention include, but are not limited to, non-Hodgkin's lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease. As Tie1 has been shown to be upregulated in acute myelogenous leukaemia and myelodysplastic syndrome (Verstovsek et al., 2001, Leuk, Lymphoma), B cell chronic lymphocytic leukaemia (Aguayo et al, 2001. Leukemia Research), ligands that interact with Tie1 can be used to detect, treat, or prevent these diseases.

Methods of administering Tie1-binding ligands are described in "Pharmaceutical Compositions". Suitable dosages of the molecules used will depend on the age and weight of the subject and the particular drug used. The ligands can be used as competitive agents to inhibit, reduce an undesirable interaction, e.g., between a natural or pathological agent and the Tie1.

In one embodiment, the Tie1-binding ligands are used to inhibit (e.g., inhibit at least one activity of, reduce proliferation, migration, growth or viability) of a cell, e.g., an endothelial cell in vivo. The ligands can be used by themselves or conjugated to an agent, e.g., a cytotoxic drug, radioisotope. This method includes: administering the ligand alone or attached to a cytotoxic drug, to a subject requiring such treatment.

The terms "cytotoxic agent" and "cytostatic agent" and "anti-tumor agent" are used interchangeably herein and refer to agents that have the property of inhibiting the growth or proliferation (e.g., a cytostatic agent), or inducing the killing, of hyperproliferative cells, e.g., an aberrant cancer cell. In cancer therapeutic embodiment, the term "cytotoxic agent" is used interchangeably with the terms "anti-cancer" or "anti-tumor" to mean an agent, which inhibits the development or progression of a neoplasm, particularly a solid tumor, a soft tissue tumor, or a metastatic lesion.

Nonlimiting examples of anti-cancer agents include, e.g., anti-microtubule agents, topoisomerase inhibitors, antimetabolites, mitotic inhibitors, alkylating agents, intercalating agents, agents capable of interfering with a signal transduction pathway, agents that promote apoptosis, radiation, and antibodies against other tumor-associated antigens (including naked antibodies, immunotoxins and radioconjugates). Examples of the particular classes of anti-cancer agents are provided in detail as follows: antitubulin/antimicrotubule, e.g., paclitaxel, vincristine, vinblastine, vindesine, vinorelbin, taxotere; topoisomerase I inhibitors, e.g., topotecan, camptothecin, doxorubicin, etoposide, mitoxantrone, daunorubicin, idarubicin, teniposide, amsacrine, epirubicin, merbarone, piroxantrone hydrochloride; antimetabolites, e.g., 5-fluorouracil (5-FU), methotrexate, 6-mercaptopurine, 6-thioguanine, fludarabine phosphate, cytarabine/Ara-C, trimetrexate, gemcitabine, acivicin, alanosine, pyrazofurin, N-Phosphoracetyl-L-Asparate=PALA, pentostatin, 5-azacitidine, 5-Aza 2'-deoxycytidine, ara-A, cladribine, 5-fluorouridine, FUDR, tiazofurin, N-[5-[N-(3,4-dihydro-2-methyl-4-oxoquinazolin-6-ylmethyl)-N-methylamino]-2-thenoyl]-L-glutamic acid; alkylating agents, e.g., cisplatin, carboplatin, mitomycin C, BCNU=Carmustine, melphalan, thiotepa, busulfan, chlorambucil, plicamycin, dacarbazine, ifosfamide phosphate, cyclophosphamide, nitrogen mustard, uracil mustard, pipobroman, 4-ipomeanol; agents acting via other mechanisms of action, e.g., dihydrolenperone, spiromustine, and desipeptide; biological response modifiers, e.g., to enhance anti-tumor responses, such as interferon; apoptotic agents, such as actinomycin D; and anti-hormones, for example anti-estrogens such as tamoxifen or, for example antiandrogens such as 4'-cyano-3-(4-fluorophenyl-sulphonyl)-2-hydroxy-2-methy-3'1(trifluoromethyl) propionanilide.

Since the Tie1-binding ligands recognize Tie1-expressing endothelial cells and0 can bind to endothelial cells that are associated with (e.g., in proximity of or intermingled with) cancer cells, e.g., cancerous lung, liver, colon, breast, ovarian, epidermal, laryngeal, and cartilage cells, and particularly metastatic cells thereof, Tie1-binding ligands can be used to inhibit (e.g., inhibit at least one activity, reduce growth and proliferation, or kill) any such cells to which the ligands bind. Reducing endothelial cell activity near a cancer can indirectly inhibit (e.g., inhibit at least one activity, reduce growth and proliferation, or kill) the cancer cells which may be dependent on the endothelial cells for nutrients, growth signals and so forth.

Alternatively, the ligands bind to cells in the vicinity of the cancerous cells, but are sufficiently close to the cancerous cells to directly or indirectly inhibit (e.g., inhibit at least one activity, reduce growth and proliferation, or kill) the cancers cells. aThus, the Tie1-binding ligands (e.g., modified with a toxin, e.g., a cytotoxin) can be used to selectively inhibit (e.g., kill or ablate cells in cancerous tissue (including the cancerous cells themselves and endothelial cells associated with or invading the cancer).

The ligands may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters, as described herein.

Enzymatically active toxins and fragments thereof are exemplified by diphtheria toxin A fragment, non-binding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. Procedures for preparing enzymatically active polypeptides of the immunotoxins are described in WO84/03508 and WO85/03508, and in the appended Examples below. Examples of cytotoxic moieties that can be conjugated to the antibodies include adriamycin, chlorambucil, daunomycin, methotrexate, neocarzinostatin, and platinum.

In the case of polypeptide toxins, recombinant nucleic acid techniques can be used to construct a nucleic acid that encodes the ligand (or a protein component thereof) and the cytotoxin (or a protein component thereof) as translational fusions. The recombinant nucleic acid is then expressed, e.g., in cells and the encoded fusion polypeptide isolated.

Procedures for conjugating protein ligands (e.g., antibodies) with the cytotoxic agents have been previously described. Procedures for conjugating chlorambucil with antibodies are described by Flechner (1973) *European Journal of Cancer,* 9:741-745; Ghose et al. (1972) *British Medical Journal,* 3:495-499; and Szekerke, et al. (1972) *Neoplasma,* 19:211-215. Procedures for conjugating daunomycin and adriamycin to antibodies are described by Hurwitz, E. et al. (1975) *Cancer Research,* 35:1175-1181 and Arnon et al. (1982) *Cancer Surveys,* 1:429-449. Procedures for preparing antibody-ricin conjugates are described in U.S. Pat. No. 4,414,148 and by Osawa, T., et al. (1982) *Cancer Surveys,* 1:373-388 and the references cited therein. Coupling procedures as also described in EP 86309516.2.

To kill or ablate normal, benign hyperplastic, or cancerous cells, a first protein ligand is conjugated with a prodrug which is activated only when in close proximity with a prodrug activator. The prodrug activator is conjugated with a second protein ligand, preferably one which binds to a non-competing site on the target molecule. Whether two protein ligands bind to competing or non-competing binding sites can be determined by conventional competitive binding assays. Drug-prodrug pairs suitable for use in the practice of the invention are described in Blakely et al., (1996) *Cancer Research,* 56:3287-3292.

Alternatively, the Tie1-binding ligand can be coupled to high energy radiation emitters, for example, a radioisotope, such as $^{131}$I, a γ-emitter, which, when localized at the tumor site, results in a killing of several cell diameters. See, e.g., S. E. Order, "Analysis, Results, and Future Prospective of the Therapeutic Use of Radiolabeled Antibody in Cancer Therapy", *Monoclonal Antibodies for Cancer Detection and Therapy,* R. W. Baldwin et al. (eds.), pp 303-316 (Academic Press 1985). Other suitable radioisotopes include α-emitters, such as $^{212}$Bi, $^{213}$Bi, and $^{211}$At, and β-emitters, such as $^{186}$Re and $^{90}$Y. Moreover, $Lu^{117}$ may also be used as both an imaging and cytotoxic agent.

Radioimmunotherapy (RIT) using antibodies labeled with $^{131}$I, $^{90}$Y, and $^{177}$Lu is under intense clinical investigation. There are significant differences in the physical characteristics of these three nuclides and as a result, the choice of radionuclide is very critical in order to deliver maximum radiation dose to the tumor. The higher beta energy particles of $^{90}$Y may be good for bulky tumors. The relatively low energy beta particles of $^{131}$I are ideal, but in vivo dehalogenation of radioiodinated molecules is a major disadvantage for internalizing antibody. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the tumor residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers. (Mulligan T et al. (1995) *Clin Cancer Res.* 1:1447-1454; Meredith R F, et al. (1996) *J Nucl Med* 37:1491-1496; Alvarez R D, et al. (1997) *Gynecologic Oncology* 65: 94-101).

The Tie1-binding ligands can be used directly in vivo to eliminate antigen-expressing cells via natural complement-dependent cytotoxicity (CDC) or antibody-dependent cellular cytotoxicity (ADCC). The protein ligands of the invention, can include complement binding effector domain, such as the Fc portions from IgG1, -2, or -3 or corresponding portions of IgM which bind complement. In one embodiment, a population of target cells is ex vivo treated with a binding agent of the invention and appropriate effector cells. The treatment can be supplemented by the addition of complement or serum containing complement. Further, phagocytosis of target cells coated with a protein ligand of the invention can be improved by binding of complement proteins. In another embodiment target, cells coated with the protein ligand which includes a complement binding effector domain are lysed by complement.

Also encompassed by the invention is a method of killing or ablating which involves using the anti-Tie1 ligand for prophylaxis. For example, these materials can be used to prevent or delay development or progression of cancers.

Use of the therapeutic methods of the invention to treat cancers has a number of benefits. Since the protein ligands specifically recognize Tie1, other tissue is spared and high levels of the agent are delivered directly to the site where therapy is required. Treatment in accordance with the invention can be effectively monitored with clinical parameters. Alternatively, these parameters can be used to indicate when such treatment should be employed.

Tie1-binding ligands of the invention can be administered in combination with one or more of the existing modalities for treating cancers, including, but not limited to: surgery; radiation therapy, and chemotherapy.

Diagnostic Uses

Protein ligands that bind to Tie1 (e.g., antibodies, e.g., an antibody described herein) have in vitro and in vivo diagnostic, therapeutic and prophylactic utilities.

In one aspect, the invention provides a diagnostic method for detecting the presence of a Tie1, in vitro (e.g., a biological sample, such as tissue, biopsy, e.g., a cancerous tissue) or in vivo (e.g., in vivo imaging in a subject).

The method includes: (i) contacting a sample with Tie1-binding ligand; and (ii) detecting formation of a complex between the Tie1-binding ligand and the sample. The method can also include contacting a reference sample (e.g., a control sample) with the ligand, and determining the extent of formation of the complex between the ligand and the sample relative to the same for the reference sample. A change, e.g., a statistically significant change, in the formation of the complex in the sample or subject relative to the control sample or subject can be indicative of the presence of Tie1 in the sample.

Another method includes: (i) administering the Tie1-binding ligand to a subject; and (iii) detecting formation of a complex between the Tie1-binding ligand, and the subject. The detecting can include determining location or time of formation of the complex.

The Tie1-binding ligand can be directly or indirectly labeled with a detectable substance to facilitate detection of the bound or unbound antibody. Suitable detectable substances include various enzymes, prosthetic groups, fluorescent materials, luminescent materials and radioactive materials.

Complex formation between the Tie1-binding ligand and Tie1 can be detected by measuring or visualizing either the ligand bound to the Tie1 or unbound ligand. Conventional detection assays can be used, e.g., an enzyme-linked immunosorbent assays (ELISA), a radioimmunoassay (RIA) or tissue immunohistochemistry. Further to labeling the Tie1-binding ligand, the presence of Tie1 can be assayed in a sample by a competition immunoassay utilizing standards labeled with a detectable substance and an unlabeled Tie1-binding ligand. In one example of this assay, the biological sample, the labeled standards and the Tie1 binding agent are combined and the amount of labeled standard bound to the unlabeled ligand is determined. The amount of Tie1 in the sample is inversely proportional to the amount of labeled standard bound to the Tie1 binding agent.

Fluorophore and chromophore labeled protein ligands can be prepared. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer (1968) *Science,* 162:526 and Brand, L. et al. (1972) *Annual Review of Biochemistry,* 41:843-868. The protein ligands can be labeled with fluorescent chromophore groups by conventional procedures such as those disclosed in U.S. Pat. Nos. 3,940,475, 4,289,747, and 4,376, 110. One group of fluorescers having a number of the desirable properties described above is the xanthene dyes, which include the fluoresceins and rhodamines. Another group of fluorescent compounds are the naphthylamines. Once labeled with a fluorophore or chromophore, the protein ligand can be used to detect the presence or localization of the Tie1 in a sample, e.g., using fluorescent microscopy (such as confocal or deconvolution microscopy).

Histological Analysis. Immunohistochemistry can be performed using the protein ligands described herein. For example, in the case of an antibody, the antibody can synthesized with a label (such as a purification or epitope tag), or can be detectably labeled, e.g., by conjugating a label or label-binding group. For example, a chelator can be attached to the antibody. The antibody is then contacted to a histological preparation, e.g., a fixed section of tissue that is on a microscope slide. After an incubation for binding, the preparation is washed to remove unbound antibody. The preparation is then analyzed, e.g., using microscopy, to identify if the antibody bound to the preparation. The method can be used to evaluate an endothelial cell or tissue formed by endothelial cells, e.g., blood vessels.

The antibody (or other polypeptide or peptide) can be unlabeled at the time of binding. After binding and washing, the antibody is labeled in order to render it detectable.

Protein Arrays. The Tie1-binding ligand can also be immobilized on a protein array. The protein array can be used as a diagnostic tool, e.g., to screen medical samples (such as isolated cells, blood, sera, biopsies, and the like). Of course, the protein array can also include other ligands, e.g., that bind to Tie1 or to other target molecules, such as hyaluronic acid.

Methods of producing polypeptide arrays are described, e.g., in De Wildt et al. (2000) *Nat. Biotechnol.* 18:989-994; Lueking et al. (1999) *Anal. Biochem.* 270:103-111; Ge (2000) *Nucleic Acids Res.* 28, e3, I-VII; MacBeath and Schreiber (2000) *Science* 289:1760-1763; WO 01/40803 and WO 99/51773A1. Polypeptides for the array can be spotted at high speed, e.g., using commercially available robotic apparati, e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the protein ligands can be grown on a filter in an arrayed format. Polypeptide production is induced, and the expressed polypeptides are immobilized to the filter at the location of the cell.

A protein array can be contacted with a labeled target to determine the extent of binding of the target to each immobilized polypeptide from the diversity strand library. If the target is unlabeled, a sandwich method can be used, e.g., using a labeled probed, to detect binding of the unlabeled target.

Information about the extent of binding at each address of the array can be stored as a profile, e.g., in a computer database. The protein array can be produced in replicates and used to compare binding profiles, e.g., of a target and a non-target. Thus, protein arrays can be used to identify individual members of the diversity strand library that have desired binding properties with respect to one or more molecules.

FACS. (Fluorescent Activated Cell Sorting). The Tie1-binding ligand can be used to label cells, e.g., cells in a sample (e.g., a patient sample). The ligand is also attached (or attachable) to a fluorescent compound. The cells can then be sorted using fluorescent activated cell sorted (e.g., using a sorter available from Becton Dickinson Immunocytometry Systems, San Jose Calif.; see also U.S. Pat. Nos. 5,627,037; 5,030,002; and 5,137,809). As cells pass through the sorter, a laser beam excites the fluorescent compound while a detector counts cells that pass through and determines whether a fluorescent compound is attached to the cell by detecting fluorescence. The amount of label bound to each cell can be quantified and analyzed to characterize the sample.

The sorter can also deflect the cell and separate cells bound by the ligand from those cells not bound by the ligand. The separated cells can be cultured and/or characterized.

In vivo Imaging. In still another embodiment, the invention provides a method for detecting the presence of a Tie1-expressing cancerous tissues in vivo. The method includes (i) administering to a subject (e.g., a patient having a cancer or neoplastic disorder) an Tie1-binding antibody, conjugated to a detectable marker; (ii) exposing the subject to a means for detecting said detectable marker to the Tie1-expressing tissues or cells. For example, the method can be used visualize blood vessels or the location of endothelial cells, e.g., Tie1-expressing endothelial cells. The subject can be imaged, e.g., by NMR or other tomographic means.

Examples of labels useful for diagnostic imaging in accordance with the invention include radiolabels such as $^{131}$I, $^{111}$In, $^{123}$I, $^{99m}$Tc, $^{32}$P, $^{125}$I, $^{3}$H, $^{14}$C, and $^{188}$Rh, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed. The protein ligand can be labeled with such reagents using known techniques. For example, see Wensel and Meares (1983) *Radioimmunoimaging and Radioimmunotherapy*, Elsevier, N.Y. for techniques relating to the radiolabeling of antibodies and D. Colcher et al. (1986) *Meth. Enzymol.* 121: 802-816.

A radiolabeled ligand of this invention can also be used for in vitro diagnostic tests. The specific activity of a isotopically-labeled ligand depends upon the half-life, the isotopic purity of the radioactive label, and how the label is incorporated into the antibody.

Procedures for labeling polypeptides with the radioactive isotopes (such as $^{14}$C, $^{3}$H, $^{35}$S, $^{125}$I, $^{32}$P, $^{131}$I) are generally known. For example, tritium labeling procedures are described in U.S. Pat. No. 4,302,438. Iodinating, tritium labeling, and $^{35}$S labeling procedures, e.g., as adapted for murine monoclonal antibodies, are described, e.g., by Goding, J. W. (*Monoclonal antibodies: principles and practice: production and application of monoclonal antibodies in cell biology, biochemistry, and immunology* 2nd ed. London ; Orlando: Academic Press, 1986. pp 124-126) and the references cited therein. Other procedures for iodinating polypeptides, such as antibodies, are described by Hunter and Greenwood (1962) *Nature* 144:945, David et al. (1974) *Biochemistry* 13:1014-1021, and U.S. Pat. Nos. 3,867,517 and 4,376,110. Radiolabeling elements which are useful in imaging include $^{123}$I, $^{131}$I, $^{111}$In, and $^{99m}$Tc, for example. Procedures for iodinating antibodies are described by Greenwood, F. et al. (1963) *Biochem. J.* 89:114-123; Marchalonis, J. (1969) *Biochem. J.* 113:299-305; and Morrison, M. et al. (1971) *Immunochemistry* 289-297. Procedures for $^{99m}$Tc-labeling are described by Rhodes, B. et al. in Burchiel, S. et al. (eds.), *Tumor Imaging: The Radioimmunochemical Detection of Cancer*, New York: Masson 111-123 (1982) and the references cited therein. Procedures suitable for $^{111}$In-labeling antibodies are described by Hnatowich, D. J. et al. (1983) *J. Immul. Methods*, 65:147-157, Hnatowich, D. et al. (1984) *J. Applied Radiation*, 35:554-557, and Buckley, R. G. et al. (1984) *F.E.B.S.* 166:202-204.

In the case of a radiolabeled ligand, the ligand is administered to the patient, is localized to the tumor bearing the antigen with which the ligand reacts, and is detected or "imaged" in vivo using known techniques such as radionuclear scanning using e.g., a gamma camera or emission tomography. See e.g., A. R. Bradwell et al., "Developments in Antibody Imaging", *Monoclonal Antibodies for Cancer Detection and Therapy*, R. W. Baldwin et al., (eds.), pp 65-85 (Academic Press 1985). Alternatively, a positron emission transaxial tomography scanner, such as designated Pet VI located at Brookhaven National Laboratory, can be used where the radiolabel emits positrons (e.g., $^{11}$C, $^{18}$F, $^{15}$O, and $^{13}$N).

MRI Contrast Agents. Magnetic Resonance Imaging (MRI) uses NMR to visualize internal features of living subject, and is useful for prognosis, diagnosis, treatment, and surgery. MRI can be used without radioactive tracer compounds for obvious benefit. Some MRI techniques are summarized in EP-A-0 502 814. Generally, the differences related to relaxation time constants T1 and T2 of water protons in different environments are used to generate an image. However, these differences can be insufficient to provide sharp high resolution images.

The differences in these relaxation time constants can be enhanced by contrast agents. Examples of such contrast agents include a number of magnetic agents paramagnetic agents (which primarily alter T1) and ferromagnetic or superparamagnetic (which primarily alter T2 response). Chelates (e.g., EDTA, DTPA and NTA chelates) can be used to attach (and reduce toxicity) of some paramagnetic substances (e.g., $Fe^{+3}$, $Mn^{+2}$, $Gd^{+3}$). Other agents can be in the form of particles, e.g., less than 10 µm to about 10 nM in diameter). Particles can have ferromagnetic, antiferromagnetic or superparamagnetic properties. Particles can include, e.g., magnetite ($Fe_3O_4$), $\gamma$-$Fe_2O_3$, ferrites, and other magnetic mineral compounds of transition elements. Magnetic particles may include: one or more magnetic crystals with and without nonmagnetic material. The nonmagnetic material can include synthetic or natural polymers (such as sepharose, dextran, dextrin, starch and the like The Tie1-binding ligands can also be labeled with an indicating group containing of the NMR-active $^{19}$F atom, or a plurality of such atoms inasmuch as (i) substantially all of naturally abundant fluorine atoms are the $^{19}$F isotope and, thus, substantially all fluorine-containing compounds are NMR-active; (ii) many chemically active polyfluorinated compounds such as trifluoracetic anhydride are commercially available at relatively low cost, and (iii) many fluorinated compounds have been found medically acceptable for use in humans such as the perfluorinated polyethers utilized to carry oxygen as hemoglobin replacements. After permitting such time for incubation, a whole body MRI is carried out using an apparatus such as one of those described by Pykett (1982) *Scientific American*, 246:78-88 to locate and image cancerous tissues.

Information obtained from evaluating an Tie1-binding ligand, e.g., a ligand described herein, can be recorded on machine-compatible media, e.g., computer readable or computer accessible media. The information can be stored as a computer representation, e.g., in a database (e.g., in the case of imaging using a ligand, a database of images for one or a plurality of subjects). The term "computer representation" refers to information which is in a form that can be manipulated by a computer. The act of storing a computer representation refers to the act of placing the information in a form suitable for manipulation by a computer.

Also within the scope of the invention are kits including the protein ligand that binds to Tie1 and instructions for diagnostic use, e.g., the use of the Tie1-binding ligand (e.g., antibody or antigen-binding fragment thereof, or other polypeptide or peptide) to detect Tie1, in vitro, e.g., in a sample, e.g., a biopsy or cells from a patient having a cancer or neoplastic disorder, or in vivo, e.g., by imaging a subject. The kit can further contain a least one additional reagent, such as a label or additional diagnostic agent. For in vivo use the ligand can be formulated as a pharmaceutical composition.

The following invention is further illustrated by the following examples (commencing on the following page), which should not be construed as limiting.

EXAMPLES

Example 1

An exemplary Tie1 amino acid sequence is as follows:

(SEQ ID NO: 2)
MVWRVPPFLLPILFLASHVGAAVDLTLLANLRLTDPQRFFLTCVSGEAGA

GRGSDAWGPPLLLEKDDRIVRTPPGPPLRLARNGSHQVTLRGFSKPSDLV

GVFSCVGGAGARRTRVIYVHNSPGAHLLPDKVTHTVNKGDTAVLSARVHK

EKQTDVIWKSNGSYFYTLDWHEAQDGRFLLQLPNVQPPSSGIYSATYLEA

SPLGSAFFRLIVRGCGAGRWGPGCTKECPGCLHGGVCHDHDGECVCPPGF

TGTRCEQACREGRFGQSCQEQCPGISGCRGLTFCLPDPYGCSCGSGWRGS

QCQEACAPGHFGADCRLQCQCQNGGTCDRFSGCVCPSGWHGVHCEKSDRI

PQILNMASELEFNLETMPRINCAAAGNPFPVRGSIELRKPDGTVLLSTKA

IVEPEKTTAEFEVPRLVLADSGFWECRVSTSGGQDSRRFKVNVKVPPVPL

AAPRLLTKQSRQLVVSPLVSFSGDGPISTVRLHYRPQDSTMDWSTIVVDP

SENVTLMNLRPKTGYSVRVQLSRPGEGGEGAWGPPTLMTTDCPEPLLQPW

LEGWHVEGTDRLRVSWSLPLVPGPLVGDGFLLRLWDGTRGQERRENVSSP

QARTALLTGLTPGTHYQLDVQLYHCTLLGPASPPAHVLLPPSGPPAPRHL

HAQALSDSEIQLTWKHPEALPGPISKYVVEVQVAGGAGDPLWIDVDRPEE

TSTIIRGLNASTRYLFRMRASIQGLGDWSNTVEESTLGNGLQAEGPVQES
RAAEEGLDQQLILAVVGSVSATCLTILAALLTLVCIRRSCLHRRRTFTYQ
SGSGEETILQFSSGTLTLTRRPKLQPEPLSYPVLEWEDITFEDLIGEGNF
GQVIRAMIKKDGLKMNAAIKMLKEYASENDHRDFAGELEVLCKLGHHPNI
INLLGACKNRGYLYIAIEYAPYGNLLDFLRKSRVLETDPAFAREHGTAST
LSSRQLLRFASDAANGMQYLSEKQFIHRDLAARNVLVGENLASKIADFGL

SRGEEVYVKKTMGRLPVRWMAIESLNYSVYTTKSDVWSFGVLLWEIVSLG
GTPYCGMTCAELYEKLPQGYRMEQPRNCDDEVYELMRQCWRDRPYERPPF
AQIALQLGRMLEARKAYVNMSLFENFTYAGIDATAEEA

An exemplary nucleic acid sequence that encodes Tie1 is as follows:

```
atggtctggc gggtgccccc tttcttgctc cccatcctct tcttggcttc tcatgtgggc    60  (SEQ ID NO: 1)
gcggcggtgg acctgacgct gctggccaac ctgcggctca cggaccccca gcgcttcttc   120
ctgacttgcg tgtctgggga ggccggggcg ggaggggct cggacgcctg ggcccgccc    180
ctgctgctgg agaaggacga ccgtatcgtg cgcaccccgc ccgggccacc cctgcgcctg   240
gcgcgcaacg gttcgcacca ggtcacgctt cgcggcttct ccaagccctc ggacctcgtg   300
ggcgtcttct cctgcgtggg cggtgctggg cgcggcgca cgcgcgtcat ctacgtgcac    360
aacagccctg agcccacct gcttccagac aaggtcacac acactgtgaa caaaggtgac    420
accgctgtac tttctgcacg tgtgcacaag agaagcaga cagacgtgat ctggaagagc    480
aacggatcct acttctacac cctggactgg catgaagccc aggatgggcg gttcctgctg   540
cagctcccaa atgtgcagcc accatcgagc ggcatctaca gtgccactta cctggaagcc   600
agcccctgg gcagcgcctt ctttcggctc atcgtgcggg gttgtgggc tgggcgctgg    660
gggccaggct gtaccaagga gtgcccaggt tgcctacatg gaggtgtctg ccacgaccat   720
gacggcgaat gtgtatgccc ccctggcttc actggcaccc gctgtgaaca ggcctgcaga   780
gagggccgtt ttgggcagag ctgccaggag cagtgcccag gcatatcagg ctgccggggc   840
ctcaccttct gcctcccaga ccccctatggc tgctcttgtg atctggctg gagaggaagc   900
cagtgccaag aagcttgtgc cctggtcat tttggggctg attgccgact ccagtgccag   960
tgtcagaatg gtggcacttg tgaccggttc agtggttgtg tctgcccctc tgggtggcat  1020
ggagtgcact gtgagaagtc agaccggatc ccccagatcc tcaacatggc ctcagaactg  1080
gagttcaact tagagacgat gccccggatc aactgtgcag ctgcaggaa ccccttcccc   1140
gtgcggggca gcatagagct acgcaagcca cggcactg tgctcctgtc caccaaggcc   1200
attgtggagc cagagaagac cacagctgag ttcgaggtgc ccgcttggt tcttgcggac   1260
agtgggttct gggagtgccg tgtgtccaca tctggcggcc aagacagccg gcgcttcaag  1320
gtcaatgtga aagtgccccc cgtgcccctg gctgcacctc ggctcctgac caagcagagc  1380
cgccagcttg tggtctcccc gctggtctcg ttctctgggg atggaccat ctccactgtc   1440
cgcctgcact accggcccca ggacagtacc atgactggt cgaccattgt ggtggacccc   1500
agtgagaacg tgacgttaat gaacctgagg ccaaagacag gatacagtgt tcgtgtgcag  1560
ctgagccggc caggggaagg aggagaggggg gcctggggc ctcccaccct catgaccaca  1620
gactgtcctg agcctttgtt gcagccgtgg ttggagggct ggcatgtgga aggcactgac  1680
cggctgcgag tgagctggtc cttgccttg gtgccgggc cactggtggg cgacggtttc    1740
ctgctgcgcc tgtgggacgg gacacggggg caggagcggc gggagaacgt ctcatccccc  1800
caggcccgca ctgccctcct gacgggactc acgcctggca cccactacca gctggatgtg  1860
```

```
                                    -continued
cagctctacc actgcaccct cctgggcccg gcctcgcccc ctgcacacgt gcttctgccc  1920
cccagtgggc ctccagcccc ccgacacctc cacgcccagg ccctctcaga ctccgagatc  1980
cagctgacat ggaagcaccc ggaggctctg cctgggccaa tatccaagta cgttgtggag  2040
gtgcaggtgg ctgggggtgc aggagaccca ctgtggatag acgtggacag gcctgaggag  2100
acaagcacca tcatccgtgg cctcaacgcc agcacgcgct acctcttccg catgcgggcc  2160
agcattcagg ggctcgggga ctggagcaac acagtagaag agtccaccct gggcaacggg  2220
ctgcaggctg agggcccagt ccaagagagc cgggcagctg aagagggcct ggatcagcag  2280
ctgatcctgg cggtggtggg ctccgtgtct gccacctgcc tcaccatcct ggccgccctt  2340
ttaaccctgg tgtgcatccg cagaagctgc ctgcatcgga gacgcacctt cacctaccag  2400
tcaggctcgg gcgaggagac catcctgcag ttcagctcag ggaccttgac acttacccgg  2460
cggccaaaac tgcagcccga gcccctgagc tacccagtgc tagagtggga ggacatcacc  2520
tttgaggacc tcatcgggga ggggaacttc ggccaggtca tccgggccat gatcaagaag  2580
gacgggctga agatgaacgc agccatcaaa atgctgaaag agtatgcctc tgaaaatgac  2640
catcgtgact ttgcgggaga actggaagtt ctgtgcaaat tggggcatca ccccaacatc  2700
atcaacctcc tgggggcctg taagaaccga ggttacttgt atatcgctat tgaatatgcc  2760
ccctacggga acctgctaga ttttctgcgg aaaagccggg tcctagagac tgacccagct  2820
tttgctcgag agcatgggac agcctctacc cttagctccc ggcagctgct gcgtttcgcc  2880
agtgatgcgg ccaatggcat gcagtacctg agtgagaagc agttcatcca cagggacctg  2940
gctgcccgga atgtgctggt cggagagaac ctagcctcca agattgcaga cttcggcctt  3000
tctcggggag aggaggttta tgtgaagaag acgatggggc gtctccctgt gcgctggatg  3060
gccattgagt ccctgaacta cagtgtctat accaccaaga gtgatgtctg gtcctttgga  3120
gtccttcttt gggagatagt gagccttgga ggtacaccct actgtggcat gacctgtgcc  3180
gagctctatg aaaagctgcc ccagggctac cgcatggagc agcctcgaaa ctgtgacgat  3240
gaagtgtacg agctgatgcg tcagtgctgg cgggaccgtc cctatgagcg accccccttt  3300
gcccagattg cgctacagct aggccgcatg ctggaagcca ggaaggccta tgtgaacatg  3360
tcgctgtttg agaacttcac ttacgcgggc attgatgcca cagctgagga ggcctga     3417
```

Example 2

Selection and Primary Screening

We have used phage display to select Tie1-specific antibodies from a very large phage library that displays immunoglobulins as Fab fragments. To isolate antibodies specific to Tie1, a phage displayed Fab antibody library was selected against the Tie1 extracellular domain fused to human Fc or to a histidine purification tag.

Selection in solution was done using biotin labelled antigen which was captured on streptavidin coated magnetic beads (M-280-DYNAL). Selection on cells expressing Tie1 was performed using a Kingfisher automated magnetic bead capture device. Selection on immobilized antigen was performed using Tie1-Fc coated onto immunotubes.

Several selection strategies were used:

Strategy 1: Round 1 (500 mM biotin labelled Tie1/magnetic beads), Round 2 (1×10⁷ Tie1 expressing cells/Kingfisher), Round 3 (1×10⁷ Tie1 expressing cells/Kingfisher)

Strategy 2: Round 1 (500 mM biotin labelled Tie1/magnetic beads), Round 2 (1×10⁷ Tie1 expressing cells/Kingfisher), (300 mM biotin labelled Tie1/magnetic beads)

Strategy 3: Round 1 (Tie1 Fc coated immunotubes at 5 μg/ml), Round 2 (Tie1-Fc coated immunotubes), Round 3 (Tie1 Fc coated immunotubes plus depletion with human IgG)

Library members recovered from the selection strategies were tested for antigen binding in phage ELISA. Each isolate was tested for binding to coated Tie1 Fc. Strategy 1 did not identify any binding clones whereas strategy 2 identified 13 positive clones (n=95). Strategy 3 identified 86 binding clones (n=95).

Sequence analysis of the selected clones were grouped on the basis of the CDR3 selected of the heavy chain and resulted in 23 different antibodies with unique VH-CDR3 sequences.

We reformatted the selected Fabs as completely human antibodies by recloning the VH and VL coding sequences from the display library vector into two vectors of a mammalian expression vector system. These vectors contain the human kappa constant domain and the human gamma-1 heavy chain constant region. The vectors were co-transfected into mammalian CHO-K1 cells for expression and production of the corresponding complete IgGs. These antibodies were characterized using several assays as described below, including:

1. Western blotting and immunoprecipitation of Tie1 transfected cells and primary human endothelial cells;
2. Immunofluorescence of Tie1 transfected cells and primary human endothelial cells;
3. Stimulation and inhibition of Tie1 in Ba/F3 cells and primary human endothelial cells; and
4. Immunostaining of human tissues.

We identified 23 antibodies that interact with Tie1. See also Table 1, below.

After sequence confirmation of the reformatted clones they were used in a transient transfection of Hek293T cells. After growth the IgG was purified from culture supernatants using a protein A column. The quality of purified IgG1 was determined using SDS-PAGE.

The specificity of the Tie1 specific IgG's can be determined in a whole cell ELISA on mouse lung microvascular endothelial cells (LEII) and LEII-Tie1 cells transfected with a Tie1 expression construct. Cells are seeded into 96 well plates at a density of 10,000 cells/well and were fixed using 4% paraformaldehyde. Staining and detection of binding of IgG1 to LE11 cells are detected using standard labelling with a HRP conjugated rabbit anti human HRP and TMB staining. Binding of purified IgG1 to LEII-Tie1 transfected cells can also be corrected for Tie1 protein that is expressed endogenously. Alternatively cells that have little or no endogenous Tie1 can be used for the analysis.

At least one of the binding antibodies—E3—functions as a Tie1 activating antibody in the BaF3 cell bioassay. We studied Tie1 phosphorylation in response to E3 IgG treatment in transiently transfected COS1 cells and human primary endothelial cells. Our results indicate that E3 IgG activates the Tie1 receptor. E3 can be used, instead of possible natural ligands to characterize several functions of Tie1 in vitro and in vivo. The region of Tie1 which interacts with E3 can be the target for small molecular weight compounds for Tie1 activation or inhibition. Although E3 functions in one particular Tie1 activating assay, E3 and other positives in this assay may also have inhibitory effect as to other functions or in other contexts. For example, E3 can inhibit tube formation by HUVEC cells. See below.

In addition, we found two antibodies that inhibit the survival effect conferred by E3 in the BaF3 cell bioassay. These two antibodies may inhibit dimerization of Tie1 induced by E3 in the BaF3 assay. Two antibodies, B2 and D11, completely blocked the viability of Tie1/EpoR cells when used in combination with E3. Thus, B2 and D11 antibodies can be used to inhibit Tie1 in vivo.

Methods

Cell Culture

COS1 cells were cultured in Dulbecco's modified Eagle's medium (DMEM) supplemented with 10% fetal calf serum (FCS), glutamine and antibiotics. The murine Ba/F3 pre-B lymphocytes were cultured in DMEM supplemented with 10% FCS, glutamine, antibiotics and 2 ng/ml interleukin-3 (Calbiochem). Human dermal microvascular endothelial cells (HDMVECs), obtained from PromoCell (Heidelberg, Germany) were cultured in endothelial cell medium provided by the supplier and used at passages 4-7.

Western Blotting and Immunoprecipitation

COS1 cells were transfected with pcDNA3-Tie1-V5 (1 µg DNA per 10 cm cell culture plate) using FUGENE 6 (Roche) according to manufacturer's instruction and incubated for 48 h before stimulation. For immunoprecipitation, Tie1 transfected cells and HMVEC cells were lysed in DOC-RIPA lysis buffer (50 mM Tris-HCl pH 8.0, 150 mM NaCl, 1% Triton-X-100, 0.1% SDS, 1% DOC, 10 mM EDTA) supplemented with aprotinin, leupeptin, PMSF and sodium vanadate. Immunoprecipitation was carried out from equal amount of cell lysates by incubating with polyclonal anti-human Tie1 antibodies (R&D), monoclonal anti-V5 antibodies (Invitrogen) or altogether 23 anti-Tie1 antibodies (1 µg/ml) for 1 to 2 h followed by incubation with protein G-Sepharose (Amersham Pharmacia Biotech AB) for 1 h. The immunoprecipitates were washed twice with PBS-T and twice with PBS, followed by elution with the Laemmli buffer and separation in 8% SDS-PAGE. The blots were probed with the 23 anti-Tie1 antibodies (5 µg/ml) and subsequently anti-human Fc antibodies conjugated with HRP.

Immunofluorescence Staining

COS1 cells on the glass coverslips were transiently transfected with pcDNA3-Tie1-V5 (the V5-epitope was added to the 3' terminus of pcDNA3-Tie1) (1 µg DNA per 10 cm cell culture plate) using FUGENE™ 6 (Roche) according to manufacturer's instruction and incubated for 48 h before staining. Cells were fixed in 4% paraformaldehyde for 10 min at 4° C. If required, the cells were permeabilized with 0.2% Triton X-100 in PBS for 5 min. Unspecific binding sites were blocked by incubation with 1% BSA in PBS for 30 min. The cells were then stained with anti-Tie1 antibodies (5 µg/ml) and anti-V5 antibodies for 1 h at room temperature, followed by incubation with FITC-conjugated anti-human antibodies (DAKO, 40 µg/ml) and TRITC-conjugated anti-mouse antibodies (DAKO, 15 µg/ml) for 30 min. Hoechst 33258 fluorochrome (Sigma, 0.5 µg/ml) was used for the staining of the nuclei.

Ba/F3 Bioassay

To generate Tie1-EpoR expressing Ba/F3 cells for the bioassay, Ba/F3 pre-B cells were stably transfected with a nucleic acid that expresses chimeric receptor containing the extracellular domain of human Tie1 fused with the transmembrane and cytoplasmic domains of the mouse erythropoietin receptor. The nucleic acid used was a Tie1-EpoR chimeric cDNA in a pEF-BOS expression vector. The nucleic acid encoding the chimeric receptor was constructed by cloning the PCR amplified extracellular part of human Tie1 (bp 37-2316 of X60975) as EcoRI-BglII fragment into mEpoR-pcDNA vector. The cDNA encoding for the chimeric receptor consisting of the extracellular part of Tie1 fused with the transmembrane and intracellular domains of EpoR was subcloned into the pEF-BOS expression vector. Vector was linearized and co-transfected into Ba/F3 cells with pcDNA3.1(+) Zeo vector (Invitrogen). Stable cell pools were generated by selection with 250 µg/ml Zeocin. The expression of Tie1/EpoR fusion protein in several clones was analyzed by Western blotting with an antibody against EpoR.

To perform the assays, Ba/F3 cells expressing the Tie1-EpoR chimera were split in 96-well microtiter plates at 50 000 cells/well in the presence of the indicated concentrations of anti-Tie1 antibodies. As controls, Zeocin resistant pools not expressing the Tie1-EpoR were used. After 48 h, the viability of the cells was determined by adding MTT (3-(4, 5-dimethylthiazol-2-yl)-2,5-diphenyl tetrazolium bromide (Sigma), 0.5 mg/ml), followed by further 2 h of culture, addition of an equal volume of cell lysis solution (10% SDS, 10 mM HCl) and incubation overnight at 37° C. Absorbance was measured at 540 nm.

Tie1 Phosphorylation Assay

COS1 cells were transfected with pcDNA3-Tie1-V5. After 24 h of transfection, the cells were serum starved for 8 h and then treated with E3 IgG. For the Tie1 phosphorylation assay, HDMVECs were cultured on 10 cm dishes to near confluence, starved (8-16 h) in serum free medium and stimulated as indicated. After the stimulations, the cells were lysed in lysis buffer (RIPA-DOC: 50 mM Tris-HCl pH 8.0, 150 mM NaCl, 1% Triton-X-100, 0.1% SDS, 0.5% DOC, 10 mM EDTA, supplemented with aprotinin, leupeptin, PMSF and sodium vanadate). Clarified lysates from transfected COS1 cells or HDMVECs were immunoprecipitated with anti-V5 or anti-Tie1 B9, respectively. Proteins were separated by SDS-PAGE, transferred to nitrocellulose and immunoblotted using the anti-phosphotyrosine and anti-Tie1 (R&D systems) antibodies.

Immunostaining of Human Tissues

To evaluate reactivity of anti-Tie1 antibodies in immunohistochemistry, 5 μm cryosections of human kidney and lung were dried at room temperature for 30 min and fixed with cold acetone for 10 min. Slides were washed with PBS and treated with 0.03% $H_2O_2$ in PBS for 15 min to reduce endogenous peroxidase activity. TNB (30 min at room temperature) was used to block non-specific binding and sections were incubated with Tie1 antibodies at concentration of 10 μg/ml overnight at +4° C. After several washings with PBS, biotinylated anti human antibody (1:300, Zymed) was added to the tissues. Signal was amplified by using a TSA kit and detected with AEC staining.

Results

Western blotting, immunoprecipitation and immunofluorescence of Tie1 transfected cells and primary human endothelial cells (see Table 1).

TABLE 1

Assay Summary

| Clone | WB: Tie1-transfected | WB: HDMEC | IP: Tie1-transfected | IP: HDMEC | IF: Tie1-transfected | IF: HDMEC | BaF3 assay |
|---|---|---|---|---|---|---|---|
| E3 | + | + | ND | − | + | + | + |
| G2 | + | + | ++ | + | + | ++ | − |
| A2 | + | + | ++ | + | + | ++ | − |
| A10 | + | + | ++ | + | + | + | − |
| B2 | + | + | + | − | + | + | − |
| B9 | + | + | ++ | ++ | ++ | + | − |
| C2 | + | + | ++ | ++ | + | ++ | − |
| C7 | + | + | ++ | + | + | + | − |
| C10 | + | + | ++ | ++ | ++ | + | − |
| D11 | + | + | + | − | + | ++ | − |
| E11 | + | + | ++ | + | + | ++ | − |
| G10 | + | + | ++ | + | ++ | + | − |
| H1 | + | + | ++ | + | ++ | + | − |
| H4 | + | + | ++ | + | + | + | − |
| P-A1 | + | + | ++ | ++ | + | ++ | − |
| P-A10 | + | + | ++ | − | + | + | − |
| P-B1 | + | + | + | − | weak | + | − |
| P-B3 | + | + | − | − | + | + | − |
| P-C6 | + | + | + | − | + | ++ | − |
| P-D12 | + | + | + | − | + | + | − |
| P-F3 | + | + | − | − | ++ | ++ | − |
| P-F4 | + | + | ++ | − | cross | ++ | − |
| P-G3 | + | + | ++ | + | + | + | − |
| PH1 | − | − | − | − | − | − | − |

To confirm the binding ability of the 23 selected anti-Tie1 antibodies, we first performed western blotting and immunoprecipitation using COS1 cells transfected with pcDNA3-Tie1-V5 (V5 tagged) and primary endothelial cells. Next, to find out if the anti-Tie1 antibodies recognize Tie1 in living cells, those cells were studied by immunofluorescence staining. All the antibodies analyzed recognized both transfected and endogenous Tie1, although differences were detected in the binding affinity as shown in Table 1.

Stimulation and Inhibition of Tie1 in Tie1-EpoR Transfected Ba/F3 Cells and Human Primary Endothelial Cells Although no ligand for Tie1 has been identified, we used the following efficient screening method for Tie1-binding ligands. Interleukin-3 dependent pre-B-lymphocyte (Ba/F3) cells were transfected with a construct that expresses a Tie1-EpoR fusion protein. Since Ba/F3 cells are IL-3 dependent, they die unless IL-3 is provided. However, Tie-EpoR receptor expressing Ba/F3 cells can survive and proliferate if the medium contains a Tie1-binding ligand, either a natural ligand or an artificial mimetic. Cell survival can be quantitated, e.g., by calorimetric MTT-assay, which measures mitochondrial activity.

The results from the BaF3 cell assays indicated that, of the 23 different monoclonal antibodies tested, only E3 IgG was able to promote survival of Tie1-EpoR cells whereas the viability of EpoR Ba/F3 cells used as a control was not affected by E3 IgG. The IgG part of the immunoglobulin molecule was needed for the survival effect of E3 IgG, as the E3 Fab fragment had no effect on the viability of Tie1-EpoR cells. A concentration of 50 ng/ml of E3 IgG gave almost maximal viability in Tie1-EpoR cell survival assays.

To test if the E3 IgG binding to the extracellular region of Tie1 induces autophosphorylation of Tie1, the Tie1 receptor phosphorylation level in response to E3 IgG treatment was studied in transiently transfected COS1 cells and human primary endothelial cells. COS1 cells were transfected with an expression vector containing a V5-tagged full length Tie1 cDNA, and, after serum starvation, the cells were treated with E3 IgG (200 ng/ml). Cell lysates were extracted at several time points and Tie1 was immunoprecipitated with anti-V5 followed by western blotting using anti-phosphotyrosine and anti-Tie1 antibodies. The results indicated that Tie1 is tyrosine phosphorylated after 10 to 30 min of E3 IgG stimulation. To determine if E3 IgG induces Tie1 phosphorylation in primary endothelial cells, HDMVEC cells were serum starved and stimulated with several concentrations of E3 for 60 min. Tie1 was then immunoprecipitated from cell lysates and subjected to anti-phosphotyrosine blotting analysis, which showed receptor phosphorylation following E3 IgG stimulation at 50-200 ng/ml. Also higher concentrations of E3 (500-1000 ng/ml) induced Tie1 phosphorylation but the response was more rapid and was most prominent after 5 min of stimulation.

To study the kinetics of E3 IgG induced Tie1 activation, cells were stimulated with E3 IgG (200 ng/ml) and receptor phosphorylation was studied at various time points. Tie1 phosphorylation was highest 15-30 min after E3 IgG treatment but phosphorylation persisted for up to 1 h.

To determine if any of the other monoclonal antibodies tested inhibit the survival effect of E3 IgG in Tie1-EpoR Ba/F3 assay, antibodies were studied in combination with E3 IgG. A concentration of 100 ng/ml of E3 IgG together with 100 (1:1) or 500 (1:5) ng/ml of the other antibodies were used and the viability of Tie1-EpoR cells was measured. The results from both combinations of E3 IgG and the test antibody (in 1:1 and 1:5 ratios) were similar and indicated that two of the 23 antibodies (B2 and D11) blocked completely the survival effect of E3 IgG (Table 2). Several antibodies (A2, A10, P-B1, P-B3 and P-C6) inhibited the viability effect of E3 IgG to some extent and two of the antibodies (G2 and C7) promoted the survival of Tie1/EpoR Ba/F3 cells in combination with E3 IgG.

TABLE 2

| Treatment | BaF3 Assay Average MTT activity in BaF3 cell assay | St. Dev. |
|---|---|---|
| IL3, 2 | 0.48 | 0.038 |
| 0 | 0.01 | 0.003 |
| E3 | 0.61 | 0.032 |
| E3 + G2 | 0.74 | 0.034 |
| E3 + A2 | 0.38 | 0.016 |
| E3 + A10 | 0.52 | 0.011 |
| E3 + B2 | 0.00 | 0.001 |
| E3 + B9 | 0.65 | 0.011 |
| E3 + C2 | 0.62 | 0.016 |
| E3 + C7 | 0.84 | 0.086 |
| E3 + C10 | 0.67 | 0.004 |
| E3 + D11 | 0.01 | 0.003 |
| E3 + E11 | 0.61 | 0.048 |
| E3 + G10 | 0.65 | 0.010 |
| E3 + H1 | 0.60 | 0.017 |
| E3 + H4 | 0.65 | 0.026 |
| E3 + PA1 | 0.60 | 0.035 |
| E3 + PA10 | 0.65 | 0.041 |
| E3 + PB1 | 0.47 | 0.011 |
| E3 + P-B3 | 0.51 | 0.007 |
| E3 + PC6 | 0.35 | 0.008 |
| E3 + PD12 | 0.60 | 0.038 |
| E3 + PF3 | 0.55 | 0.032 |
| E3 + PF4 | 0.56 | 0.009 |
| E3 + PG3 | 0.77 | 0.030 |
| E3 + PH1 | 0.63 | 0.040 |

Immunostaining of Human Tissues

The anti-Tie1 antibodies react with human Tie1 in cultured cells. It is also possible to determine whether they could stain human tissue samples from lung and kidney as well as from tumors by using biotinylated anti-Tie1 antibodies and detecting bound antibodies using labeled streptavidin or avidin.

In one embodiment, Tie ligands (such as the Tie1 antibodies described herein can be produced from gene-based vectors, such as transgenes or via adenoviral delivery.

Example 3

Exemplary Sequences

The following are sequences of exemplary immunoglobulin variable domains:

Translation of Reverse_Complement_VH-PA1-Tie1-phagemid.TXT(1-396)

Universal code

Total amino acid number: 132, MW=14169

Max ORF: 1-396, 132 AA, MW=14169

```
  1 GAAGTTCAATTGTTAGAGTCTGGTGGCGGTCTTGTTCAGCCTGGTGGTTCTTTACGTCTT  (SEQ ID NO: 3)
  1 E  V  Q  L  L  E  S  G  G  G  L  V  Q  P  G  G  S  L  R  L   (SEQ ID NO: 4)

61 TCTTGCGCTGCTTCCGGATTCACTTTCTCTATTTACAAGATGTCTTGGGTTCGCCAAGCT
 21 S  C  A  A  S  G  F  T  F  S  I  Y  K  M  S  W  V  R  Q  A

121 CCTGGTAAAGGTTTGGAGTGGGTTTCTTCTATCTATCCTTCTGGTGGCCAGACTAAGTAT
 41 P  G  K  G  L  E  W  V  S  S  I  Y  P  S  G  G  Q  T  K  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81 L  Q  M  N  S  L  R  A  E  D  T  A  V  Y  Y  C  A  R  V  N

301 TACTATGATAGTAGTGGTTACGGTCCTATAGCTCCTGGACTTGACTACTGGGGCCAGGGA
101 Y  Y  D  S  S  G  Y  G  P  I  A  P  G  L  D  Y  W  G  Q  G

361 ACCCTGGTCACCGTCTCAAGCGCCTCCACCAAGGGC
121 T  L  V  T  V  S  S  A  S  T  K  G
```

Translation of VL-PA1-Tie1-phagemid.TXT(1-311)
Universal code
Total amino acid number: 103, MW=11169
Max ORF: 1-309, 103 AA, MW=11169

Translation of VL-PA5-Tie1-phagemid.TXT(1-308)
Universal code
Total amino acid number: 101, MW=10801
Max ORF: 85-306, 74 AA, MW=7983

```
  1 CAAGACATCCAGATGACCCAGTCTCCAGGCACCCTGTCTTTGTCTCCAGGGGAAAGAGCC  (SEQ ID NO: 5)
  1 Q  D  I  Q  M  T  Q  S  P  G  T  L  S  L  S  P  G  E  R  A   (SEQ ID NO: 6)

61 ACCCTCTCCTGCAGGGCCAGTCAGAGTGTTAGCAGCAGCTACTTAGCCTGGTACCAGCAG
 21 T  L  S  C  R  A  S  Q  S  V  S  S  S  Y  L  A  W  Y  Q  Q

121 AAACCTGGCCAGGCTCCCAGGCTCCTCATCTATGGTGCATCCAGCAGGGCCACTGGCATC
 41 K  P  G  Q  A  P  R  L  L  I  Y  G  A  S  S  R  A  T  G  I

181 CCAGACAGGTTCAGTGGCAGTGGGTCTGGGACAGACTTCACTCTCACCATCAGCAGACTG
 61 P  D  R  F  S  G  S  G  S  G  T  D  F  T  L  T  I  S  R  L

241 GAGCCTGAAGATTTTGCAGTGTATTACTGTCAGCAGTATGGTAGCTCCCGGTGGACGTTC
 81 E  P  E  D  F  A  V  Y  Y  C  Q  Q  Y  G  S  S  R  W  T  F

301 GGCCAAGGGAC
101 G  Q  G
```

Translation of Reverse_Complement_VH-PA5-Tie1-phagemid.TXT(1-396)
Universal code
Total amino acid number: 132, MW=14309
Max ORF: 1-396, 132 AA, MW=14309

```
  1 GAAGTTCAATTGTTAGAGTCTGGTGGCGGTCTTGTTCAGCCTGGTGGTTCTTTACGTCTT  (SEQ ID NO: 7)
  1 E  V  Q  L  L  E  S  G  G  G  L  V  Q  P  G  G  S  L  R  L   (SEQ ID NO: 8)

61 TCTTGCGCTGCTTCCGGATTCACTTTCTCTTATTACCTTATGTATTGGGTTCGCCAAGCT
 21 S  C  A  A  S  G  F  T  F  S  Y  Y  L  M  Y  W  V  R  Q  A

121 CCTGGTAAAGGTTTGGAGTGGGTTTCTTCTATCTATCCTTCTGGTGGCTGGACTGTTTAT
 41 P  G  K  C  L  E  W  V  S  S  I  Y  P  S  G  G  W  T  V  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81 L  Q  M  N  S  L  R  A  E  D  T  A  V  Y  Y  C  A  R  V  N

301 TACTATGATAGTAGTGGTTACGGTCCTATAGCTCCTGGACTTGACTACTCGGGCCAGGGA
101 Y  Y  D  S  S  G  Y  G  P  I  A  P  G  L  D  Y  W  G  Q  G

361 ACCCTGGTCACCGTCTCAAGCGCCTCCACCAAGGGC
121 T  L  V  T  V  S  S  A  S  T  K  G
```

```
  1 CAAGACATCCAGATGACCCAGTCTCCATCCTCCCTGTCTGCATCTGTCGGAGACAGAGTC   (SEQ ID NO: 9)
  1 Q  D  I  Q  M  T  Q  S  P  S  S  L  S  A  S  V  G  D  R  V    (SEQ ID NO: 10)

61 ACCATCACTTGCCGGGCAAGTTAGAGCATTAGCACCTCTTTAAATTGGTATCAGCAAAAA
 21 T  I  T  C  R  A  S  *  S  I  S  T  S  L  N  W  Y  Q  Q  K

121 TCAGGGAAAGCCCCTAAGCTCCTGATATATGCTGCATCCAGTTTGCAAAGTGAAGTCCCA
 41 S  G  K  A  P  K  L  L  I  Y  A  A  S  S  L  Q  S  E  V  P

181 TCAAGGTTCAGTGGCAGTGGATCTGGGACAGATTTCACTCTCACCATCACCAGTCTGCAA
 61 S  R  F  S  G  S  G  S  G  T  D  F  T  L  T  I  T  S  L  Q

241 CCTGAAGATTTTGCAACTTACTACTGTCAACAGAGTTACAGTACCCCTCCGACTTTCGGC
 81 P  E  D  F  A  T  Y  Y  C  Q  Q  S  Y  S  T  P  P  T  F  G

301 CAAGGGAC
101 Q  G
```

Translation of VH-PA6-Tie1-phagemid.TXT(1-439)
Universal code
Total amino acid number: 146, MW=15647
Max ORF: 1-438, 146 AA, MW=15647

Translation of VH-PA10-Tie1-phagemid.TXT(1-439)
Universal code
Total amino acid number: 146, MW=15499
Max ORF: 1-438, 146 AA, MW=15499

```
  1 GAAGTTCAATTGTTAGAGTCTGGTGGCGGTCTTGTTCAGCCTGGTGGTTCTTTACGTCTT   (SEQ ID NO: 11)
  1 E  V  Q  L  L  E  S  G  G  G  L  V  Q  P  G  G  S  L  R  L    (SEQ ID NO: 12)

61 TCTTGCGCTGCTTCCGGATTCACTTTCTCTATGTACGTTATGAAGTGGGTTCGCCAAGCT
 21 S  C  A  A  S  G  F  T  F  S  M  Y  V  M  K  W  V  R  Q  A

121 CCTGGTAAAGGTTTGGAGTGGGTTTCTTCTATCTATCCTTCTGGTGGCTATACTCGTTAT
 41 P  G  K  G  L  E  W  V  S  S  I  Y  P  S  G  G  Y  T  R  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81 L  Q  M  N  S  L  R  A  E  D  T  A  V  Y  Y  C  A  R  V  N

301 TACTATGATAGTAGTGGTTACGGTCCTATAGCTCCTGGACTTGACTACTGGGGCCAGGGA
101 Y  Y  D  S  S  G  Y  G  P  I  A  P  G  L  D  Y  W  G  Q  G

361 ACCCTGGTCACCGTCTCAAGCGCCTCCACCAAGGGCCCATCGGTCTTCCCGCTAGCACCC
121 T  L  V  T  V  S  S  A  S  T  K  G  P  S  V  F  P  L  A  P

421 TCCTCCAAGAGCACCTCTG
141 S  S  K  S  T  S
```

Translation of VL-PA6-Tie1-phagemid.TXT(1-311)
Universal code
Total amino acid number: 103, MW=11056
Max ORF: 1-309, 103 AA, MW=11056

```
  1 CAAGACATCCAGATGACCCAGTCTCCAGGCACCCTGTCTTTGTCTCCAGGGGAAAGAGCC   (SEQ ID NO: 13)
  1 Q  D  I  Q  M  T  Q  S  P  G  T  L  S  L  S  P  G  E  R  A    (SEQ ID NO: 14)

61 ACCCTCTCCTGCAGGGCCAGTCAGAGTGTTAGCAGCAGCTACTTAGCCTGGTACCAGCAG
 21 T  L  S  C  R  A  S  Q  S  V  S  S  S  Y  L  A  W  Y  Q  Q

121 AAACCTGGCCAGGCTCCCAGGCTCCTCATCTATGGTGCATCCAGCAGGGCCACTGGCATC
 41 K  P  G  Q  A  P  R  L  L  I  Y  G  A  S  S  R  A  T  G  I

181 CCAGACAGGTTCAGTGGCAGTGGGTCTGGGACAGACTTCACTCTCACCATCAGCAGACTG
 61 P  D  R  F  S  G  S  G  S  G  T  D  F  T  L  T  I  S  R  L

241 GAGCCTGAAGATTTTGCAGTGTATTACTGTCAGCAGTATGGTAGCTCCCTATTCACTTTC
 81 E  P  E  D  F  A  V  Y  Y  C  Q  Q  Y  G  S  S  L  F  T  F

301 GGCCCTGGGAC
101 G  P  G
```

```
  1 GAAGTTCAATTGTTAGAGTCTGGTGGCGGTCTTGTTCAGCCTGGTGGTTCTTTACGTCTT  (SEQ ID NO: 15)
  1 E  V  Q  L  L  E  S  G  G  G  L  V  Q  P  G  G  S  L  R  L   (SEQ ID NO: 16)

61 TCTTGCGCTGCTTCCGGATTCACTTTCTCTTCTTACAAGATGGGTTGGGTTCGCCAAGCT
 21 S  C  A  A  S  G  F  T  F  S  S  Y  K  M  G  W  V  R  Q  A

121 CCTGGTAAAGGTTTGGAGTGGGTTTCTTGGATCTATCCTTCTGGTGGCGGTACTACTTAT
 41 P  G  K  G  L  E  W  V  S  W  I  Y  P  S  G  G  G  T  T  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81 L  Q  M  N  S  L  R  A  E  D  T  A  V  Y  Y  C  A  R  V  N

301 TACTATGATAGTAGTGGTTACGGTCCTATAGCTCCTGGACTTGACTACTGGGGCCAGGGA
101 Y  Y  D  S  S  G  Y  G  P  I  A  P  G  L  D  Y  W  G  Q  G

361 ACCCTGGTCACCGTCTCAAGCGCCTCCACCAAGGGCCCATCGGTCTTCCCGCTAGCACCC
121 T  L  V  T  V  S  S  A  S  T  K  G  P  S  V  F  P  L  A  P

421 TCCTCCAAGAGCACCTCTG
141 S  S  K  S  T  S
```

Translation of VL-PA10-Tie1-phagemid.TXT(1-311)
Universal code
Total amino acid number: 103, MW=11110
Max ORF: 1-309, 103 AA, MW=11110

```
  1 CAAGACATCCAGATGACCCAGTCTCCAGGCACCCTGTCTTTGTCTCCAGGGGAAAGAGCC  (SEQ ID NO: 17)
  1 Q  D  I  Q  M  T  Q  S  P  G  T  L  S  L  S  P  G  E  R  A   (SEQ ID NO: 18)

61 ACCCTCTCCTGCAGGGCCAGTCAGAGTGTTAGCAGCAGCTACTTAGCCTGGTACCAGCAG
 21 T  L  S  C  R  A  S  Q  S  V  S  S  S  Y  L  A  W  Y  Q  Q

121 AAACCTGGCCAGGCTCCCAGGCTCCTCATCTATGGTGCATCCAGCAGGGCCACTGGCATC
 41 K  P  G  Q  A  P  R  L  L  I  Y  G  A  S  S  R  A  T  G  I

181 CCAGACAGGTTCAGTGGCAGTGGGTCTGGGACAGACTTCACTCTCACCATCAGCAGACTG
 61 P  D  R  F  S  G  S  G  S  G  T  D  F  T  L  T  I  S  R  L

241 GAGCCTGAAGATTTTGCAGTGTATTACTGTCAGCAGTATGGTAGCTCACCGTGGACGTTC
 81 E  P  E  D  F  A  V  Y  Y  C  Q  Q  Y  G  S  S  P  W  T  F

301 GGCCAAGGGAC
101 G  Q  G
```

Translation of VH-PB1-Tie1-phagemid.TXT(1-446)
Universal code
Total amino acid number: 148, MW=15809
Max ORF: 1-444, 148 AA, MW=15809

```
  1 GAAGTTCAATTGTTAGAGTCTGGTGGCGGTCTTGTTCAGCCTGGTGGTTCTTTACGTCTT  (SEQ ID NO: 19)
  1 E  V  Q  L  L  E  S  G  G  G  L  V  Q  P  G  G  S  L  R  L   (SEQ ID NO: 20)

61 TCTTGCGCTGCTTCCGGATTCACTTTCTCTCGTTACCCTATGGTTTGGGTTCGCCAAGCT
 21 S  C  A  A  S  G  F  T  F  S  R  Y  P  M  V  W  V  R  Q  A

121 CCTGGTAAAGGTTTGGAGTGGGTTTCTGTTATCTCTCCTTCTGGTGGCCAGACTTTTTAT
 41 P  G  K  G  L  E  W  V  S  V  I  S  P  S  G  G  Q  T  F  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGGGGTC
 81 L  Q  M  N  S  L  R  A  E  D  T  A  V  Y  Y  C  A  R  G  V

301 CTCACCACCGCTTTTGATATCTGGGGCCAAGGGACAATGGTCACCGTCTCAAGCGCCTCC
101 L  T  T  A  F  D  I  W  G  Q  G  T  M  V  T  V  S  S  A  S

361 ACCAAGGGCCCATCGGTCTTCCCGCTAGCACCCTCCTCCAAAGCACCTCTGGGGGCACAG
121 T  K  G  P  S  V  F  P  L  A  P  S  S  K  A  P  L  G  A  Q

421 CGGCCCTGGGCTGCCTGGTCAAGGAC
141 R  P  W  A  A  W  S  R
```

Translation of VL-PB1-Tie1-phagemid.TXT(1-308)
Universal code
Total amino acid number: 102, MW=11057
Max ORF: 1-306, 102 AA, MW=11057

```
  1 CAAGACATCCAGATGACCCAGTCTCCATCCTCCCTGTCTGCATCTGTGGGAGACAGAGTC  (SEQ ID NO: 21)
  1 Q  D  I  Q  M  T  Q  S  P  S  S  L  S  A  S  V  G  D  R  V   (SEQ ID NO: 22)

61 ACCATCACTTGCCGGGCAAGTCAGAACATTAACAGCTATTTAAATTGGTATCAGCAGAAA
 21 T  I  T  C  R  A  S  Q  N  I  N  S  Y  L  N  W  Y  Q  Q  K

121 CCAGGGCAAGCCCCTAAACTCCTGATCTATGCTGCCTCCAATTTGGAAACTGCGGTCCCA
 41 P  G  Q  A  P  K  L  L  I  Y  A  A  S  N  L  E  T  A  V  P

181 TCAAGGTTCAGCGGCAGTGGATCTGGGACAGATTTCACTCTCACCATCAGTAGCCTGCAG
 61 S  R  F  S  G  S  G  S  C  T  D  F  T  L  T  I  S  S  L  Q

241 CCTGAAGATTTTGCAACTTATTATTGTCAACAATTTAATACTTACCCTCTCACTTTCGGC
 81 P  E  D  F  A  T  Y  Y  C  Q  Q  F  N  T  Y  P  L  T  F  G

301 GGAGGGAC
101 G  C
```

Translation of VH-PC6-Tie1-phagemid.TXT(1-429)
Universal code
Total amino acid number: 143, MW=14727
Max ORF: 1-429, 143 AA, MW=14727

Translation of VH-PB3-Tie1-phagemid.TXT(1-393)
Universal code
Total amino acid number: 131, MW=13931
Max ORF: 1-393, 131 AA, MW=13931

```
  1 GAAGTTCAATTGTTAGAGTCTGGTGGCGGTCTTGTTCAGCCTGGTGGTTCTTTACGTCTT  (SEQ ID NO: 23)
  1 E  V  Q  L  L  E  S  G  G  G  L  V  Q  P  G  G  S  L  R  L   (SEQ ID NO: 24)

61 TCTTGCGCTGCTTCCGGATTCACTTTCTCTCGTTACGGTATGCATTGGGTTCGCCAAGCT
 21 S  C  A  A  S  G  F  T  F  S  R  Y  G  M  H  W  V  R  Q  A

121 CCTGGTAAAGGTTTGGAGTGGGTTTCTGTTATCTCTCCTTCTGGTGGCATGACTTATTAT
 41 P  G  K  G  L  E  W  V  S  V  I  S  P  S  G  G  M  T  Y  Y

181 GCTGACTCCGTTAAAGGTCGCTTCACTATCTCTAGAGACAACACTAAGAATACTCTCTAC
 61 A  D  S  V  K  G  R  F  T  I  S  R  D  N  T  K  N  T  L  Y

241 TTGCAGATGAACAGCTTAAGGGCTGAGGACACTGCAGTCTACTATTGTGCGAGAGTGGGA
 81 L  Q  M  N  S  L  R  A  E  D  T  A  V  Y  Y  C  A  R  V  G

301 GCTACCGGGCCTTTTGATATCTGGGGCCAAGGGACAATGGTCACCGTCTCAAGCGCCTCC
101 A  T  G  P  F  D  I  W  G  Q  C  T  M  V  T  V  S  S  A  S

361 ACCAAGGGCCCATCGGTCTTCCCGCTAGCACCC
121 T  K  G  P  S  V  F  P  L  A  P
```

Translation of VL-PB3-Tie1-phagemid.TXT(1-308)
Universal code
Total amino acid number: 102, MW=11032
Max ORF: 1-306, 102 AA, MW=11032

```
  1 CAAGACATCCAGATGACCCAGTCTCCAGCCACCCTGTCTTTGTCTCCAGGGGAAAGAGCC  (SEQ ID NO: 25)
  1 Q  D  I  Q  M  T  Q  S  P  A  T  L  S  L  S  P  G  E  R  A   (SEQ ID NO: 26)

61 ACCCTCTCCTGCAGGGCCAGTCAGAGTGTTAGCACCTACTTAGCCTGGTACCAACAGAAA
 21 T  L  S  C  R  A  S  Q  S  V  S  T  Y  L  A  W  Y  Q  Q  K

121 CCTGGCCAGGCTCCCAGGCTTCTCATCTATGATGCATCCAACAGGGCCACTGGCATCCCA
 41 P  G  Q  A  P  R  L  L  I  Y  D  A  S  N  R  A  T  G  I  P

181 GGCAGGTTCAGTGGCAGTGGGTCTGGGACAGACTTCACTCTCACCATCAGCAGCCTAGAG
 61 G  R  F  S  G  S  G  S  G  T  D  F  T  L  T  I  S  S  L  E

241 GCTGAAGACTTTGCAGTTTATTACTGTCAGCAGCGTAGCAGCTGGCCGATCACCTTCGGC
 81 A  E  D  F  A  V  Y  Y  C  Q  Q  R  S  S  W  P  I  T  F  G

301 CAAGGGAC
101 Q  G
```

```
  1 GAAGTTCAATTGTTAGAGTCTGGTGGCGGTCTTGTTCAGCCTGGTGGTTCTTTACGTCTT  (SEQ ID NO: 27)
  1 E  V  Q  L  L  E  S  G  G  G  L  V  Q  P  G  G  S  L  R  L   (SEQ ID NO: 28)

61 TCTTGCGCTGCTTCCGGATTCACTTTCTCTCATTACGGTATGACTTGGGTTCGCCAAGCT
 21 S  C  A  A  S  G  F  T  F  S  H  Y  G  M  T  W  V  R  Q  A

121 CCTGGTAAAGGTTTGGAGTGGGTTTCTGTTATCTCTCCTTCTGGTGGCCAGACTGGTTAT
 41 P  G  K  G  L  E  W  V  S  V  I  S  P  S  G  G  Q  T  G  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGGGTGGTGGC
 81 L  Q  M  N  S  L  R  A  E  D  T  A  V  Y  Y  C  A  G  G  G

301 TACGCAGCCTTTGACTACTGGGGCCAGGGAACCCTGGTCACCGTCTCAAGCGCCTCCACC
101 Y  A  A  F  D  Y  W  G  Q  G  T  L  V  T  V  S  S  A  S  T

361 AAGGGCCCATCGGTCTTCCCGCTAGCACCCTCCTCCAAGAGCACCTCTGGGGGCACAGCG
121 K  G  P  S  V  F  P  L  A  P  S  S  K  S  T  S  G  G  T  A

421 GCCCTGGGC
141 A  L  G
```

Translation of VL-PC6-Tie1-phagemid.TXT(1-308)
Universal code
Total amino acid number: 102, MW=11014
Max ORF: 1-306, 102 AA, MW=11014

```
  1 CAAGACATCCAGATGACCCAGTCTCCAGCCACCCTGTCTTTGTCTCCAGGGGAAAGAGCC  (SEQ ID NO: 29)
  1 Q  D  I  Q  M  T  Q  S  P  A  T  L  S  L  S  P  G  E  R  A   (SEQ ID NO: 30)

61 ACCCTCTCCTGCAGGGCCAGTCAGAGTGTTAGCAGCTACTTAGCCTGGTACCAACAGAAA
 21 T  L  S  C  R  A  S  Q  S  V  S  S  Y  L  A  W  Y  Q  Q  K

121 CCTGGCCAGGCTCCCAGGCTCCTCATCTATGATGCATCCAACAGGGCCACTGGCATCCCA
 41 P  G  Q  A  P  R  L  L  I  Y  D  A  S  N  R  A  T  G  I  P

181 GCCAGGTTCAGTGGCAGTGGGTCTGGGACAGACTTCACTCTCACCATCAGCAGCCTAGAG
 61 A  R  F  S  G  S  G  S  G  T  D  F  T  L  T  I  S  S  L  E

241 CCTGAACATTTTGCAGTTTATTACTGTCAGCAGCGTAGCAACTGGCCTCTCACTTTCGGC
 81 P  E  D  F  A  V  Y  Y  C  Q  Q  R  S  N  W  P  L  T  F  G

301 GGAGGGAC
101 G  G
```

Translation of Reverse_Complement_VH-PD6-Tie1-ph-
agemid.TXT(1-396)
Universal code
Total amino acid number: 132, MW=14217
Max ORF: 1-396, 132 AA, MW=14217

```
  1 GAAGTTCAATTGTTAGAGTCTGGTGGCGGTCTTGTTCAGCCTGGTGGTTCTTTACGTCTT  (SEQ ID NO: 31)
  1 E  V  Q  L  L  E  S  G  G  G  L  V  Q  P  G  G  S  L  R  L   (SEQ ID NO: 32)

61 TCTTGCGCTGCTTCCGGATTCACTTTCTCTGCTTACCGTATGGAGTGGGTTCGCCAAGCT
 21 S  C  A  A  S  G  F  T  F  S  A  Y  R  M  E  W  V  R  Q  A

121 CCTGGTAAAGGTTTGGAGTGGGTTTCTTCTATCTATCCTTCTGGTGGCATTACTTATTAT
 41 P  G  K  G  L  E  W  V  S  S  I  Y  P  S  G  G  I  T  Y  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81 L  Q  M  N  S  L  R  A  E  D  T  A  V  Y  Y  C  A  R  V  N

301 TACTATGATAGTAGTGGTTACGGTCCTATAGCTCCTGGACTTGACTACTGGGGCCAGGGA
101 Y  Y  D  S  S  G  Y  G  P  I  A  P  G  L  D  Y  W  G  Q  G

361 ACCCTGGTCACCGTCTCAAGCGCCTCCACCAAGGGC
121 T  L  V  T  V  S  S  A  S  T  K  G
```

Translation of VL-PD6-Tie1-phagemid.TXT (1-308)
Universal code
Total amino acid number: 101, MW=10731
Max ORF: 115-306, 64 AA, MW=6731

```
  1 CAAGACATCCAGATGACCCAGTCTCCATCCTCCCTGTCTGCATCTGTAGGAGACAGAGTT  (SEQ ID NO: 33)
  1  Q  D  I  Q  M  T  Q  S  P  S  S  L  S  A  S  V  G  D  R  V   (SEQ ID NO: 34)

61 ACCATCACTTGCCGGGCAAGTCAGGGCATTACCACTTATTTAGGCTGGTATTAGCAGAAA
 21  T  I  T  C  R  A  S  Q  G  I  T  T  Y  L  G  W  Y  *  Q  K

121 CCAGGGAAAGCCCCTAAGCTCCTGATCTATGCTGCATCCACTTTGCAAAGTGGGGTCCCA
 41  P  G  K  A  P  K  L  L  I  Y  A  A  S  T  L  Q  S  G  V  P

181 GCAAAGTTCAGCGGCAGTGGATCTGGGACACTTTTCACTCTCACCATCAGCGGTCTGCAA
 61  A  K  F  S  G  S  G  S  G  T  L  F  T  L  T  I  S  G  L  Q

241 CCTGAAGATTCTGCAACTTACTACTGTCACCAGAGTTACAATACCCCTTGGACGTTCGGC
 81  P  E  D  S  A  T  Y  Y  C  H  Q  S  Y  N  T  P  W  T  F  G

301 CAAGGGAC
101  Q  G
```

Translation of VH-PD12-Tie1-phagemid.TXT(1-444)
Universal code
Total amino acid number: 148, MW=15535
Max ORF: 1-444, 148 AA, MW=15535

Translation of VH-PD10-Tie1-phagemid.TXT(1-412)
Universal code
Total amino acid number: 136, MW=14313
Max ORF: 181-411, 77 AA, MW=8216

```
  1 GAAGTTCAATTGTTAGAGTCTGGTGGCGGTCTTGTTCAGCCTGGTGGTTCTTTACGTCTT  (SEQ ID NO: 35)
  1  E  V  Q  L  L  E  S  G  G  G  L  V  Q  P  G  G  S  L  R  L   (SEQ ID NO: 36)

61 TCTTGCGCTGCTTCCGGATTCACTTTCTCTGGTTACGGTATGCATTGGGTTCGCCAAGCT
 21  S  C  A  A  S  G  F  T  F  S  G  Y  G  M  H  W  V  R  Q  A

121 CCTGGTAAAGGTTTGGAGTGGGTTTCTGTTATCTCTCCTTCTGGTGGCCAGACTTGGTAG
 41  P  G  K  G  L  E  W  V  S  V  I  S  P  S  G  G  Q  T  W  *

181 GCTGACTCCGTTAAAGGTCGCTTCACTATCTCTAGAGACAACTCTAAGAATACTCTCTAC
 61  A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGGCGGG
 81  L  Q  M  N  S  L  R  A  E  D  T  A  V  Y  Y  C  A  R  G  G

301 ACCAGTAACCCACTGTTTTACTGGGGCCAGGGAACCCTGGTCACCGTCTCAAGCGCCTCC
101  T  S  N  P  L  F  Y  W  G  Q  G  T  L  V  T  V  S  S  A  S

361 ACCAAGGGCCCATCGGTCTTCCCGCTAGCACCCTCCTCCAAGAGCACCTCTG
121  T  K  G  P  S  V  F  P  L  A  P  S  S  K  S  T  S
```

Translation of VL-PD10-Tie1-phagemid.TXT(1-308)
Universal code
Total amino acid number: 102, MW=11069
Max ORF: 1-306, 102 AA, MW=11069

```
  1 CAAGACATCCAGATGACCCAGTCTCCAGCCACCCTGTCTTTGTCTCCAGGGGAAAGAGCC  (SEQ ID NO: 37)
  1  Q  D  I  Q  M  T  Q  S  P  A  T  L  S  L  S  P  G  E  R  A   (SEQ ID NO: 38)

61 ACCCTCTCCTGCAGGGCCAGTCAGAGTGTTAGCAGCTACTTAGCCTGGTACCAACAGAAA
 21  T  L  S  C  R  A  S  Q  S  V  S  S  Y  L  A  W  Y  Q  Q  K

121 CCTGGCCAGGCTCCCAGGCTCCTCATCTATGATGCATCCAACAGGGCCACTGGCATCCCA
 41  P  G  Q  A  P  R  L  L  I  Y  D  A  S  N  R  A  T  G  I  P

181 GCCAGGTTCAGTGGCAGTGGGTCTGGGACAGACTTCACTCTCACCATCAGCAGCCTAGAG
 61  A  R  F  S  G  S  G  S  G  T  D  F  T  L  T  I  S  S  L  E

241 CCTGAAGATTTTGCAGTTTATTACTGTCAGCAGCGTAGCAACTGGCCTCCGACTTTTGGC
 81  P  E  D  F  A  V  Y  Y  C  Q  Q  R  S  N  W  P  P  T  F  G

301 CAGGGGAC
101  Q  G
```

```
  1 GAAGTTCAATTGTTAGAGTCTGGTGGCGGTCTTGTTCAGCCTGGTGGTTCTTTACGTCTT   (SEQ ID NO: 39)
  1 E  V  Q  L  L  E  S  G  G  G  L  V  Q  P  G  G  S  L  R  L   (SEQ ID NO: 40)

61 TCTTGCGCTGCTTCCGGATTCACTTTCTCTGGTTACGGTATGCATTGGGTTCGCCAAGCT
 21 S  C  A  A  S  G  F  T  F  S  G  Y  G  M  H  W  V  R  Q  A

121 CCTGGTAAAGGTTTGGAGTGGGTTTCTGTTATCTCTCCTTCTGGTGGCCAGACTTCTTAT
 41 P  G  K  G  L  E  W  V  S  V  I  S  P  S  G  G  Q  T  S  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGATAGG
 81 L  Q  M  N  S  L  R  A  E  D  T  A  V  Y  Y  C  A  R  D  R

301 CAGTATTACTATGGTTCGGGGAGTCTTGACTACTGGGGCCAGGGAACCCTGGTCACCGTC
101 Q  Y  Y  Y  G  S  G  S  L  D  Y  W  G  Q  G  T  L  V  T  V

361 TCAAGCGCCTCCACCAAGGGCCCATCGGTCTTCCCGCTAGCACCCTCCTCCAAGAGCACC
121 S  S  A  S  T  K  G  P  S  V  F  P  L  A  P  S  S  K  S  T

421 TCTGGGGGCACAGCGGCCCTGGCC
141 S  G  G  T  A  A  L  G
```

Translation of VL-PD12-Tie1-phagemid.TXT(1-308)
Universal code
Total amino acid number: 102, MW=11060
Max ORF: 1-306, 102 AA, MW=11060

```
  1 CAAGACATCCAGATGACCCAGTCTCCATCCTCCCTGTCTGCATCTGTAGGAGACAGAGTC   (SEQ ID NO: 41)
  1 Q  D  I  Q  M  T  Q  S  P  S  S  L  S  A  S  V  G  D  R  V   (SEQ ID NO: 42)

61 ACCGTCACTTGCCGGGCAAGTCAGAGCATTAGCAGTTATTTAAATTGGTATCAGCAGAAA
 21 T  V  T  C  R  A  S  Q  S  I  S  S  Y  L  N  W  Y  Q  Q  K

121 CCAGGGAAAGCCCCTAAACTCCTGATCTATGCTGCATCCAGTTTGCAAAGTGGGGTCCCA
 41 P  G  K  A  P  K  L  L  I  Y  A  A  S  S  L  Q  S  G  V  P

181 TCAAGGTTCAGTGGCGGTGGATCTGGGACAGATTTCACTCTCACCATCAGCAGTCTGCAA
 61 S  R  F  S  G  G  G  S  G  T  D  F  T  L  T  I  S  S  L  Q

241 CCTGAAGATTTTGCAACTTATTTCTGTCTACAAGATTACAAATACCCGTGGACGTTCGGC
 81 P  E  D  F  A  T  Y  F  C  L  Q  D  Y  K  Y  P  W  T  F  G

301 CAAGGGAC
101 Q  G
```

Translation of Reverse_Complement_VH-PF3-Tie1-ph-
   agemid.TXT(1-375)
Universal code
Total amino acid number: 125, MW=13201
Max ORF: 1-375, 125 AA, MW=13201

```
  1 GAAGTTCAATTGTTAGAGTCTGGTGGCGGTCTTGTTCAGCCTGGTGGTTCTTTACGTCTT   (SEQ ID NO: 43)
  1 E  V  Q  L  L  E  S  G  G  G  L  V  Q  P  G  G  S  L  R  L   (SEQ ID NO: 44)

61 TCTTGCGCTGCTTCCGGATTCACTTTCTCTATGTACGGTATGGGTTGGGTTCGCCAAGCT
 21 S  C  A  A  S  G  F  T  F  S  M  Y  G  M  G  W  V  R  Q  A

121 CCTGGTAAAGGTTTGGAGTGGGTTTCTGTTATCTCTCCTTCTGGTGGCCAGACTGCTTAT
 41 P  G  K  G  L  E  W  V  S  V  I  S  P  S  G  G  Q  T  A  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTGGCC
 81 L  Q  M  N  S  L  R  A  E  D  T  A  V  Y  Y  C  A  R  V  A

301 TTGCTCCTGGGCCACGCTTTTGATATCTGGGGCCAAGGGACAATGGTCACCGTCTCAAGC
101 L  L  L  G  H  A  F  D  I  W  G  Q  G  T  M  V  T  V  S  S

361 GCCTCCACCAAGGGC
121 A  S  T  K  G
```

Translation of VL-PF3-Tie1-phagemid.TXT(1-308)
Universal code
Total amino acid number: 102, MW=11162
Max ORF: 1-306, 102 AA, MW=11162

```
  1 CAAGACATCCAGATGACCCAGTCTCCTTCCACCCTGTCTGCATCTTTAGGAGACAGAGTC    (SEQ ID NO: 45)
  1  Q  D  I  Q  M  T  Q  S  P  S  T  L  S  A  S  L  G  D  R  V    (SEQ ID NO: 46)

61 ACCATCACTTGCCGGGCCAGTGAGAGTATTAGTAGGTGGTTGGCCTGGTATCAGCAGAAA
 21  T  I  T  C  R  A  S  E  S  I  S  R  W  L  A  W  Y  Q  Q  K

121 CCAGGGAAAGCCCCTAAGCTCCTGATGTATGAGGCATCCACTTTAGAAAGTGGGGTCCCA
 41  P  G  K  A  P  K  L  L  M  Y  E  A  S  T  L  E  S  G  V  P

181 TCAAGGTTCACCGGCACTGGATCTGGGACAGAATTCACTCTCACCATCAGCAGCCTGCAG
 61  S  R  F  T  G  T  G  S  G  T  E  F  T  L  T  I  S  S  L  Q

241 CCCGATGATTTTGCAACTTATTACTGTCAGCAGCGTAGCAACTGGCCCCTCACTTTCGGC
 81  P  D  D  F  A  T  Y  Y  C  Q  Q  R  S  N  W  P  L  T  F  G

301 GGAGGGAC
101  G  G
```

Translation of VH-PF4-Tie1-phagemid.TXT(1-429)
Universal code
Total amino acid number: 143, MW=14996
Max ORF: 1-429, 143 AA, MW=14996

```
  1 GAAGTTCAATTGTTAGAGTCTGGTGGCGGTCTTGTTCAGCCTGGTGGTTCTTTACGTCTT    (SEQ ID NO: 47)
  1  E  V  Q  L  L  E  S  G  G  G  L  V  Q  P  G  G  S  L  R  L    (SEQ ID NO: 48)

61 TCTTGCGCTGCTTCCGGATTCACTTTCTCTGCTTACATGATGTCTTGGGTTCGCCAAGCT
 21  S  C  A  A  S  G  F  T  F  S  A  Y  M  M  S  W  V  R  Q  A

121 CCTGGTAAAGGTTTGGAGTGGGTTTCTTCTATCTATCCTTCTGGTGGCTATACTTATTAT
 41  P  G  K  G  L  E  W  V  S  S  I  Y  P  S  G  G  Y  T  Y  Y

181 GCTGACTCCGTTAAAGGTCGCTTCACTATCTCTAGAGACAACTCTAAGAATACTCTCTAC
 61  A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGGCTTA
 81  L  Q  M  N  S  L  R  A  E  D  T  A  V  Y  Y  C  A  R  G  L

301 CGGGGAGGTCCTGACTACTGGGGCCAGGGAACCCTGGTCACCGTCTCAAGCGCCTCCACC
101  R  G  G  P  D  Y  W  G  Q  G  T  L  V  T  V  S  S  A  S  T

361 AAGGGCCCATCGGTCTTCCCGCTAGCACCCTCCTCCAAGAGCACCTCTGGGGGCACAGCG
121  K  G  P  S  V  F  P  L  A  P  S  S  K  S  T  S  G  G  T  A

421 GCCCTGGGC
141  A  L  G
```

Translation of VL-PF4-Tie1-phagemid.TXT(1-308)
Universal code
Total amino acid number: 102, MW=10966
Max ORF: 1-306, 102 AA, MW=10966

```
  1 CAAGACATCCAGATGACCCAGTCTCCTTCCACCCTGTCTGCATATGTAGGAGACAGTGTC    (SEQ ID NO: 49)
  1  Q  D  I  Q  M  T  Q  S  P  S  T  L  S  A  Y  V  G  D  S  V    (SEQ ID NO: 50)

61 ACCATCACTTGCCGGGCCAGTCAGAGTGTGAGAAGGTCGTTGGCCTGGTATCAGCAGAGA
 21  T  I  T  C  R  A  S  Q  S  V  R  R  S  L  A  W  Y  Q  Q  R

121 CCAGGGAAAGCCCCCAAGTCCCTCATCTATAAGGCGTCTACTTTAGAGACTGGGGTCCCA
 41  P  G  K  A  P  K  S  L  I  Y  K  A  S  T  L  E  T  G  V  P

181 CCAAGGTTCAGCGGCAGTGGATCTGGGACAGAATTCACTCTCACCATCAGCAGCCTGCAG
 61  P  R  F  S  G  S  G  S  G  T  E  F  T  L  T  I  S  S  L  Q

241 CCTGAAGATTCTGCAATTTATTACTGCCAACAATATGGTAGTTTTCCGCTCACTTTCGGC
 81  P  E  D  S  A  I  Y  Y  C  Q  Q  Y  G  S  F  P  L  T  F  G

301 GGAGGGAC
101  G  G
```

Translation of VH-PG3-Tie1-phagemid.TXT(1-441)
Universal code
Total amino acid number: 147, MW=15647
Max ORF: 1-441, 147 AA, MW=15647

```
  1 GAAGTTCAATTGTTAGAGTCTGGTGGCGGTCTTGTTCAGCCTGGTGGTTCTTTACGTCTT   (SEQ ID NO: 51)
  1 E  V  Q  L  L  E  S  G  G  G  L  V  Q  P  G  G  S  L  R  L    (SEQ ID NO: 52)

61 TCTTGCGCTGCTTCCGGATTCACTTTCTCTCATTACATGATGGTTTGGGTTCGCCAAGCT
 21 S  C  A  A  S  G  F  T  F  S  H  Y  M  M  V  W  V  R  Q  A

121 CCTGGTAAAGGTTTGGAGTGGGTTTCTTCTATCTATCCTTCTGGTGGCTGGACTTATTAT
 41 P  G  K  G  L  E  W  V  S  S  I  Y  P  S  G  G  W  T  Y  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGGCTGGAC
 81 L  Q  M  N  S  L  R  A  E  D  T  A  V  Y  Y  C  A  R  L  D

301 TACGGTGGTAATTCCGCCTACTTTGACTACTGGGGCCAGGGAACCCTGGTCACCGTCTCA
101 Y  G  G  N  S  A  Y  F  D  Y  W  G  Q  G  T  L  V  T  V  S

361 AGCGCCTCCACCAAGGGCCCATCGGTCTTCCCGCTAGCACCCTCCTCCAAGAGCACCTCT
121 S  A  S  T  K  G  P  S  V  F  P  L  A  P  S  S  K  S  T  S

421 GGGGGCACAGCGGCCCTGGGC
141 G  G  T  A  A  L  G
```

Translation of VL-PG3-Tie1-phagemid.TXT(1-327)
Universal code
Total amino acid number: 109, MW=11792
Max ORF: 1-327, 109 AA, MW=11792

```
  1 CAGAGCGTCTTGACTCAGCCGCACTCTGTGTCGGCCTCTCCGGGGAAGACGGTAACCATC   (SEQ ID NO: 53)
  1 Q  S  V  L  T  Q  P  H  S  V  S  A  S  P  G  K  T  V  T  I    (SEQ ID NO: 54)

61 TCCTGCACCCGCAGCAGTGGCAACATTGCCAGCAACTTTGTCCAGTGGTACCAACAGCGC
 21 S  C  T  R  S  S  G  N  I  A  S  N  F  V  Q  W  Y  Q  Q  R

121 CCGGGCAGTGTCCCCACCACTGTGATTTATGAAGATGACCGAAGACCCTCTGGGGTCCCT
 41 P  G  S  V  P  T  T  V  I  Y  E  D  D  R  R  P  S  G  V  P

181 GATCGCTTTTCTGGCTCCATCGACAGTTCCTCCAACTCTGCTTTCCTCAGCATCTCTGGA
 61 D  R  F  S  G  S  I  D  S  S  S  N  S  A  F  L  S  I  S  G

241 CTGAAGACTGAGGACGAGGCAGACTATTACTGTCAGTCTCATGATCGTACCACCCGTGCT
 81 L  K  T  E  D  E  A  D  Y  Y  C  Q  S  H  D  R  T  T  R  A

301 TGGGTGTTCGGCGGAGGGACCAAGCTG
101 W  V  F  G  G  G  T  K  L
```

Translation of VH-SA2-Tie1-phagemid.TXT(1-413)
Universal code
Total amino acid number: 137, MW=14682
Max ORF: 1-411, 137 AA, MW=14682

```
  1 GAAGTTCAATTGTTAGAGTCTGGTGGCCGTCTTGTTCAGCCTGGTGGTTCTTTACGTCTT   (SEQ ID NO: 55)
  1 E  V  Q  L  L  E  S  G  G  G  L  V  Q  P  G  G  S  L  R  L    (SEQ ID NO: 56)

61 TCTTGCGCTGCTTCCGGATTCACTTTCTCTCGTTACACTATGATGTGGGTTCGCCAAGCT
 21 S  C  A  A  S  G  F  T  F  S  R  Y  T  M  M  W  V  R  Q  A

121 CCTGGTAAAGGTTTGGAGTGGGTTTCTGGTATCTATCCTTCTGGTGGCGTTACTCTTTAT
 41 P  G  K  G  L  E  W  V  S  G  I  Y  P  S  G  G  V  T  L  Y

181 GCTGACTCCGTTAAAGGTCGCTTCACTATCTCTAGACACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81 L  Q  M  N  S  L  R  A  E  D  T  A  V  Y  Y  C  A  R  V  N

301 TACTATGATAGTAGTGGTTACGGTCCTATAGCTCCTGGACTTGACTACTGGGGCCAGGGA
101 Y  Y  D  S  S  G  Y  G  P  I  A  P  G  L  D  Y  W  G  Q
```

```
361 ACCCTGGTCACCGTCTCAAGCGCCTCCACCAAGGGCCCATCGGTCTTCCCGCT
121  T  L  V  T  V  S  S  A  S  T  K  G  P  S  V  F  P
```

Translation of VL-SA2-Tie1-phagemid.TXT(1-339)
Universal code
Total amino acid number: 113, MW=12358
Max ORF: 1-339, 113 AA, MW=12358

```
  1 CACAGTGCACAAGACATCCAGATGACCCAGTCTCCAGGCACCCTGTCTTTGTCTCCAGGG   (SEQ ID NO: 57)
  1 H  S  A  Q  D  I  Q  M  T  Q  S  P  G  T  L  S  L  S  P  G   (SEQ ID NO: 58)

61 GAAAGAGCCACACTCTCCTGCAGGGCCAGTCGGAGTGTGATCATCAGCTACGTAGCCTGG
 21 E  R  A  T  L  S  C  R  A  S  R  S  V  I  I  S  Y  V  A  W

121 TACCAGCAGAAACCTGGCCAGGCTCCCAGGCTCCTCATCTATGGAGCGTCCACCAGGGCC
 41 Y  Q  Q  K  P  G  Q  A  P  R  L  L  I  Y  G  A  S  T  R  A

181 ACTGGCATCCCAGACAGGTTCAGTGGCAGTGGGTCTGGGACAGACTTCACTCTCACCATC
 61 T  G  I  P  D  R  F  S  G  S  G  S  G  T  D  F  T  L  T  I

241 AGCAGACTGGAGCCTGAAGACTTTGCAGTGTATTTCTGTCAGCTTTATGGTAGGTCACCA
 81 S  R  L  E  P  E  D  F  A  V  Y  F  C  Q  L  Y  G  R  S  P

301 CGGATCATCTTCGGCCAAGGGACACGACTGGAGATTAAA
101 R  I  I  F  G  Q  G  T  R  L  E  I  K
```

Translation of VH-SA10-Tie1-phagemid.TXT(1-369)
Universal code
Total amino acid number: 123, MW=13314
Max ORF: 1-369, 123 AA, MW=13314

```
  1 GAAGTTCAATTGTTAGAGTCTGGTGGCGGTCTTGTTCAGCCTGGTGGTTCTTTACGTCTT   (SEQ ID NO: 59)
  1 E  V  Q  L  L  E  S  G  G  G  L  V  Q  P  G  G  S  L  R  L   (SEQ ID NO: 60)

61 TCTTGCGCTGCTTCCGGATTCACTTTCTCTAATTACGTTATGGTTTGGGTTCGCCAAGCT
 21 S  C  A  A  S  G  F  T  F  S  N  Y  V  M  V  W  V  R  Q  A

121 CCTGGTAAAGGTTTGGAGTGGGTTTCTGGTATCTATCCTTCTGGTGGCCATACTAAGTAT
 41 P  G  K  G  L  E  W  V  S  G  I  Y  P  S  G  G  H  T  K  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81 L  Q  M  N  S  L  R  A  E  D  T  A  V  Y  Y  C  A  R  V  N

301 TACTATGATAGTAGTGGTTACGGTCCTATAGCTCCTGGACTTGACTACTGGGGCCAGGGA
101 Y  Y  D  S  S  G  Y  G  P  I  A  P  G  L  D  Y  W  G  Q  G

361 ACCCTGGTC
121 T  L  V
```

Translation of VL-SA10-Tie1-phagemid.TXT(1-339)
Universal code
Total amino acid number: 113, MW=12445
Max ORF: 1-339, 113 AA, MW=12445

```
  1 CACAGTGCACAAGACATCCAGATGACCCAGTCTCCAGGCACCCTGTCTTTGTCTCCAGGG   (SEQ ID NO: 61)
  1 H  S  A  Q  D  I  Q  M  T  Q  S  P  G  T  L  S  L  S  P  G   (SEQ ID NO: 62)

61 GAAAGAGCCACCCTCTTCTGCAGGGCCAGTCAGCGTGTTACCAGCAACTCCTTGGCCTGG
 21 E  R  A  T  L  F  C  R  A  S  Q  R  V  T  S  N  S  L  A  W

121 TACCAGCAGAGACCTGGCCAGGCTCCCAGGCTCCTCATCTATGATGCATCCACCAGGGCC
 41 Y  Q  Q  R  P  G  Q  A  P  R  L  L  I  Y  D  A  S  T  R  A

181 ACTGGCATCCCAGACCGCTTCAGTGGCAGTGGGTCGGGAGGGACTTCACTCTCACCATC
 61 T  G  I  P  D  R  F  S  G  S  G  S  G  R  D  F  T  L  T  I

241 AGCAGACTGGAGCCTGAAGATTTTGCAGTTTATTACTGTCAGCGATATGGTAGTTCAGTG
 81 S  R  L  E  P  E  D  F  A  V  Y  Y  C  Q  R  Y  G  S  S  V
```

```
301 TTGTACTCTTTTGGCCAGGGGACGAAGTTGGAAATCACA
101  L   Y   S   F   G   Q   G   T   K   L   E   I   T
```

Translation of VH-SB2-Tie1-phagemid.TXT(1-383)
Universal code
Total amino acid number: 127, MW=13611
Max ORF: 1-381, 127 AA, MW=13611

```
  1 GAAGTTCAATTGTTAGAGTCTGGTGGCGGTCTTGTTCAGCCTGGTGGTTCTTTACGTCTT  (SEQ ID NO: 63)
  1  E   V   Q   L   L   E   S   G   G   G   L   V   Q   P   G   G   S   L   R   L   (SEQ ID NO: 64)

61 TCTTGCGCTGCTTCCGGATTCACTTTCTCTATTTACGGTATGGCTTGGGTTCGCCAAGCT
 21  S   C   A   A   S   G   F   T   F   S   I   Y   G   M   A   W   V   R   Q   A

121 CCTGGTAAAGGTTTGGAGTGGGTTTCTGTTATCTCTCCTTCTGGTGGCCAGACTTTTTAT
 41  P   G   K   G   L   E   W   V   S   V   I   S   P   S   G   G   Q   T   F   Y

181 GCTGACTCCGTTAAAGGTCGCTTCACTATCTCTAGAGACAACTCTAAGAATACTCTCTAC
 61  A   D   S   V   K   G   R   F   T   I   S   R   D   N   S   K   N   T   L   Y

241 TTGCAGATGAACAGCTTAAGGGCTGAGGACACTGCAGTCTACTATTGTGCGAGAGTTTAC
 81  L   Q   M   N   S   L   R   A   E   D   T   A   V   Y   Y   C   A   R   V   Y

301 TACTACGGTATGGACGTCTGGGGCCAAGGGACCACGGTCACCGTCTCAAGCGCCTCCACC
101  Y   Y   G   M   D   V   W   G   Q   G   T   T   V   T   V   S   S   A   S   T

361 AAGGGCCCATCGGTCTTCCCGCT
121  K   G   P   S   V   F   P
```

Translation of VL-SB2-Tie1-phagemid.TXT(1-333)
Universal code
Total amino acid number: 111, MW=12221
Max ORF: 1-333, 111 AA, MW=12221

```
  1 CACAGTGCACAAGACATCCAGATGACCCAGTCTCCAGCCACCCTGTCTTTGTCTCCAGGG  (SEQ ID NO: 65)
  1  H   S   A   Q   D   I   Q   M   T   Q   S   P   A   T   L   S   L   S   P   G   (SEQ ID NO: 66)

61 GAAAGAGCCACCCTCTCCTGCAGGGCCAGTCAGAGTGTTAGCAGCTACTTAGCCTGGTAC
 21  E   R   A   T   L   S   C   R   A   S   Q   S   V   S   S   Y   L   A   W   Y

121 CAACAAAAACCTGGCCAGGCTCCCAGGCTCCTCATTTATGATGCATCCAACAGGGCCACT
 41  Q   Q   K   P   G   Q   A   P   R   L   L   I   Y   D   A   S   N   R   A   T

181 GGCATCCCAGCCAGGTTCAGTGGCAGTGGGTCTGAGACAGACTTCACTCTCACCATCAGC
 61  G   I   P   A   R   F   S   G   S   G   S   E   T   D   F   T   L   T   I   S

241 AGCCTAGAGCCTGAAGATTTTGCAGTTTATTACTGTCAGCAGCGTAGCAAGTGGCCTCGG
 81  S   L   E   P   E   D   F   A   V   Y   Y   C   Q   Q   R   S   K   W   P   R

301 ACTTTTGGCCAGGGGACCAAGCTGGAGATCAAA
101  T   F   G   Q   G   T   K   L   E   I   K
```

Translation of VH-SB9-Tie1-phagemid.TXT(1-413)
Universal code
Total amino acid number: 137, MW=14778
Max ORF: 1-411, 137 AA, MW=14778

```
  1 GAAGTTCAATTGTTAGAGTCTGGTGGCGGTCTTGTTCAGCCTGGTGGTTCTTTACGTCTT  (SEQ ID NO: 67)
  1  E   V   Q   L   L   E   S   G   G   G   L   V   Q   P   G   G   S   L   R   L   (SEQ ID NO: 68)

61 TCTTGCGCTGCTTCCGGATTCACTTTCTCTTCTTACGTTATGATGTGGGTTCGCCAAGCT
 21  S   C   A   A   S   G   F   T   F   S   S   Y   V   M   M   W   V   R   Q   A

121 CCTGGTAAAGGTTTGGAGTGGGTTTCTGGTATCTATCCTTCTGGTGGCTGGACTTATTAT
 41  P   G   K   G   L   E   W   V   S   G   I   Y   P   S   G   G   W   T   Y   Y

181 ACTGACTCCGTTAAAGGTCGCTTCACTATCTCTAGAGACAACTCTAAGAATACTCTCTAC
 61  T   D   S   V   K   G   R   F   T   I   S   R   D   N   S   K   N   T   L   Y

241 TTGCAGATGAACAGCTTAAGGGCTGAGGACACTGCAGTCTACTATTGTGCGAGAGTCAAT
 81  L   Q   M   N   S   L   R   A   E   D   T   A   V   Y   Y   C   A   R   V   N
```

```
301 TACTATGATAGTAGTGGTTACGGTCCTATAGCTCCTGGACTTGACTACTGGGGCCAGGGA
101  Y  Y  D  S  S  G  Y  G  P  I  A  P  G  L  D  Y  W  G  Q  G

361 ACCCTGGTCACCGTCTCAAGCGCCTCCACCAAGGGCCCATCGGTCTTCCCGCT
121  T  L  V  T  V  S  S  A  S  T  K  G  P  S  V  F  P
```

Translation of VL-SB9-Tie1-phagemid.TXT(1-336)
Universal code
Total amino acid number: 112, MW=12010
Max ORF: 1-336, 112 AA, MW=12010

```
  1 CACAGTGCACAAGACATCCAGATGACCCAGTCTCCATCCTCCCTGTCTGCATCTGTTGGA  (SEQ ID NO: 69)
  1  H  S  A  Q  D  I  Q  M  T  Q  S  P  S  S  L  S  A  S  V  G  (SEQ ID NO: 70)

61 GATAGAGTCACCATCACTTGCCGGGCAAGTCAGAGTGTCAGCAGTCATTTAAGTTGGTTT
 21  D  R  V  T  I  T  C  R  A  S  Q  S  V  S  S  H  L  S  W  F

121 CAGCAGAGACCAGGGAAAGCCCCCAACCTCCTGATCTATCATGCATCCAGTTTGCAAAGT
 41  Q  Q  R  P  G  K  A  P  N  L  L  I  Y  H  A  S  S  L  Q  S

181 GGGGTCCCATCAAGGTTCAGTGGCAGTGGGTCTGGGACAGATTTCACGCTCACCATCAGC
 61  G  V  P  S  R  F  S  G  S  G  S  G  T  D  F  T  L  T  I  S

241 AGTCTGCAACCTGAAGATTTTGCAACTTACTACTGTCAGCAGAGTTACGCTACTTCCTCG
 81  S  L  Q  P  E  D  F  A  T  Y  Y  C  Q  Q  S  Y  A  T  S  S

301 ATCACCTTCGGCCAGGGGACACGACTGGACATTAAA
101  I  T  F  G  Q  G  T  R  L  D  I  K
```

Translation of VH-SC2-Tie1-phagemid.TXT(1-413)
Universal code
Total amino acid number: 137, MW=14650
Max ORF: 1-411, 137 AA, MW=14650

```
  1 GAAGTTCAATTGTTAGAGTCTGGTGGCGGTCTTGTTCAGCCTGGTGGTTCTTTACGTCTT  (SEQ ID NO: 71)
  1  E  V  Q  L  L  E  S  G  G  G  L  V  Q  P  G  G  S  L  R  L  (SEQ ID NO: 72)

61 TCTTGCGCTGCTTCCGGATTCACTTTCTCTCGTTACAAGATGAAGTGGGTTCGCCAAGCT
 21  S  C  A  A  S  G  F  T  F  S  R  Y  K  M  K  W  V  R  Q  A

121 CCTGGTAAAGGTTTGGAGTGGGTTTCTGTTATCTATCCTTCTGGTGGCGGTACTGGTTAT
 41  P  G  K  G  L  E  W  V  S  V  I  Y  P  S  G  G  G  T  G  Y

181 GCTGACTCCGTTAAAGGTCGCTTCACTATCTCTAGAGACAACTCTAAGAATACTCTCTAC
 61  A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81  L  Q  M  N  S  L  R  A  E  D  T  A  V  Y  Y  C  A  R  V  N

301 TACTATGATAGTAGTGGTTACGGTCCTATAGCTCCTGGACTTGACTACTGGGGCCAGGGA
101  Y  Y  D  S  S  G  Y  G  P  I  A  P  G  L  D  Y  W  G  Q  G

361 ACCCTGGTCACCGTCTCAAGCGCCTCCACCAAGGGCCCATCGGTCTTCCCGCT
121  T  L  V  T  V  S  S  A  S  T  K  G  P  S  V  F  P
```

Translation of VL-SC2-Tie1-phagemid.TXT(1-428)
Universal code
Total amino acid number: 142, MW=15044
Max ORF: 1-426, 142 AA, MW=15044

```
  1 CACAGTGCACAGAGCGTCTTGACTCAGCCTGACTCCGTGTCTGGGTCTCCTGGAGAGTCG  (SEQ ID NO: 73)
  1  H  S  A  Q  S  V  L  T  Q  P  D  S  V  S  G  S  P  G  E  S  (SEQ ID NO: 74)

61 ATCACCATCTCCTGCACTGGAAGCAGCAGAGACGTTGGTGGTTATAACTATGTCTCCTGG
 21  I  T  I  S  C  T  G  S  S  R  D  V  G  G  Y  N  Y  V  S  W

121 TACCAACAACACCCAGGCAAAGCCCCCAAACTCTTGCTTTATGATGTCACTTATCGGCCC
 41  Y  Q  Q  H  P  G  K  A  P  K  L  L  L  Y  D  V  T  Y  R  P

181 TCAGGGATTTCTGGTCGCTTCTCTGGCTCCAAGTCTGGCGACACGGCCTCCCTGACCATC
 61  S  G  I  S  G  R  F  S  G  S  K  S  G  D  T  A  S  L  T  I
```

```
241 TCTGGGCTCCGGACTGAGGACGAGGCTGATTATTACTGCAGCTCATCTATAGGCACCAGG
 81  S  G  L  R  T  E  D  E  A  D  Y  Y  C  S  S  I  G  T  R

301 ACTTATGTCTTCGGAAGTGGGACCAAGGTCACCGTCCTACGTCAGCCCAAGGCCAACCCC
101  T  Y  V  F  G  S  G  T  K  V  T  V  L  R  Q  P  K  A  N  P

361 ACTGTCACTCTGTTCCCGCCCTCCTCTGAGGAGCTCCAAGCCAACAAGGCCACACTAGTG
121  T  V  T  L  F  P  P  S  S  E  E  L  Q  A  N  K  A  T  L  V

421 TGTCTGAT
141  C  L
```

Translation of VH-SC7-Tie1-phagemid.TXT(1-386)
Universal code
Total amino acid number: 128, MW=13785
Max ORF: 1-384, 128 AA, MW=13785

Translation of VH-SC10-Tie1-phagemid.TXT(1-413)
Universal code
Total amino acid number: 137, MW=14688
Max ORF: 1-411, 137 AA, MW=14688

```
  1 GAAGTTCAATTGTTAGAGTCTGGTGGCGGTCTTGTTCAGCCTGGTGGTTCTTTACGTCTT    (SEQ ID NO: 75)
  1  E  V  Q  L  L  E  S  G  G  G  L  V  Q  P  G  G  S  L  R  L   (SEQ ID NO: 76)

61 TCTTGCGCTGCTTCCGGATTCACTTTCTCTCGTTACGTTATGTATTGGGTTCGCCAAGCT
 21  S  C  A  A  S  G  F  T  F  S  R  Y  V  M  Y  W  V  R  Q  A

121 CCTGGTAAAGGTTTGGAGTGGGTTTCTGTTATCTATCCTTCTGGTGGCGCTACTTATTAT
 41  P  G  K  G  L  E  W  V  S  V  I  Y  P  S  G  G  A  T  Y  Y

181 GCTGACTCCGTTAAAGGTCGCTTCACTATCTCTAGAGACAACTCTAAGAATACTCTCTAC
 61  A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGACGGGGA
 81  L  Q  M  N  S  L  R  A  E  D  T  A  V  Y  Y  C  A  R  R  G

301 AGTAGTGGTGCGTTTGACTACTGGGGCCAGGGAACCCTGGTCACCGTCTCAAGCGCCTCC
101  S  S  G  A  F  D  Y  W  G  Q  G  T  L  V  T  V  S  S  A  S

361 ACCAAGGGCCCATCGGTCTTCCCGCT
121  T  K  G  P  S  V  F  P
```

Translation of VL-SC7-Tie1-phagemid.TXT(1-434)
Universal code
Total amino acid number: 144, MW=15027
Max ORF: 1-432, 144 AA, MW=15027

```
  1 CACAGTGCACAGAGCGTCTTGACTCAGCCTGCCTCCGTGTCTGGGTCTCCTGGACAGTCG    (SEQ ID NO: 77)
  1  H  S  A  Q  S  V  L  T  Q  P  A  S  V  S  G  S  P  G  Q  S   (SEQ ID NO: 78)

61 ATCACCATCTCCTGCACTGGAACCAGCAGTGACATTGGTCGTTATAACTATGCCTCCTGG
 21  I  T  I  S  C  T  G  T  S  S  D  I  G  R  Y  N  Y  A  S  W

121 TACCAACAACGCCCAGGCAAATCCCCCAAACTCCTGATTTATGAGGTCAGTGATCGGCCC
 41  Y  Q  Q  R  P  G  K  S  P  K  L  L  I  Y  E  V  S  D  R  P

181 TCAGGGGTTTCTAATCGCTTCTCTGGCTCCAAGTCTGGCAACACGGCCTCCCTGATCATC
 61  S  G  V  S  N  R  F  S  G  S  K  S  G  N  T  A  S  L  I  I

241 TCTGGGCTCCAGGCTGAGGACGAGGCTGATTATTACTGCAGCTCATATTCAAGCACCAAC
 81  S  G  L  Q  A  E  D  E  A  D  Y  Y  C  S  S  Y  S  S  T  N

301 AGTCTCCAAGTGGTATTCGGCGGAGGGACCAAGCTGAGCGTCCTAGGTCAGCCCAAGGCT
101  S  L  Q  V  V  F  G  G  G  T  K  L  S  V  L  G  Q  P  K  A

361 GCCCCCTCGGTCACTCTGTTCCCGCCCTCCTCTGAGGAGCTTCAAGCCAACAAGGCCACA
121  A  P  S  V  T  L  F  P  P  S  S  E  E  L  Q  A  N  K  A  T

421 CTGGTGTGTCTCAT
141  L  V  C  L
```

```
  1 GAAGTTCAATTGTTAGAGTCTGGTGGCGGTCTTGTTCAGCCTGGTGGTTCTTTACGTCTT   (SEQ ID NO: 79)
  1 E  V  Q  L  L  E  S  G  G  G  L  V  Q  P  G  G  S  L  R  L    (SEQ ID NO: 80)

61 TCTTGCGCTGCTTCCGGATTCACTTTCTCTGCTTACGGTATGTCTTGGGTTCGCCAAGCT
 21 S  C  A  A  S  G  F  T  F  S  A  Y  G  M  S  W  V  R  Q  A

121 CCTGGTAAAGGTTTGGAGTGGGTTTCTGTTATCTATCCTTCTGGTGGCTGGACTTATTAT
 41 P  G  K  G  L  E  W  V  S  V  I  Y  P  S  G  G  W  T  Y  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81 L  Q  M  N  S  L  R  A  E  D  T  A  V  Y  Y  C  A  R  V  N

301 TACTATGATAGTAGTGGTTACGGTCCTATAGCTCCTGGACTTGACTACTGGGGCCAGGGA
101 Y  Y  D  S  S  G  Y  G  P  I  A  P  G  L  D  Y  W  G  Q  G

361 ACCCTGGTCACCGTCTCAAGCGCCTCCACCAAGGGCCCATCGGTCTTCCCGCT
121 T  L  V  T  V  S  S  A  S  T  K  G  P  S  V  F  P
```

Translation of VL-SC10-Tie1-phagemid.TXT(1-336)
Universal code
Total amino acid number: 112, MW=12256
Max ORF: 1-336, 112 AA, MW=12256

Translation of VL-SD11-Tie1-phagemid.TXT(1-333)
Universal code
Total amino acid number: 111, MW=12194
Max ORF: 1-333, 111 AA, MW=12194

```
  1 CACAGTGCACAAGACATCCAGATGACCCAGTCTCCAGGCACCCTGTCTTTGTCTCCAGGG   (SEQ ID NO: 81)
  1 H  S  A  Q  D  I  Q  M  T  Q  S  P  G  T  L  S  L  S  P  G    (SEQ ID NO: 82)

61 GAAAGAGCCACCCTCTCCTGCAGGGCCAGTCAGAGTGTTAGCAGCAGCTACTTAGCCTGG
 21 E  R  A  T  L  S  C  R  A  S  Q  S  V  S  S  S  Y  L  A  W

121 TACCAGCAGAAACCTGGCCAGGCTCCCAGGCTCCTCATCTATGGTGCATCCAGCAGGGCC
 41 Y  Q  Q  K  P  G  Q  A  P  R  L  L  I  Y  G  A  S  S  R  A

181 ACTGGCATCCCAGACAGGTTCAGTGGCAGTGGGTCTGGGACAGACTTCACTCTCACCATC
 61 T  G  I  P  D  R  F  S  G  S  G  S  G  T  D  F  T  L  T  I

241 AGCAGACTGGAGCCTGAAGATTTTGCAGTGTATTACTGTCAGCAGTATAATAACTGGCCT
 81 S  R  L  E  P  E  D  F  A  V  Y  Y  C  Q  Q  Y  N  N  W  P

301 CGGACGTTCGGCCAAGGGACCAAGGTGGAAATCAAA
101 R  T  F  G  Q  G  T  K  V  E  I  K
```

Translation of VH-SD11-Tie1-phagemid.TXT(1-395)
Universal code
Total amino acid number: 131, MW=14005
Max ORF: 1-393, 131 AA, MW=14005

```
  1 GAAGTTCAATTGTTAGAGTCTGGTGGCGGTCTTGTTCAGCCTGGTGGTTCTTTACGTCTT   (SEQ ID NO: 83)
  1 E  V  Q  L  L  E  S  G  G  G  L  V  Q  P  G  G  S  L  R  L    (SEQ ID NO: 84)

61 TCTTGCGCTGCTTCCGGATTCACTTTCTCTGGTTACGCTATGTGGTGGGTTCGCCAAGCT
 21 S  C  A  A  S  G  F  T  F  S  G  Y  A  M  W  W  V  R  Q  A

121 CCTGGTAAAGGTTTGGAGTGGGTTTCTTCTATCTCTCCTTCTGGTGGCGCTACTGCTTAT
 41 P  G  K  G  L  E  W  V  S  S  I  S  P  S  G  G  A  T  A  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGATGCG
 81 L  Q  M  N  S  L  R  A  E  D  T  A  V  Y  Y  C  A  R  D  A

301 GGGAGTTATTATTGGGGCTGGTTCGACCCCTGGGGCCAGGGAACCCTGGTCACCGTCTCA
101 G  S  Y  Y  W  G  W  F  D  P  W  G  Q  G  T  L  V  T  V  S

361 AGCGCCTCCACCAAGGGCCCATCGGTCTTCCCGCT
121 S  A  S  T  K  G  P  S  V  F  P
```

```
  1 CACAGTGCACAAGACATCCAGATGACCCAGTCTCCAGCCACCTTGTCTTTGTCTCCAGGG  (SEQ ID NO: 85)
  1 H  S  A  Q  D  I  Q  M  T  Q  S  P  A  T  L  S  L  S  P  G   (SEQ ID NO: 86)

61 GAAAGAGCCACCCTCTCCTGCAGGGCCAGTCAGAGTATTAGCAGCTACTTAGCCTGGTAC
 21 E  R  A  T  L  S  C  R  A  S  Q  S  I  S  S  Y  L  A  W  Y

121 CAACAGAAACCTGGCCAGCCTCCCAGGCTCCTCATCTATGATGCATCCAGCAGGGTTACT
 41 Q  Q  K  P  G  Q  P  P  R  L  L  I  Y  D  A  S  S  R  V  T

181 GGCATCCCAGCCAGGTTCAGTGGCAGTGGCTTTGGGACAGACTTCACTCTCACCATTAGT
 61 G  I  P  A  R  F  S  G  S  G  F  G  T  D  F  T  L  T  I  S

241 AGCCTGGAGCCTGAAGATTTTGCAGTTTATTACTGTCTCCAGCGTAGCAGCTGGCCCCGA
 81 S  L  E  P  E  D  F  A  V  Y  Y  C  L  Q  R  S  S  W  P  R

301 ACTTTTGGCCAGGGGACCAAGCTGGAGATCAAA
101 T  F  G  Q  G  T  K  L  E  I  K
```

Translation of VH-SE11-Tie1-phagemid.TXT(1-413)
Universal code
Total amino acid number: 137, MW=14670
Max ORF: 1-411, 137 AA, MW=14670

Translation of VH-SG4-Tie1-phagemid.TXT(1-395)
Universal code
Total amino acid number: 131, MW=14168
Max ORF: 1-393, 131 AA, MW=14168

```
  1 GAAGTTCAATTGTTAGAGTCTGGTGGCGGTCTTGTTCAGCCTGGTGGTTCTTTACGTCTT  (SEQ ID NO: 87)
  1 E  V  Q  L  L  E  S  G  G  G  L  V  Q  P  G  G  S  L  R  L   (SEQ ID NO: 88)

61 TCTTGCGCTGCTTCCGGATTCACTTTCTCTGGTTACGTTATGTTTTGGGTTCGCCAAGCT
 21 S  C  A  A  S  G  F  T  F  S  G  Y  V  M  F  W  V  R  Q  A

121 CCTGGTAAAGGTTTGGAGTGGGTTTCTGGTATCTATCCTTCTGGTGGCTGGACTGTTTAT
 41 P  G  K  G  L  E  W  V  S  G  I  Y  P  S  G  G  W  T  V  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGTCAAT
 81 L  Q  M  N  S  L  R  A  E  D  T  A  V  Y  Y  C  A  R  V  N

301 TACTATGATAGTAGTGGTTACGGTCCTATAGCTCCTGGACTTGACTACTGGGGCCAGGGA
101 Y  Y  D  S  S  G  Y  G  P  I  A  P  G  L  D  Y  W  G  Q  G

361 ACCCTGGTCACCGTCTCAAGCGCCTCCACCAAGGGCCCATCGGTCTTCCCGCT
121 T  L  V  T  V  S  S  A  S  T  K  G  P  S  V  F  P
```

Translation of VL-SE11-Tie1-phagemid.TXT(1-333)
Universal code
Total amino acid number: 111, MW=11962
Max ORF: 1-333, 111 AA, MW=11962

```
  1 CACAGTGCACAAGACATCCAGATGACCCAGTCTCCAGGCACCCTGTCTTTGTCTCCAGGG  (SEQ ID NO: 89)
  1 H  S  A  Q  D  I  Q  M  T  Q  S  P  G  T  L  S  L  S  P  G   (SEQ ID NO: 90)

61 GAAAGAGCCACCCTCTCCTGCAGGGCCAGTCAGAGTGTTAGCAGCAGCTACTTAGCCTGG
 21 E  R  A  T  L  S  C  R  A  S  Q  S  V  S  S  S  Y  L  A  W

121 TACCAGCAGAAACCTGGCCAGGCTCCCAGGCTCCTCATCTATGGTGCATCCAGCAGGGCC
 41 Y  Q  Q  K  P  G  Q  A  P  R  L  L  I  Y  G  A  S  S  R  A

181 ACTGGCATCCCAGACAGGTTCAGTGGCAGTGGGTCTGGGACAGACTTCACTCTCACCATC
 61 T  G  I  P  D  R  F  S  G  S  G  S  G  T  D  F  T  L  T  I

241 AGCAGACTGGAGCCTGAAGATTTTGCAGTGTATTACTGTCAGCAATATGGTAGCTCACGG
 81 S  R  L  E  P  E  D  F  A  V  Y  Y  C  Q  Q  Y  G  S  S  R

301 ACGTTCGGCCAAGGGACCAACGTGGAAATCAAA
101 T  F  G  Q  G  T  N  V  E  I  K
```

```
  1 GAAGTTCAATTGTTAGAGTCTGGTGGCGGTCTTGTTCAGCCTGGTGGTTCTTTACGTCTT  (SEQ ID NO: 91)
  1 E  V  Q  L  L  E  S  G  G  G  L  V  Q  P  G  G  S  L  R  L   (SEQ ID NO: 92)

61 TCTTGCGCTGCTTCCGGATTCACTTTCTCTTCTTACATGATGACTTGGGTTCGCCAAGCT
 21 S  C  A  A  S  G  F  T  F  S  S  Y  M  M  T  W  V  R  Q  A

121 CCTGGTAAAGGTTTGGAGTGGGTTTCTTCTATCTATCCTTCTGGTGGCTATACTTATTAT
 41 P  G  K  G  L  E  W  V  S  S  I  Y  P  S  G  G  Y  T  Y  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGGAGGG
 81 L  Q  M  N  S  L  R  A  E  D  T  A  V  Y  Y  C  A  R  G  G

301 TATGGCGACTCGTCATTTTTTTTGACTACTGGGGCCAGGGAACCCTGGTCACCGTCTCA
101 Y  G  D  S  S  F  F  F  D  Y  W  G  Q  G  T  L  V  T  V  S

361 AGCGCCTCCACCAAGGGCCCATCGGTCTTCCCGCT
121 S  A  S  T  K  G  P  S  V  F  P
```

Translation of VL-SG4-Tie1-phagemid.TXT(1-333)
Universal code
Total amino acid number: 111, MW=11832
Max ORF: 1-333, 111 AA, MW=11832

```
  1 CACAGTGCACAAGACATCCAGATGACCCAGTCTCCAGCCACCCTGTCTGTGTCTCCAGGG  (SEQ ID NO: 93)
  1 H  S  A  Q  D  I  Q  M  T  Q  S  P  A  T  L  S  V  S  P  G   (SEQ ID NO: 94)

61 GAAGGAGCCACCCTCTCTTGCAGGGCCAGTCGGAGTGTTGGCAGCAACTTAGCCTGGTAC
 21 E  G  A  T  L  S  C  R  A  S  R  S  V  G  S  N  L  A  W  Y

121 CAGCAGAAGCCTGGCCAGGCTCCCAGGCTCCTCATCTATGATGCATCCACCAGGGCCACT
 41 Q  Q  K  P  G  Q  A  P  R  L  L  I  Y  D  A  S  T  R  A  T

181 GGTATCCCCGCCAGGTTCAGTGGCAGTGGGTCTGGGACAAAGTTCACTCTCACCATCAGC
 61 G  I  P  A  R  F  S  G  S  G  S  G  T  K  F  T  L  T  I  S

241 AGCCTCCAGTCTGAAGATTTTGCAGTTTATTACTGTCAGCAGCGTAGCAATTGGCCTCTC
 81 S  L  Q  S  E  D  F  A  V  Y  Y  C  Q  Q  R  S  N  W  P  L

301 ACTTTCGGCGGAGGGACCAAGGTGGAGATCAAA
101 T  F  G  G  G  T  K  V  E  I  K
```

Complete sequence VH-SG9 not known
Translation of VL-SG9-Tie1-phagemid.TXT(1-428)
Universal code
Total amino acid number: 142, MW=14993
Max ORF: 1-426, 142 AA, MW=14993

```
  1 CACAGTGCACAGAGCGTCTTGACTCAGCCTGCCTCCGTGTCTGGGTCTCCTGGACAGTCG  (SEQ ID NO: 95)
  1 H  S  A  Q  S  V  L  T  Q  P  A  S  V  S  G  S  P  G  Q  S   (SEQ ID NO: 96)

61 ATCACCATCTCCTGCACTGGAACCAGCAGTGACGTTGGTGATGATAACTATGTCTCCTGG
 21 I  T  I  S  C  T  G  T  S  S  D  V  G  D  D  N  Y  V  S  W

121 TACCAACAACACCCAGACAAAGCCCCCAAACTCATGATTTATGAGGTCAGTTATCGGCCC
 41 Y  Q  Q  H  P  D  K  A  P  K  L  M  I  Y  E  V  S  Y  R  P

181 TCAGGGGTTTCTAATCGCTTCTCTGGCTCCAAGTCTGGCAACACGGCCTCCCTGACCATC
 61 S  G  V  S  N  R  F  S  G  S  K  S  G  N  T  A  S  L  T  I

241 TCTGGGCTCCAGACTGAGGACGAGGCTGATTATTATTGCGGCTCATATCGCGTCAGCAGC
 81 S  G  L  Q  T  E  D  E  A  D  Y  Y  C  G  S  Y  R  V  S  S

301 TCCTATGTCTTCGGAACTGGGACCAAGGTCACCGTCCTAGGTCAGCCCAAGGCCAACCCC
101 S  Y  V  F  G  T  G  T  K  V  T  V  L  G  Q  P  K  A  N  P

361 ACTGTCACTCTGTTCCCGCCCTCCTCTGAGGAGCTCCAAGCCAACAAGGCCACACTAGTG
121 T  V  T  L  F  P  P  S  S  E  E  L  Q  A  N  K  A  T  L  V

421 TGTCTGAT
141 C  L
```

Translation of VH-SG10-Tie1-phagemid.TXT(1-363)
Universal code
Total amino acid number: 121, MW=13390
Max ORF: 1-363, 121 AA, MW=13390

```
  1 GAAGTTCAATTGTTAGAGTCTGGTGGCGGTCTTGTTCAGCCTGGTGGTTCTTTACGTCTT    (SEQ ID NO: 97)
  1 E  V  Q  L  L  E  S  G  G  G  L  V  Q  P  G  G  S  L  R  L     (SEQ ID NO: 98)

61 TCTTGCGCTGCTTCCGGATTCACTTTCTCTCGTTACAAGATGTTTTGGGTTCGCCAAGCT
 21 S  C  A  A  S  G  F  T  F  S  R  Y  K  M  F  W  V  R  Q  A

121 CCTGGTAAAGGTTTGGAGTGGGTTTCTGTTATCTATCCTTCTGGTGGCCCTACTATGTAT
 41 P  G  K  C  L  E  W  V  S  V  I  Y  P  S  G  G  P  T  M  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCGAGAGGGATG
 81 L  Q  M  N  S  L  R  A  E  D  T  A  V  Y  Y  C  A  R  G  M

301 GTCCGTGGATATAGTGGCTACGATTACCCTTTCTTGGACTACTGGGGCCAGGGAACCCTG
101 V  R  G  Y  S  G  Y  D  Y  P  F  L  D  Y  W  G  Q  G  T  L

361 GTC
121 V
```

Translation of VL-SG10-Tie1-phagemid.TXT(1-333)
Universal code
Total amino acid number: 111, MW=11981
Max ORF: 1-333, 111 AA, MW=11981

```
  1 CACAGTGCACAAGACATCCAGATGACCCAGTCTCCATCTTCCCTGTCTGCATCTGTAGGG    (SEQ ID NO: 99)
  1 H  S  A  Q  D  I  Q  M  T  Q  S  P  S  S  L  S  A  S  V  G     (SEQ ID NO: 100)

61 GACAGAGTCACCATCACTTGCCGAGCAAGTCAGACCATTAGCAGCTATTTAAATTGGTAT
 21 D  R  V  T  I  T  C  R  A  S  Q  T  I  S  S  Y  L  N  W  Y

121 CAGCAGAAGCCAGGGAAAGCCCCTAAGCTCCTGATCTATGCTGCATCCAGTTTGCAAAGT
 41 Q  Q  K  P  G  K  A  P  K  L  L  I  Y  A  A  S  S  L  Q  S

181 GGGGTCCCATCAAGGTTCAGTGGCAGTGGATCTGGGACAGATTTCACTCTCACCATCAGC
 61 G  V  P  S  R  F  S  G  S  G  S  G  T  D  F  T  L  T  I  S

241 AGTCTGCAACCTGAAGATTTTGCAACTTACTACTGTCAACAGAGTTACAGTACCCCTCGT
 81 S  L  Q  P  E  D  F  A  T  Y  Y  C  Q  Q  S  Y  S  T  P  R

301 ACGTTCGGCCAAGGGACCAAGGTGGAAATCAAA
101 T  F  G  Q  G  T  K  V  E  I  K
```

Translation of VH-SH1-Tie1-phagemid.TXT(1-386)
Universal code
Total amino acid number: 128, MW=13767
Max ORF: 1-384, 128 AA, MW=13767

```
  1 GAAGTTCAATTGTTAGAGTCTGGTGGCGGTCTTGTTCAGCCTGGTGGTTCTTTACGTCTT    (SEQ ID NO: 101)
  1 E  V  Q  L  L  E  S  G  G  G  L  V  Q  P  G  G  S  L  R  L     (SEQ ID NO: 102)

61 TCTTGCGCTGCTTCCGGATTCACTTTCTCTGCTTACCAGATGGTTTGGGTTCGCCAAGCT
 21 S  C  A  A  S  G  F  T  F  S  A  Y  Q  M  V  W  V  R  Q  A

121 CCTGGTAAAGGTTTGGAGTGGGTTTCTTCTATCTATCCTTCTGGTGGCTGGACTTATTAT
 41 P  G  K  G  L  E  W  V  S  S  I  Y  P  S  G  G  W  T  Y  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCACATGAACAGCTTAAGGGCTGAGGACACTGCAGTCTACTATTGTGCGAGAGGCACG
 81 L  Q  M  N  S  L  R  A  E  D  T  A  V  Y  Y  C  A  R  G  T

301 CACCTCCCGGGGGTTGACTACTGGGGCCAGGGAACCCTGGTCACCGTCTCAAGCGCCTCC
101 H  L  P  G  V  D  Y  W  G  Q  G  T  L  V  T  V  S  S  A  S

361 ACCAAGGGCCCATCGGTCTTCCCGCT
121 T  K  G  P  S  V  F  P
```

Translation of VL-SH1-Tie1-phagemid.TXT(1-339)
Universal code
Total amino acid number: 113, MW=12225
Max ORF: 1-339, 113 AA, MW=12225

```
  1 CACAGTGCACAAGACATCCAGATGACCCAGTCTCCAGGCACCCTGTCTTTGTCTCCAGGG     (SEQ ID NO: 103)
  1 H  S  A  Q  D  I  Q  M  T  Q  S  P  G  T  L  S  L  S  P  G     (SEQ ID NO: 104)

61 GAAAGAGCCACCCTCTCCTGCAGGGCCAGTCAGAGTGTTAGCAGCAGCTACTTAGCCTGG
 21 E  R  A  T  L  S  C  R  A  S  Q  S  V  S  S  S  Y  L  A  W

121 TACCAGCAGAAACCTGGCCAGGCTCCCAGGCTCCTCATCTATGGTGCATCCAGCAGGGCC
 41 Y  Q  Q  K  P  G  Q  A  P  R  L  L  I  Y  G  A  S  S  R  A

181 ACTGGCATCCCAGACAGGTTCAGTGGCAGTGGGTCTGGGACAGACTTCACTCTCACCATC
 61 T  G  I  P  D  R  F  S  G  S  G  S  G  T  D  F  T  L  T  I

241 AGCAGACTGGAGCCTGAAGATTTTGCAGTGTATTACTGTCAGCAGTATGGTAGCTCCCCC
 81 S  R  L  E  P  E  D  F  A  V  Y  Y  C  Q  Q  Y  G  S  S  P

301 ATGTACACTTTTGGCCAGGGGACCAAGCTGGAGATCAAA
101 M  Y  T  F  G  Q  G  T  K  L  E  I  K
```

Translation of VH-SH4-Tie1-phagemid.TXT(1-339)
Universal code
Total amino acid number: 113, MW=12481
Max ORF: 1-339, 113 AA, MW=12481

```
  1 GAAGTTCAATTGTTAGAGTCTGGTGGCGGTCTTGTTCAGCCTGGTGGTTCTTTACGTCTT     (SEQ ID NO: 105)
  1 E  V  Q  L  L  E  S  G  G  G  L  V  Q  P  G  G  S  L  R  L     (SEQ ID NO: 106)

61 TCTTGCGCTGCTTCCGGATTCACTTTCTCTTCTTACAAGATGGGTTGGGTTCGCCAAGCT
 21 S  C  A  A  S  G  F  T  F  S  S  Y  K  M  G  W  V  R  Q  A

121 CCTGGTAAAGGTTTGGAGTGGGTTTCTTCTATCTATCCTTCTGGTGGCTGGACTCATTAT
 41 P  G  K  G  L  E  W  V  S  S  I  Y  P  S  G  G  W  T  H  Y

181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

241 TTGCAGATGAACAGCTTAAGGGCTGAGGACACTGCAGTCTACTATTGTGCAAGAGTACTA
 81 L  Q  M  N  S  L  R  A  E  D  T  A  V  Y  Y  C  A  R  V  L

301 CTACACTACTTTGACTACTGGGGCCAGGGAACCCTGGTC
101 L  H  Y  F  D  Y  W  G  Q  G  T  L  V
```

Translation of VL-SH4-Tie1-phagemid.TXT(1-415)
Universal code
Total amino acid number: 138, MW=14287
Max ORF: 1-414, 138 AA, MW=14287

```
  1 CACAGTGCACAGAGCGTCTTGACTCAGCCTGCCTCCGTGTCTGGGTCTCCTGGACAGTCG     (SEQ ID NO: 107)
  1 H  S  A  Q  S  V  L  T  Q  P  A  S  V  S  G  S  P  G  Q  S     (SEQ ID NO: 108)

61 ATCACCATCTCCTGCACTGGAACCAGCAGTGACGTTGGTGGTTATAAATATGTCTCCTGG
 21 I  T  I  S  C  T  G  T  S  S  D  V  G  G  Y  K  Y  V  S  W

121 TACCAACAGCACCCAGGCAAAGCCCCCAAACTCATTATTTCTGACGTCAATAATCGGCCC
 41 Y  Q  Q  H  P  G  K  A  P  K  L  I  I  S  D  V  N  N  R  P

181 TCAGGGGTTTCTGATCGCTTCTCTGGCTCCAAGTCTGGCAACACGGCCTCCCTGACCATC
 61 S  G  V  S  D  R  F  S  G  S  K  S  G  N  T  A  S  L  T  I

241 TCTGGGCTCCAGGCTGAGGACGACGGTGATTATTACTGCAGTTCCTACGCAAGTAGTTCC
 81 S  G  L  Q  A  E  D  D  G  D  Y  Y  C  S  S  Y  A  S  S  S

301 TATACAAGCAGTACCACTTGGGTGTTCGGCGGGGGGACCAAGCTGACCGTCCTAGGTCAG
101 Y  T  S  S  T  T  W  V  F  G  G  G  T  K  L  T  V  L  G  Q

361 CCCAAGGCTGCCCCCTTGGTCACTCTGTTCCCACCCTCCTCTGAGGAGCTTCAAG
121 P  K  A  A  P  L  V  T  L  F  P  P  S  S  E  E  L  Q
```

Translation of Reverse_Complement_K2086117(1-471)
Universal code
Total amino acid number: 157, MW=16967
Max ORF: 1-471, 157 AA, MW=16967
T-G2-Tie1-heavy Translation of DNAMAN12 (1-425)
Universal code
Total amino acid number: 141, MW=14855
Max ORF: 1-423, 141 AA, MW=14855
T-E3-Tie1-heavy

```
         ---------------------------Fr1------------------------------
  1 GAAGTTCAATTGTTAGAGTCTGGTGGCGGTCTTGTTCAGCCTGGTGGTTCTTTACGTCTT   (SEQ ID NO: 109)
  1 E   V   Q   L   L   E   S   G   G   G   L   V   Q   P   G   G   S   L   R   L   (SEQ ID NO: 110)

----------------Fr1----------|....CDR1......|-----Fr2-------
 61 TCTTGCGCTGCTTCCGGATTCACTTTCTCTTCTTACAAGATGGGTTGGGTTCGCCAAGCT
 21 S   C   A   A   S   G   F   T   F   S   S   Y   K   M   G   W   V   R   Q   A

--------------Fr2----------|............CDR2..................
121 CCTGGTAGAGGTTTGGAGTGGGTTTCTTCTATCTATCCTTCTGGTGGCTGGACTCATTAT
 41 P   G   R   G   L   E   W   V   S   S   I   Y   P   S   G   G   W   T   H   Y

......CDR2........|-----------------Fr3----------------------
181 GCTGACTCCGTTAAAGGTCGCTTCACTATCTCTAGAGACAACTCTAAGAATACTCTCTAC
 61 A   D   S   V   K   G   R   F   T   I   S   R   D   N   S   K   N   T   L   Y

-------------------------Fr3--------------------------|.CDR3.
241 TTGCAGATGAACAGCTTAAGGGCTGAGGACACTGCAGTCTACTATTGTGCAAGAGTACTA
 81 L   Q   M   N   S   L   R   A   E   D   T   A   V   Y   Y   C   A   R   V   L

.......CDR3......|--------------Fr4-----------------
301 CTACACTACTTTGACTACTGGGGCCAGGGAACCCTGGTCACCGTCTCAAGCGCCTCCACC
101 L   H   Y   F   D   Y   W   G   Q   G   T   L   V   T   V   S   S   A   S   T

361 AAGGGCCCATCGGTCTTCCCCCTGGCACCCTCCTCCAAGAGCACCTCGGGGGCACAGCGG
121 K   G   P   S   V   F   P   L   A   P   S   S   K   S   T   S   G   A   Q   R

421 CCCTGGGCTGCCTGGTCAAGGACTACTTCCCGCGATACCGGTGACGGTGTC
141 P   W   A   A   W   S   R   T   T   S   R   D   T   G   D   G   V
```

Translation of C3-G2_pUCrev(1-325)
Universal code
Total amino acid number: 108, MW=11191
Max ORF: 1-324, 108 AA, MW=11191
T-G2-Tie1-lambda-light
2a2.272A12/DPL11

```
         ----------------------------Fr1------------------------------
  1 CAGAGCGTCTTGACTCAGCCTGCCTCCGTGTCTGGGTCTCCTGGACAGTCGATCACCATC   (SEQ ID NO: 111)
  1 Q   S   V   L   T   Q   P   A   S   V   S   G   S   P   G   Q   S   I   T   I   (SEQ ID NO: 112)

-Fr1-|.....................CDR1.................|----Fr2-----
 61 TCCTGCACTGGAACCAGCAGTGACGTTGGTGGTTATAAATATGTCTCCTGGTACCAACAG
 21 S   C   T   G   T   S   S   D   V   G   G   Y   K   Y   V   S   W   Y   Q   Q

-------------Fr2----------------|.........CDR2.......|-Fr3--
121 CACCCAGGCAAAGCCCCCAAACTCATTATTTCTGACGTCAATAATCGGCCCTCAGGGGTT
 41 H   P   G   K   A   P   K   L   I   I   S   D   V   N   N   R   P   S   G   V

---------------------------Fr3-------------------------------
181 TCTGATCGCTTCTCTGGCTCCAAGTCTGGCAACACGGCCTCCCTGACCATCTCTGGGCTC
 61 S   D   R   F   S   G   S   K   S   G   N   T   A   S   L   T   I   S   G   L

---------------Fr3-----------|...............CDR3............
241 CAGGCTGAGGACGACGGTGATTATTACTGCAGTTCCTACGCAAGTAGTTCCTATACAAGC
 81 Q   A   E   D   D   G   D   Y   Y   C   S   S   Y   A   S   S   S   Y   T   S

....CDR3...|----Fr4------
301 AGTACCACTTGGGTGTTCGGCGGGG
101 S   T   T   W   V   F   G   G
```

```
                    -----------------------------Fr1-----------------------------
  1 GAAGTTCAATTGTTAGAGTCTGGTGGCGGTCTTGTTCAGCCTGGTGGTTCTTTACGTCTT  (SEQ ID NO: 113)
  1 E  V  Q  L  L  E  S  G  G  G  L  V  Q  P  G  G  S  L  R  L   (SEQ ID NO: 114)

----------------Fr1------------|.....CDR1.....|------Fr2------
 61 TCTTGCGCTGCTTCCGGATTCACTTTCTCTATGTACGGTATGGTTTGGGTTCGCCAAGCT
 21 S  C  A  A  S  G  F  T  F  S  M  Y  G  M  V  W  V  R  Q  A

----------------Fr2--------|...............CDR2...............
121 CCTGGTAAAGGTTTGGAGTGGGTTTCTGTTATCTCTCCTTCTGGTGGCAATACTGGTTAT
 41 P  G  K  G  L  E  W  V  S  V  I  S  P  S  G  G  N  T  G  Y

........CDR2.....|-------------------Fr3---------------------
181 GCTGACTCCGTTAAAGGTCGCTTCACTATCTCTAGAGACAACTCTAAGAATACTCTCTAC
 61 A  D  S  V  K  G  R  F  T  I  S  R  D  N  S  K  N  T  L  Y

--------------------------Fr3-------------------------|.CDR3.
241 TTGCAGGTGAACAGCTTAAGGGCTGAGGACACTGCAGTCTACTATTGTGCGAGAGCCCCA
 81 L  Q  V  N  S  L  R  A  E  D  T  A  V  Y  Y  C  A  R  A  P

..............CDR3..........|---------------Fr4----------------
301 CGTGGATACAGCTATGGTTACTACTACTGGGGCCAGGGAACCCTGGTCACCGTCTCAAGC
101 R  G  Y  S  Y  G  Y  Y  Y  W  G  Q  G  T  L  V  T  V  S  S

361 GCCTCCACCAAGGGCCCATCGGTCTTCCCGCTAGCACCCTCCTCCAAGAGCACCTCTGGG
121 A  S  T  K  G  P  S  V  F  P  L  A  P  S  S  K  S  T  S  G

421 GGCAC
141 G
```

Translation of C1-E3_pUCrev(1-322)
Universal code
Total amino acid number: 107, MW=11650
Max ORF: 1-321, 107 AA, MW=11650
T-E3-Tie1-kappa-light DPK4/A20+
jk5

NO:20, SEQ ID NO:24, SEQ ID NO:28, SEQ ID NO:40, SEQ ID NO:44, SEQ ID NO:48, SEQ ID NO:52, SEQ ID NO:60, SEQ ID NO:102, SEQ ID NO:56, SEQ ID NO:64, SEQ ID NO:68, SEQ ID NO:80, SEQ ID NO:72, SEQ ID NO:76, SEQ ID NO:84, SEQ ID NO:88, SEQ ID NO:98, SEQ ID NO:106, SEQ ID NO:110, SEQ ID NO:114.

```
    -----------------------------Fr1-----------------------------
  1 GACATCCAGATGACCCAGTCTCCACTCTCCCTGTCTGCATCTGTAGGAGACAGAGTCACC  (SEQ ID NO: 115)
  1 D  I  Q  M  T  Q  S  P  L  S  L  S  A  S  V  G  D  R  V  T   (SEQ ID NO: 116)

--Fr1---|..............CDR1................|--------Fr2--------
 61 ATCACTTGCCGGGCGAGTCAGGGCATTGGCCATTATTTAGCCTGGTATCAGCAGAAACCA
 21 I  T  C  R  A  S  Q  G  I  G  H  Y  L  A  W  Y  Q  Q  K  P

-----------Fr2-------------|..........CDR2.......|----Fr3-----
121 GGGAAAGTTCCTAAGCTCCTGATCTATACTGCATCCACTTTGCAATCAGGGGTCCCATCT
 41 G  K  V  P  K  L  L  I  Y  T  A  S  T  L  Q  S  G  V  P  S

----------------------------Fr3-----------------------------
181 CGGTTCAGTGGCAGTGGATCTGGGACAGATTTCACTCTCACCATCAACAGCCTGCAGCCT
 61 R  F  S  G  S  G  S  G  T  D  F  T  L  T  I  N  S  L  Q  P

-----------Fr3---------|..........CDR3.........|-----Fr4----
241 GAGGATGTTGCAACTTATTACTGTCAACAGTTTAATAGTTACCCTCACACCTTCGGCCAA
 81 E  D  V  A  T  Y  Y  C  Q  Q  F  N  S  Y  P  H  T  F  G  Q

----------Fr4---------
301 GGGACACGACTGGATATTAAAC
101 G  T  R  L  D  I  K
```

Example 4

Alignment

Tables 3 and 4 the list CDR and FR regions of exemplary antibodies, the sequences of which are listed herein.

The sequences listed in Table 3 correspond to an amino-terminal portion of the variable heavy chain sequences of, respectively, SEQ ID NO:4, SEQ ID NO:16, SEQ ID NO:20, SEQ ID NO:24, SEQ ID NO:28, SEQ ID NO:40, SEQ ID NO:44, SEQ ID NO:48, SEQ ID NO:52, SEQ ID NO:60, SEQ ID NO:102, SEQ ID NO:56, SEQ ID NO:64, SEQ ID NO:68, SEQ ID NO:80, SEQ ID NO:72, SEQ ID NO:76, SEQ ID NO:84, SEQ ID NO:88, SEQ ID NO:98, SEQ ID NO:106, SEQ ID NO:110, SEQ ID NO:114.

The sequences listed in Table 4 correspond to an amino-terminal portion of the variable light chain sequences of, respectively, SEQ ID NO:6, SEQ ID NO:18, SEQ ID NO:22, SEQ ID NO:26, SEQ ID NO:30, SEQ ID NO:42, SEQ ID NO:46, SEQ ID NO:50, SEQ ID NO:54, SEQ ID NO:62, SEQ ID NO:104, SEQ ID NO:58, SEQ ID NO:66, SEQ ID NO:70, SEQ ID NO:82, SEQ ID NO:74, SEQ ID NO:78, SEQ ID NO:86, SEQ ID NO:90, SEQ ID NO:100, SEQ ID NO:108, SEQ ID NO:112, SEQ ID NO:116.

TABLE 3

Heavy Chain Sequences

| Isolate name | H-FR1 | H-CDR1 | FR2 | H-CDR2 | H-FR3 | H-CDR3 |
|---|---|---|---|---|---|---|
| p-A1 | EVQLLESGGGLVQPGGSL RLSCAASGFTFS | IYKMS | WVRQAPGKGLEWVS | SIYPSGGQTKYADSVKQ | RFTISRDNSKNTLYLQMNS LRAEDTAVYYCAR | VNYYDSSYGPIAPGLDY |
| p-A10 | EVQLLESGGGLVQPGGSL RLSCAASGFTFS | SYKMG | WVRQAPGKGLEWVS | WIYPSGGGTTYADSVKC | RFTISRDNSKNTLYLQMNS LRAEDTAVYYCAR | VNYYDSSYGPIAPGLDY |
| p-B1 | EVQLLESGGGLVQPGQSL RLSCAASGFTFS | RYPMV | WVRQAPGKGLEWVS | VISPSGGQTFYADSVKG | RFTISRDNSKNTLYLQMNS LRAEDTAVYYCAR | GVLTTAFDI |
| p-B3 | EVQLLESGGGLVQPGGSL RLSCAASGFTFS | RYGMH | WVRQAPGKGLEWVS | VISPSGGMTYYADSVKG | RFTISRDNTKNTLYLQMNS LRAEDTAVYYCAR | VGATGPFDI |
| p-C6 | EVQLLESGGGLVQPGGSL RLSCAASGFTFS | HYGMT | WVRQAPGKGLEWVS | VISPSGGQTGYADSVKG | RFTISRDNSKNTLYLQMNS LRAEDTAVYYCAG | GGYAAFDY |
| p-D12 | EVQLLESGGGLVQPGGSL RLSCAASGFTFS | GYGMH | WVRQAPGKGLEWVS | VISPSGGQTSYADSVKG | RFTISRDNSKNTLYLQMNS LRAEDTAVYYCAR | DRQYYYGSGSLDY |
| p-F3 | EVQLLESGGGLVQPGGSL RLSCAASGFTFS | MYGMG | WVRQAPGKGLEWVS | VISPSGGQTAYADSVKG | RFTISRDNSKNTLYLQMNS LRAEDTAVYYCAR | VALLLGHAFDI |
| p-F4 | EVQLLESGGGLVQPGGSL RLSCAASGFTFS | AYMMS | WVRQAPGKGLEWVS | SIYPSGGYTYYADSVKG | RFTISRDNSKNTLYLQMNS LRAEDTAVYYCAR | GLRGGPDY |
| p-G3 | EVQLLESGGGLVQPGGSL RLSCAASGFTFS | HYMMV | WVRQAPGKGLEWVS | SIYPSGGMTYYADSVKG | RFTISRDNSKNTLYLQMNS LRAEDTAVYYCAR | LDYGGNSAYFDY |
| s-A10 | EVQLLESGGGLVQPGGSL RLSCAASGFTFS | NYVMV | WVRQAPGKGLEWVS | GIYPSGGHTKYADSVKG | RFTISRDNSKNTLYLQMNS LRAEDTAVYYCAR | VNYYDSSYGPIAPGLDY |
| s-H1 | EVQLLESGGGLVQPGGSL RLSCAASGFTFS | AYQMV | WVRQAPGKGLEWVS | SIYPSGGWTYYADSVKG | RFTISRDNSKNTLYLQMNS LRAEDTAVYYCAR | GTHLPGVDY |
| s-A2 | EVQLLESGGGLVQPGGSL RLSCAASGFTFS | RYTMM | WVRQAPGKGLEWVS | GIYPSGGVTLYADSVKG | RFTISRDNSKNTLYLQHNS LRAEDTAVYYCAR | VNYYDSSYGPIAPGLDY |
| s-B2 | EVQLLESGGGLVQPGGSL RLSCAASGFTFS | IYGMA | WVRQAPGKGLEWVS | VISPSGGQTFYADSVKG | RFTISRDNSKNTLYLQMNS LRAEDTAVYYCAR | VYYYGMDV |
| s-B9 | EVQLLESGGGLVQPGGSL RLSCAASGFTFS | SYVMM | WVRQAPGKGLEWVS | GIYPSGGWTYYTDSVKG | RFTISRDNSKNTLYLQMNS LRAEDTAVYYCAR | VNYYDSSYGPIAPGLDY |
| s-C10 | EVQLLESGGGLVQPGGSL RLSCAASGFTFS | AYGMS | WVRQAPGKGLEWVS | VIYPSGGWTYYADSVKG | RFTISRDNSKNTLYLQMNS LRAEDTAVYYCAR | VNYYDSSYGPIAPGLDY |
| s-C2 | EVQLLESGGGLVQPGGSL RLSCAASGFTFS | RYKMK | WVRQAPGKGLEWVS | VIYPSGGGTGYADSVKG | RFTISRDNSKNTLYLQMMS LRAEDTAVYYCAR | VNYYDSSYGPIAPGLDY |
| s-C7 | EVQLLESGGGLVQPGGSL RLSCAASGFTFS | RYVHY | WVRQAPGKGLEWVS | VIYPSGGATYYADSVKG | RFTISRDNSKNTLYLQMNS LRAEDTAVYYCAR | RGSSGAFDY |
| s-D11 | EVQLLESGGGLVQPGGSL RLSCAASGFTFS | GYAMW | WVRQAPGKGLEWVS | SISPSGGATAYADSVKG | RFTISRDNSKNTLYLQMNS LRAEDTAVYYCAR | DAGSYYWGWFDP |
| a-E11 | EVQLLESGGGLVQPGGSL RLSCAASGFTFS | GYVMF | WVRQAPGRGLEWVS | GIYPSGGWTVYADSVKG | RFTISRDNSKNTLYLQMNS LRAEDTAVYYCAR | VNYYDSSYGPIAPGLDY |
| s-G10 | EVQLLESGGGLVQPGGSL RLSCAASGFTFS | RYKMF | WVRQAPGKGLEWVS | VIYPSGGPTMYADSVKG | RFTISRDNSKNTLYLQMNS LRAEDTAVYYCAR | GMVRGYSGYDYPFLDY |
| a-H4 | EVQLLESGGGLVQPGGSL RLSCAASGFTFS | SYKMG | WVRQAPGKGLEWVS | SIYPSGGWTHYADSVKG | RFTISRDNSKNTLYLQMMS LRAEDTAVYYCAR | VLLHYFDY |
| G2 | EVQLLESGGGLVQPGGSL RLSCAASGFTFS | SYKMG | WVRQAPGRGLEWVS | SIYPSGGWTHYADSVKG | RFTISRDNSKNTLYLQMMS LRAEDTAVYYCAR | VLLHYFDY |
| E3 | EVQLLESGGGLVQPGGSL RLSCAASGFTFS | MYGMV | WVRQAPGKGLEWVS | VISPSGGNTGYADSVKG | RFTISRDNSKNTLYLQVNS LRAEDTAVYYCAR | APRGYSYGYYY |

TABLE 4

Light Chain Sequences

| Isolatename | L-FR1 | L-CDR1 | L-FR2 | L-CDR2 | L-FR3 | L-CDR3 |
|---|---|---|---|---|---|---|
| p-A1 | QDIQMTQSPGTLSLSPGE RATLSC | RASQSVSSSYLA | WYQQKPGQAPRLLIY | GASSRAT | GIPDRFSGSGSGTDFTL TISRLEPEDFAVYYC | QQYGSSRWT |
| p-A10 | QDIQMTQSPGTLSLSPGE RATLSC | RASQSVSSSYLA | WYQQKPGQAPRLLIY | GASSRAT | GIPDRFSGSQSCTDFTL TISRLEPEDFAVYYC | QQYGSSPWT |
| p-B1 | QDIQMTQSPSSLSASVGD RVTITC | RASQNINSYLN | WYQQKPGQAPKLLIY | AASNLET | AVPSRFSGSGSGTDFTL TISSLQPEDFATYYC | QQFNTYPLT |
| p-B3 | QDIQMTQSPATLSLSPGE RATLSC | RASQSVSTYLA | WYQQKPQQAPRLLIY | DASNRAT | GIPGRFSGSCSGPDFTL TISSLEAEDEAVYYC | QQRSSWPIT |
| p-C6 | QDIQMTQSPATLSLSPGE RATLSC | RASQSVSSYLA | WYQQKPGQAPRLLIY | DASNRAT | GIPARFSGSGSGTDFTL TISSLEPEDFAVYYC | QQRSNWPLT |
| p-D12 | QDIQMTQSPSSLSASVGD RVTVTC | RASQSISSYLN | WYQQKPGKAPKLLIY | AASSLQS | GVPSRFSQGQGSTDFTL TISSLQPEDEATYPC | LQDYKYPWT |
| p-F3 | QDIQMTQSPSTLASLGD RVTITC | RASESISRWLA | WYQQKPGKAPKLLMY | EASTLES | QVPSRFTGTGSGTEFTL TISSLQPDDFATYYC | QQRSNWPLT |
| p-F4 | QDIQMTQSPSTLSAYVGD SVTITC | RASQSVRRSLA | WYQQRPGKAPKSLIY | KASTLET | GVPPRFSGSGSGTEFTL TISSLQPEDSAIYYC | QQYGSFPLT |
| p-G3 | QSVLTQPHSVSASPGKTV TISC | TRSSGNIASNFVQ | WYQQRPGSVPTTVIY | EDDRRPS | GVPDRFSGSIDSSSNSA FLSISGLKTEDEADYYC | QSHDRTTRAWV |
| s-A10 | QDIQMTQSPGTLSLSPGE RATLFC | RASQRVTSNSLA | WYQQRPGQAPRLLIY | DASTRAT | GIPDRFSGSGSGRDFTL TISRLEPEDFAVYYC | QRYGSSVLYS |
| s-H1 | QDIQMTQSPGTLSLSPGE RATLSC | RASQSVSSSYLA | WYQQKPGQAPRLLIY | GASSRAT | GIPDRFSGSGSGTDFTL TISRLEPEDFAVYYC | QQYGSSPMYT |
| s-A2 | QDIQMTQSPGTLSLSPGE RATLSC | RASRSVIISYVA | WYQQKPGQAPRLLIY | GASTRAT | GIPDRFSGSGSGTDFTL TISRLEPEDFAVYFC | QLYGRSPRII |
| s-B2 | QDIQMTQSPATLSLSPGE RATLSC | RASQSVSSYLA | WYQQKPOQAPRLLIY | DASNRAT | GIPARFSGSGSETDFTL TISSLEPEDFAVYYC | QQRSKWPRT |
| s-B9 | QDIQMTQSPSSLSASVGD RVTITC | RASQSVSSHLS | WFQQRPGKAPNLLIY | HASSLQS | GVPSRFSGSGSGTDFTL TISSLQPEDFATYYC | QQSYATSSIT |
| s-C10 | QDIQMTQSPGTLSLSPGE RATLSC | RASQSVSSSYLA | WYQQKPQQAPRLLIY | GASSRAT | GIPDRFSGSGSGTDFTL TISRLEPEDFAVYYC | QQYNNWPRT |
| s-C2 | QSVLTQPDSVSOSPQESI TISC | TGSSRDVQGYNYVS | WYQQHPGKAPKLLLY | DVTYRPS | GISGRFSQSKSGDTASL TISGLRTEDEADYYC | SSSIGTRTYV |
| s-C7 | QSVLTQPASVSGSPGQSI TISC | TGTSSDIGRYNYAS | WYQQRPQKSPKLLIY | EVSDRPS | GVSNRFSGSKSGNTASL IISGLQAEDEADYYC | SSYSSTNSLQVV |
| s-D11 | QDIQMTQSPATLSLSPGE RATLSC | RASQSISSYLA | WYQQKPGQPPRLLIY | DASSRVT | GIPARFSGSGFGTDFTL TISSLEPEDPAVYYC | LQRSSWPRT |
| s-E11 | QDIQMTQSPGTLSLSPGE RATLSC | RASQSVSSSYLA | WYQQKPGQAPRLLIY | GASSRAT | GIPDRFSGSGSGTDFTL TISRLEPEDFAVYYC | QQYGSSRT |
| s-G10 | QDIQMTQSPSSLSASVGD RVTITC | RASQTISSYLN | WYQQKPGKAPKLLIY | AASSLQS | GVPSRFSGSGSGTDFTL TISSLQPEDFATYYC | QQSYSTPRT |
| s-H4 | QSVLTQPASVSGSPGQSI TISC | TGTSSDVGGYKYVS | WYQQHPGKAPKLIIS | DVNNRPS | GVSDRFSGSKSGNTASL TISGLQAEDDGDYYC | SSYASSSYTSSTTWV |
| G2 | QSVLTQPASVSGSPGQSI TISC | TGTSSDVGGYKYVS | WYQQHPGKAPKLIIS | DVNNRPS | GVSDRFSGSKSGNTASL TISGLQAEDDGDYYC | SSYASSSYTSSTTWV |
| E3 | DIQMTQSPLSLSASVGDR VTITC | RASQGIGHYLA | WYQQKPGKVPKLLIY | TASTLQS | GVPSRFSGSGSGTDFTL TINSLQPEDVATYYC | QQFNSYPHT |

Example 5

Sequence Alignment of B2 and D11

B2 and D11 are both antagonists of Tie1 since they counteract the agonistic activity of E3 in the BaF3 activation assay. B2 and D11 both have a kappa light chain and are similar in sequence (8 amino acid differences):

```
                        ←---CDR1--→                    ←-CDR2-→
1  (B2)  DIQMTQSPATLSLSPGERATLSCRASQSVSSYLAWYQQKPGQAPRLLIYDASNRAT
         |||||||||||||||||||||||||||:||||||||||||:|||||||||.|.|
1  (D11) DIQMTQSPATLSLSPGERATLSCRASQSISSYLAWYQQKPGQPPRLLIYDASSRVT

←-CDR3-→
61  GIPARFSGSGSETDFTLTISSLEPEDFAVYYCQQRSKWPRTFGQGTKLEIK SEQ ID NO:157
    |||||||||||:||||||||||||||||||||||||||.|||||||||||
61  GIPARFSGSGFGTDFTLTISSLEPEDFAVYYCLQRSSWPRTFGQGTKLEIK SEQ ID NO:158
```

Example 6

Inhibition of Tube Formation by HUVECS Cells Using Anti Tie1 E3-IgG

To demonstrate the ability of E3 to inhibit angiogenesis in vitro, purified E3 was tested for its ability to inhibit tube formation by human umbilical cord endothelial cells (HUVECS). Human Umbilical vein endothelial cells (HUVEC) were obtained by treating fresh human umbilical cord veins with Trypsin-EDTA (1×) (Gibco/Invitrogen) for 20-25 minutes at 37° C. The cells were cultured in a T-25 flask coated with attachment factor (AF), (Cascade Biologics) in RPMI 1640 medium supplemented with 10% FCS, 0.4% BBE, 1% 1-glutamin, 1% penicillin/streptomycin. Primary cultures were detached with warm Trypsin-EDTA and used when confluent at the second or third passage. The cells were maintained in a proliferative state by culturing them in a split ratio 1:2 at an approximate density of the monolayer of about 60-80%. To dissociate the cells, HUVEC monolayers were treated with trypsin/EDTA (500 l/dish) at 37° C. for 3 min. Trypsin activity was stopped by adding 3 volumes of complete RPMI medium. The cells were carefully scraped, separated by repeated pipetting, and finally washed with PBS.

After 2 passages HUVECs were seeded in their culture medium ($40.10^3$/50 μl/well of a 96-well plate) on a collagen gel (50 μl of collagen I 1.5 mg/ml) prepared by mixing 7.5 volumes of 2 mg/ml collagen (Collagen R; Serva, Heidelberg, Germany), 1 volume of 10× MEM, 1.5 volume of $NaHCO_3$ (15.6 mg/ml) and ~1 volume of NaOH to adjust the pH to 7.4. After 1 h30, the culture medium was then discarded and the cells were covered with a new layer of collagen (1.5 mg/ml, new preparation, 50 μl/well). After polymerization of the gel, culture medium was added to each well in presence or in absence of E3 antibody (1 ng/ml to 10 μg/ml). The assay was performed with a streptavidin antibody used as a control (from 1 ng/ml to 10 μg/ml). The total length of the tube network on the culture surface was quantified at ×40 magnification by the METAVUE™ Software (Universal Imaging Corporation). Results from triplicate wells were expressed as mean vessel area per field ±SEM (relative units). Each assay was performed at least three times.

E3 is a potent inhibitor of tube formation by HUVECS even at a concentration of 10 ng/ml. The control anti streptavidin has no effect on the ability of HUVECS to form tubes. This results indicates that E3 can inhibit one aspect of angiogenesis.

Example 7

Immunohistochemical Analysis of E3 Binding to Matched Tumor and Normal Tissue Sections To evaluate the binding of E3 to Tie1 in primary tumor and normal tissue the antibody was produced as an IgG and biotin labeled. The E3 antibody and two other anti Tie1 antibodies B2 and D11 were reformatted as full length IgG molecules. Nucleic acids encoding these IgGs were transiently transfected into HEK293T cells. Plasmid preparations for transient cell transfections were performed using the HP-GENELUTE™ MIDI prep kit (Sigma, cat. no. NA0200). HEK293T cells (GenHunter Corp. cat. no. Q401) were seeded 24 hours before transfection; $6×10^6$ cells were plated per 10-cm culture dish. Transfections were carried out using LIPOFECTAMINE™ 2000 reagent (Invitrogen, cat. no. 11668019) following the manufacturer's instructions. Five micrograms of plasmid DNA was used per 10-cm dish. Cells were cultured in DMEM (Invitrogen, cat. no. 31966021) supplemented with 10% "ultra-low IgG" fetal calf serum (Invitrogen, cat. no. 16250078), at 37° C., 5% $CO_2$, in a water saturated atmosphere. Conditioned media were harvested 72 hours and 144 hours after transfection, pooled and sterile filtered.

One hundred microliters of Protein A beads (rProtein A Sepharose 4 Fast Flow, Amersham Biosciences, cat. no. 17-1279-01) equilibrated in PBS were added to the cell culture supernatants, and these were rotated overnight at 4° C., e.g., in 50 ml tubes. The beads were collected by centrifugation, transferred to a 96-well filter plate (UNIFILTER 800 GF/B, Whatman, cat. no. 7700-2803) and washed extensively with PBS using a vacuum manifold (Macherey Nagel, cat. no. 760681). Elution of the antibodies was achieved by resuspending the beads in 400 μl of 12.5 mM citric acid. After a 30 to 60 second incubation, the bead eluates were collected, using the vacuum manifold, into the wells of a 96-well collection plate (UNIPLATE 750, Whatman, cat. no. 7701-5750). Each well of the collection plate contained 60 μl of 1 M HEPES pH 7.5 buffer to immediately neutralize the eluted fractions. The elution step was performed twice to maximize antibody recovery. The eluted samples were then dialyzed against PBS using dialysis cassettes (Slide-A-Lyser Dialysis Cassettes, MWCO 10,000, Pierce, cat. no. 66380) and protein concentration was determined from the absorbance at 280 nm assuming that a 1 mg/ml solution has an absorbance of 1.35. The quality of the preparations was analyzed by reducing and non-reducing SDS-PAGE.

The Tie-1 antibodies were biotinylated using the EZ-link Sulfo-NHS-SS-Biotin (Pierce, Cat. 21331). For Tie-1/Fc and Tie-1-His, the reaction was performed for 2 hours on ice in 50 mM sodium carbonate buffer, pH 9.6, in the presence of a 5-fold molar excess of biotinylating agent. For the antibodies, the reaction was performed for 2 hours on ice in PBS, in the presence of a 15-fold molar excess of EZ-link Sulfo-NHS-SS-Biotin. The reaction was stopped by the addition of Tris-HCl, pH 7.5 (50 mM final concentration) followed by a 1-hour incubation on ice. Samples were then dialyzed against PBS.

Various normal and tumor tissue sections were stained with biotinylated antibodies. A mouse monoclonal anti-Tie1 antibody (7e8) (Alitalo laboratory, University of Helsinki) was used as a positive control. Sections without primary antibody served as negative control. All samples were fresh frozen tissues and staining was performed with the TSA-kit (Perkin-Elmer Life Sciences). After acetone fixation (10-20 min, −20° C.) the slides were treated with 0.73% $H_2O_2$ for 10 min to reduce endogenous peroxidase activity followed by blocking for 30 min with TNB buffer. Sections (5-10 mm thick) were incubated with primary antibodies (10 μg/ml) overnight at 4° C. Sections with the mouse monoclonal anti-tie1 antibody (7e8) were treated with biotinylated antimouse antibodies (VectaStain) before the addition of streptavidin-HRP. Signal was amplified by using a TSA kit and the visualized by AEC (235 ml NaAc,15 ml AEC (stock solution: 1600 mg 3-amino-9-ethyl-carbazole and 480 ml N-dimethylformamide), 250 μl $H_2O_2$).

In general, Tie-1 expression was upregulated in tumor tissue when compared with matching normal tissue. However, in the tumor tissues the anti Tie1 antibodies stained other structures in addition to the vessels. Furthermore, some tissue specificity in the expression of certain epitopes was observed. For example, the E3 antibody stained vessels in the lung and kidney but not in the skin while the B2 antibody stained vessels very faintly in other normal tissues than in the breast. Shedding of the ectodomain of Tie-1 into the tumor tissues can explain observed differences.

In skin tissue, the E3, B2, and D11 antibodies stained blood vessels very faintly whereas the murine 7e8 control antibody gave a clear staining in the normal skin. In melanoma tissue, the 7e8 antibody stained vessels only but the E3, B2, and D11 antibodies also stained other surrounding structures. The staining pattern was similar with all three of the E3, B2, and D11 antibodies antibodies.

In lung tissue, we observed that the E3 antibody stained especially clearly the large veins in the lung, whereas D11 and 7e8 gave a faint staining. B2 did not stain the same veins. The expression of Tie-1 was dramatically upregulated in lung carcinoma and all the antibodies stained vessels more strongly in samples with lung carcinoma than in samples from normal lung. In the lung tumors, the E3, B2, and D11 antibodies stained structures other than vessels.

In kidney, the E3 and D11 antibodies stained kidney tubules in addition to the vessels. B2 gave only very faint staining of either tubules or vessels while 7e8 stained only vessels. In hypernephroma tissue, only the E3 antibody gave a clear staining.

In breast, E3 gave the brightest staining in the veins and capillaries of the mammary tissue, B2 and 7e8 gave a similar staining while D11 stained those structures rather faintly. In breast carcinoma the Tie-1 expression was substantially upregulated, and the E3, B2, and D11 antibodies stained also other structures in addition to vessels.

Example 8

Binding to Mouse Endothelial Cell Lines of Anti Tie1 E3-IgG Using Flow Cytometry We evaluated if E3 cross reacts with mouse Tie1 in situ and thus if we can evaluate E3 activity in mouse tumor xenograft models binding to mouse endothelial cells was tested and compared with human and transfected cell lines.

Specific binding of the Tie-1 antibodies and of control Mabs to mouse endothelial cells was measured by flow cytometry analysis (FACSscan, Becton Dickinson, Oxnard, Epics, Coulter). Mouse endothelial cell lines MS1, Le-2 (Alitalo) Bend3, SVEC (ATCC, Rockville) and Tie-1 transfected Le-2 cells (Alitalo) were stained. Cell staining was modified from existing protocols. About 200,000 cells were used in each experiment: after trypsinization, cells were washed one time in PBS and resuspended PBS, 10% Heat inactivated human serum (incubation buffer). To test specificity, antibodies were incubated at different dilutions for 1 h at room temperature. Cells were spun down by centrifugation for 3 min at 611 g. Between incubations cells were washed twice with PBS. Then relevant biotinylated antibodies (A2 against streptavidin, E3 against Tie-1, were added and incubated for 1 h at room temperature). This was followed by incubation with Strepatvidin-R-phycoerythrin (Dako, Glostrup, Denmark) for 1 hour at room temperature in incubation buffer. After the final incubation step bound antibodies were detected by means of flow cytometry on a FACSCan and Epics Altra (Becton Dickinson, Oxnard, Coulter,) and results analyzed.

Intracellular Tie-1 was measured as described above, except for the addition of Saponin to the incubation buffer to a final concentration of 0.1% during incubations. The anti-Tie-1 antibody E3 binds to mouse endothelial cell lines indicating a cross reactivity of E3 with mouse and human Tie1 in situ. The binding pattern in mouse cell lines detected by flow cytometry is different from the binding pattern in HUVEC in that in mouse cells there is a greater cell surface staining than that compared to primary human endothelial cell lines.

Example 9

Determination of Anti Tie1 E3-IgG Binding to Human Platelets Using Flow Cytometry Binding experiments with a purified polyclonal goat antiserum against Tie-1 (R&D systems) had showed binding to human platelets in a previous study (Tsiamis et al., 2000). The conclusion form this study was that platelets represent a large pool of Tie-1 immunoreactivity which could present a problem for development of Tie1 as a therapeutic target. To determine if the antibody E3 binds to platelets we performed flow cytrometric analysis on both activated and inactivated platelets and compared the staining pattern with the purified anti Tie1 polyclonal serum.

To avoid platelet activation, human platelets were isolated from plasma of healthy donors using the platelet GelSep kit (Biocytex, Marseille, France) kit according to the guidelines of the manufacturer. Platelets were activated by the addition of thrombin to a final concentration of 0.8 U/ml. To distinguish activated from non-activated platelets double staining was performed with Tie-1 antibodies/control antibodies and antibody CD42 (total platelets) or CD62 (activated platelets).

After preparation, platelets were resuspended in buffer 2 of the GelSep kit, 10% heat inactivated human serum (incubation buffer) and incubated for 1 hour. To test specificity, biotinylated antibodies human anti-Tie1 (E3), human anti-streptavidin (A2), human anti-FITC and goat anti-Tie (R&D systems) were incubated with 500 000 platelets per test for 1 hour at different dilutions (2 µg/ml, 10 µg/ml) for 1 h at room temperature. Platelets were spun down by centrifugation for 10 min at 611 g. Between incubations platelets were washed twice with Buffer 1 of the GelSep kit. Then, Strepatvidin-R-phycoerythrin together with anti-CD42-PercP or anti-CD62-PercP were incubated for 30 minutes at room temperature in incubation buffer After the last incubation and washing detection of bound antibodies was performed by means of flow cytometry on a FACSscan and Epics Altra (Becton Dickinson, Oxnard, Coulter,) and results analyzed. Cells were gated on SSC and anti-CD42-PercP for the total platelets in case non-activated platelets were used and on SSC and anti-CD62-PercP for the activated platelets.

The polyclonal goat anti-Tie-1 antibody indeed binds to platelets under the conditions tested. This binding is lower when platelets are activated. In contrast, the human anti-Tie1 antibody E3 shows no significant binding to total platelets, nor to activated platelets.

Example 10

Assessment of Tie1 Immunoreactivity in Human Platelets Using Immunoprecipitation with Anti Tie1 E3-IgG (Paula Henderikx, Laetitia Devy)

A previous study with a purified polyclonal goat antiserum against Tie-1 (R&D Systems) had showed binding to human platelets (Tsiamis et al., 2000). The conclusion from this study was that platelets represent a large pool of Tie-1 immunoreactivity which could present a problem for development of Tie1 as a therapeutic target. To exclude the possibility that the antibody E3 binds to platelets immunoprecipitation of lysates prepared from platelets and HUVECS were performed. Both, activated and inactivated platelets were tested. Anti-Tie-1 antibodies B2, D11, E3, the goat polyclonal AF619 (R&D) and negative control antibodies anti-FITC and anti-Streptavidin were used. HUVECS were retrieved from culture dishes by trypsinization and platelets were prepared with the platelet GelSep kit (Biocytex, Marseille, France) kit according to the guidelines of the manufacturer. Per immunoprecipitation experiment 3-5e10$^6$ and 3e10$^8$ cells platelets were used for each antibody tested. Platelets and cells were washed with PBS and spun down at 1400 rpm for 4 minutes and supernatant was removed. Then cells were lysed in 1 ml lysis buffer containing 50 mM Tris HCL pH 7.5, 150 mM NaCl, 0.5% Deoxycholic acid (DOC) and 0.5% NP-40 for 5 minutes. The lysed cells were spin down for 10 minutes at 14.000 rpm and 5 µg/ml antibody was added to the supernatant and incubated at 4° C. on a rotator. 100 µl/sample protein A beads (Uppsala, Sweden) were washed 3 times with lysis buffer (centrifugation speed: 15 seconds, 2000 rpm) then cell lysates incubated with antibody were added for 30 minutes 4° C. Then beads were washed three times with washing buffer containing 50 mM Tris HCL pH 7.5, 400 mM NaCl, 0.5% DOC, 0.5% NP-40. Finally, beads are spun down and the pellets was resuspended in an equal amount in sample buffer to perform SDS-page and Western blotting. In Western blotting Tie-1 was detected with the polyclonal goat anti-Tie-1 antibody. The conclusions of this study are that E3 is able to immune precipitate Tie-1 in HUVEC but not in platelets.

Example 11

Distribution of Tie1 in HUVECS Cells Determined by Staining with Anti Tie1 E3-IgG We analyzed the staining pattern of E3 in HUVECS using confocal microscopy. HUVEC were trypsinised, washed with PBS and spotted at a density of 60 000 cells on a gelatine coated microscope slide and incubated for 24 hours in a humidified incubator at 37° C. Cells were air dried and fixed with 4% paraformaldehyde for 20 minutes at room temperature. The slides were washed with PBS. The slides were incubated with 10% Heat inactivated human serum (incubation buffer).

For measuring specific binding to Tie-1, biotinylated antibody E3 and biotinylated negative control antibody A2 were used at a concentration of 10 µg/ml and incubated for 1 hour at room temperature. Slides were washed twice with PBS. Then, Strepatvidin-R-phycoerythrin (Dako, Glostrup, Denmark) was added and incubated for 1 hour at room temperature. After the last incubation and washing detection of bound antibodies was performed by means of confocal microscopy.

E3 binds specifically to HUVEC as detected by confocal microscopy. The staining is pre-dominantly located inside of the cell which suggests a large intracellular pool of Tie1 relative to a smaller pool of cell surface localized Tie1. The localization of E3 was consistent with co-localization of Tie1 with a cytoskeletal protein.

Example 12

Conversion of Somatic Mutations Positioned in the Framework Region of Anti Tie1 E3 to Germline Residues To reduce potential immunogenicity of E3 in humans, all non germline amino acid residues in the LC framework regions were corrected back to germline. An initial analysis was performed which aligned the LC of E3 with a database containing all kappa and lambda light chain germline genes. The LC of E3 was shown to have closest homology to DPK4 and three substitutions in E3 relative to the germline framework regions were identified.

We constructed a germlined version of E3 in which the LC framework regions were altered to include sequences identical to the DPK4 germline framework regions. The germlined E3 antibody was constructed by engineering a nucleic acid encoding the desired sequence. Changes to nucleic acids encoding the E3 LC variable domain were made by PCR and other standard molecular biological techniques and verified by nucleic acid sequencing.

The germlined E3 sequence is as follows:

(SEQ ID NO: 159)
DIQMTQSPSSLSASVGDRVTITCRASQGIGHYLAWYQQKPGKVPKLLIYT

ASTLQSGVPSRFSGSGSGTDFTLTISSLQPEDVATYYCQQFNSYPHTFGQ

GTRLEIK

The altered positions are underscored.

We produced the germlined version of the E3 antibody as both a soluble Fab and as an IgG. The Fab cassette of the positive sFAB-expressing clone was PCR amplified with oligonucleotides, ligated into a mammalian expression vector containing the human IgG4 Fc region and electroporated into XL1 Blue MRF' cells. The prokaryotic ribosomal binding sequence and gene three leader sequence were replaced with a mammalian internal ribosomal entry and heavy chain leader sequences. Reformatted antibody clones were sequenced to confirm accuracy following the cloning procedure. Endotoxin-free DNA was prepared and used for transient transfection studies.

Example 13

Production and Testing of Germlined Anti Tie1 E3-Fab for Binding to Recombinant Tie1-Fc in ELISA To evaluate if the conversion of any of the somatic mutations in the framework of E3 back to germline residues had any effect on binding activity the soluble Fabs were produced. The soluble expression vector containing the parental E3 Fab and the germlined E3 Fab construct were grown overnight at 30° C. in 2x+TY broth containing 100 µg/ml ampicillin and 2% glucose and use 4 ml of this overnight culture to inoculate 400 ml of 2x TY broth containing 100 µg/ml ampicillin and 0.1% glucose. Cells were grow at 37° C. until an $OD_{600}$ of 0.8-1.0, 1 mM IPTG was added and the culture was maintained at 30° C. for 4 hours. The cultures were spun down at 4,000 rpm for 15 min at 4° C. The supernatants were discarded and resuspend the pellets resuspended in 4.8 ml of ice cold TES buffer (0.2 M Tris-HCl, 0.5 mM EDTA, 0.5 M sucrose, pH 8.0) containing proteases inhibitors (protease inhibitor cocktail tablets [Roche]: dissolve 1 tablet in 1 ml of water and dilute 50-times in TES buffer). Transfer to 50 ml Falcon tubes and place on ice for 5-10 min. During this incubation, wash the centrifugation bottles with 5.25 ml $TES:H_2O$ (1:3) containing proteases inhibitors and add this to the cells. Incubate for 20 more min on ice. Spin at 3000 g for 15 min at 4° C. and transfer the supernatants into new centrifugation tubes. Resuspend the cell pellets in 6 ml TES containing 15 mM $MgSO_4$ and proteases inhibitors and incubate on ice for 15 min. Centrifuge at 3000 g for 15 min at 4° C. Transfer the supernatants into the centrifugation tubes and spin at 8000 g for 20 min at 4° C. Collect the supernatants and dialyze against PBS. The Fabs were purified by metal chelate chromatography. Incubate the dialyzed periplasmic extracts with 1 ml of TALON™ Metal Affinity Resin (Clontech) and rotate at room temperature for 2 hours. Transfer the beads into empty gravity column (Poly-Prep chromatography columns, Bio-Rad, Cat. 731-1550). Wash the beads with 5 mM imidazole in PBS and elute the Fabs with 150 mM imidazole in PBS. Dialyze against PBS using dialysis cassettes (SLIDE-A-LYSER™ Dialysis Cassettes, MWCO 10,000, Pierce, cat. no. 66380) and determine the protein concentration from the absorbance at 280 nm assuming that a 1 mg/ml solution has an absorbance of 0.86. The quality of the preparations can be analyzed by reducing and non-reducing SDS-PAGE.

Wells of an IMMULON™ 2 HB plate coated overnight with 500 ng or 50 ng of purified recombinant human Tie-1-Fc target antigen per 100 microliters 0.1 M sodium bicarbonate buffer, pH 8.5. Parental E3, E3 germlined (E3g) or a negative control soluble Fab were loaded into wells at either 5 micrograms or 1 microgram per 100 microliters of PBST. Recombinant human Tie-1-Fc target antigen is dissolved in an appropriate amount of acetic acid and subsequently diluted into 0.1 M sodium bicarbonate buffer, pH 9.6 at final concentrations of 500 ng and 50 ng per 100 microliters. After addition of the target antigen to the wells the microtitre plate is incubated overnight at 4° C. The plate is subsequently washed 5 times with PBST and blocked with 1% BSA in PBS at 37° C. for 2 hours. The plate is again washed plate times with wash buffer, PBST and 100 microliters per well of purified Fab at 5 or 1 micrograms per 100 microliter PBST was added followed by incubation at room temperature for 1 hour. After washing plate 7 times with PBST 100 microliters of a 1:5000 dilution of anti-sFab-HRP in PBST was added (Pierce Product #31414). After washing the wells seven times 100 microliters TMB-H2O2 solution was added to each well and the plate read at 630 nm in an ELISA. Both E3 and germlined E3 bound to the recombinant human Tie-1-Fc target antigen by this assay.

Example 14

Production and Testing of Germlined Anti Tie1-E3-Fab for Binding to Recombinant Human Tie1 in BIAcore Recombinant purified human Tie1-Fc antigen (Stock 2.45 mg/ml) was biotinylated using the EZ-link Sulfo-NHS-SS-Biotin (Pierce, Cat. 21331). The reaction was performed for 2 hours on ice in 50 mM sodium carbonate buffer, pH 9.6, in the presence of a 5-fold molar excess of biotinylating agent and was stopped by the addition of Tris-HCl, pH 7.5 (50 mM final concentration) followed by a 1-hour incubation on ice. Samples were then dialyzed against PBS. The antigen was then diluted 1/100 fold in HBS and was then captured onto a streptavidin chip. This was coated to a density of 830 RU (resonance units). All analysis was performed in HBS buffer. The parental Fab E3 and germlined E3 Fab were prepared as described above. A stock solution of 0.587 mg/ml (11740 nM) was diluted 1/587 in HBS+BSA to obtain a stock of 20 nM and the germlined Fab E3 0.025 mg/ml (500 nM) was diluted 1/25 in HBS+BSA to obtain a stock of 20 nM. Serial dilutions were made of each Fab preparation to obtain 10 nM, 5 nM, 2.5 nM, and 1.25 nM solutions. For the association phase samples were injected at 30 µl/min for 4 minutes using kinject program. This was followed by a 10 minutes dissociation phase, any remaining sample was stripped from the Tie-1 Fc surface at a flow of 50 µl/min with a single injection of 5 mM NaOH+1M NaCl for 18 seconds. All samples were run and analyzed in duplicate.

Sensorgrams were analyzed using the simultaneous ka/kd fitting program with 1:1 model in the BIAEVALUATION™ software 3.1. From the analysis we can see that the germlining of the E3 antibody has had minimal effect on the binding activity of the antibody.

TABLE 5

Comparison of the binding affinity of parental and germlined E3 Fab

| E3 Fab | Tie-1 Fc | ka (1/Ms) | kd (1/s) | KD (1) nM |
|---|---|---|---|---|
| parental | Human | 3.00E+05 | 6.10E−04 | 2.0 |
| germlined | Human | 3.00E+05 | 1.02E−03 | 3.4 |

Example 15

Comparison of Affinity of Germlined Anti Tie1 E3-IgG to Parental Anti Tie1 E3 for Binding to Recombinant Human Tie1 Using BIAcore In order to evaluate if the binding behavior had been affected in any way by the conversion of the somatic mutations back to germline residues, the germlined antibody was produced and tested as an IgG. The germlined E3-IgG construct used to transiently transfect HEK293T cells and purified.

The gernlined E3 IgG1 stock solution 0.63 mg/ml was diluted 1/50 in a buffer of pH4.5 and the parental E3 IgG1 stock solution 0.56 mg/ml (2143-001) was diluted 1/50 in a buffer of pH 4.5. The IgG were directly coated onto a CM5 chip. The surface of the chips was activated with a 7 minute pulse of 0.05M NHS/0.2M EDC and the IgG was flowed over until 780 RU germlined E3-IgG and 728 non germlined E3 IgG was coated onto the surface. All flow cells were subsequently deactivated with a 7 minute pulse of 1M ethanolamine hydrochloride pH 8.5. All analysis was performed in HBS buffer. Purified recombinant human Tie-1 Fc was diluted 1/28.7 in HBS to obtain a 400 nM stock solution. Serial dilutions were made to obtain 200 nM, 100 nM, 50 nM and 25 nM Tie-1 Fc stocks. For analysis of the association phase samples were injected at 30 µl/min for 8.3 minutes using kinject program. This was followed by a 40 minutes dissociation phase. Any antigen remaining associated to the surface was stripped from the IgG surface at a flow of 50 µl/min with two injections of 10 mM glycine pH 1.5 for 30 secods. All samples were run and analyzed in duplicate Sensorgrams were analyzed using the simultaneous ka/kd fitting program with 1:1 model in the BIAEVALUATION™ software 3.1. Germlining had minimal impact on the binding activity of the E3 IgG with respect to human Tie1 Fc.

TABLE 6

Comparison of the binding affinity of parental and germlined E3 IgG

| E3 IgG | Tie-1 Fc | ka (1/Ms) | kd (1/s) | KD (1) nM |
|---|---|---|---|---|
| parental | Human | 6.19E+03 | 3.61E−05 | 5.83 |
| germlined | Human | 7.09E+03 | 3.67E−05 | 5.17 |

Example 16

Production and Testing of Germlined Anti Tie1-E3-Fab for Binding to Recombinant Mouse Tie1 in BIAcore Mouse Tie 1-Fc antigen (0.5 mg/ml stock) was biotinylated using established procedures and after dilution 1/100 fold in HBS this was then used for capturing to a streptavidin chip. This was coated to a resonance value of 740 RU. All analysis was performed in HBS buffer. The parental Fab E3 0.587 mg/ml (11740 nM) was diluted 1/587 in HBS+BSA to obtain a stock of 20 nM and the germlined Fab E3 0.025 mg/ml (500 nM) was diluted 1/25 in HBS+BSA to obtain a stock of 20 nM. Serial dilutions were made of each Fab preparation to obtain 10 nM, 5 nM, 2.5 nM, and 1.25 nM. For the association phase samples were injected at 30 µl/min for 4 minutes using kinject program. This was followed by a 10 minutes dissociation phase, any remaining sample was stripped from the Tie-1 Fc surface at a flow of 50 µl/min with a single injection of 50 mM NaOH+1 M NaCl for 18 seconds. All samples were run and analyzed in duplicate.

Sensorgrams were analyzed using the simultaneous ka/kd fitting program with 1:1 model in the BIAEVALUATION™ software 3.1. The germlining of the E3 antibody has had minimal effect on the binding activity of the antibody.

TABLE 7

Comparison of the binding affinity of parental and germlined E3 Fab

| E3 Fab | Tie-1 Fc | ka (1/Ms) | kd (1/s) | KD (1) nM |
|---|---|---|---|---|
| parental | Mouse | 2.46E+05 | 9.50E−04 | 3.9 |
| germlined | Mouse | 3.40E+05 | 1.04E−03 | 3.1 |

Example 17

Comparison of Affinity of Germlined Anti Tie1 E3-IgG to Parental Anti Tie1 E3 for Binding to Recombinant Mouse Tie1 Using BIAcore In order to evaluate if the binding behavior had been affected in any way by the conversion of the somatic mutations back to germline, the germlined antibody was produced and tested as a IgG. The germlined E3 was reformatted to an IgG as described. This was then used to transiently transfect HEK293T cells using established procedures. The IgG was purified from the culture supernatant using protein A column chromatography using established procedures and the subsequent IgG was then tested for binding activity using surface plasmon resonance (BIAcore). The germlined E3 IgG1 stock solution 0,63 mg/ml (2146-002) was diluted 1/50 in a buffer of pH 4.5 and the parental E3 IgG1 stock solution 0,56 mg/ml (2143-001) was diluted 1/50 in a buffer of pH 4.5. The IgG were directly coated via onto a CM5 chip. The surface of the chips was activated with a 7 minute pulse of 0.05M NHS/0.2M EDC and the IgG was flowed over until 780 RU germlined E3-IgG and 728 non germlined E3 IgG was coated onto the surface. All flow cells were subsequently deactivated with a 7 minute pulse of 1 M ethanolamine hydrochloride pH 8,5. All analysis was performed in HBS buffer. Purified recombinant mouse Tie-1 Fc was diluted 1/6,5 in HBS to obtain a 400 nM stock solution. Serial dilutions were made to obtain 200 nM, 100 nM, 50 nM and 25 nM Tie-1 Fc stocks. For analysis of the association phase samples were injected at 30 µl/min for 8,3 minutes using kinject program. This was followed by a 40 minutes dissociation phase. Any antigen remaining associated to the surface was stripped from the IgG surface at a flow of 50 µl/min with two injections of 10 mM glycine pH1,5 for 30 seconds. All samples were run and analyzed in duplicate Sensorgrams were analyzed using the simultaneous ka/kd fitting program with 1:1 model in the BIAEVALUATION™ software 3.1. The germlining process had minimal impact on the binding activity of the E3 IgG with respect to mouse Tie1-Fc.

TABLE 8

Comparison of the binding affinity of parental and germlined E3 IgG

| E3 IgG | Tie-1 Fc | ka (1/Ms) | kd (1/s) | KD (1) nM |
|---|---|---|---|---|
| parental | Mouse | 6.17E+03 | 9.20E−05 | 14.9 |
| germlined | Mouse | 6.00E+03 | 8.99E−05 | 15 |

Example 18

Comparison of IC50 of Germlined Anti Tie1-E3 and Parental Anti Tie1-E3 in Tube Formation Assays Using HUVECS Germlined E3 and its parental antibody were evaluated in the tube formation assay in a collagen type-I matrix. Human Umbilical vein endothelial cells (HUVEC) (freshly isolated) were obtained by treating human umbilical cord veins with Trypsin-EDTA (1×) (Gibco/Invitrogen) for 20-25 minutes at 37° C. The cells were then cultured in a T-25 flask coated with attachment factor (AF), (Cascade Biologics) in RPMI 1640 medium supplemented with 10% FCS, 0.4% BBE, 1% 1-glutamin, 1% penicillin/streptomycin. Primary cultures were detached with warm Trypsin-EDTA and used when confluent at the second or third passage. During culturing, the cells were kept in a proliferative state by culturing them in a split ratio 1:2 at an approximate density of the monolayer of about 60-80%. HUVEC monolayers were treated with trypsin/EDTA (500 µl/dish) at 37° C. for 3 min. Trypsin activity was stopped by adding 3 volumes of complete RPMI medium. The cells were carefully scraped, separated by repeated pipetting, and finally washed with PBS. HUVECs (passage 2) were seeded in their culture medium ($40.10^3/50$ l/well of a 96-well plate) on a collagen gel (50 µl of coll I 1.5 mg/ml) prepared by mixing 7.5 volumes of 2 mg/ml collagen (Collagen R; Serva, Heidelberg, Germany), 1 volume of 10× MEM, 1.5 volume of NaHCO3 (15.6 mg/ml) and ~1 volume of NaOH to adjust the pH to 7.4. After 1 h30, the culture medium was then discarded and the cells were covered with a new layer of collagen (1.5 mg/ml, new preparation, 50 µl/well). After polymerization of the gel, culture medium was added to each well in presence or in absence of E3 antibody or germlined E3 antibody (0.1 ng/ml to 100 ng/ml). The total length of the tube network on the culture surface was quantified at 40× magnification by the Metavue Software (Universal Imaging Corporation). Results from triplicate wells were expressed as mean vessel area per field ±SEM (relative units). Each assay was performed at least three times (FIG. 16, FIG. 17). The conclusions are that conversion of the 3 somatic mutations to germline amino acids in E3 has had little effect on the potency of E3. Both parental E3 and germlined E3 inhibit tube formation in vitro with an essentially identical $IC_{50}=10$ ng/ml, i.e. 66 pM)

Example 19

Analysis of Germlined Anti Tie1-E3 in Tube Formation Assays with Mouse Endothelial Cells In order to assess mouse Tie-1 cross-reactivity and biological activity on mouse Tie1, both E3 and germlined E3 were evaluated for their ability to inhibit tube formation in vitro using mouse endothelial cell line (LEII).

LEII lung mouse endothelial cell line (ATCC) was cultured in a T-25 flask in MEM medium with GLUTAMAX™ (Life Technologies Ltd., Paisley, Scotland) supplemented with 10% FCS, and 1% penicillin/streptomycin. During culturing, the cells were kept in a proliferative state by culturing them in a split ratio 1:5 at an approximate density of the monolayer of about 80%. LEII monolayers were treated with trypsin/EDTA (500 µl/dish) at 37° C. for 3 min. Trypsin activity was stopped by adding 3 volumes of complete MEM medium. The cells were carefully scraped, separated by repeated pipetting, and finally washed with PBS.LEII cells were seeded in their culture medium ($20$-$40 \times 10^3/50$ µl/well of a 96-well plate) on a basement membrane (BIOCOAT™ Angiogenesis System; Becton Dickinson). After polymerization of the MATRIGEL™ (30 min at 37° C., 5% $CO_2$ environment) the endothelial cell suspension resuspended in complete culture medium in the presence of the desired molecules ($4.10^5$ cells/ml; 50 µl/well) was added to each well. The angiogenesis assay plate was then incubated for 16 to 18 hours at 37° C., 5% $CO_2$ atmosphere. The total length of the tube network was then quantified at 40× magnification by the METAVUE™ Software (Universal Imaging Corporation). Results from triplicate wells were expressed as mean vessel area per field ±SEM (relative units). Each assay was performed at least two times. Germlined E3 is a potent inhibitor of tube formation in mouse endothelial cells.

Example 20

Immunohistochemical Analysis of Mouse Tumor Tissue Sections Using Anti Tie1-E3

We determined if antibody E3 binds to mouse endothelial cells in mouse xenographs. Immunohistochemistry was performed with biotinylated antibody E3 and control antibodies anti-CD3 1 (endothelial cell specific marker) and anti-PCNA (proliferating cell nuclear antigen). Formalin-fixed tumor tissues from a mouse-xenograph containing SW480 cells (ATCC) were tested for the binding pattern of the human anti-Tie1 antibody E3. 5 µm sections of paraffin embedded tissues were deparaffinized, rehydrated and pretreated with warm the citrate buffer (0.01 M sodium citrate, pH6 at 95° C.) for 45 min. The slides were cooled down in fresh citrate buffer for 20 min and rinsed with distilled water. The slides were hydrogen peroxide treated, (0.3% $H_2O_2$ in PBS), and preincubated with PBS, 5% FCS, 5% heat inactivated human serum (HS) for 1 hour. Between antibody incubations slides were washed 3 times 5 minutes in PBS. Biotinylated antibodies E3 and A2 were diluted to a concentration of 10 µg/ml in PBS, 10% HS and incubated for 1 hour at RT. Slides were then incubated with an avidin-HRP (Dako) for 30 minutes at room temperature. Staining was detected by AEC (Vector Laboratories, Burlingame) and $H_2O_2$. The peroxidase reaction was stopped with water and slides were counter-stained with haematoxylin. The tissues were evaluated for their binding reactivity. The staining pattern was consistent with staining of mouse endothelial cell Tie-1 and also with Tie1 expressed by the E3 binds to Tie-1 expressed by SW480 tumor cells in a mouse xenograft.

What is claimed is:

1. An isolated antibody comprising a heavy chain immunoglobulin variable domain sequence and a light chain immunoglobulin variable domain sequence, wherein the antibody binds to Tie1 ectodomain and comprises:

(1) the heavy chain immunoglobulin variable domain comprising a CDR1 that consists of MYGMV (amino acids 31-35 of SEQ ID NO:114), a CDR2 that consists of VISPSGGNTGYADSVKG (amino acids 50-66 of SEQ ID NO:114), and a CDR3 that consists of APRGYSYGYYY (amino acids 99-109 of SEQ ID NO:114) and the light chain immunoglobulin variable domain comprising a CDR1 that consists of RASQGIGHYLA (amino acids 24-34 of SEQ ID NO:116), a CDR2 that consists of TASTLQS (amino acids 50-56 of SEQ ID NO:116), and a CDR3 that consists of QQFNSYPHT (amino acids 89-96 of SEQ ID NO:116);

(2) the heavy chain immunoglobulin variable domain comprising a CDR1 that consists of IYGMA (amino acids 31-35 of SEQ ID NO:64), a CDR2 that consists of VISPSGGQTFYADSVKG (amino acids 50-66 of SEQ ID NO:64), and a CDR3 that consists of VYYYGMDV (amino acids 99-106 of SEQ ID NO:64) and the light chain immunoglobulin variable domain comprising a CDR1 that consists of RASQSVSSYLA (amino acids 28-38 of SEQ ID NO:66), a CDR2 that consists of DASNRAT (amino acids 54-60 of SEQ ID NO:66), and a CDR3 that consists of QQRSKWPRT (amino acids 93-101 of SEQ ID NO:66); or (3) the heavy chain immunoglobulin variable domain comprising a CDR1 that consists of GYAMW (amino acids 31-35 of SEQ ID NO:84), a CDR2 that consists of SISPSGGATAYADSVKG (amino acids 50-66 of SEQ ID NO:84), and a CDR3 that consists of DAGSYYWGWFDP (amino acids 99-110 of SEQ ID NO:84) and the light chain immunoglobulin variable domain comprising a CDR1 that consists of RASQSISSYLA (amino acids 28-38 of SEQ ID NO:86), a CDR2 that consists of DASSRVT (amino acids 54-60 of SEQ ID NO:86), and a CDR3 that consists of LQRSSWPRT (amino acids 93-101 of SEQ ID NO:86).

2. The antibody of claim 1 wherein the amino acid sequences of the heavy chain variable domain sequence comprises CDR1, CDR2, and CDR3 sequences from SEQ ID NO:114, and the light chain variable domain sequence comprises CDR1, CDR2, and CDR3 sequences from SEQ ID NO:116.

3. An isolated antibody comprising a heavy chain immunoglobulin variable domain sequence and a light chain variable domain sequence, wherein the heavy chain immunoglobulin variable domain sequence comprises CDR1, CDR2, and CDR3 sequences from SEQ ID NO:114, and the light chain variable domain sequence comprises SEQ ID NO:159.

4. The antibody of claim 2 wherein the heavy chain variable domain sequence comprises SEQ ID NO:114.

5. The antibody of claim 1 wherein the heavy chain and light chain framework regions are human.

6. The antibody of claim 1 further comprising an Fc domain.

7. The antibody of claim 6 that comprises the constant domains of a human IgG1, IgG2, IgG3, or IgG4.

8. A composition comprising the antibody of any one of claims 1 or 2-7 and a pharmaceutically acceptable carrier.

9. A method for detecting the presence of a Tie1 protein, in a sample, in vitro, the method comprising:
- (i) contacting the sample with the antibody according to claim 1, under conditions that allow interaction of the antibody and the Tie1 protein to occur; and
- (ii) detecting formation of a complex between the antibody and the Tie1 protein in the sample.

10. A method for detecting the presence of Tie1 in vivo, the method comprising:
- (i) administering to a human subject the antibody according to claim 1, under conditions that allow interaction of the antibody and the Tie1 protein to occur; and
- (ii) detecting formation of a complex between the antibody and the Tie1 protein in the subject.

* * * * *